United States Patent
Krum et al.

(10) Patent No.: US 11,273,153 B2
(45) Date of Patent: Mar. 15, 2022

(54) MAPK INHIBITORS

(71) Applicant: EverBrilliant Pharma Pty Ltd, Melbourne (AU)

(72) Inventors: Henry Krum, Malvern (AU); Peter Scammells, North Balwyn (AU); Bing Wang, Camberwell (AU); Natalie Vinh, Vermont South (AU); Jamie Simpson, Brunswick (AU); David Chalmers, Clayton (AU)

(73) Assignee: EverBrilliant Pharma Pty Ltd, Melbourne (AU)

( * ) Notice: Subject to any disclaimer, the term of this patent is extended or adjusted under 35 U.S.C. 154(b) by 0 days.

(21) Appl. No.: 16/006,308

(22) Filed: Jun. 12, 2018

(65) Prior Publication Data

US 2018/0289684 A1 Oct. 11, 2018

Related U.S. Application Data

(63) Continuation of application No. 15/505,942, filed as application No. PCT/AU2015/050490 on Aug. 25, 2015, now abandoned.

(30) Foreign Application Priority Data

Aug. 25, 2014 (AU) .................................. 2014903342

(51) Int. Cl.
| | | |
|---|---|---|
| C07D 409/04 | (2006.01) | |
| A61K 31/4436 | (2006.01) | |
| C07D 409/14 | (2006.01) | |
| A61K 31/444 | (2006.01) | |
| C07D 333/02 | (2006.01) | |
| C07D 409/00 | (2006.01) | |

(52) U.S. Cl.
CPC ........ *A61K 31/4436* (2013.01); *A61K 31/444* (2013.01); *C07D 333/02* (2013.01); *C07D 409/00* (2013.01); *C07D 409/04* (2013.01); *C07D 409/14* (2013.01)

(58) Field of Classification Search
CPC .......................... C07D 409/04; A61K 31/4436
USPC ........................................ 546/280.4; 514/336
See application file for complete search history.

(56) References Cited

U.S. PATENT DOCUMENTS

| | | |
|---|---|---|
| 4,174,405 A | 11/1979 | Relyea et al. |
| 4,381,311 A | 4/1983 | Haber |
| 4,749,712 A | 6/1988 | Haber |
| 5,571,810 A | 11/1996 | Matsuo et al. |
| 2003/0004559 A1 | 1/2003 | Lentz et al. |
| 2003/0019570 A1 | 1/2003 | Chen et al. |
| 2004/0147515 A1 | 7/2004 | Umbricht et al. |
| 2004/0147525 A1 | 7/2004 | Umbricht et al. |
| 2004/0242673 A1 | 12/2004 | Lockhart et al. |
| 2010/0063104 A1 | 3/2010 | Nakai et al. |

FOREIGN PATENT DOCUMENTS

| | | |
|---|---|---|
| CN | 1059142 A | 6/1991 |
| DE | 10343757 A1 | 4/2005 |
| JP | 57-134480 A | 8/1982 |
| JP | 2007-500219 A | 1/2007 |
| JP | 2008-001596 A | 1/2008 |
| JP | 2010-209141 A | 9/2010 |
| WO | 9119708 A1 | 12/1991 |
| WO | 1998047892 A1 | 10/1998 |
| WO | 2006/092059 A1 | 9/2006 |
| WO | 2006025517 A1 | 9/2006 |
| WO | 2006092059 A1 | 9/2006 |
| WO | 2007/040208 A1 | 4/2007 |
| WO | 2007/118149 A2 | 10/2007 |
| WO | 2013119895 A1 | 8/2013 |

OTHER PUBLICATIONS

Li et al., "Selective inhibition, etc.," Am J Physiol Heart Circ Physiol 291: H1972-H1977. (Year: 2006).*
Zwerina et al., "Activation of p38, etc.," Arthritis & Rheumatism, 54(2), pp. 463-472. (Year: 2006).*
Chopra et al., "Therapeutic potential, etc.," Expert Opin. Investig. Drigs, 17(10), 1411-1425. (Year: 2008).*
Simone, Oncology: Introduction, Cecil Textbook of Medicine, ed. Bennett et al. W.B. Saunders CO. 20ed. vol. 1, pp. 1004-1010. (Year: 1996).*
Gura, Systems for Identifiying New Drugs Are Often Faulty, Cancer Models, Science, vol. 278 No. 5340. pp 1041-1042. (Year: 1997).*
Johnson et al., Relationships between drug activity in NCI preclinical in vitro and in vivo and early clinical trials, British J of Cancer, 64(10): 1424-1431. (Year: 2001).*
Pearce et al., Failure modes in anticancer drug discovery and development, Cancer Drug Design and Discovery ed by Stephen Neidle, chap. 18, pp. 424-435. (Year: 2008).*
Khorasanizadeh et al., "Mitogen-activated, etc.," Pharmacology & Therapeutics 174, 112-126. (Year: 2017).*
Lee et al., "Targeting the, etc.," Expert Opin. Ther. Targets, 6(6), 659-678. (Year: 2002).*
Braicu et al., "A Comphrehensive, etc.," Cancers, 11, 1618, pp. 1-25. (Year: 2019).*
Kumar,et al., "Mitogen-Activated, etc.," Pharmaceutical, 13, 9, pp. 1-11. (Year: 2020).*
Newton et al., "Inhibitors, etc.," Biodrugs, 17(2), 113-129. (Year: 2003).*
Yuan et al., "The MAPK, etc.," Journal of Hematology & Oncology, 13:113, pp. 1-19. (Year: 2020).*
Fujiwara et al. "Preparation of, etc.," CA 138:204948. (Year 2003).
Fujita et al. , "Bicyclic thiophenes, etc.," CA 126:304061 (Year: 2002).

(Continued)

*Primary Examiner* — Patricia L Morris
(74) *Attorney, Agent, or Firm* — Reichel Stohry Dean LLP; Natalie J. Dean

(57) ABSTRACT

The present invention relates to certain novel substituted thiophene compounds and the finding that they display useful efficacy in the inhibition of the p38α MAPK enzyme. This provides for use of the compounds in various treatment methodologies related to MAPK inhibition, including the treatment of inflammation.

18 Claims, 12 Drawing Sheets

(56) References Cited

OTHER PUBLICATIONS

L. Ackermann and al: "Ruthenium-catalysed direct C—H bond arylations of heteroarenes", Organic Letters, vol. 13, No. 13, Apr. 22, 2011 (Apr. 22, 2011), pp. 3332-3335, XP002776033.
Matloubi Moghaddam E et al: "A versatile one-pot synthesis of 2,3,5-tri-substituted thiophenes from thiomorpholides", Tetrahedron Let., Elsevier, Amsterdam, NL, vol. 44, No. 33, Aug. 11, 2003 (Aug. 11, 2003), pp. 6253-6255, XP004439058, ISSN: 0040-4039, DOI:10.1016/S0040-4039(03)01548-X.
Blay G et al: "Indirect regioselective heteroarylation of indoles through a Friedel-Crafts reaction with (E)-1,4-diaryl-2-buten-1,4-diones", Tetrahedron, Elsevier Science Publishers, Amsterdam, NL, vol. 65, No. 45, Nov. 7, 2009 (Nov. 7, 2009), pp. 9264-9270, XP026675264, ISSN: 0040-4020, DOI: 10.1016/J.TET.2009.09.011 [retrieved on Sep. 9, 2009].
Markus K.R. Fischer et al: "Functionalized Dendritic Oligothiophenes: Ruthenium Phthalocyanine Complexes and Their Application in Bulk Heterojunction Solar Cells", Journal of the American Chemical Society, vol. 131, No. 24, Jun. 24, 2009 (Jun. 24, 2009, pp. 8669-8676, XP55428757, US ISSN: 0002-7863, DOI: 10.1021/ja901537d.
Ullrich Mitschke et al: "Synthesis, characterization, and electrogenerated chemiluminescence of phenyl-substituted, phenyl-annulated, and spirofluorenyl-bridged oligothiophenes", Royal Chemical Society. Journal. Perkin Transactions 1, No. 7, Jan. 1, 2001 (Jan. 1, 2001), pp. 740-753, XP55235012, GB ISSN: 1472-7781, DOI:10.1039/b006553f.
Alfred Mitschker et al: "Neue ringsysteme durch photocyclisierung heterocyclischer triarene (1)", Tetrahedron Letters, vol. 15, No. 27, Jan. 1, 1974 (Jan. 1, 1974), pp. 2343-2346, XP55428549, Amsterdam, NL ISSN: 0040-4039, DOI: 10.1016/S0040-4039(00)92250-6.
Pinto D J P et al: "Chemistry and pharmacokinetics of diarylthiophenes and terphenyls as selective COX-2 inhibitors", Bioorganic & Medicinal Chemistry Letters, Pergamon, Amsterdam, NL, vol. 6, No. 24, Dec. 17, 1996 (Dec. 17, 1996), pp. 2907-2912, XP004135925, ISSN: 0960-894X, DOI: 10.1016/S0960-894X(96)00513-6.
Masakazu Fujita et al: "Design, synthesis and bioactivities of novel diarylthiophenes: inhibitors of tumor necrosis factor-alpha (TNF-alpha) production", Bioorganic & Medicinal Chemistry, vol. 10, No. 10, Oct. 1, 2002 (Oct. 1, 2002), pp. 3113-3122, XP55033743, ISSN: 0968-0896, DOI: 10.1016/S0968-0896(02)00224-9.
Peifer Christian et al: "New approaches to the treatment of inflammatory disorders small molecule inhibitors of p38 MAP kinase", Current Topics in Medicinal Chemistry, Bentham Science Publishers Ltd, Hilversum: NL, vol. 6, No. 2, Jan. 1, 2006 (Jan. 1, 2006), pp. 113-149, XP002673577, ISSN: 1568-0266, DOI: 10.2174/156802606775270323.
Biftu T. et al: "Synthesis and SAR of 2,3-diarylpyrrole inhibitors of parasite cGMP-dependent protein kinase as novel anticoccidial agents", Bioorganic & Medicinal Chemistry Letters, vol. 15, No. 13, Jul. 1, 2005 (Jul. 1, 2005), pp. 3296-3301, XP004947959, DOI: 10.1016/J.BMCL.2005.04.060.

Ducharme Y. et al: "2,3-Diarylthiophenes as selective EP 1 receptor antagonists", Bioorganic & Medicinal Chemistry Letters, vol. 15, No. 4, Feb. 15, 2005 (Feb. 15, 2005), pp. 1155-1160, XP004730411, DOI: 10.1016/J.BMCL.2004.12.005.
Vinh N. B. et al. "Design, Synthesis, and Biological Evaluation of Tetra-Substituted Thiophenes as Inhibitors of p38a MAPK" ChemistryOpen (2015) 4(1): pp. 56-64, DOI: 10.1002/open.201402076.
Acharya A. et al. "Sequential, One-Pot Synthesis of Tri- and Tetrasubstituted Thiophenes and Fluorescent Push-Pull Thiophene Acrylates Involving (Het)aryl Dithioesters as Thiocarbonyl Precursors" Journal of Organic Chemistry (2015) 80(1): pp. 414-427, DOI: 10.1021/jo502429c.
Vinh N. B. et al. "Virtual Screening using a confirmationally flexible target protein: models for ligand binding to p38a MAPK" Journal of Computer-Aided Molecular Design (2012) 26(4): pp. 409-423, DOI: 10.1007/S10822-012-9569-7.
Meanwell N.A. "Synopsis of Some Recent Tactical Applications of Bioisosteres in Drug Design" Journal of Medicinal Chemistry (2011) 54(8): pp. 2529-2591; See pp. Z to AB, DOI: 10.1021/jm1013693.
Thurmond R. L. et al. "Kinetics of small molecule inhibitor binding to p38 kinase" European Journal of Biochemistry (2001) 268(22): pp. 5747-5754.
Gallagher T.F. et al. "Regulation of Stress-Induced Cytokine Production by Pyridinylimidazoles; Inhibition of CSBP Kinase" Bioorganic & Medicinal Chemistry (1997) 5(1):pp. 49-64.
Japan Patent Office (JPO), Examination Report for Japan Application Serial No. JP2017525770, dated May 7, 2019, Japan.
Pillai et al., Design, synthesis, and pharmacological evaluation of some 2-[4-morpholino]-3-aryl-5-substituted thiophenes as novel anti-inflammatory agents: generation of a novel anti-inflammatory pharmacophore, Bioorganic & Medicinal Chemistry, vol. 12, Jul. 24, 2004, pp. 4667-4671, Elsevier Ltd.
Pillai et al., Novel drug designing approach for dual inhibitors as anti-inflammatory agents: implication of pyridine template, Biochemical and Biophysical Research Communications, vol. 301, 2003, pp. 183-186, Academic Press, Elsevier Science, USA.
Molvi et al., Synthesis and Anti-inflammatory Activity of Some Novel Trisubstituted Thiophene Analogues, Ethiop Pharm J, vol. 24, 2006, pp. 84-90, Ethiopia.
Marber et al., The p38 mitogen-activated protein kinase pathway—a potential target for intervention in infarction, hypertrophy and heart failure, J Mol Cell Cardiol. Oct. 2011; 51(4) 485-490, National Institute of Health, US.
Yang et al., Functional roles of p38 mitogen-activated protein kinase in macrophage-mediated inflammatory responses, Mediators Inflamm. 2014; 2014: 352371, Hindawi Publishing Corporation, GB.
Schett et al., The p38 mitogen-activated protein kinase (MAPK) pathway in rheumatoid arthritis, Ann Rheum Dis. Jul. 2008; 67(7): 909-916, National Institute of Health, US.
Koul et al., Role of p38 MAP kinase signal transduction in solid tumors, Genes & Cancer, Sep. 2013; 4(9-10) 342-359, SAGE Publications, US.
Kim and Choi, Pathological roles of MAPK signaling pathways in human diseases, Biochim Biophys Acta. Apr. 2010;1802(4): 396-405, Elsevier, NL.

\* cited by examiner

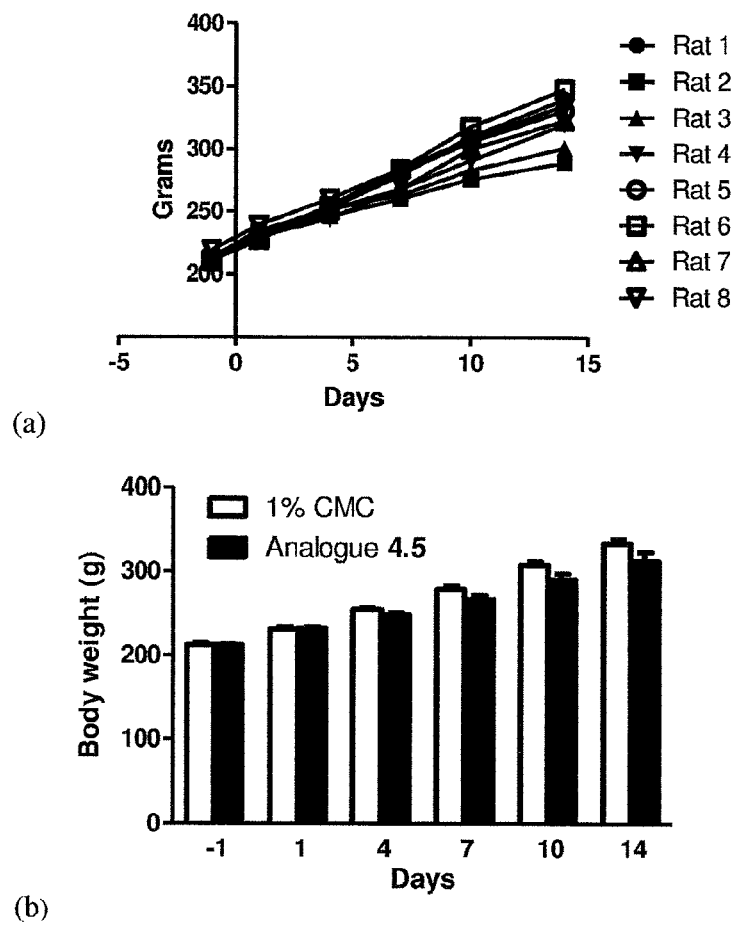
FIG 10 (a) and (b)
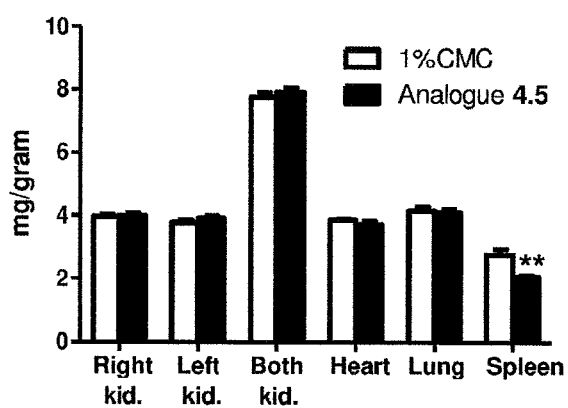
FIG 11

MAPK INHIBITORS

CROSS-REFERENCE TO RELATED APPLICATIONS

This application is a continuation of U.S. patent application Ser. No. 15/505,942 filed Feb. 23, 2017, which claims the benefit of PCT Application No. PCT/AU2015/050490 filed Aug. 25, 2015, which in turn claims the benefit of Australian Patent Application No. 2014903342 filed Aug. 25, 2014.

FIELD OF THE INVENTION

The invention relates to the field of medical treatment. More particularly, this invention relates to novel thiophene compounds and their use in treating a disease or condition responsive to mitogen-activated protein kinase (MAPK) inhibition.

BACKGROUND TO THE INVENTION

Any reference to background art herein is not to be construed as an admission that such art constitutes common general knowledge in Australia or elsewhere.

A number of drugs are commonly used to treat inflammation and include non-steroidal anti-inflammatory drugs (NSAIDs), corticosteroids and anti-cytokine biologics. NSAIDs exert their anti-inflammatory effect by inhibiting the cyclooxygenase enzymes (COX-1 and COX-2) which are responsible for the synthesis of prostanoids. These drugs however, are relatively non-selective and are often associated with gastrointestinal side effects. Although selective COX-2 inhibitors were developed and found to reduce these side effects, many were withdrawn from the market over safety concerns associated with cardiovascular and thrombotic adverse effects.

Among the most widely used anti-inflammatory drugs are the corticosteroids which act at multiple stages of the inflammatory cascade, including the up-regulation of anti-inflammatory genes and suppression of pro-inflammatory genes. However, prolonged use of corticosteroids can be associated with adverse effects including growth retardation in children, immunosuppression, hypertension, impairment of wound healing, osteoporosis and metabolic disturbances. Resistance has also been reported and as a consequence there are variations in patient response and in many cases a reduced efficacy with disease progression.

Aside from the more traditional anti-inflammatory therapies, anti-cytokine biologics developed using recombinant DNA and monoclonal antibody technology have become available for the treatment of several chronic inflammatory conditions. Despite their effectiveness as anti-inflammatory agents, these biologics have drawbacks that limit their use. Poor cellular penetration and activity, low oral bioavailability resulting in subcutaneous or intravenous administration, short half-life, rapid metabolism and a high cost of manufacture render them less desirable drugs. Given the limitations of existing anti-inflammatory drug therapies, there remains a need to identify alternative drug targets for the treatment of chronic inflammatory diseases.

With a greater understanding of the molecular basis of the inflammatory response and the mechanisms involved, a number of molecular targets for the treatment of inflammation have been identified. One signalling network found to play an important role in inflammation is the p38α mitogen-activated protein kinase (MAPK) pathway.

p38α MAPK (also named p38, reactivating kinase (RK) and p40) is a serine/threonine kinase that becomes phosphorylated and activated in response to various stimuli including endotoxin, hyperosmolarity, sodium arsenite, heat shock, and interleukin-1 (IL-1).

The p38α MAPK isoform plays a central role in the immune and inflammatory process. Its function is critical for the production of the inflammatory response of a number of proteins. Of particular importance, p38α MAPK is responsible for the biosynthesis of inflammatory cytokines through transcription-dependent mechanisms and post-transcriptional regulation. In addition to regulating cytokine biosynthesis, p38α MAPK is known to act downstream of cytokines. Therefore, p38α MAPK inhibition can not only stop production of cytokines but also reduce the deleterious effects of any cytokines that may still be produced which would provide greater efficacy in disease than inhibitors that act on mediators alone.

Pharmacological inhibition of p38α MAPK has shown anti-inflammatory activity in a number of experimental disease models including models for arthritis, inflammatory bowel disease, asthma and psoriasis. Further links have been established in myocardial injury, cardiac remodelling and renal fibrosis, stroke, cancer, Alzheimer's disease and human immunodeficiency virus.

p38α MAPK inhibitors to date suffer from a number of drawbacks including sub-optimal efficacy, poor physicochemical characteristics and undesirable side effects. There is, therefore, a need for alternative compounds for the treatment of diseases responsive to MAPK inhibition generally and, particularly, p38α MAPK inhibition.

OBJECT OF THE INVENTION

It is an aim of this invention to provide for a heterocyclic compound suitable for treating a disease responsive to MAPK inhibition which overcomes or ameliorates one or more of the disadvantages or problems described above, or which at least provides a useful alternative.

Other preferred objects of the present invention will become apparent from the following description.

SUMMARY OF INVENTION

According to a first aspect of the invention, there is provided a compound of formula (I), or a pharmaceutically acceptable salt thereof:

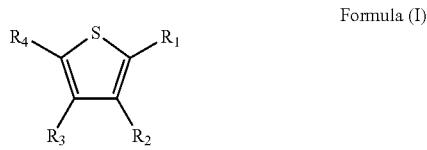

Formula (I)

wherein, $R_1$ is selected from the group consisting of hydrogen, alkyl, alkenyl, alkynyl, alkanoyl, carboalkoxy, acyloxy, aryl, aroyl, heteroaryl, heteroaroyl, heterocyclyl, heterocycloyl, cycloalkyl, O-alkyl and O-aryl, O-heteroaryl, amino and amido, all of which groups may be substituted or unsubstituted;

$R_2$ is selected from the group consisting of hydrogen, alkyl, alkenyl, alkynyl, aryl, alkylaryl, heterocyclyl and heteroaryl, all of which may be substituted or unsubstituted; and $R_3$ and $R_4$ are independently selected from the group consisting of aryl, heteroaryl, heterocyclyl and cycloalkyl, all of which groups may be substituted or unsubstituted.

In one embodiment, the compound of the first aspect is a non-naturally occurring compound.

According to a second aspect of the invention there is provided a pharmaceutical composition comprising an effective amount of a compound of the first aspect, or a pharmaceutically acceptable salt thereof, and a pharmaceutically acceptable carrier, diluent and/or excipient.

Suitably, the pharmaceutical composition is for the treatment or prophylaxis of a disease, disorder or condition responsive to MAPK inhibition, preferably p38 MAPK inhibition, more preferably p38α MAPK inhibition.

A third aspect of the invention resides in a method of treating a patient suffering from a disease, disorder or condition responsive to MAPK inhibition including the step of administering an effective amount of a compound of the first aspect, or a pharmaceutically effective salt thereof, or the pharmaceutical composition of the second aspect to the patient.

A fourth aspect of the invention provides for a compound of the first aspect, or a pharmaceutically effective salt thereof, or the pharmaceutical composition of the second aspect for use in the treatment of a disease, disorder or condition responsive to MAPK inhibition.

A fifth aspect of the invention provides for use of a compound of the first aspect, or a pharmaceutically effective salt thereof, in the manufacture of a medicament for the treatment of a disease, disorder or condition responsive to MAPK inhibition.

A sixth aspect of the invention provides for a complex of a compound of the first aspect, or a pharmaceutically effective salt thereof, with a p38 MAPK enzyme.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein:

FIGS. 10 (a) and (b) is a series of graphical representations showing (a) Individual body weight gain (rats 1-4 were administered compound 4.5 and rats 5-8 represent the vehicle group and (b) Difference in the body weight on average to the vehicle group;

FIG. 11 is a graphical representation of the average mass of tissues relative to the vehicle group for testing of compound 4.5;

DETAILED DESCRIPTION

Figure 1:
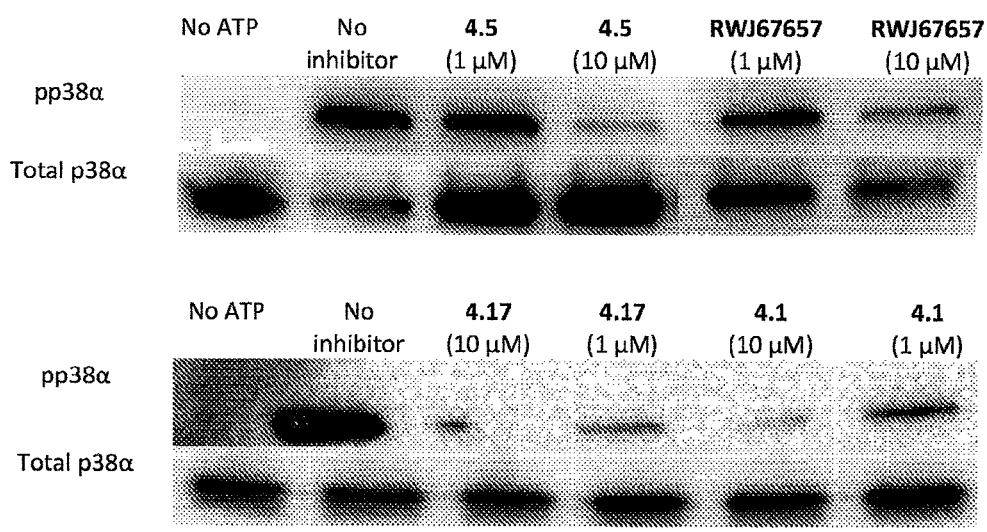
FIG. 1 is a series of western blots showing the effects of the tested compounds on p38α MAPK activation (phosphorylation)

The present invention is predicated, at least in part, on the finding that certain substituted thiophene compounds display useful efficacy in the treatment of inflammation through inhibition of the p38α MAPK enzyme.

Definitions

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

Unless defined otherwise, all technical and scientific terms used herein have the same meaning as would be commonly understood by those of ordinary skill in the art to which this invention belongs.

As used herein, "effective amount" refers to the administration of an amount of the relevant active agent sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight etc. An appropriate dosage or dosage regime can be ascertained through routine trial.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, amine, glucosamine, chloride, sulphate, sulphonate, bisulphate, nitrate, citrate, tartrate, bitartrate, phosphate, carbonate, bicarbonate, malate, maleate, napsylate, fumarate, succinate, acetate, benzoate, terephthalate, palmoate, piperazine, pectinate and S-methyl methionine salts and the like.

The term "alkyl" refers to a straight-chain or branched alkyl substituent containing from, for example, 1 to about 12 carbon atoms, preferably 1 to about 9 carbon atoms, more preferably 1 to about 6 carbon atoms, even more preferably from 1 to about 4 carbon atoms. Examples of such substituents include methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl and the like. The number of carbons relates to the carbon backbone and carbon branching but does not include carbon atoms belonging to any substituents, for example the carbon atoms of an alkoxy substituent branching off the main carbon chain.

The term "alkenyl" refers to optionally substituted unsaturated linear or branched hydrocarbon groups, having 2 to 12 carbon atoms, preferably 2 to 9 carbon atoms, more preferably 2 to 6 carbon atoms and having at least one carbon-carbon double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-1,3-diene, hex-1,3-diene, non-1,3,5-triene and the like.

The term "alkynyl" as used herein means alkyl moieties wherein at least one saturated C—C bond is replaced by a triple bond. In particular embodiments, alkynyl refers to groups comprising 2 to 12 carbon atoms ($C_2$-$C_{12}$ alkynyl). In further embodiments, alkynyl refers to groups comprising 2 to 6 carbon atoms ($C_2$-$C_6$ alkynyl). In specific embodiments, alkynyl can be ethynyl, 1-propynyl, 2-propynyl, 1-butynyl, 2-butynyl, 3-butynyl, I-pentynyl, 2-pentynyl, 3-pentynyl, 4-pentynyl, 1-hexynyl, 2-hexynyl, 3-hexynyl, 4-hexynyl, or 5-hexynyl.

The term "carboalkoxy" refers to an alkyl ester of a carboxylic acid, wherein alkyl has the same definition as found above. Examples include carbomethoxy, carboethoxy, carboisopropoxy and the like.

The term "cycloalkyl" refers to optionally substituted saturated mono-cyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

The term "aryl" refers to an unsubstituted or substituted aromatic carbocyclic substituent, as commonly understood in the art. It is understood that the term aryl applies to cyclic substituents that are planar and comprise $4n+2\pi$ electrons, according to Hickel's Rule.

The term "heteroaryl" refers to an aryl group containing from one or more (particularly one to four) non-carbon atom(s) (particularly N, O or S) or a combination thereof, which heteroaryl group is optionally substituted at one or more carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one heteroatom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 6-membered heteroaryls with one heteroatom (e.g., pyridine, quinoline, isoquinoline, benzoquinoline, acridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. "Substituted heteroaryl" means a heteroaryl having one or more non-interfering groups as substituents.

"Heterocyclyl" as used herein specifically in relation to certain 'R' groups refers to a non-aromatic ring having 5 to 7 atoms in the ring and of those atoms 1 to 4 are heteroatoms, said ring being isolated or fused to a second ring wherein said heteroatoms are independently selected from O, N and S. Heterocyclic includes partially and fully saturated heterocyclic groups. Heterocyclic systems may be attached to another moiety via any number of carbon atoms or heteroatoms and may be both saturated and unsaturated. Non-limiting examples of heterocyclic include pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

"Aroyl", "heteroaroyl" and "heterocycloyl" as used herein relate to aryl, heteroaryl and heterocyclyl groups, as described above, when attached to a carbonyl group which is also attached to the thiophene ring.

The term "halo" or "halogen" as used herein means fluorine, chlorine, bromine, or iodine.

The term "arylalkyl" as used herein refers to an aryl group, as defined above, linked to the thiophene ring or other moiety through an alkyl group as defined above.

The term "amino" as used herein means a moiety represented by the structure $NR_{10}$, and includes primary amines, and secondary and tertiary amines substituted by alkyl (i.e., alkylamino). Thus, $R_{10}$ may represent, for example, two hydrogen atoms, two alkyl moieties, or one hydrogen atom and one alkyl moiety.

The term "alkanoyl" or "acyl" as used herein means a group formed by removing the hydroxyl group from a carboxylic acid, in which the non-carbonyl moiety of the group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted, C1-6 alkyl or C1-6 alkoxy; and substituted benzyl.

"Substituted" as used herein in reference to a substituent group refers to substituent groups which may be substituted with one or more moieties, for example, those selected from the group consisting of optionally substituted C1-8 alkyl (e.g., optionally substituted C1-6 alkyl); optionally substituted C1-8 alkoxy (e.g., optionally substituted C1-6 alkoxy); optionally substituted C2-8 alkenyl; optionally substituted C2-8 alkynyl; optionally substituted C5-6 aryl; aryloxy; optionally substituted heteroaryl; optionally substituted heterocycle; halo (e.g., Cl, F, Br, and I); hydroxyl; halogenated alkyl (e.g., $CF_3$, 2-Br-ethyl, $CH_2F$, $CH_2CF_3$, and $CF_2CF_3$);

amino (e.g., $NH_2$, $NR_{10}H$, and $NR_{10}R_{10}$); alkylamino; arylamino; acyl; amido; CN; $NO_2$; $N_3$; $CH_2OH$; $CONH_2$; $CONR_{10}R_{10}$; $CO_2R_{10}$; $CH_2OR_{10}$; $NHCOR_{10}$; $NHCO_2R_{10}$; $CF_3S$; and $CF_3SO_2$; and each $R_{10}$ is independently selected from H or optionally substituted C1-6 alkyl Whenever a range of the number of atoms in a structure is indicated (e.g., a $C_1$-$C_{12}$, $C_1$-$C_{10}$, $C_1$-$C_9$, $C_1$-$C_6$, $C_1$-$C_4$, or $C_2$-$C_{20}$, $C_2$-$C_{12}$, $C_2$-$C_{10}$, $C_2$-$C_9$, $C_2$-$C_8$, $C_2$-$C_6$, $C_2$-$C_4$ alkyl, alkenyl, etc.), it is specifically contemplated that any sub-range or individual number of carbon atoms falling within the indicated range also can be used. Thus, for instance, the recitation of a range of 1-12 carbon atoms (e.g., $C_1$-$C_{12}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment for a disease or condition caused by or related to inflammation. However, it will be understood that the aforementioned terms do not imply that symptoms are necessarily present.

According to a first aspect of the invention, there is provided a compound of formula (I), or a pharmaceutically acceptable salt thereof:

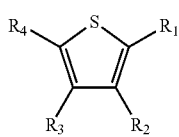

Formula (I)

wherein, $R_1$ is selected from the group consisting of hydrogen, alkyl, alkenyl, alkynyl, alkanoyl, carboalkoxy, acyloxy, aryl, aroyl, heteroaryl, heteroaroyl, heterocyclyl, heterocycloyl, cycloalkyl, O-alkyl and O-aryl, O-heteroaryl, amino and amido, all of which groups may be substituted or unsubstituted;
$R_2$ is selected from the group consisting of hydrogen, alkyl, alkenyl, alkynyl, aryl, alkylaryl, heterocyclyl and heteroaryl, all of which may be substituted or unsubstituted; and
$R_3$ and $R_4$ are independently selected from the group consisting of aryl, heteroaryl, heterocyclyl and cycloalkyl, all of which groups may be substituted or unsubstituted.

In one embodiment, $R_1$ is selected from the group consisting of hydrogen, $C_1$-$C_{12}$ alkyl, $C_2$-$C_{12}$ alkenyl, $C_2$-$C_{12}$ alkynyl, $C_2$-$C_{12}$ alkanoyl, $C_5$-$C_7$ aryl, $C_5$-$C_7$ aroyl, $C_5$-$C_7$ heteroaryl, $C_5$-$C_7$ heteroaroyl, $C_5$-$C_7$ heterocyclyl, $C_5$-$C_7$ heterocycloyl and $C_5$-$C_7$ cycloalkyl, all of which groups may be substituted or unsubstituted;
$R_2$ is selected from the group consisting of hydrogen, $C_1$-$C_{12}$ alkyl, $C_2$-$C_{12}$ alkenyl, $C_2$-$C_{12}$ alkynyl, $C_5$-$C_7$ aryl and alkyl-$C_5$-$C_7$ aryl, all of which may be substituted or unsubstituted;
$R_3$ is selected from the group consisting of $C_5$-$C_7$ heteroaryl and $C_5$-$C_7$ heterocyclyl, each of which groups may be substituted or unsubstituted; and
$R_4$ is substituted or unsubstituted $C_5$-$C_7$ aryl or $C_5$-$C_7$ heteroaryl.

In one embodiment, $R_1$ is selected from the group consisting of $C_2$-$C_6$ alkynyl, $C_2$-$C_6$ alkanoyl, $C_5$-$C_6$ aryl, $C_5$-$C_6$ aroyl, $C_5$-$C_6$ heteroaryl, $C_5$-$C_6$ heteroaroyl, $C_5$-$C_6$ heterocyclyl and $C_5$-$C_6$ heterocycloyl, all of which groups may be substituted or unsubstituted;
$R_2$ is hydrogen;
$R_3$ is selected from the group consisting of $C_6$ nitrogen heteroaryl and $C_6$ nitrogen heterocycyl, each of which groups may be substituted or unsubstituted; and
$R_4$ is substituted or unsubstituted phenyl.

In one embodiment, $R_1$ is selected from the group consisting of $C_2$-$C_6$ alkynyl, $C_2$-$C_6$ alkanoyl, $C_5$-$C_6$ aryl, $C_5$-$C_6$ aroyl, $C_5$-$C_6$ heteroaryl, $C_5$-$C_6$ heteroaroyl, $C_5$-$C_6$ heterocyclyl and $C_5$-$C_6$ heterocycloyl, all of which groups may be substituted or unsubstituted;
$R_2$ is hydrogen;
$R_3$ is selected from the group consisting of pyridyl, piperidyl, pyrazyl, pyrimidyl and pyridazyl, each of which groups may be substituted or unsubstituted; and
$R_4$ is phenyl substituted with a substituent selected from the group consisting of halo, haloalkyl, hydroxy and nitro.

In one embodiment, there is provided a compound of formula (II), or a pharmaceutically acceptable salt thereof:

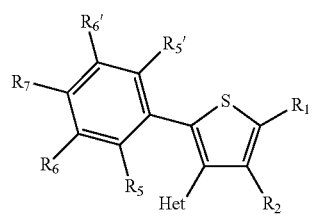

Formula (II)

wherein $R_1$ and $R_2$ are as described in any one or more of the above embodiments;
Het is selected from the group consisting of $C_5$-$C_7$ heteroaryl and $C_5$-$C_7$ heterocyclyl,
each of which groups may be substituted or unsubstituted; and
$R_5$, $R_5'$, $R_6$, $R_6'$ and $R_7$ are independently selected from the group consisting of hydrogen, halo, haloalkyl, hydroxy and nitro.

Preferably, $R_1$ is selected from the group consisting of $C_1$-$C_{12}$ alkyl, $C_2$-$C_{12}$ alkenyl, $C_2$-$C_{12}$ alkynyl, $C_2$-$C_{12}$ alkanoyl, $C_5$-$C_7$ aryl, $C_5$-$C_7$ aroyl, $C_5$-$C_7$ heteroaryl, $C_5$-$C_7$ heteroaroyl, $C_5$-$C_7$ heterocyclyl, $C_5$-$C_7$ heterocycloyl and $C_5$-$C_7$ cycloalkyl, all of which groups may be substituted or unsubstituted;

$R_2$ is hydrogen;
Het is selected from the group consisting of pyridyl, piperidyl, pyrazyl, pyrimidyl and pyridazyl, each of which groups may be substituted or unsubstituted; and
$R_5$, $R_5'$, $R_6$, $R_6'$ and $R_7$ are independently selected from the group consisting of hydrogen, halo and haloalkyl.

Preferably, $R_1$ is selected from the group consisting of $C_2$-$C_6$ alkynyl, $C_2$-$C_6$ alkanoyl, $C_5$-$C_6$ aryl, $C_5$-$C_6$ aroyl, $C_5$-$C_6$ heteroaryl, $C_5$-$C_6$ heteroaroyl, $C_5$-$C_6$ heterocyclyl and $C_5$-$C_6$ heterocycloyl, all of which groups may be substituted or unsubstituted;
$R_2$ is hydrogen;
Het is selected from the group consisting of pyridyl, piperidyl and pyrimidyl, each of which groups may be substituted or unsubstituted; $R_5$, $R_5'$, $R_6$ and $R_6'$ are hydrogen; and $R_7$ is selected from the group consisting of halo and haloalkyl.

In one embodiment, there is provided a compound of formula (III), or a pharmaceutically acceptable salt thereof:

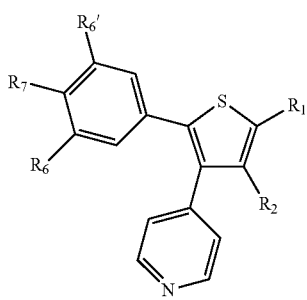

Formula (III)

wherein $R_1$, $R_2$, $R_6$, $R_6'$ and $R_7$ are as described in any one or more of the above embodiments for formula (I) or formula (II).

Suitably, in one embodiment of the compound of formula (III):
$R_1$ is selected from the group consisting of $C_1$-$C_{12}$ alkyl, $C_2$-$C_{12}$ alkenyl, $C_2$-$C_{12}$ alkynyl, $C_2$-$C_{12}$ alkanoyl, $C_5$-$C_7$ aryl, $C_5$-$C_7$ aroyl, $C_5$-$C_7$ heteroaryl, $C_5$-$C_7$ heteroaroyl, $C_5$-$C_7$ heterocyclyl, $C_5$-$C_7$ heterocycloyl and $C_5$-$C_7$ cycloalkyl, all of which groups may be substituted or unsubstituted;
$R_2$ is hydrogen; and
$R_6$, $R_6'$ and $R_7$ are independently selected from the group consisting of hydrogen, halo, haloalkyl, hydroxy and nitro.

In one embodiment, wherein $R_1$ is selected from the group consisting of $C_2$-$C_6$ alkynyl, $C_2$-$C_6$ alkanoyl, $C_5$-$C_6$ aryl, $C_5$-$C_6$ aroyl, $C_5$-$C_6$ heteroaryl, $C_5$-$C_6$ heteroaroyl, $C_5$-$C_6$ heterocyclyl and $C_5$-$C_6$ heterocycloyl, all of which groups may be substituted or unsubstituted;
$R_2$ is hydrogen;
$R_6$ and $R_6'$ are hydrogen; and
$R_7$ is selected from the group consisting of halo and haloalkyl.

Compounds of formula (III) wherein $R_2$ is hydrogen have proven to be particularly efficacious as inhibitors of the p38 α MAPK enzyme and are therefore useful in reducing inflammation in a subject.

In one embodiment of formula (III) the compound is a compound of the below formula, or a pharmaceutically acceptable salt thereof:

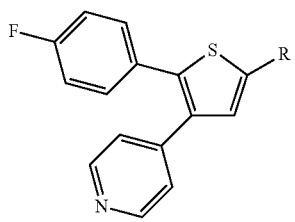

wherein R is selected from the groups shown in the below table

| R* |
|---|
| 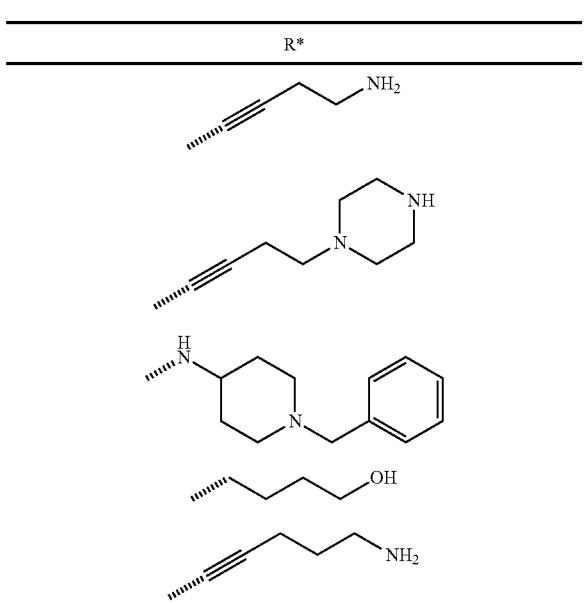 |
| !! EMBED ChemDraw.Document.6.0 |
| 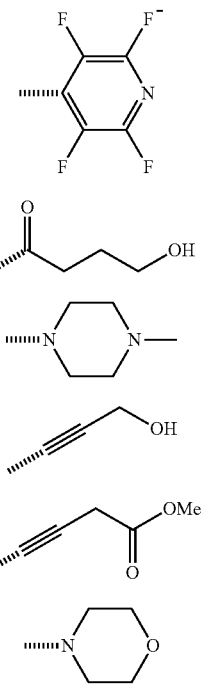 |

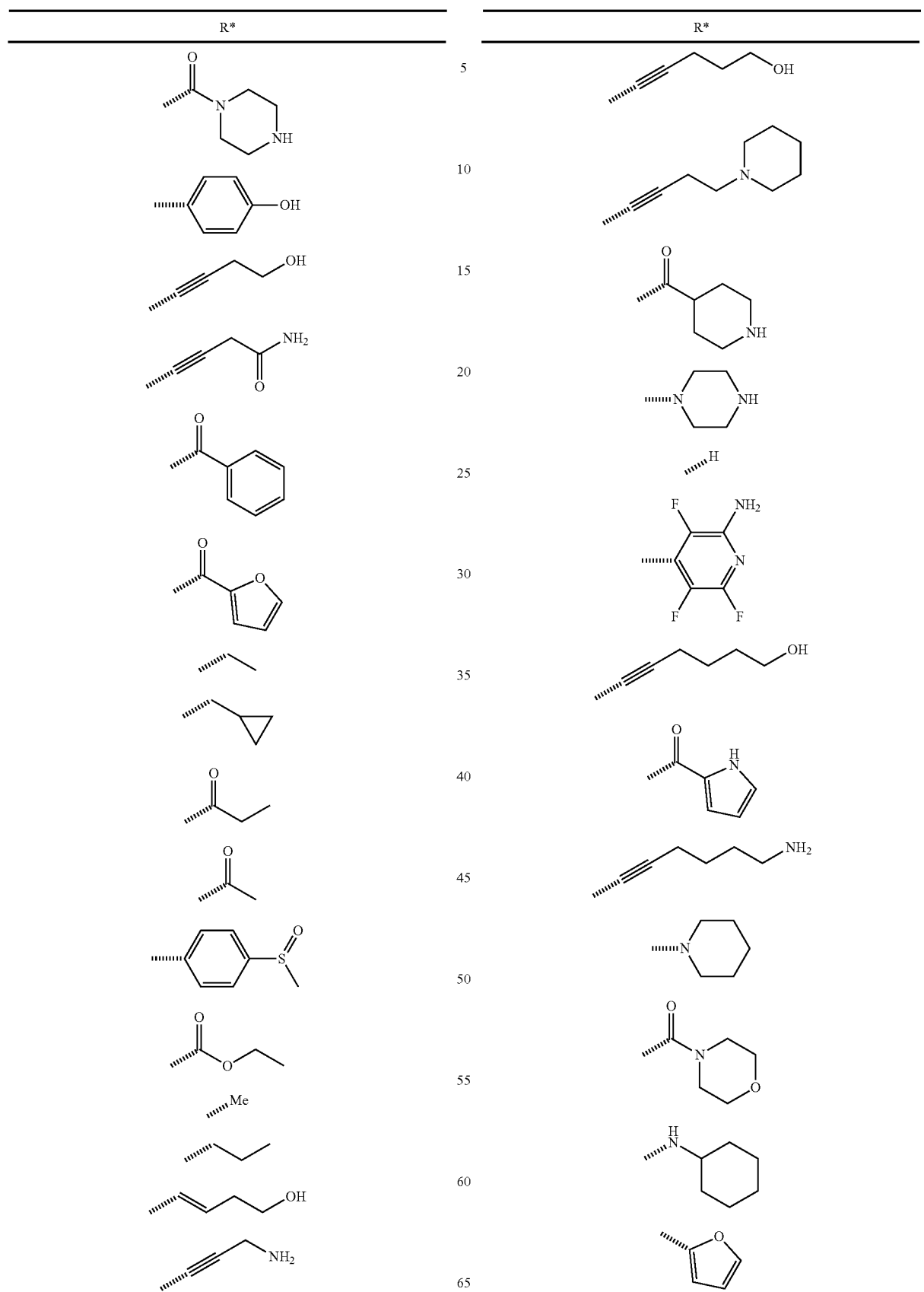

-continued

| R* |
|---|
| 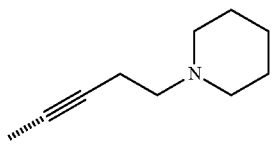 |
| 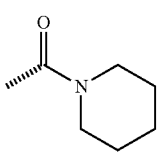 |
| 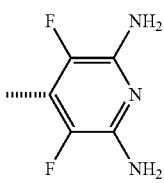 |
| 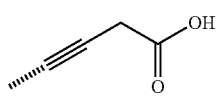 |
|  |

*Hashed line depicts the bond that is formed.

In one preferred embodiment, there is provided a compound of formula (I) to formula (III), or a pharmaceutically acceptable salt thereof, selected from the group consisting of:

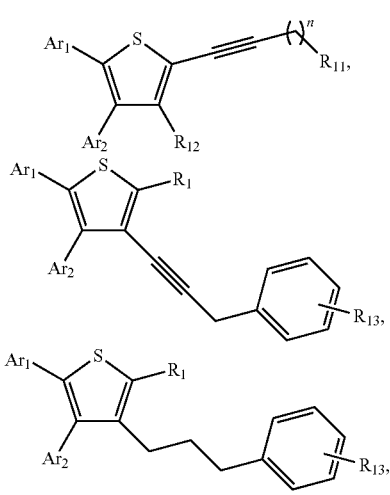

-continued

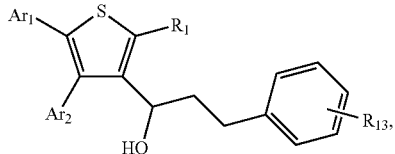

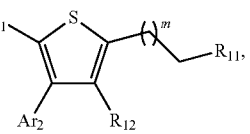

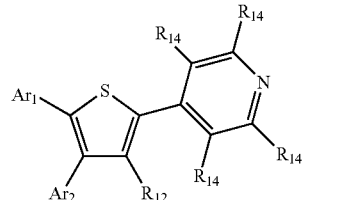

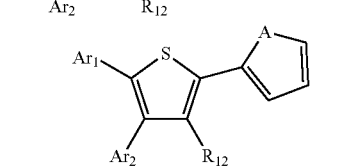

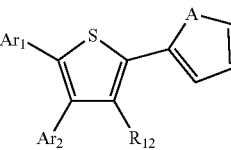

wherein, $Ar_1$ and $Ar_2$ are independently substituted or unsubstituted aryl or heteroaryl, A is selected from oxygen, sulphur or nitrogen, n is 1 or 2, m is 0 to 6, $R_1$ is as described in any one of the embodiments for formula (I) to (III), $R_{11}$ is selected from the group consisting of hydroxy, amino, $C_1$-$C_6$ alkyl, phenyl, furan, morpholine, piperazine and N-phthalimide;

$R_{12}$ is selected from the group consisting of hydrogen, alkylphenyl and hydroxyalkyl phenyl wherein the phenyl ring may be substituted with $R_{13}$;

$R_{13}$, when present, is selected from the group consisting of halo, amino, hydroxy, haloalkyl, $C_1$-$C_6$ alkyl and $C_1$-$C_6$ alkanoyl; and each incidence of $R_{14}$ is independently selected from the group consisting of hydrogen, fluoro, chloro, bromo, iodo, amino and aminoalkyl.

In one embodiment, $Ar_1$ is substituted or unsubstituted phenyl.

In any one of the preceding embodiments, $Ar_2$ is substituted or unsubstituted pyridyl.

In any one of the preceding embodiments A is preferably oxygen.

In any one of the preceding embodiments $R_{12}$ is preferably hydrogen.

In any one of the preceding embodiments it is preferred if $R_{13}$ is not present.

In any one of the preceding embodiments each incidence of $R_{14}$ is independently selected from fluoro or amino.

In any one of the preceding embodiments, $Ar_1$ is 4-fluorophenyl.

In any one of the preceding embodiments, $Ar_2$ is 4-pyridyl.

In any one of the preceding embodiments, the compound of the first aspect is selected from the group consisting of:

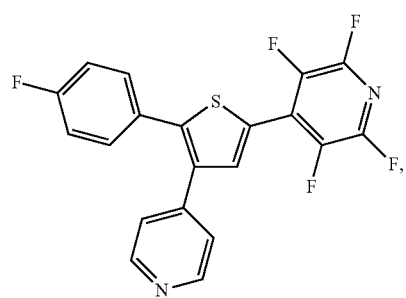
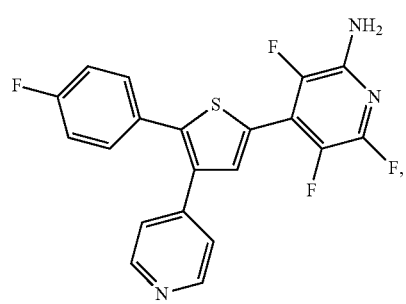
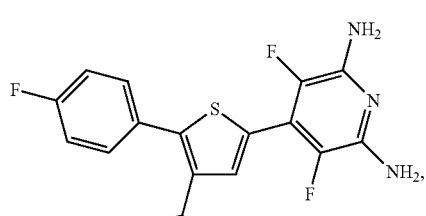
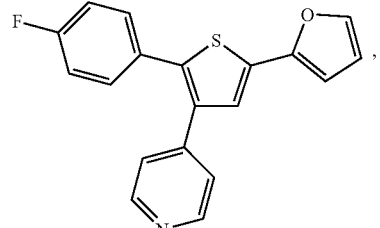
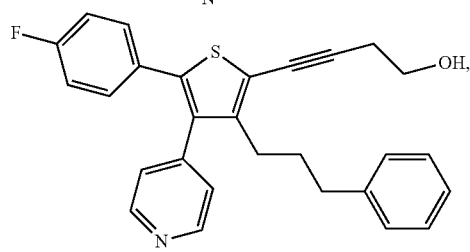
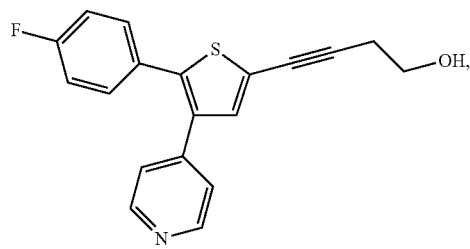
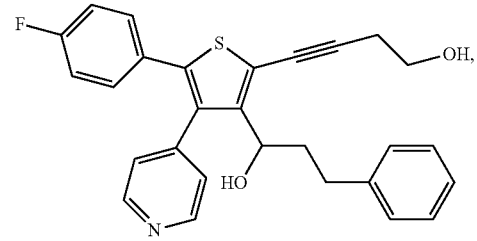
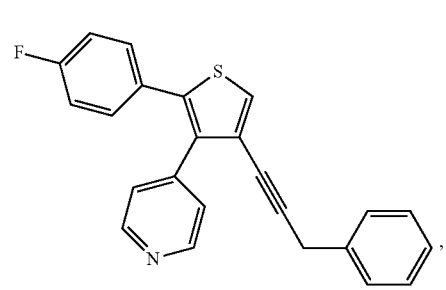
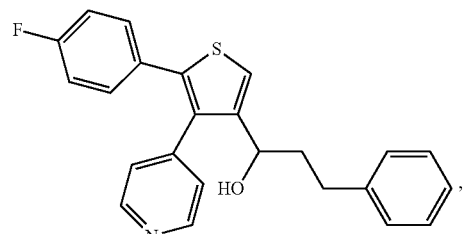
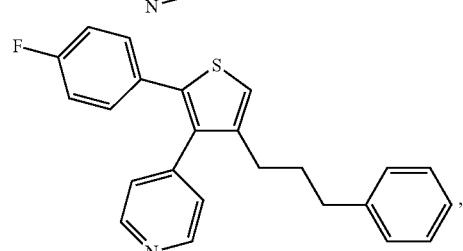
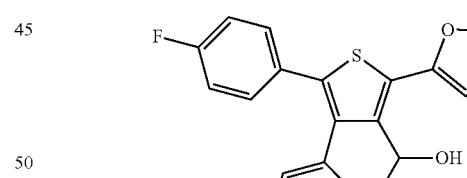
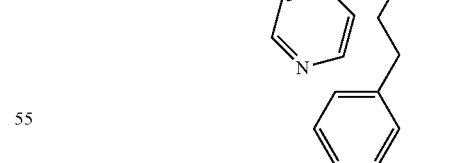
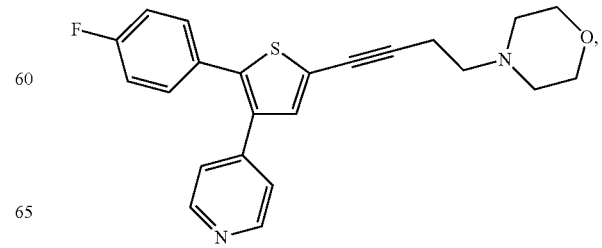

-continued

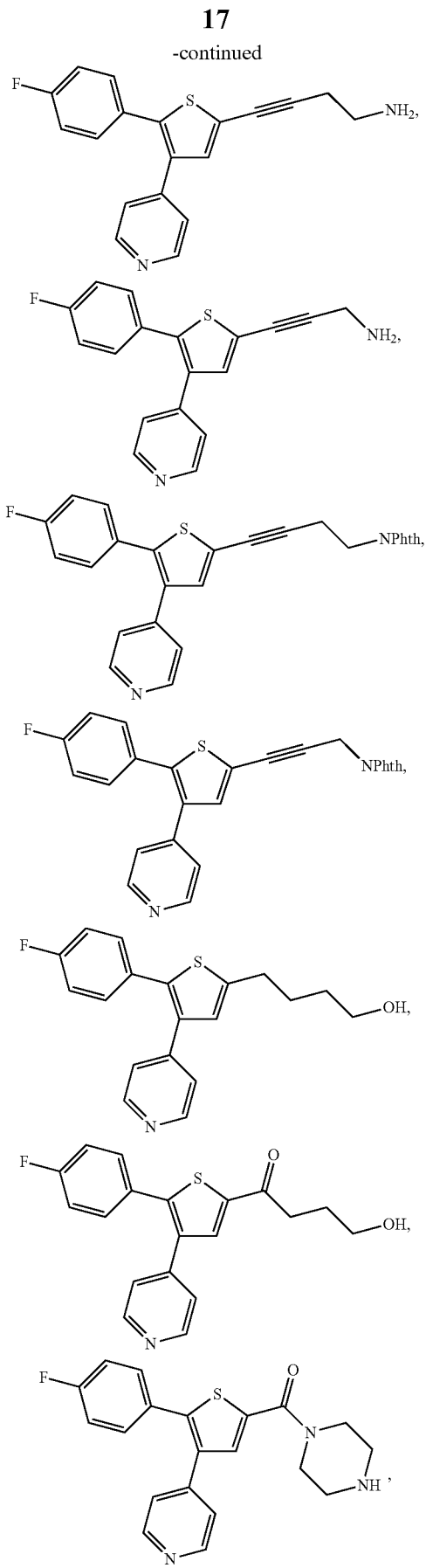

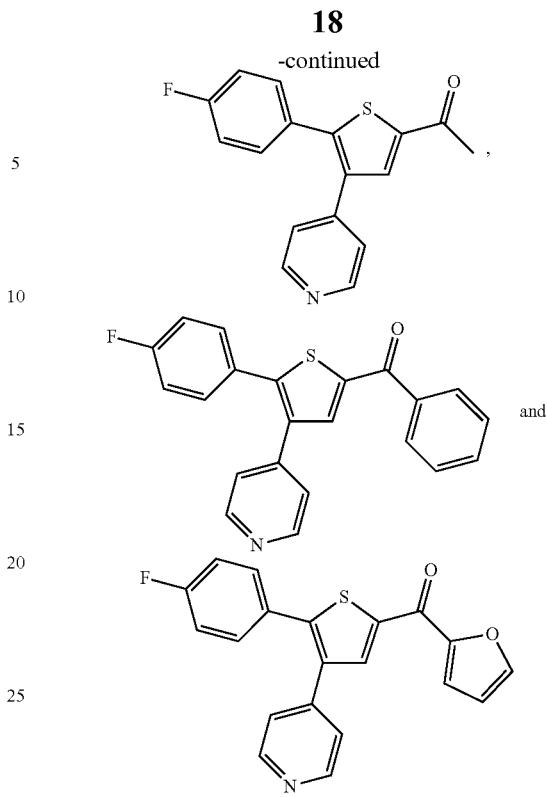

or a pharmaceutically acceptable salt thereof.

The compounds may be synthesised by a number of pathways which are outlined in the experimental section.

It will be recognised that certain compounds of the invention may possess asymmetric centres and would therefore be capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be obtained by asymmetric synthesis, for example using chiral intermediates, or by chiral resolution. The compounds of the invention may, in some examples, exist as geometrical isomers. The invention also relates to compounds in substantially pure cis (Z) or trans (E) forms or mixtures thereof.

According to a second aspect of the invention there is provided a pharmaceutical composition comprising an effective amount of a compound of the first aspect, or a pharmaceutically acceptable salt thereof, and a pharmaceutically acceptable carrier, diluent and/or excipient.

Suitably, the pharmaceutical composition is for the treatment or prophylaxis of a disease, disorder or condition responsive to MAPK inhibition, preferably p38 MAPK inhibition, more preferably p38α MAPK inhibition.

The pharmaceutical composition may include more than one compound of the first aspect. When the composition includes more than one compound then the compounds may be in any ratio. The composition may further comprise known co-actives, delivery vehicles or adjuvants.

The compound of the first aspect is present in the pharmaceutical composition in an amount sufficient to inhibit or ameliorate the disease, disorder or condition which is the subject of treatment. Suitable dosage forms and rates of the compounds and the pharmaceutical compositions containing such may be readily determined by those skilled in the art.

Dosage forms may include tablets, dispersions, suspensions, injections, solutions, syrups, troches, capsules, suppositories, aerosols, transdermal patches and the like. These dosage forms may also include injecting or implanting devices designed specifically for, or modified to, controlled release of the pharmaceutical composition. Controlled release of the therapeutic agent may be effected by coating the same, for example, with hydrophobic polymers including acrylic resins, waxes, higher aliphatic alcohols, polylactic and polyglycolic acids and certain cellulose derivates such as hydroxypropylmethyl cellulose. In addition, the controlled release may be affected by using other polymer matrices, liposomes and/or microspheres. Pharmaceutically acceptable carriers for systemic administration may also be incorporated into the compositions of this invention.

Suitably, the pharmaceutical composition comprises a pharmaceutically-acceptable excipient. By "pharmaceutically-acceptable excipient" is meant a solid or liquid filler, diluent or encapsulating substance that may be safely used in systemic administration. Depending upon the particular route of administration, a variety of carriers, well known in the art may be used. These carriers or excipients may be selected from a group including sugars, starches, cellulose and its derivates, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a patient with the pharmaceutical composition of the invention. For example, oral, rectal, parenteral, sublingual, buccal, intravenous, intraarticular, intra-muscular, intra-dermal, subcutaneous, inhalational, intraocular, intraperitoneal, intracerebroventricular, transdermal and the like may be employed.

Pharmaceutical compositions of the present invention suitable for administration may be presented in discrete units such as vials, capsules, sachets or tablets each containing a predetermined amount of one or more pharmaceutically active compounds of the invention, as a powder or granules or as a solution or a suspension in an aqueous liquid, a non-aqueous liquid, an oil-in-water emulsion or a water-in-oil emulsion. Such compositions may be prepared by any of the method of pharmacy but all methods include the step of bringing into association one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

A third aspect of the invention resides in a method of treating a patient suffering from a disease, disorder or condition responsive to MAPK inhibition including the step of administering an effective amount of a compound of the first aspect, or a pharmaceutically effective salt thereof, or the pharmaceutical composition of the second aspect to the patient.

A fourth aspect of the invention provides for a compound of the first aspect, or a pharmaceutically effective salt thereof, or the pharmaceutical composition of the second aspect for use in the treatment of a disease, disorder or condition responsive to MAPK inhibition.

A fifth aspect of the invention provides for use of a compound of the first aspect, or a pharmaceutically effective salt thereof, in the manufacture of a medicament for the treatment of a disease, disorder or condition responsive to MAPK inhibition.

Suitably, the disease, disorder or condition of the third, fourth and fifth aspect is responsive to p38 MAPK inhibition.

Preferably, the disease, disorder or condition of the third, fourth and fifth aspect is responsive to p38α MAPK inhibition.

The method of the third aspect and use of the fourth and fifth aspects may be a method of reducing inflammation, or use in treating inflammation, in a patient by inhibiting MAPK, particularly by inhibiting p38 MAPK, more particularly by inhibiting p38α MAPK.

The disease, disorder or condition of the third, fourth and fifth aspects may be one or more of arthritis, inflammatory bowel disease, asthma, psoriasis, myocardial injury, cardiac remodelling, renal fibrosis, stroke, cancer, Alzheimer's disease, HIV, COPD, multiple myeloma, myelodysplastic syndrome, acute respiratory distress syndrome, coronary heart disease, acute coronary syndrome, major depressive disorder, dental pain, artherosclerosis, neuropathic pain and inflammation associated with any one or more of these aforementioned diseases, disorders or conditions.

Preferably, the patient is a domestic or livestock animal or a human. Most preferably, the patient or subject is a human in need of a treatment to reduce inflammation.

A sixth aspect of the invention provides for a complex of a compound of the first aspect, or a pharmaceutically effective salt thereof, with a p38 MAPK enzyme.

In one embodiment, the p38 MAPK enzyme is a p38α MAPK enzyme.

The following experimental section describes in more detail the characterisation of certain compounds of the invention and their binding to p38α MAPK. The intention is to illustrate certain specific embodiments of the compounds of the invention and their efficacy without limiting the invention in any way. SYNTHETIC APPROACHES AND RESULTS A synthetically accessible 3-iodothiophene 3.6 was employed as the starting material nucleophile in a metal-halogen exchange reaction. 3-Iodothiophene 3.6 was treated with isopropylmagnesium chloride lithium chloride complex at −78° C. in tetrahydrofuran. The organomagnesiate of thiophene 3.6 provides a key intermediate that could be used in a variety of organometallic reactions.

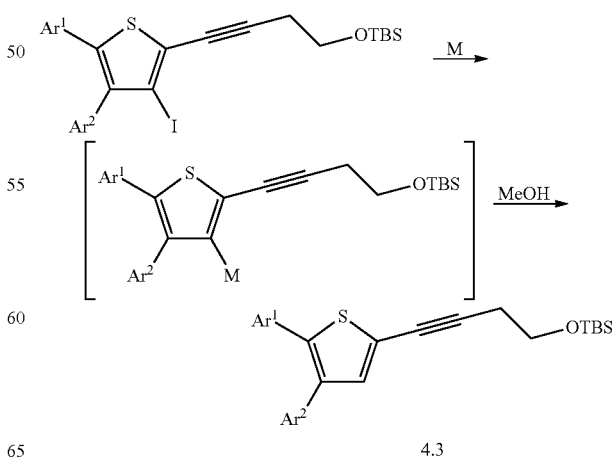

4.3

Synthesis of Thiophene Compounds 4.3 and 4.6

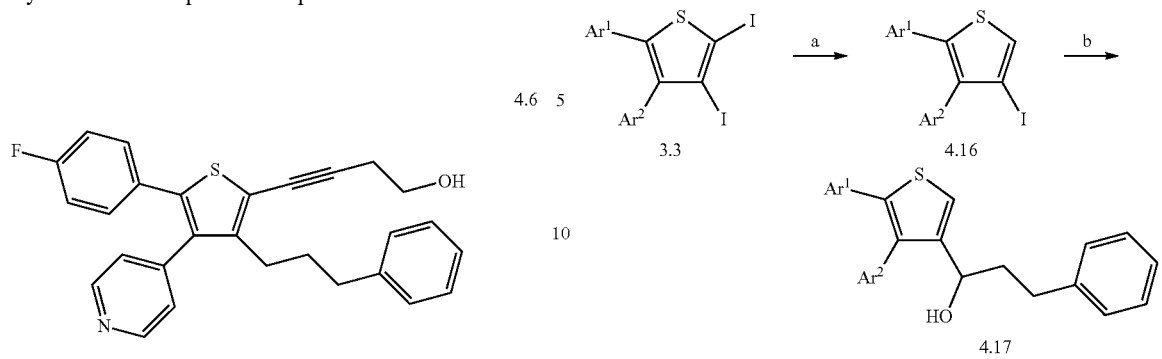

Reaction of the organomagnesium compound with hydrocinnamaldehyde gave hydroxylated analogue 4.4 in 64% yield as well as the reduced by-product 4.3. TBS deprotection of compounds 4.3 and 4.4 with ammonium fluoride, as shown in the scheme below, gave compounds 4.5 and 4.6.

Synthesis of the analogue 4.17 (Ar$^1$=4-F-Ph, Ar$^2$=Pyr). Reagents and conditions: (a) iPrMgCl.LiCl, THF, −78° C., 30 min, 95%; (b) iPrMgCl.LiCl, THF, −78° C., 30 min, hydrocinnamaldehyde, 0° C., 1 h, 63%.

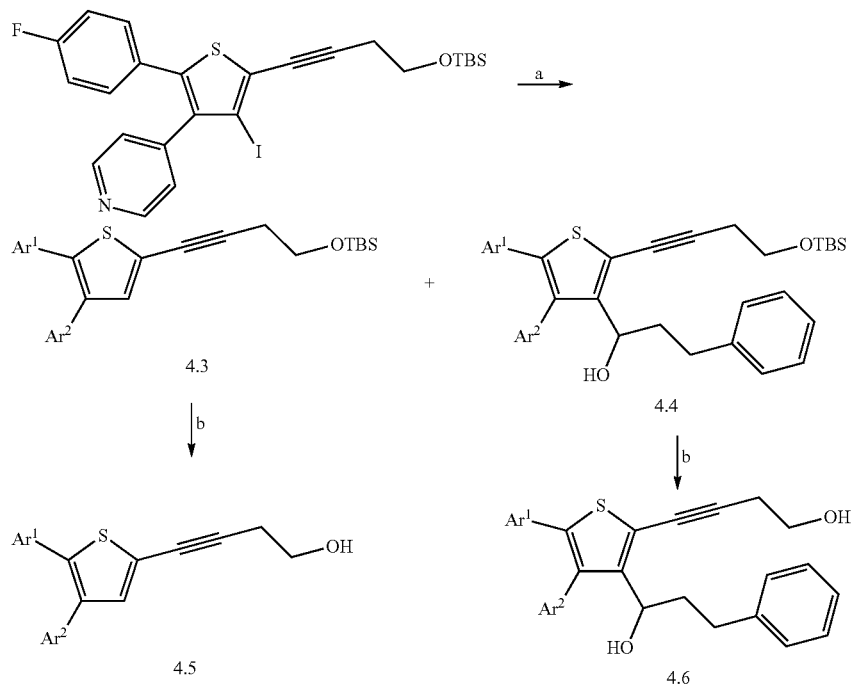

Synthesis of hydroxylated analogue 4.6 (Ar$^1$=4-F-Ph; Ar$^2$=Pyr). Reagents and conditions: (a) iPrMgCl.LiCl, THF, −78° C., 30 min, hydrocinnamaldehyde, 0° C., 1 h, 4.3: 36%, 4.4: 64%; (b) NH$_4$F, MeOH, reflux, 16 h, 4.5: 95%, 4.6: 99%.

Compound 4.17 was synthesised in two steps from the di-iodinated thiophene 3.3 (Scheme below). First, a dehalogenation reaction at the α-position of the thiophene was conducted to avoid substitution at this position. Compound 3.3 was treated with isopropylmagnesium chloride lithium chloride complex at −78° C. and subsequently quenched with methanol to give the mono-iodinated compound 4.16 in 95% yield. Compound 4.16 was again metallated and reacted with hydrocinnamaldehyde to form the hydroxylated analogue 4.17 in 63% yield.

To synthesise 3-phenylpropylthiophene 4.18 a Sonogashira cross coupling reaction with the 3-iodothiophene intermediate 4.16 was conducted followed by hydrogenation. Reaction of 3-iodothiophene 4.16, 3-phenyl-1-propyne and the bis(triphenylphosphine)palladium(II) dichloride catalyst under basic conditions afforded alkyne 4.19 in 28% yield (Scheme shown below). Reduction of the triple bond was carried out using standard hydrogenation conditions to give 3-phenylpropylthiophene 4.18 quantitatively. Iodination of the thiophene at the α-position using silver nitrate and potassium iodide formed 2-iodothiophene 4.20 quantitatively. Synthesis of 2-iodothiophene 4.20 allowed a Sonogashira reaction with the TBS protected but-3-yn-1-ol to give the protected thiophene 4.2 in 58% yield. Reaction of compound 4.2 with ammonium fluoride in methanol at reflux gave the final product 4.1 in 96% yield.

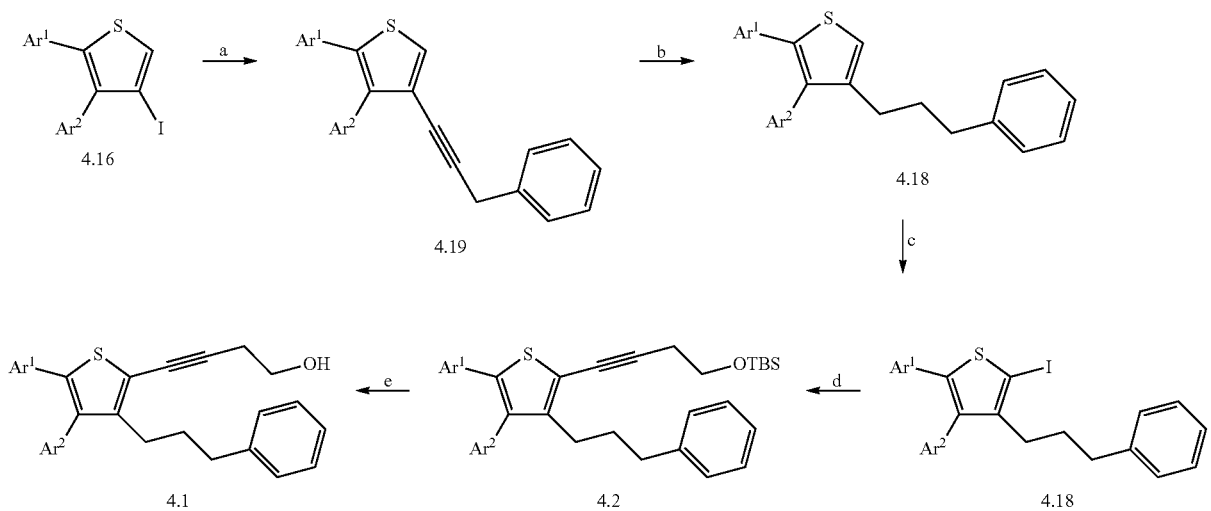

Synthesis of 4.1 (Ar$^1$=4-F-Ph, Ar$^2$=Pyr). Reagents and conditions: (a) 3-phenyl-1-propyne, CuI, PPh$_3$, PdCl$_2$(PPh$_3$)$_2$, Et$_3$N, THF, 120° C., 2 h, 28%; (b) H$_2$, Pd/C, EtOH, rt, 3 d, quant.; (c) AgNO$_3$, I$_2$, MeCN, rt, 1.5 h, quant.; (d) (but-3-yn-1-yloxy)(tert-butyl)dimethylsilane 3.5, CuI, PPh$_3$, PdCl$_2$(PPh$_3$)$_2$, Et$_3$N, THF, 120° C., 2 h, 58%; (e) NH$_4$F, MeOH, reflux, 16 h, 96%.

Biological Evaluation of Compound 4.1 and Related Thiophene Analogues

The objective of the biological studies on the compound 4.1 thiophene and analogues was to determine the binding affinities to both the inactive and active forms of p38α MAPK and subsequently their inhibitory activity. Certain compounds were also selected for study in an in vitro activation assay to determine whether they also inhibit the phosphorylation of p38α MAPK. Further evaluation in cellular assays was carried out to establish whether the compounds suppress production of pro-inflammatory cytokines TNF-α and IL-6. These inflammatory mediators are known to play a role in cardiac remodelling and heart failure progression and therefore cellular assays on cardiac myocytes and fibroblasts were conducted to investigate the effects of the compounds on cardiac hypertrophy and fibrosis. An important factor is to determine the metabolic and toxicity profiles of the synthesised compounds.

The binding affinity of 4.1 and intermediates and related compounds were determined using a fluorescence polarisation (FP) binding assay using both the inactive non-phosphorylated and the active phosphorylated forms of p38α MAPK. A number of compounds were also assessed for the inhibition of p38α MAPK activity (www.kinase-screen.mr-c.ac.uk) in which a radioactive ($^{33}$P-labelled ATP) filter binding assay was used to directly measure phosphate incorporation. Table 1 summarises the binding affinities of the synthesised compounds to both forms of the enzyme as well as the inhibitory activities against p38α MAPK. By way of enabling a comparison with a non-thiophene compound the biological testing was also carried out for known inhibitor RWJ67657, shown in table 1.

TABLE 1

| Compound | K$_i$ (μM, mean ± SEM) inactive p38α | K$_i$ (μM, mean ± SEM) active p38α | IC$_{50}$ (μM, mean) |
|---|---|---|---|
| | 0.21 ± 0.04 | 0.013 ± 0.006 | lit. 0.03 ± 0.003 |

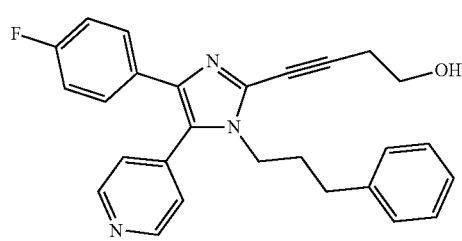

RWJ67657 (1.49)

TABLE 1-continued
| Compound | $K_i$ (μM, mean ± SEM) inactive p38α | $K_i$ (μM, mean ± SEM) active p38α | IC$_{50}$ (μM, mean) |
|---|---|---|---|
| 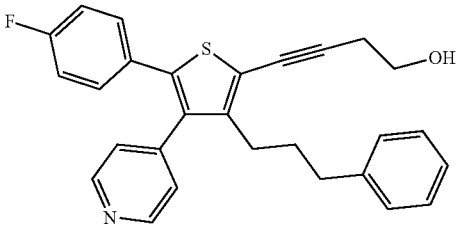 4.1 | 2.3 ± 0.2 | 0.6 ± 0.1 | 0.18 |
| 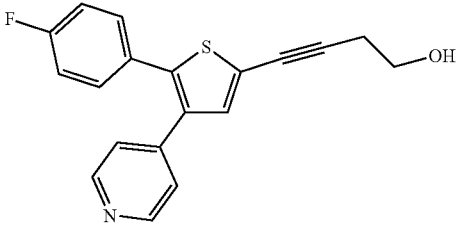 4.5 | 2.0 ± 0.2 | 0.56 ± 0.06 | 0.16 |
| 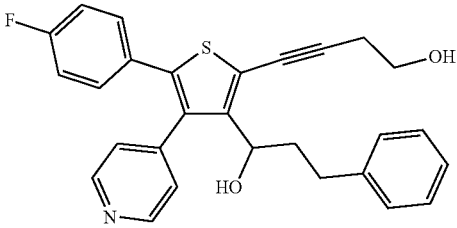 4.6 | >10.0 | 3.85 | 4.72 |
| 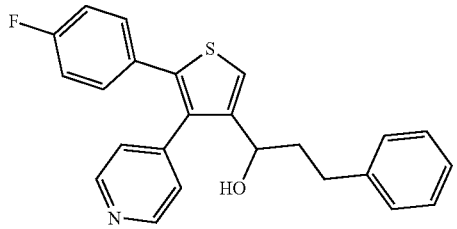 4.17 | 1.9 ± 0.3 | 0.99 ± 0.09 | 0.26 |
| 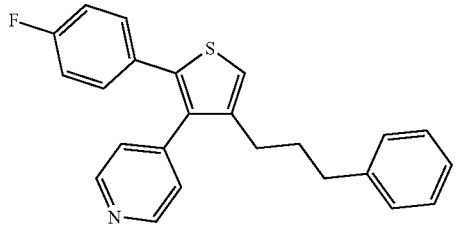 4.18 | 1.5 ± 0.5 | 0.72 ± 0.03 | 0.27 |

TABLE 1-continued

| Compound | $K_i$ (µM, mean ± SEM) inactive p38α | $K_i$ (µM, mean ± SEM) active p38α | $IC_{50}$ (µM, mean) |
|---|---|---|---|
| 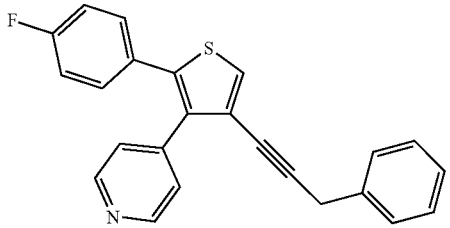<br>4.19 | >10.0 | 9.44 | n.d. | n.d. not determined. For compounds with $K_i$ values below 3 µM; binding assay was carried out in triplicate with n = 3 experiments using inactive p38α MAPK and in duplicate with n = 2-3 experiments using active p38α MAPK. $IC_{50}$ values were determined by taking the average of two experiments.

It was observed that the binding affinities of the thiophene compounds were often two- to four-fold stronger for the phosphorylated form of the enzyme relative to the non-phosphorylated form. Some structure activity relationships can be deduced from the data. Addition of a benzylic hydroxyl group resulted in some loss of activity with compound 4.6 having an $IC_{50}$ value of 4.72 µM. Interestingly, the removal of the alkyne substituent in compound 4.17, compared to the tetra-substituted compound 4.6, significantly improves the activity giving an $IC_{50}$ of 0.26 µM. Compound 4.18 was equipotent with an $IC_{50}$ of 0.27 µM. Having an alkyne in the 3-position of the thiophene in compound 4.19 results in the complete loss of binding, suggesting that the rigidity of the alkyne at this position may be detrimental to activity. However, removing the substituent at the 3-position while keeping the butynol moiety resulted in good binding with compound 4.5 having a $K_i$ value of 0.56 µM to active p38α MAPK and moderate inhibitory activity with an $IC_{50}$ of 0.16 µM. In summary, the similarity in the inhibitory activity values of the two best compounds, 4.1 and 4.5, suggest that the addition of a fourth substituent to the thiophene core is not necessary for activity. Compounds 4.17 and 4.18, which have moderate $IC_{50}$ values, also indicate that three substituents around the thiophene core are preferred for binding and inhibition.

In Vitro Activation Assay

The most potent compounds were also assessed in an in vitro activation assay using a published method. The assay was analysed by immunoblotting using antibodies against pan p38 MAPK and activated (phosphorylated) p38α MAPK. The assay evaluates whether compounds bind to the inactive non-phosphorylated p38α enzyme and prevent its activation by upstream MKK6. The protocol involves pre-incubating inactive non-phosphorylated p38α MAPK with the test compounds at 10 and 1 µM concentrations for 30 minutes. The reaction is initiated by the addition of ATP and MKK6 and proceeds for 15 minutes. Ethylenediaminetetracetic acid (EDTA) was used to stop the reaction and subsequent western blot analysis was carried out to qualitatively determine the extent of inhibition of p38α MAPK activation (phosphorylation). FIG. 1 shows the western blots of the activation assays. All compounds were found to inhibit phosphorylation of p38α MAPK at 10 µM concentration. Initial ligand binding experiments showed these compounds bind weakly to the inactive non-phosphorylated form of p38α MAPK (Table 1). This would suggest that the compounds to some extent occupy the active site of the non-phosphorylated enzyme causing conformational changes that prevent its activation.

Cellular Assays

Assays were conducted to determine the anti-inflammatory effects of the synthesised thiophene 4.1 and its analogues by inhibition of cytokine gene expression. Further downstream effects were also investigated. Pro-inflammatory cytokines are known to adversely affect cardiac function by stimulation of cardiac remodelling including hypertrophy and collagen synthesis (fibrosis). Therefore the effects of the synthesised compounds on cardiac remodelling were also determined.

Anti-Inflammatory Effects of 4.1 and Analogues

Figure 2:
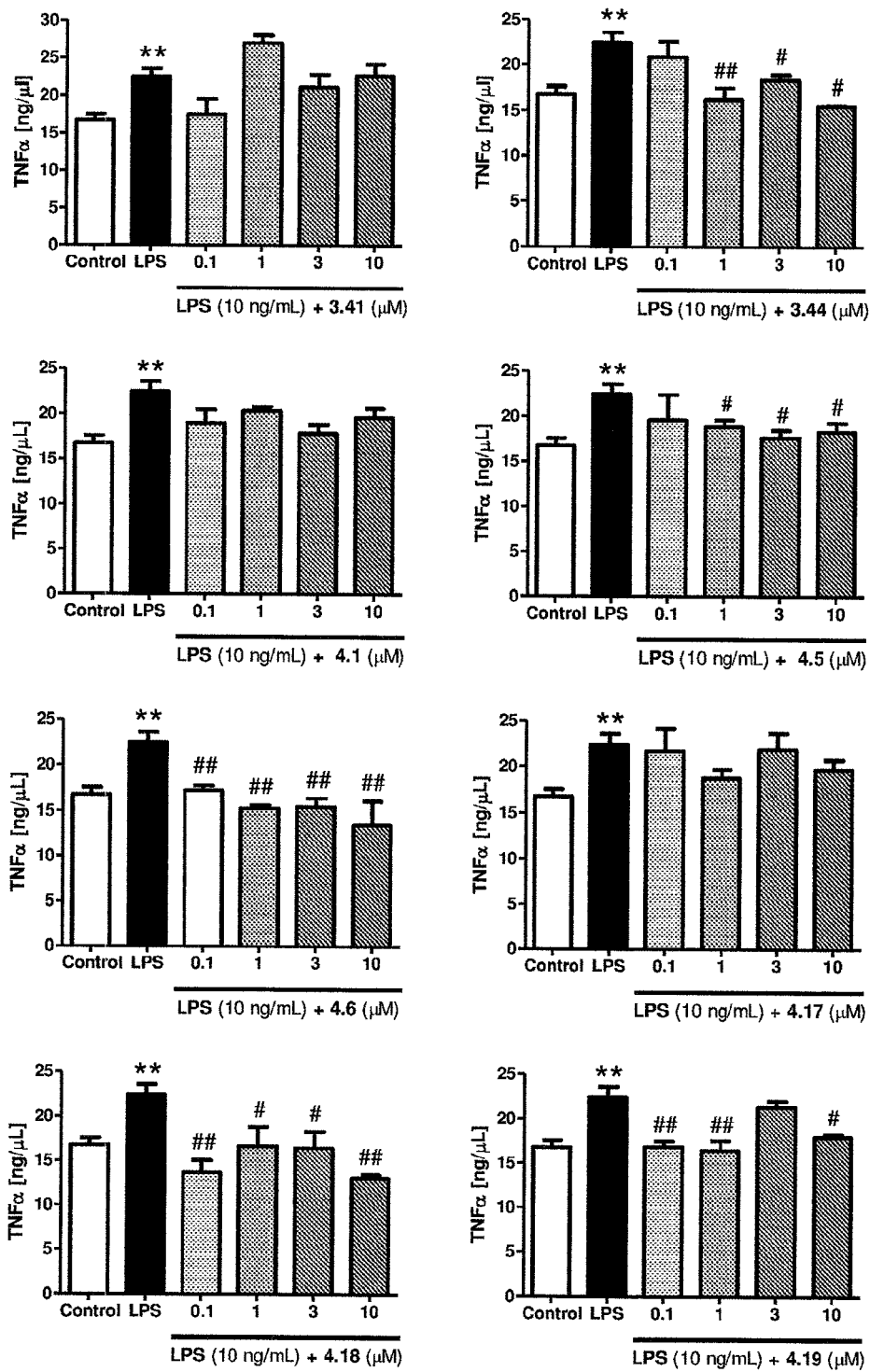
FIG. 2 is a graphical representation of the effects of a number of compounds of the present invention on monocytic cells (THP-1) TNF-α gene expression (** $p<0.01$ vs. unstimulated control; # $p<0.05$, ## $p<0.01$ vs. stimulated control (LPS))
Figure 3:
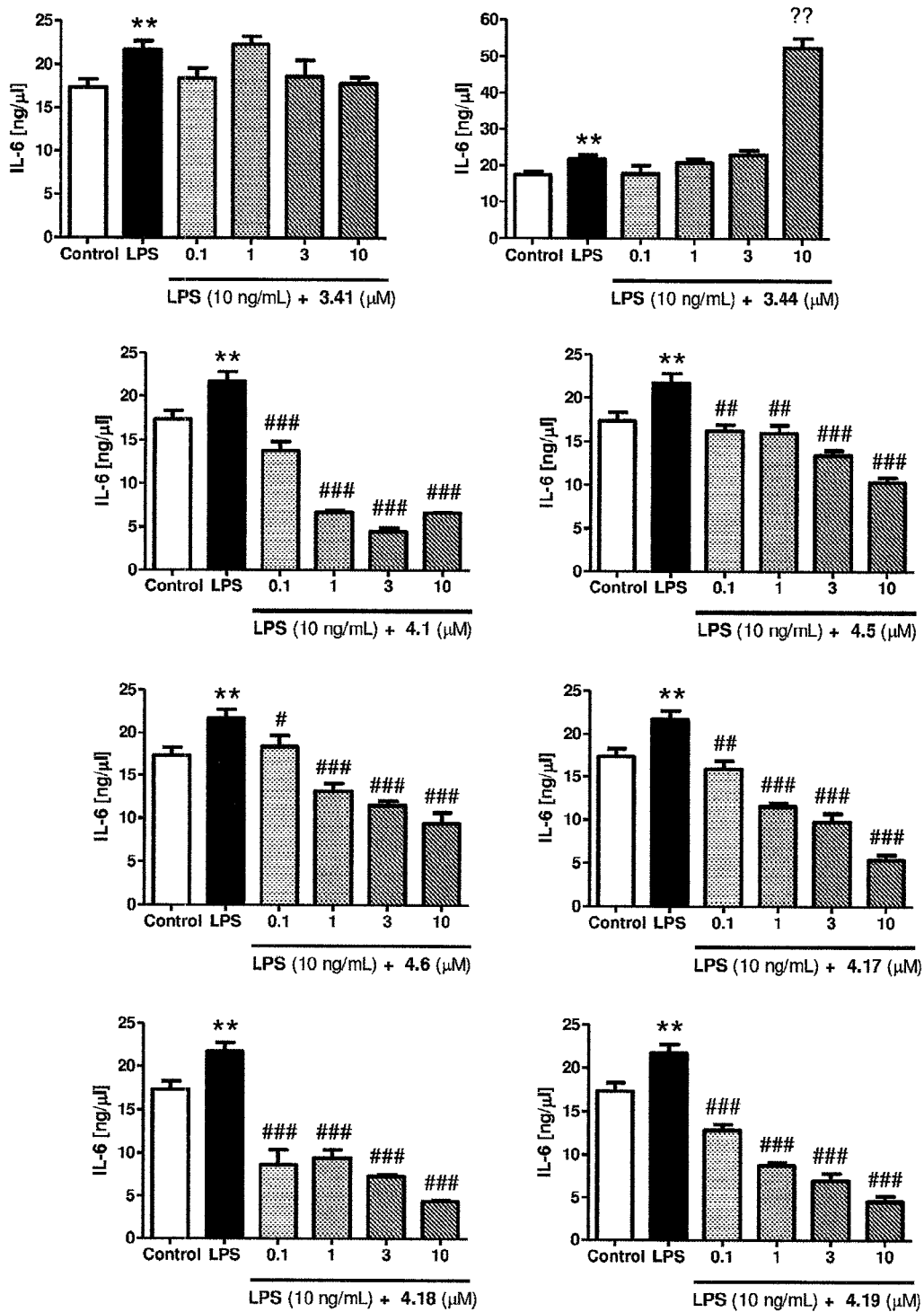
FIG. 3 is a graphical representation of the effects of a number of compounds of the present invention on monocytic cells (THP-1) IL-6 gene expression (** $p<0.01$ vs. unstimulated control; # $p<0.05$, ## $p<0.01$, ### $p<0.001$ vs. stimulated control (LPS))

Certain of the compounds were tested in a cellular assay for suppression of TNF-α and IL-6 gene expression in monocytic (THP-1) cells and the assay results are depicted in FIGS. 2 and 3. A published method was used whereby treating THP-1 cells with LPS induces TNF-α and IL-6 gene expression. FIGS. 2 and 3 include the cytokine suppression by the two most potent compounds synthesised, compound 4.1 and the tri-substituted thiophene 4.5. The tri-substituted thiophene 4.5 showed inhibition of TNF-α gene expression at 1 µM concentration and higher (FIG. 2). All of the tested analogues showed strong inhibition of LPS-induced IL-6 gene expression, including 4.1 and 4.5 as shown in FIG. 3.

Effects on Cellular Functions Relevant to Cardiac Remodeling

Measurement of Neonatal Rat Cardiac Myocyte Hypertrophy

Figure 4:
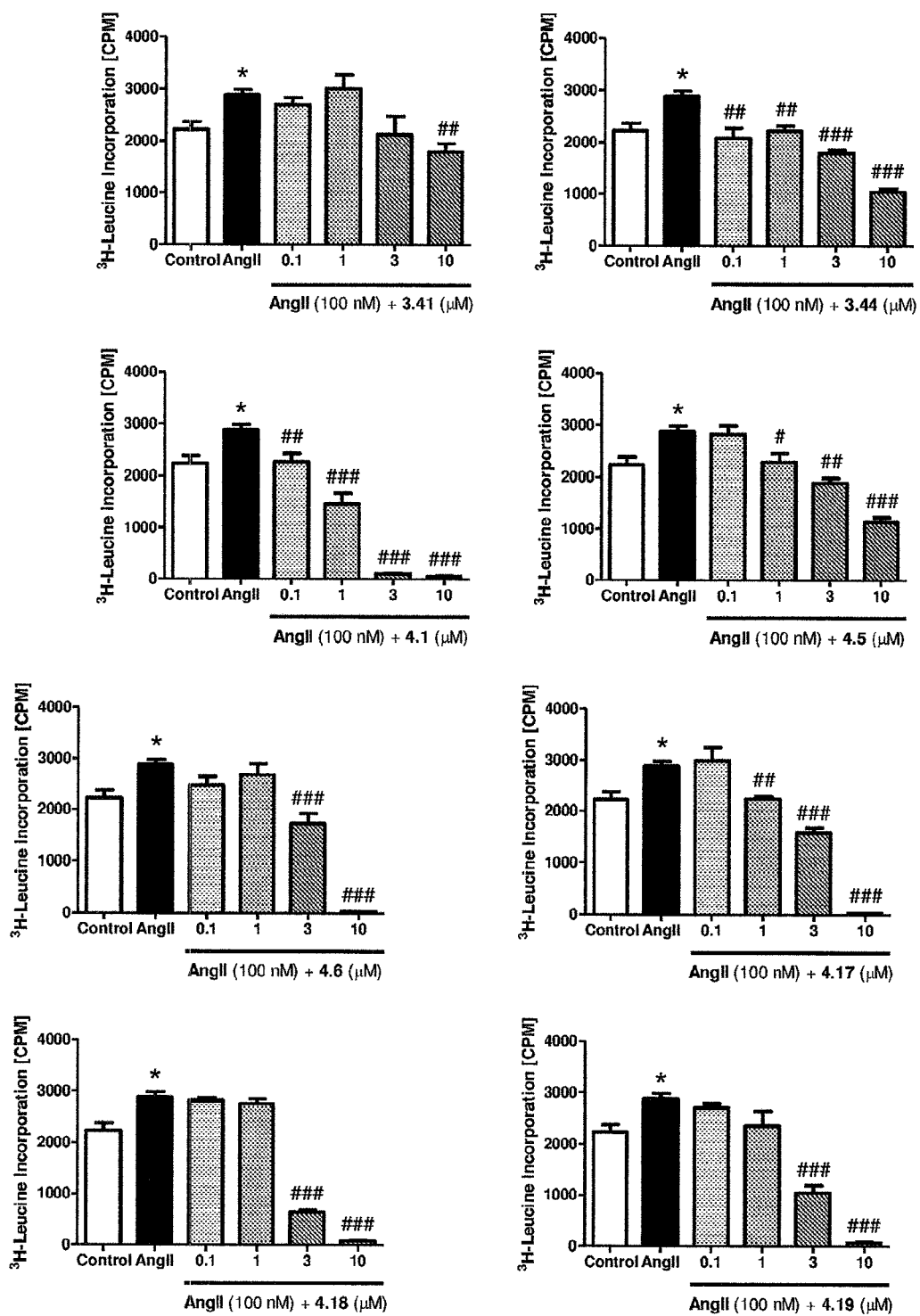
FIG. 4 is a graphical representation of the effects of a number of compounds of the present invention on NCM hypertrophy stimulated by AngII (* $p<0.05$ vs. unstimulated control; # $p<0.05$, ## $p<0.01$, ### $p<0.001$ vs. stimulated control (AngII))
Figure 5:
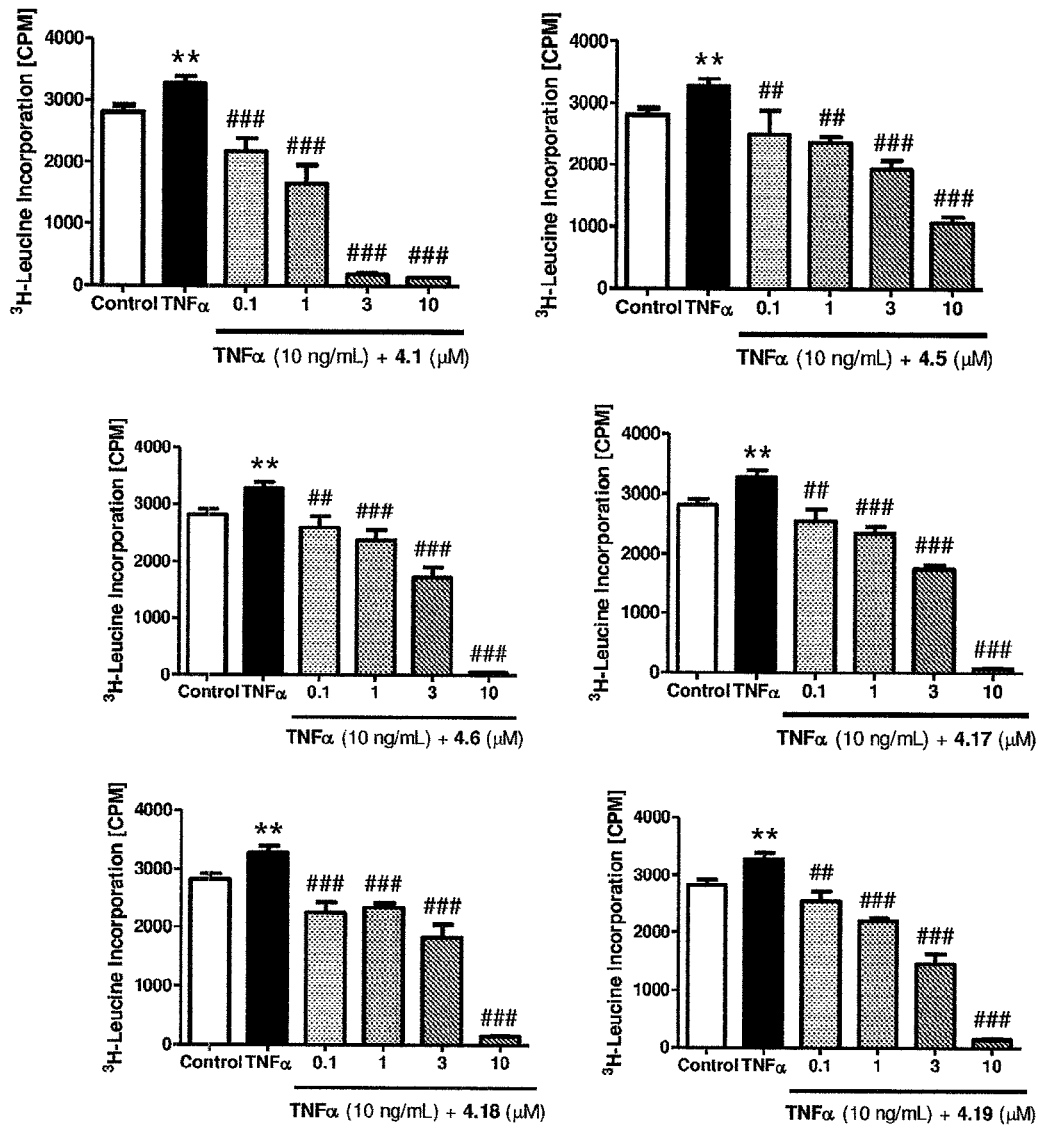
FIG. 5 is a graphical representation of the effects of a number of compounds of the present invention on NCM hypertrophy stimulated by TNF-α (** $p<0.01$ vs. unstimulated control; # $p<0.05$, ## $p<0.01$, ### $p<0.001$ vs. stimulated control (TNF-α))

Neonatal rat cardiac myocyte (NCM) hypertrophy was determined by $^3$H-leucine incorporation following a published protocol on the above synthesised compounds using either Angiotensin II (AngII, 100 nM) or TNF-α (10 ng/mL) as the stimulus. $^3$H levels were counted in scintillation fluid on a beta counter to determine levels of $^3$H-leucine incorporation. Both AngII and TNF-α are known activators of p38α MAPK and as expected AngII and TNF-α significantly stimulated NCM hypertrophy. All of the tested analogues dose-dependently suppressed both AngII- and TNF-α-induced NCM hypertrophy. FIGS. 4 and 5 show the suppression of NCM hypertrophy by a number of compounds of the present invention, including compounds 4.1 and 4.5.

Measurement of Neonatal Rat Cardiac Fibroblast Collagen Synthesis

Figure 6:
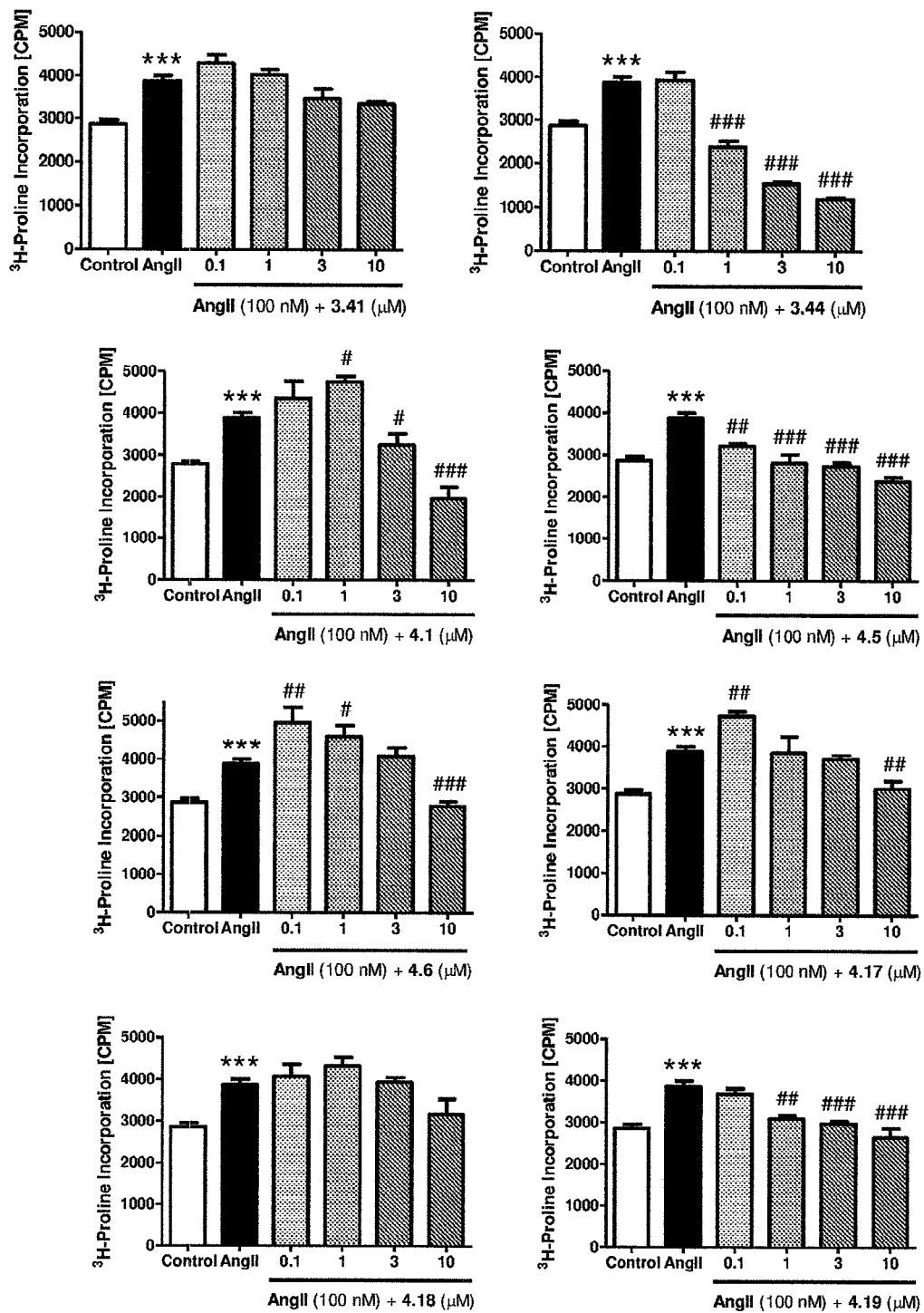
FIG. 6 is a graphical representation of the effects of a number of compounds of the present invention on NCF collagen synthesis stimulated by AngII (*** $p<0.001$ vs. unstimulated control; # $p<0.05$, ## $p<0.01$, ### $p<0.001$ vs. stimulated control (AngII))

The effect of the compounds on neonatal rat cardiac fibroblasts (NCF) collagen synthesis was determined by measuring $^3$H-proline incorporation following a published protocol using AngII (100 nM) as the stimulus. $^3$H-proline incorporation was determined in the same way as the cardiac myocyte hypertrophy assay described above. AngII significantly stimulated NCF collagen synthesis. Compound 4.5 showed a dose-dependent inhibition of AngII-simulated NCF collagen synthesis (FIG. 6). However, compound 4.1 did not suppress AngII-induced NCF collagen synthesis at 1 µM concentration.

Measurement of Cell Viability in Neonatal Rat Cardiac Fibroblasts

Figure 9:
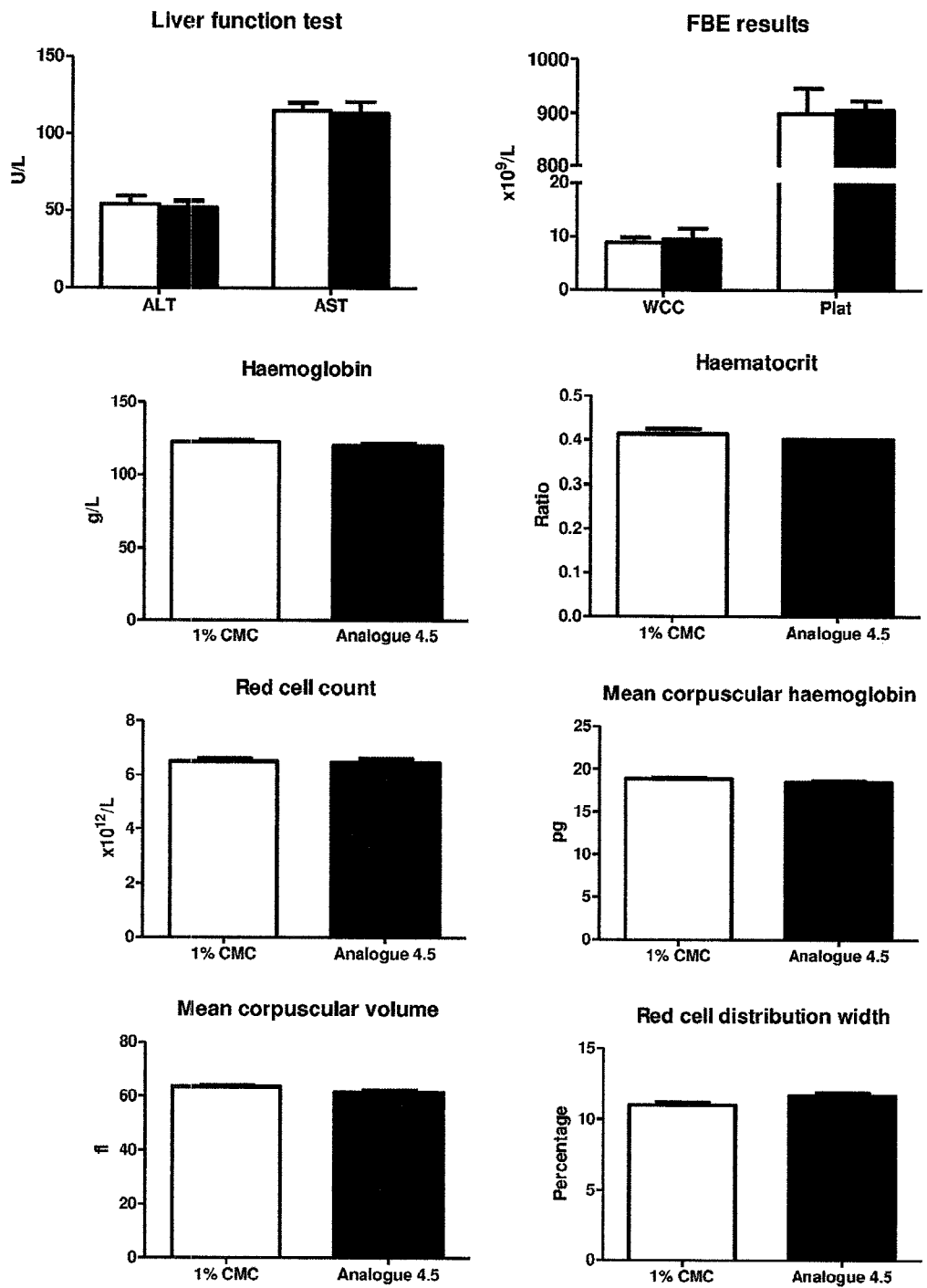
FIG. 9 is a graphical representation of the effects of analogues 4.1 and 4.5 on NCF viability.

Measurement of NCF cell viability was carried out using a published method with the 3-(4,5-dimethylthiazol-2-yl)-2,5-diphenyltetraxolium bromide (MTT) assay. Both compounds 4.1 and 4.5 demonstrated good toxicity profiles having no affect on NCF cell viability at 10 and 25 µM concentration, respectively (FIG. 9).

number of drug metabolising enzymes, such as the CYP450 enzymes. An in vitro metabolic stability study was conducted using human, rat and mouse liver microsomes as a prediction of the in vivo metabolic clearance. Table 2 shows the metabolic stability parameters for the two compounds. From the results, the rates of apparent compound degradation in human, rat and mouse liver microsomes were in agreement with the moderate to high microsome-predicted extraction ratios ($E_H$) for both compounds 4.1 and 4.5. Compound 4.5 had a better metabolic stability profile in all three species of liver microsomes. This compound had an acceptable intrinsic clearance and $E_H$ values in human microsomes, though the half life is relatively short.

TABLE 2

| Compound | Species | Apparent Degradation half-life (min) | In vitro $CL_{int}$ (µL/min/mg protein) | Microsome predicted $E_H$ |
|---|---|---|---|---|
| 4.1 | Human | 8 | 219 | 0.92 |
|  | Rat | 5* | 319* | 0.91* |
|  | Mouse | 5* | 342* | 0.94* |
| 4.5 | Human | 71 | 24 | 0.58 |
|  | Rat | 16 | 110 | 0.78 |
|  | Mouse | 9 | 184 | 0.89 |

Metabolic stability parameters for compounds 4.1 and 4.5 based on nicotinamide adenine dinucleotide phosphate (NADPH)-dependent degradation profiles in human, rat and mouse liver microsomes. *Value is an approximation as concentrations were only above the analytical lower limit of quantification (LLQ) up to 5 min and degradation parameters were estimated using the initial two time points only (i.e. 2 and 5 min).

Effects on Cellular Functions Related to Renal Fibrosis

Measurement of Rat Mesangial Cell Collagen Synthesis

Figure 8:
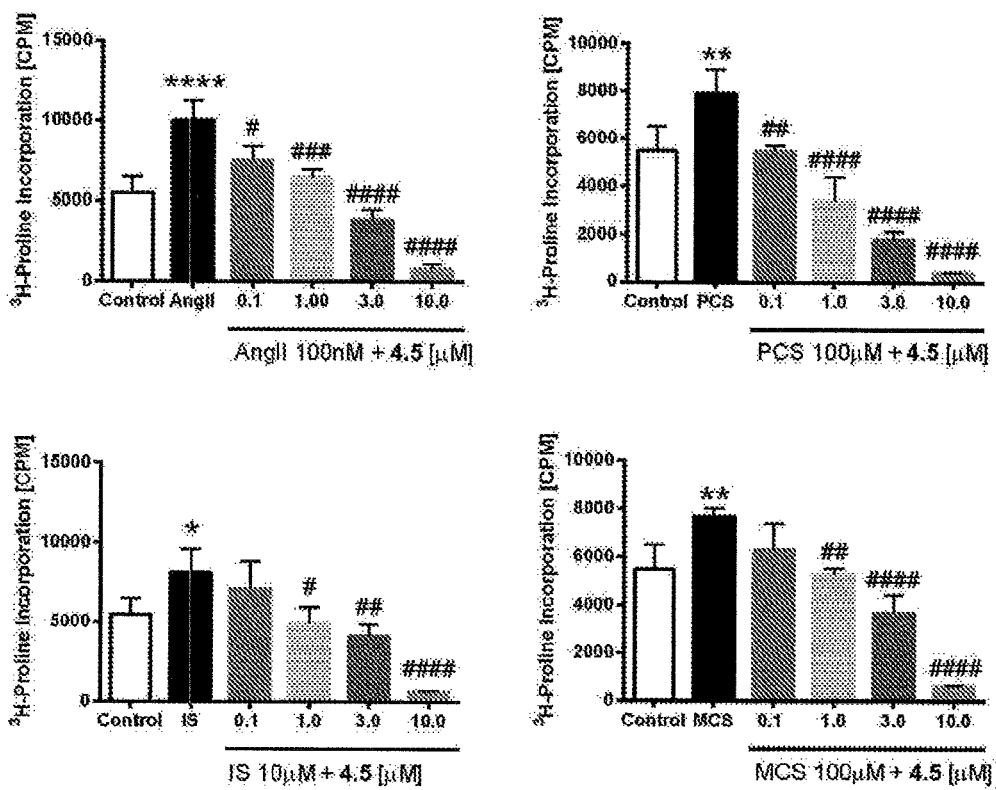
FIG. 8 is a graphical representation of the effect of 4.5 on RMC collagen synthesis stimulated by AngII, IS, PCS or MCS (* $p<0.05$, $P<0.01$, ** $p<0.0001$ vs. unstimulated control; # $p<0.05$, ## $p<0.01$, ### $p<0.001$, ####$p<0.0001$ vs. stimulated control (AngII, IS, PCS or MCS))

The effects of the compounds on rat mesangial cell (RMC) collagen synthesis were determined by measuring ³H-proline incorporation following a published protocol using AngII (100 nM), uremic toxins: indoxyl sulphate (IS, 10 µM), p-cresol sulphate (PCS, 100 µM) and m-cresol sulphate (MCS, 100 µM) as the stimulus. ³H-proline incorporation was determined in the same way as the NCF collagen synthesis assay described above. AngII, IS, PCS and MCS significantly stimulated RMC collagen synthesis. Compound 4.5 showed a dose-dependent inhibition of AngII-, IS-, PCS- and MCS-simulated RMC collagen synthesis (FIG. 8).

In Vitro Metabolism of Compounds 4.1 and 4.5

Figure 7:
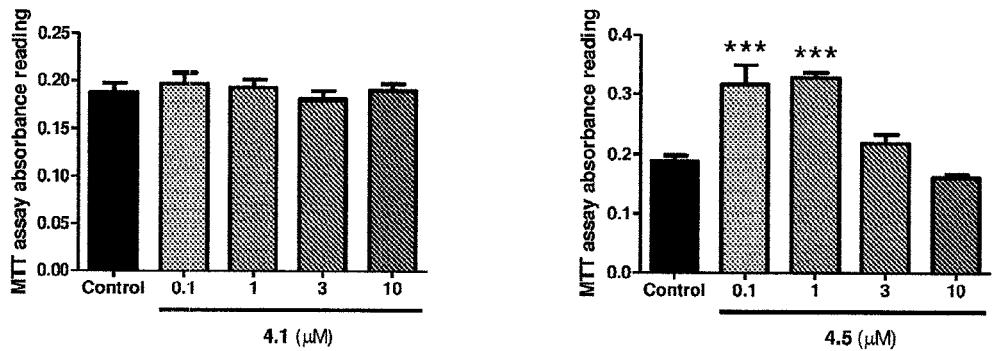
FIG. 7 is a graphical representation of the blood results from an acute toxicity study for compound 4.5.

The metabolic stability of compounds 4.1 and 4.5 was assayed in an in vitro assay which employed liver microsomes. Liver microsomes are valuable models for the determination of hepatic clearance because they contain a Acute Toxicity Study An acute toxicity study of compound 4.5 was carried out. In this toxicity study, four male Sprague-Dawley (SD) rats received 150 mg/kg of compound 4.5 twice daily by oral gavage over a period of two weeks. The control group consisting of four male SD rats received 1% carboxymethylcellulose (CMC) in water. Blood samples were collected for analysis at 1 and 12 hours after the first dose and at the 7 and 14 day troughs. The rats were then sacrificed and organs collected for analysis. Individual body weights were measured at day −1, 2, 4, 7, 10 and 14. FIG. 7 indicates the blood results from an acute toxicity study for 4.5. FIG. 10*a* shows the individual body weight gain of each rat over the course of two weeks. There was no difference in the average body weight compared to the vehicle group (FIG. 10*b*). The weights of the kidneys, heart and liver were the same as the vehicle group but a loss in the mass of the spleen was observed (FIG. 11).

The full blood, haemoglobin, haemocrit, red cell count, mean corpuscular haemoglobin, mean corpuscular volume, red cell distribution width, mean corpuscular haemoglobin concentration and liver function were all assessed. No differences were observed between treated and vehicle groups. Given that liver toxicity has resulted in the failure of many p38α MAPK inhibitors, it was promising to see that there were no changes to liverfunction. The CDCO analysed blood samples using HPLC-MS to determine the concentrations of compound 4.5 in rat plasma at different time points (Table 3). An intake of 300 mg/kg/day of compound 4.5 resulted in peak plasma levels two to nine times higher than the enzyme $IC_{50}$ value. This suggests that there is a sufficient amount of compound in circulation. Overall, the results of the acute toxicity study indicate that compound 4.5 is well tolerated in rats.

TABLE 3

Concentrations (nM) of compound 4.5 in rat plasma.

| Sample Time | Rat 1 | Rat 2* | Rat 3 | Rat 4 |
| --- | --- | --- | --- | --- |
| 1 hour post first dose | 1357 | 0.9 | 325 | 327 |
| 12 hours post first dose | 8 | 7 | 147 | 5 |
| 7 day trough | 5 | 424 | 58 | 6 |
| 14 day trough | 7 | 105 | 32 | 14 |

*The concentration profile for rat 2 appears atypical however data were confirmed by analysis of the second (duplicate) sample set from this animal. Data for rat 2 was excluded from the analysis.

Summary for Compound 4.1 and Related Compounds

Most of the synthesised analogues tested above showed potent inhibitory activity against p38α MAPK and therefore, were expected to show anti-inflammatory properties. In vitro, the synthesised thiophene analogues were all shown to suppress IL-6 production from LPS-stimulated THP-1 cells in a dose dependent manner. Some inhibition of TNF-α production was also observed. Additional assays were conducted to determine whether the compounds could affect cardiac remodelling. Investigation into two major mechanisms of cardiac remodelling, cardiac myocyte hypertrophy and cardiac fibroblast collagen synthesis, have given positive results. Both AngII and TNF-α induced cardiac myocyte hypertrophy were inhibited by all synthesised analogues in a dose-dependent manner. At high concentrations, these compounds also suppress cardiac fibroblast collagen synthesis. Given that inflammatory cytokines are known to adversely affect cardiac remodelling, inhibition of the p38α MAPK pathway is a potential avenue for attenuating cardiac remodelling associated with cardiac disease. As an example, compound 4.5 dose-dependently inhibited Angiotensin II and uremic toxins (IS, PCS and MCS) stimulated rat mesangial cell collagen synthesis. Given that the renin angiotensin aldosterone system, inflammatory cytokines and uremic toxins are known to adversely affect renal fibrosis, inhibition of the p38α MAPK pathway is a potential avenue for attenuating renal fibrosis associated with kidney disease.

Furthermore, metabolic stability profiling of the two best compounds found that both compounds 4.1 and 4.5 had high degradation rates and moderate to high microsome-predicted extraction ratios. Compound 4.5 had a better metabolic stability profile than compound 4.1 in human, rat and mouse liver microsomes and subsequently was investigated in an acute toxicity study. This compound was well tolerated in the rat model. A dose of 300 mg/kg/day resulted in peak circulating concentration between 325 and 1357 nM which is well above the concentrations required to inhibit p38α MAPK, indicating that there was sufficient amount of compound in circulation.

Studies Towards Improved Thiophene p38α MAPK Inhibitors

Further experiments focused on potentially improving the physicochemical properties of the thiophene compounds by reducing molecular weight and lipophilicity. To guide this furtherwork molecular modelling was carried out based around the thiphene core shown below:

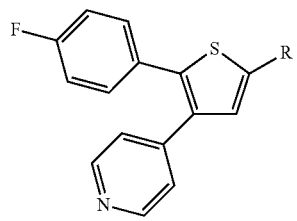

A range of potential substituents were docked into the 1 BL7 and 2EWA crystal structures to predict the binding conformation within the p38α MAPK active site. The results are shown in Table 4, below.

TABLE 4

| Rank | R* | Score |
| --- | --- | --- |
| 1 | ~~~~~~~~NH₂ (but-3-ynyl-amine) | −8.83 |
| 2 | ~~~~~~~~N-piperazine | −8.60 |
| 3 | ~~~~~~~~NH-piperidine-N-benzyl | −8.31 |
| 4 | ~~~~~~~~OH | −8.27 |
| 5 | ~~~~~~~~NH₂ | −8.21 |
| 6 | ~~~~~~~~N-morpholine | −8.12 |
| 7 | ~~~~~~~~tetrafluoropyridine | −7.96 |
| 8 | ~~~~~~~~C(O)~~~OH | −7.91 |
| 9 | ~~~~~~~~Me | −7.91 |

TABLE 4-continued

| Rank | R* | Score |
|---|---|---|
| 10 | propyl | −7.90 |
| 11 | but-2-en-1-ol | −7.85 |
| 12 | prop-2-yn-1-amine | −7.82 |
| 13 | pent-4-yn-1-ol | −7.80 |
| 14 | 1-(but-3-yn-1-yl)piperidine | −7.78 |
| 15 | 1-(piperidin-4-yl)ethanone | −7.73 |
| 16 | piperazine | −7.72 |
| 17 | 1-methylpiperazine | −7.71 |
| 18 | prop-2-yn-1-ol | −7.67 |
| 19 | methyl but-2-ynoate | −7.66 |
| 20 | morpholine | −7.66 |
| 21 | 1-(piperazin-1-yl)ethanone | −7.65 |
| 22 | 4-hydroxyphenyl | −7.61 |
| 23 | pent-3-yn-1-ol | −7.60 |
| 24 | but-2-ynamide | −7.54 |

TABLE 4-continued

| Rank | R* | Score |
|---|---|---|
| 25 | H | −7.53 |
| 26 | 2-amino-3,5,6-trifluoro-4-methylpyridine | −7.48 |
| 27 | hex-5-yn-1-ol | −7.46 |
| 28 | 1-(1H-pyrrol-2-yl)ethanone | −7.46 |
| 29 | hex-5-yn-1-amine | −7.35 |
| 30 | piperidine | −7.35 |
| 31 | 1-morpholinoethanone | −7.27 |
| 32 | cyclohexylamine | −7.26 |
| 33 | 1-phenylethanone | −7.26 |
| 34 | 1-(furan-2-yl)ethanone | −7.23 |
| 35 | ethyl | −7.22 |
| 36 | cyclopropyl | −7.20 |
| 37 | butan-2-one | −7.20 |
| 38 | propan-2-one | −7.15 |

TABLE 4-continued

| Rank | R* | Score |
|---|---|---|
| 39 | 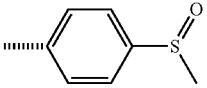 | −7.10 |
| 40 | 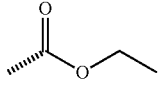 | −7.05 |
| 41 |  | −7.05 |
| 42 |  | −7.01 |
| 43 | 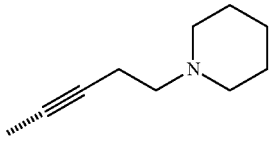 | −6.94 |
| 44 | 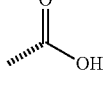 | −6.93 |
| 45 | 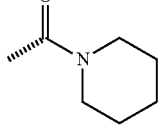 | −6.86 |
| 46 | 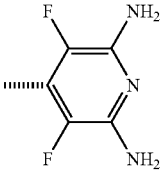 | −6.84 |
| 47 | 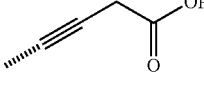 | −6.81 |

TABLE 4-continued

| Rank | R* | Score |
|---|---|---|
| 48 |  | −6.19 |

Ensemble scores of designed compounds docked into the 1BL7-2EWA crystal structures.
*Hashed line depicts the bond that is formed.

From the ensemble scores of the docked structures shown in Table 4, the best scoring compound contains a terminal amine as a replacement for the hydroxyl group. This analogue is able to form hydrogen bonding interactions with the surrounding Asp168 and Asn155 side chains. Generally the alkynyl amine analogues with differing chain lengths performed well in ensemble docking. Analogues in which the hydroxyl group was substituted with piperazine or morpholine moieties were also ranked highly. Using the rankings from the ensemble docking study the approach was undertaken to synthesise a range of compounds with differing chain lengths, terminal hydrogen bond donors, hydrogen bond acceptors in the α position and those with increased flexibility to improve potency while also monitoring physicochemical properties such as lipophilicity.

Synthesis of Tri-Substituted Thiophene Analogues
Modifications to Chain Length and Replacement of the Hydroxyl Group In order to investigate analogues with different chain lengths the synthesis of compound 4.5 was simplified (Scheme below). First, iodination of compound 3.2 at the α-position using silver nitrate and molecular iodine gave 2-iodothiophene 5.1 as a white powder in 74% yield. Sonogashira reaction of 2-iodothiophene 5.1 with the appropriate alkynyl alcohol gave the cross coupled product in high yields using copper iodide, triphenylphosphine, bis(triphenylphosphine)palladium(II) dichloride and triethylamine. The propargyl alcohol 5.2, butynyl alcohol 4.5 and the pentynyl alcohol 5.3 were synthesised in 76%, 87% and 85% yield respectively. Results from the docking study found that the alkynyl amines were able to bind to the p38α MAPK structure in a low energy conformation. Therefore the synthesised alkynyl alcohol analogues were transformed into the corresponding alkynyl amines (as shown in the below scheme). To synthesise these analogues a Mitsunobu reaction was conducted in which N,N-diisopropylazodicarboxylate was added to a mixture of the alkynyl alcohol, phthalimide and triphenylphosphine. This reaction enabled substitution of the alcohol moiety for a phthalimide group producing the propargyl phthalimide 5.4 and butynyl phthalimide 5.5 in 51% and 93% yield, respectively. Cleavage of the phthalyl group with hydrazine monohydrate gave amines 5.6 and 5.7 in 78% and 75% yield respectively.

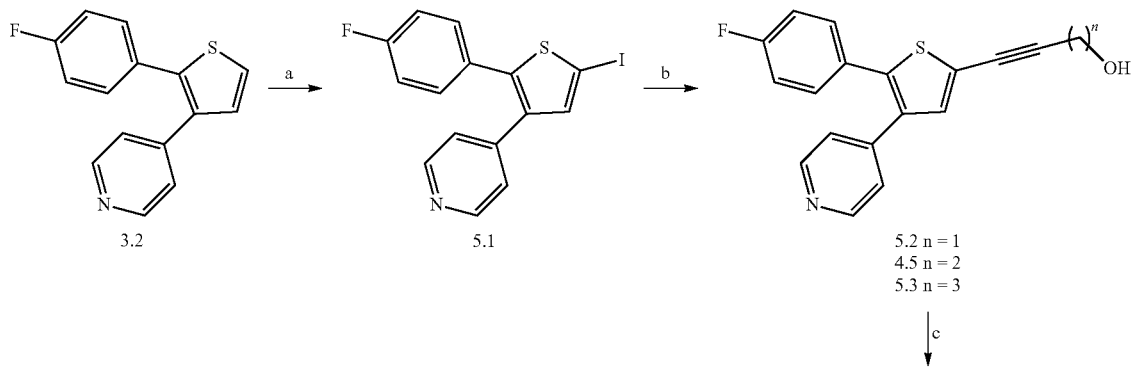

5.2 n = 1
4.5 n = 2
5.3 n = 3

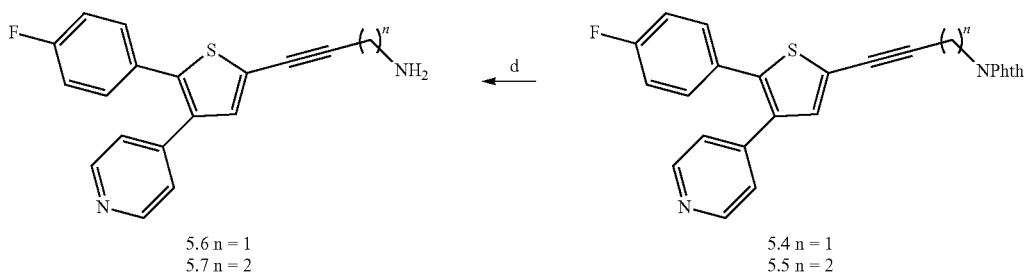

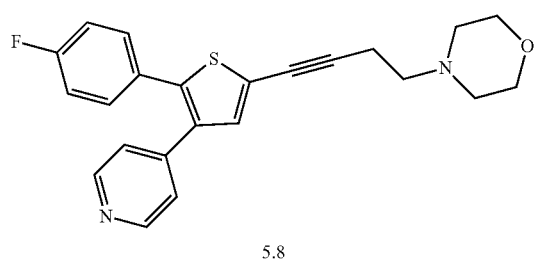

Synthesis of alkynyl alcohols 4.5, 5.2 and 5.3 and alkynyl amines 5.6 and 5.7. Reagents and conditions: (a) AgNO$_3$, I$_2$, MeCN, rt, 16 h, 74%; (b) PdCl$_2$(PPh$_3$)$_2$, alkynyl alcohol, PPh$_3$, CuI, Et$_3$N, THF, reflux, 2 h, 5.2: 76%, 4.5: 87%, 5.3: 85%; (c) Phthalimide, DIAD, PPh$_3$, THF, rt, 20 h, 5.4: 51%, 5.5: 93%; (d) NH$_2$NH$_2$.H$_2$O, MeOH/EtOH, 5.6: 65%, 5.7: 69%.

The alcohol group of compound 4.5 was also substituted with a morpholine (Scheme below). Compound 4.5 was treated with mesyl chloride then heated in morpholine at 100° C. to produce morpholine analogue 5.8 in 32% yield.

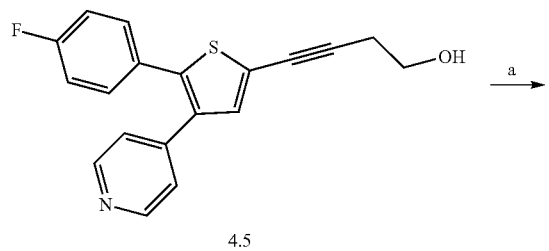

Synthesis of analogue 5.8. Reagents and conditions: (a) MsCl, CHCl$_3$, 0° C., 1 h, morpholine, 100° C., 1 h, 32%.

Modifications to the Alkyne Functional Croup

To determine whether the alkyne functionality was needed for p38α MAPK binding, the butynyl substituent was reduced to increase flexibility. Reduction of the butynyl substituent was conducted using palladium on carbon under a hydrogen atmosphere to give butanol analogue 5.9 in 40% yield (Scheme below). The alkyne of compound 4.5 was also hydrated to a ketone using sulfuric acid to give analogue 5.10 in good yield (90%).

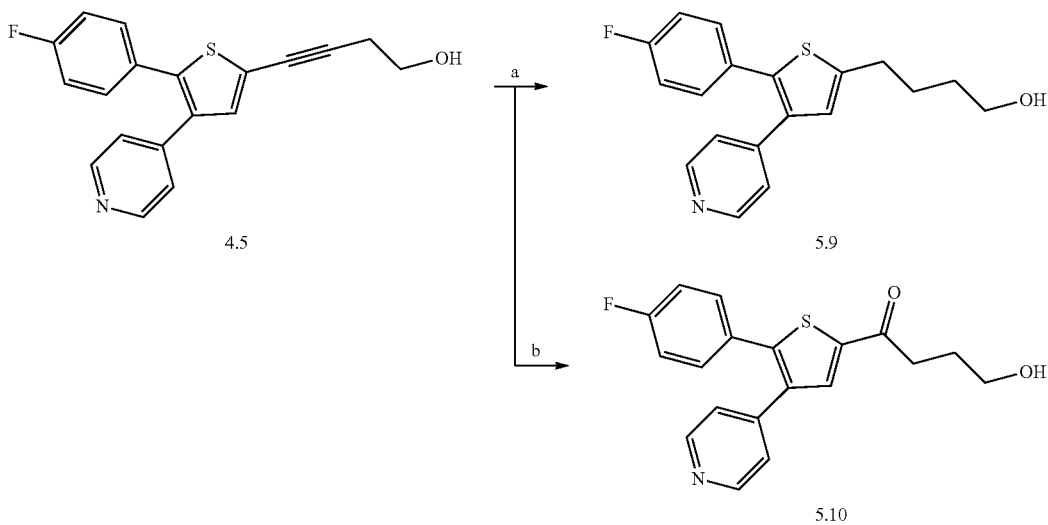 [SMILES: OCCC#Cc1cc(-c2ccncc2)c(-c2ccc(F)cc2)s1 ; OCCCCc1cc(-c2ccncc2)c(-c2ccc(F)cc2)s1 ; O=C(CCCO)c1cc(-c2ccncc2)c(-c2ccc(F)cc2)s1]

Synthesis of analogues 5.9 and 5.10. Reagents and conditions: (a) Pd/C, H$_2$, EtOH, rt, 3 d, 40%; (b) H$_2$SO$_4$, (CH$_3$)$_2$CO, 0° C.—rt, 1.5 h, 71%.

Carbonyl Derivatives

The carboxypiperazine analogue 5.14 was ranked twenty-first in the docking study. To incorporate a carbonyl moiety in the α-position of the thiophene, compound 3.2 was reacted with n-butyllithium (Scheme below). The lithiated thiophene was reacted with ethyl chloroformate to form ethyl ester 5.11 in 55% yield. Hydrolysis of ethyl ester 5.11 with aqueous sodium hydroxide in ethanol gave acid 5.12 in 85% yield. Acid 5.12 was converted to the acid chloride using oxalyl chloride and a catalytic amount of N,N-dimethylformamide and then immediately reacted with 1-boc-piperazine to form the protected carboxypiperazine analogue 5.13 in 61% yield. Boc deprotection using trifluoroacetic acid in dichloromethane gave the desired carboxypiperazine 5.14 in 72% yield.

ride and furoyl chloride all gave the desired analogues 5.15, 5.16 and 5.17 in good yields.

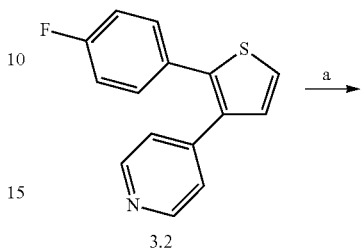

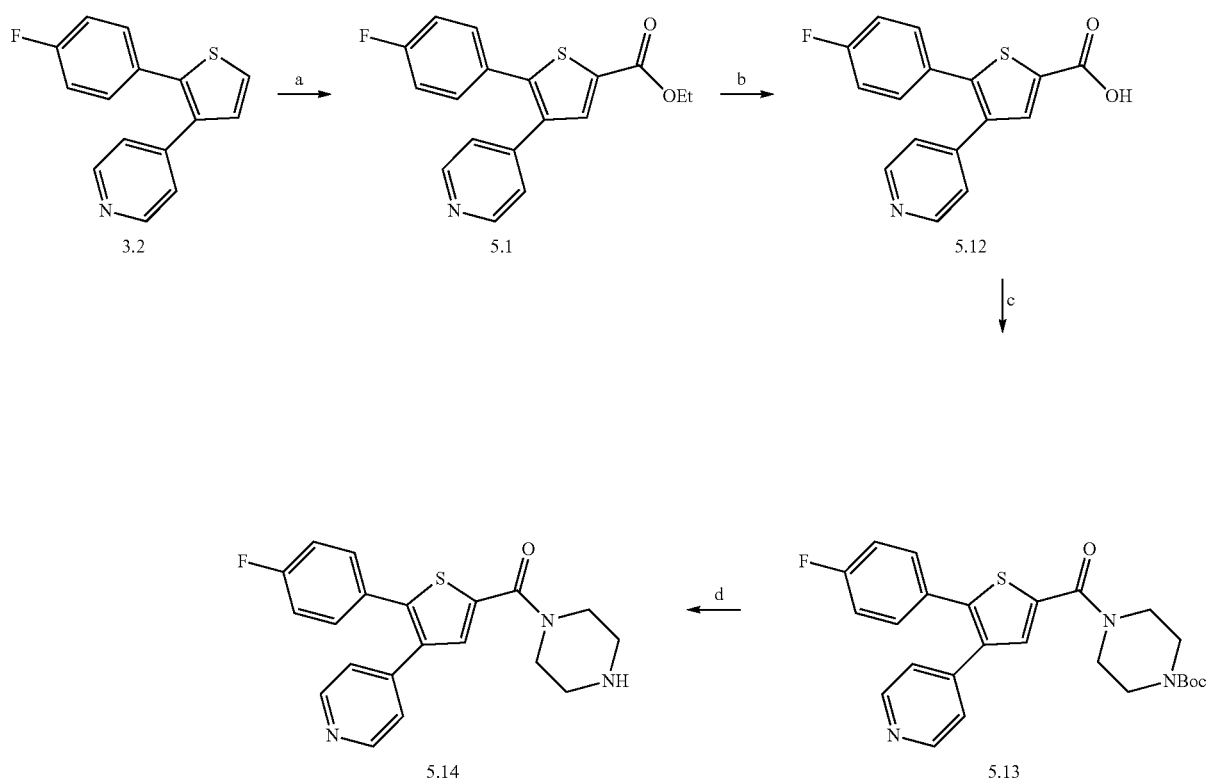

Synthesis of carboxypiperazine 5.14. Reagents and conditions: (a) nBuLi, THF, −78° C., 30 min, ClCO$_2$Et, rt, 3 h, 55%; (b) NaOH, EtOH, H$_2$O, 50° C., 2 h, 85%; (c) (COCl)$_2$, DMF, DCM, rt, 2 h, 1-Boc-piperazine, DIPEA, DCM, rt, 4 h, 61%; (d) TFA, DCM, rt, 2 h, 72%.

Other carbonyl derivatives were synthesised using a Friedel-Crafts acylation reaction (Scheme below). The acid chloride was treated with aluminium chloride in dichloromethane, and then refluxed with compound 3.2. Under these reaction conditions the acetyl chloride, benzoyl chloride -continued

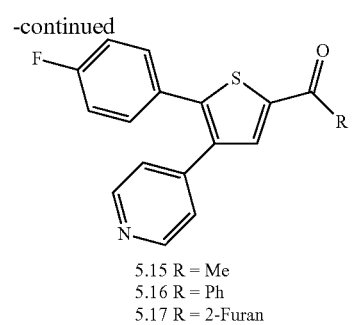

5.15 R = Me
5.16 R = Ph
5.17 R = 2-Furan

Synthesis of acyl analogues 5.15-5.17. Reagents and conditions: (a) acid chloride, AlCl₃, DCM, reflux, 16 h, 5.15: 67%. 5.16: 86%, 5.17: 85%.

Aromatic Substituents

The furan analogue 5.18 was synthesised in high yield (91%) using a Suzuki coupling reaction described in the experimental section (Scheme below).

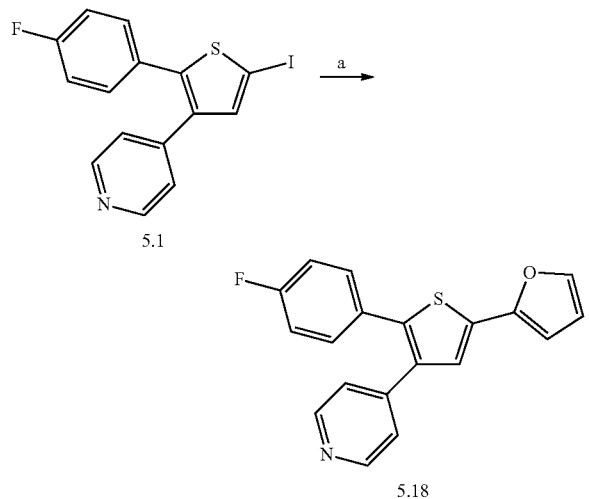

Synthesis of analogue 5.18. Reagents and conditions: (a) furan-2-boronic acid, Pd(PPh₃)₂Cl₂, Na₂CO₃, THF, μW, 100° C., 90 min, 91%.

Compound 3.2 was reacted with n-butyllithium followed by pentafluoropyridine to give analogue 5.19 in good yield (65%). Monoamination occurred easily in aqueous ammonia using N-methyl-2-pyrrolidone as a co-solvent at 120° C. for 1 hour in a sealed tube. This gave analogue 5.20 quantitatively. Diamination of tetrafluoropyridine 5.19 progressed much slower and required harsh reaction conditions with only 70% conversion after heating the reaction at 150° C. over 3 days. The diamino analogue 5.21 was isolated in 36% yield.

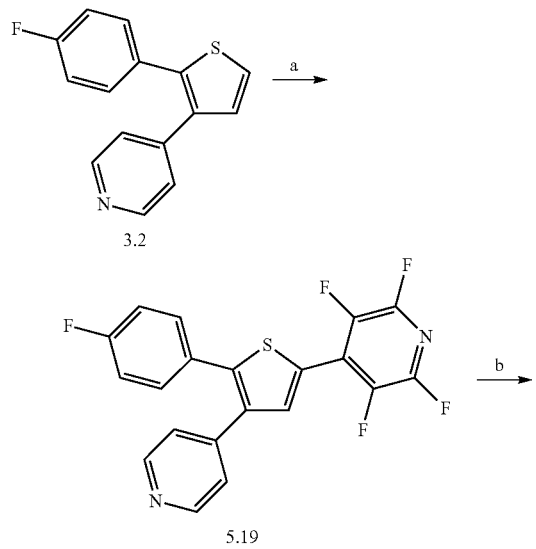

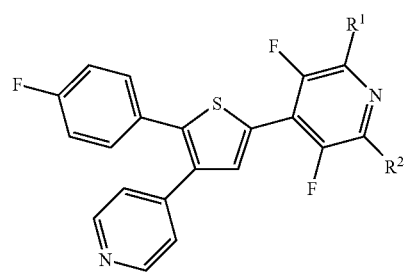

5.20 R¹, R² = NH₂, F
5.21 R¹, R² = NH₂, NH₂

Synthesis of pyridine analogues 5.19-5.21. Reagents and conditions: (a) nBuLi, THF, −78° C., 30 min, pentafluoropyridine, rt, 2 h, 65%; (b) NH₃ (aq.), NMP, 5.20: 120° C., 1 hour, quant., 5.21: 150° C., 3 d, 50%

Biological Evaluation of Tri-Substituted Thiophene Compounds

Binding Affinity to p38α MAPK

Figure 12:
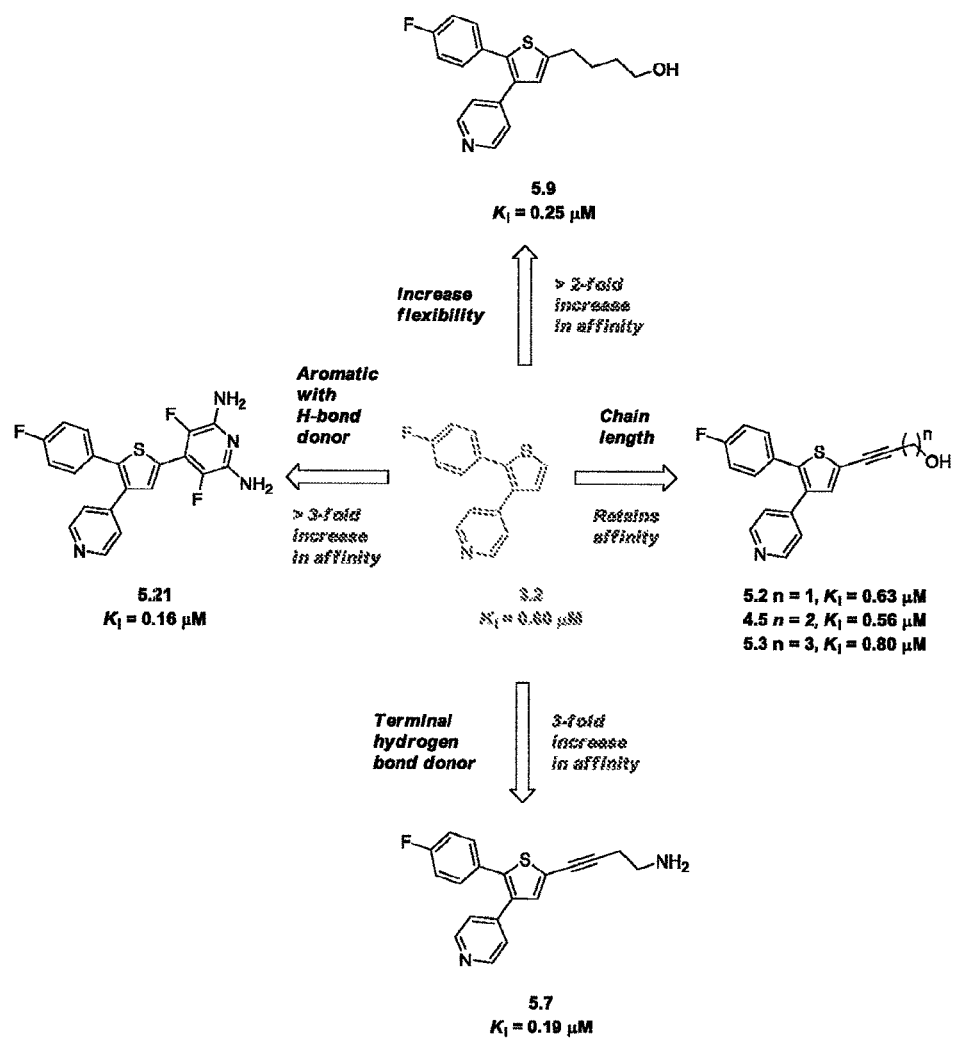
FIG. 12 is a diagrammatic representation of the SAR for a trisubstituted thiophene series.

The synthesised tri-substituted analogues were evaluated in the same fluorescence polarisation binding assay discussed above with binding affinities given in Table 5. The compounds showed stronger binding to the active form of the enzyme, consistent with the above description. Generally, the stronger the analogues bind to the inactive protein, the stronger they bind to active phosphorylated p38α MAPK. FIG. 12 describes the SAR of the synthesised analogues. Small differences in affinity are observed when modifying the chain length of the alkynyl alcohol substituent with $K_i$ values of 0.63, 0.56 and 0.80 μM for the 3, 4 and 5 carbon spacer. When compared with disubstituted thiophene 3.2, there are no significant improvements in binding affinity suggesting that the extra alkynyl alcohol functional group is not making key interactions within the binding pocket. However, a three-fold improvement in affinity is observed when converting the butynyl alcohol 4.5 to a butynyl amine 5.7 in which a $K_i$ value of 0.19 μM was achieved. Loss of the terminal hydrogen bond donor reduces binding affinity which was exemplified by the morpholine analogue 5.8 ($K_i$ 2.5 μM).

Reduction of the alkyne functional group to the fully saturated butyl group 5.9 improved binding affinity more than two-fold ($K_i$ 0.25 μM). In addition, hydration of the alkyne to a ketone 5.10 maintained affinity with a $K_i$ value of 0.67 μM. This suggests that the alkyne is not essential for p38α binding and increasing the flexibility improves affinity. Only aromatic substituents containing hydrogen bond donating functional groups were found to improve affinity. The tetrafluoropyridine analogue 5.19 had a $K_i$ value of 0.80 μM which was further improved by the substitution of a fluoro group with an amine. This mono-aminopyridine analogue 5.20 had a $K_i$ value of 0.20 μM. The diaminopyridine analogue 5.21 was the most potent analogue synthesised having a $K_i$ value 0.16 μM.

TABLE 5

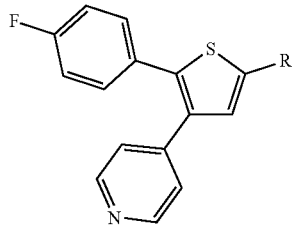

| Compound | R | $K_i$ ± SEM (μM) to inactive p38α MAPK | $K_i$ ± SEM (μM) to active p38α MAPK |
|---|---|---|---|
| RWJ67657 | n.a. | 0.21 ± 0.04 | 0.013 ± 0.006 |
| 3.2 | H | 5.0 ± 0.4 | 0.6 ± 0.1 |
| 5.1 | I | 1.9 ± 0.4 | 2.3 |
| 5.2 | C≡CCH$_2$OH | 2.1 ± 0.3 | 0.63 ± 0.04 |
| 4.5 | C≡C(CH$_2$)$_2$OH | 2.0 ± 0.2 | 0.56 ± 0.06 |
| 5.3 | C≡C(CH$_2$)$_3$OH | 1.7 ± 0.2 | 0.80 ± 0.04 |
| 5.6 | C≡CCH$_2$NH$_2$ | >10.0 | n.d. |
| 5.7 | C≡C(CH$_2$)$_2$NH$_2$ | 1.1 ± 0.2 | 0.19 ± 0.04 |
| 5.8 | C≡C(CH$_2$)$_2$morpholine | 2.2 ± 0.2 | 2.5 |
| 5.9 | (CH$_2$)$_4$OH | 0.98 ± 0.02 | 0.25 ± 0.04 |
| 5.10 | CO(CH$_2$)$_3$OH | 2.7 ± 0.3 | 0.67 ± 0.03 |
| 5.11 | CO$_2$Et | 6 ± 1 | 2.2 |
| 5.12 | CO$_2$H | 17 ± 2 | 1.4 |
| 5.14 | carboxypiperazine | 6.3 ± 0.4 | 0.9 ± 0.1 |
| 5.15 | acetyl | 6.4 ± 0.6 | 1.4 |
| 5.16 | benzoyl | 5 ± 2 | 2.8 ± 0.1 |
| 5.17 | furoyl | 5.9 ± 0.7 | 2.5 |
| 5.18 | 2-furan | >10.0 | 1.7 |
| 5.19 | 2,3,5,6-tetrafluoropyridine | 3.01 ± 0.03 | 0.8 ± 0.1 |
| 5.20 | 2-amino-3,5,6-trifluoropyridine | 0.66 ± 0.06 | 0.21 ± 0.01 |
| 5.21 | 2,6-diamino-3,5-difluoropyridine | 0.47 ± 0.01 | 0.16 ± 0.02 |

Binding affinities to inactive and active p38α MAPK. n.d. not determined. For compounds with $K_i$ < 10 μM to inactive p38α MAPK the binding assay was carried out in triplicate with n = 3 experiments. For compounds with $K_i$ < 1 μM to active p38α MAPK the binding assay was conducted in duplicate with n = 2-3 experiments.

Figure 14:
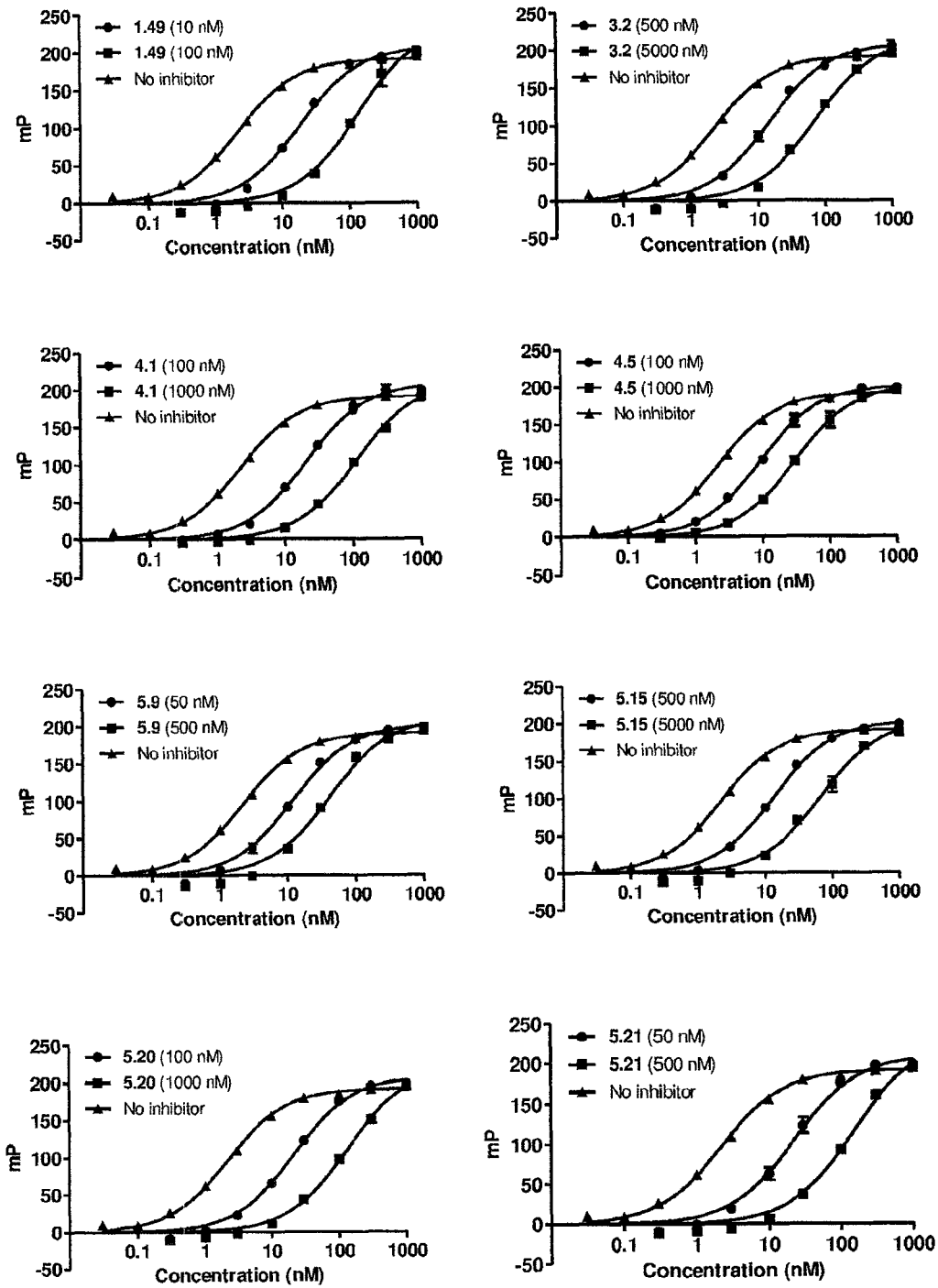
FIG. 14 is a graphical representation of the competitive binding of certain compounds of the invention with SB203580-fluorescein ligand to inactive p38α MAPK.

A number of compounds were selected for competition experiments to prove they were binding competitively with the SB203580-fluoroscein ligand and not to an allosteric site. The dose response curves are shown in FIG. 14. Using differing concentrations of the inactive non-phosphorylated p38α MAPK (0.03 to 1000 nM) it was possible to determine the change in $K_d$ value for the fluorescently labelled ligand. The affinity of SB203580-fluorescein to the inactive form of the p38α enzyme was observed to decrease with increasing concentrations of the tested analogues, indicating that the synthesised analogues were competing for the same binding site as the fluoroprobe. All of the tested compounds showed competitive binding for the ATP pocket of p38α MAPK.

In Vitro Activation Assay

Figure 13:
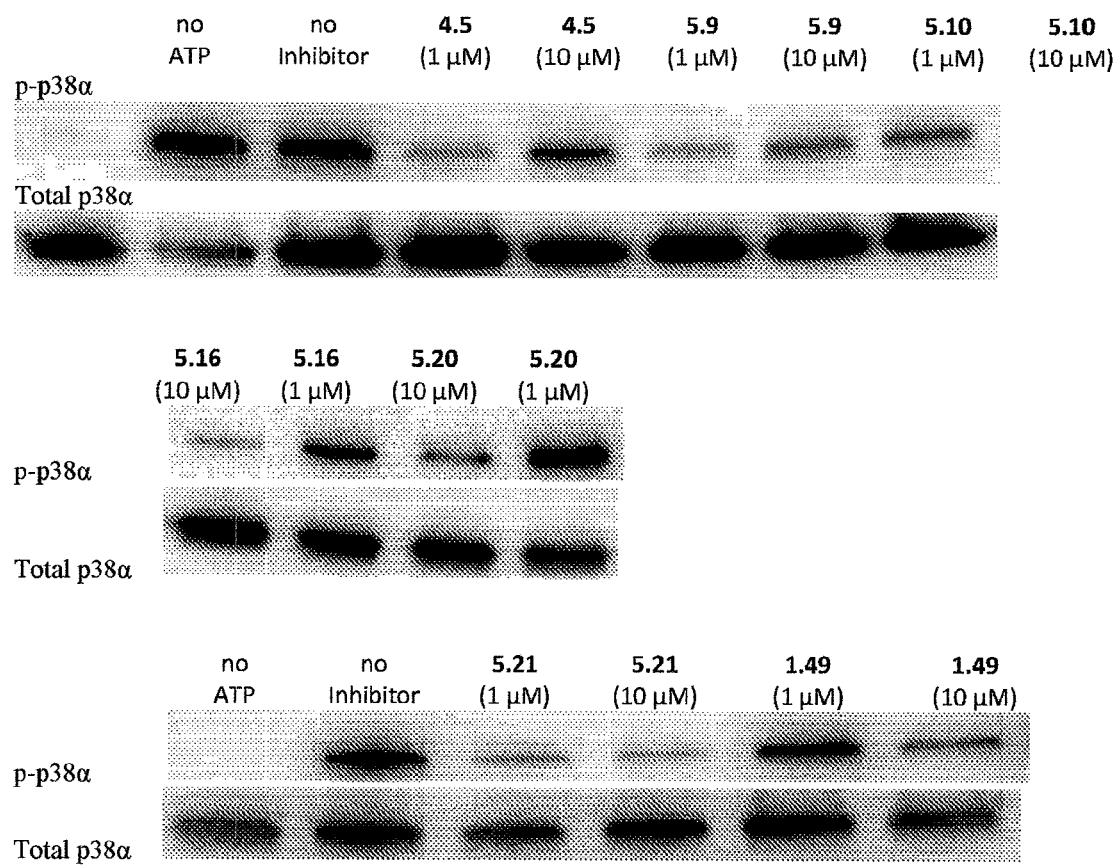
FIG. 13 is a series of western blots indicating the effects of select compounds on p38α MAPK activation (phosphorylation)

To assess whether the compounds of the present invention could also inhibit the activation of p38α MAPK a number of select compounds were tested in an in vitro activation assay following a published method. As discussed above, inactive non-phosphorylated p38α MAPK was pre-incubated with the test compounds at 10 and 1 μM concentration for 30 minutes before the addition of ATP and MKK6. Western blot analysis shows whether the compounds were able to inhibit p38α activation. FIG. 13 shows the western blots of compounds 4.5, 5.9, 5.10, 5.16, 5.20, 5.21 and RWJ67657 (1.49). The assay was analysed by immunoblotting using antibodies against pan p38 MAPK and phosphorylated p38α MAPK. All of the tested compounds showed inhibition of p38α MAPK activation at 10 μM concentration. Compound 5.21 shows significant inhibition, being able to prevent MKK6 activation of p38α MAPK at 1 μM concentration. This coincides with the binding assay data which shows that compound 5.21 was the strongest binder of the analogue series having a $K_i$ of 0.47 μM to inactive non-phosphorylated p38α MAPK.

The compounds of the first aspect, and particularly those having substitution at the 2-position ($R_1$ position) and hydrogen at the 3-position ($R_2$ position), have thereby been shown to be particularly efficacious in binding to the p38α MAPK enzyme and demonstrate good 'drug-like' characteristics in terms of their physicochemical characteristics which are further demonstrated in the experimental section.

EXPERIMENTAL

General Experimental

All chemical reagents were acquired from Sigma Aldrich, Fluka, Merck, Boron Molecular, and Matrix Scientific and were used without further purification. Flash chromatography was carried out using Scharlau silica gel 60, 0.06-0.20 mm (70-230 mesh ASTM). Melting points were determined using a Mettler Toledo MP50 melting point apparatus. NMR spectra were recorded on a 300 MHz Bruker Avance DPX 300 NMR spectrometer or a 400 MHz Bruker Avance Ultrashield Plus NMR spectrometer or a 600 MHz Varian Unity Inova NMR spectrometer. Chemical shifts (δ) were reported in parts per million (ppm) referenced to an internal standard of residual proteo-solvent ($^1$H NMR, $^{13}$C NMR): CDCl$_3$ (7.26, 77.16), CD$_3$OD (3.31, 49.00) or d$_6$-DMSO (2.50, 39.52). Multiplicity is quoted as app. (apparent), br. (broad), s (singlet), d (doublet), t (triplet), q (quartet), p (pentet) and m (multiplet). Coupling constants (J) are given in Hertz (Hz). Where possible overlapped non-equivalent $^{13}$C peaks were identified by $^{13}$C-$^1$H HSQC and HMBC NMR and are indicated with (2C) after the identified overlapped signal. Low resolution mass spectrometry (LRMS) analyses were performed using a Micromass Platform II single quadrupole mass spectrometer equipped with an atmospheric pressure (ESI/APCI) ion source. Sample management was facilitated by an Agilent 1100 series high performance liquid chromatography (HPLC) system using MassLynx version 3.5 software. High resolution mass spectrometry (HRMS) analyses were carried out on a Waters Micromass LCT Premier XE Orthogonal Acceleration time-of-flight (TOF) mass spectrometer coupled to an Alliance 2795 Separation Module using MassLynx version 4.1 software. Liquid chromatography mass spectrometry (LCMS) was performed on an Agilent 1200 Series Separation Module fitted with a 6120 quadropole detector and a Phenomenex® Luna C8(2) 100 Å (50×4.6 mm, internal diameter) 5 μm column. Samples were run in a gradient of 5-100% buffer B in buffer A (buffer A: 0.1% aqueous formic acid; buffer B: 80% acetonitrile, 19.9% water, 0.1% formic acid) over 4 minutes, followed by isocratic 100% buffer B for 3 minutes then a gradient of 100-0% buffer B over 3 minutes at a flow rate of 0.5 mL/min. Agilent Chemstation software (version B.04.01) managed the running and processing of samples. Analytical RP-HPLC was acquired on a Waters Millenium 2690 system fitted with a Phenomenex® Luna C8 100 Å (50×4.6 mm, internal diameter) 5 μm column with UV detection at 254 nm. Samples were run in a gradient of 20-100% buffer B in buffer A (buffer A: 0.1% aqueous trifluoroacetic acid; buffer B: 80% acetonitrile, 19.9% water, 0.1% trifluoroacetic acid) over 10 minutes, followed by isocratic 100% buffer B for 1 minute then a gradient of 100-20% buffer B over 1 minute followed by isocratic 20% buffer B for 10 minutes at a flow rate of 1.0 mL/minute. EmPowerPro managed the running and processing of samples. EmPowerPro managed the running and processing of samples. Microwave chemistry was performed using a Biotage Initiator Microwave Reactor according to manufacturer's instructions.

4-(2-(4-Fluorophenyl)thiophen-3-yl)pyridine (3.2)

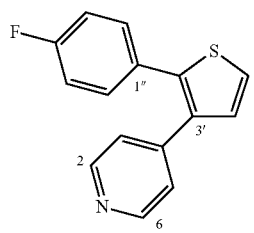 [SMILES: Fc1ccc(-c2sccc2-c2ccncc2)cc1]

To a solution of 2,3-dibromothiophene (2.38 mL, 20.7 mmol) in dimethylformamide (160 mL) was added 4-fluorophenylboronic acid (2.89 g, 20.7 mmol), sodium carbonate monohydrate (12.3 g, 99.2 mmol) and water (40 mL). The reaction mixture was bubbled with nitrogen for 15 minutes. Bis(triphenylphosphine)palladium(II) chloride (0.725 g, 1.03 mmol) was added and the reaction mixture was heated at 70° C. for 3 hours. Pyridine-4-boronic acid (3.81 g, 31.0 mmol) and bis(triphenylphosphine)palladium(II) chloride (0.725 g, 1.03 mmol) were added and the reaction mixture was heated at 120° C. for 16 hours. The reaction mixture was cooled to room temperature and passed through a plug of silica and washed with ethyl acetate (160 mL). The organic layer was washed with water (5×100 mL), then brine (50 mL), dried over magnesium sulfate and filtered. The organic layer was evaporated and the dimethylformamide removed by azeotrope with toluene to afford a yellow oil. The product was purified by column chromatography using a gradient elution (0-50% ethyl acetate/petroleum spirits) to afford a pale yellow solid. Recrystallisation in diethyl ether gave thiophene 3.2 (3.81 g, 71%) as a white powder. 3.2: $C_{15}H_{10}FNS$ ($M_r$=255.31); mp 95.8-97.6° C.; $^1H$ NMR (400 MHz, $CDCl_3$) δ (ppm) 8.51 (br. app. d, J=5.6 Hz, 2H), 7.37 (d, J=5.2 Hz, 1H), 7.28-7.23 (m, 2H), 7.18 (d, J=5.3 Hz, 1H), 7.16-7.15 (m, 2H), 7.04-6.98 (m, 2H); $^{13}C$ NMR (101 MHz, $CDCl_3$) δ (ppm) 162.3 (d, $^1J_{CF}$=248.5 Hz), 149.8, 143.6, 139.7, 135.1, 130.9 (d, $^3J_{CF}$=8.1 Hz), 129.33 (d, $^4J_{CF}$=3.4 Hz), 129.27, 125.0, 123.4, 115.6 (d, $^2J_{CF}$=21.7 Hz); ESI-HRMS-TOF calcd for $C_{15}H_{11}FNS^+$ (M+H)$^+$ 256.0591, found 256.0589; ESI-LCMS $R_t$=4.9 min, 256.1 (M+H)$^+$; RP-HPLC $R_t$=6.5 min, 99%.

4-(2-(4-Fluorophenyl)-4,5-diiodothiophen-3-yl)pyridine (3.3)

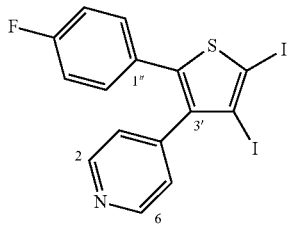 [SMILES: Fc1ccc(-c2sc(I)c(I)c2-c2ccncc2)cc1]

To a solution of compound 3.2 (0.861 g, 3.37 mmol) in acetic acid (18 mL) was added mercuric acetate (3.23 g, 10.1 mmol). The solution was heated at 70° C. for 16 hours. Concurrently, iodine (5.14 g, 20.2 mmol) and potassium iodide (3.36 g, 20.2 mmol) were dissolved in water (38 mL) over 16 hours in a separate round bottom flask. After 16 hours, the acetic acid mixture was concentrated in vacuo and poured into ice/water (100 mL). The resulting white precipitate was filtered and washed with water then diethyl ether to afford the mercuric acetate intermediate as a white powder. The intermediate was added to the potassium triiodide solution. Tetrahydrofuran (1 mL) was added to break the surface tension and the mixture was stirred at room temperature for 16 hours. Saturated sodium thiosulfate (100 mL) was added and the resulting yellow solid was filtered and washed with water (50 mL). The solid was dissolved in tetrahydrofuran/ethyl acetate (100 mL) and washed further with saturated sodium thiosulfate (3×50 mL). The organic extract was dried over magnesium sulfate, filtered and concentrated in vacuo to afford thiophene 3.3. Recrystallisation from tetrahydrofuran/ethanol (1:1) afforded compound 3.3 (1.39 g, 81%) as yellow crystals. 3.3: $C_{15}H_8FI_2NS$ ($M_r$=507.10); mp 212.8° C. (decomposition); $^1H$ NMR (400 MHz, $d_6$-DMSO) δ (ppm) 8.59-8.58 (m, 2H), 7.20-7.12 (m, 6H); $^{13}C$ NMR (101 MHz, $d_6$-DMSO) δ (ppm) 162.0 (d, $^1J_{CF}$=247.0 Hz), 149.7, 145.1, 145.0, 140.1, 130.9 (d, $^3J_{CF}$=8.5 Hz), 128.4 (d, $^4J_{CF}$=3.2 Hz), 125.5, 115.8 (d, $^2J_{CF}$=21.9 Hz), 101.8, 87.6; ESI-HRMS-TOF calcd for $C_{15}H_9FI_2NS^+$ (M+H)$^+$ 507.8524, found 507.8521; ESI-LCMS $R_t$=6.4 min, 507.9 (M+H)$^+$; RP-HPLC $R_t$=8.4 min, >99%.

(But-3-yn-1-yloxy)(tert-butyl)dimethylsilane (3.5)

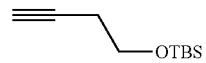

Compound 3.5 was synthesised using a similar procedure by Nadeau et al. To a solution of 3-butyn-1-ol (3.00 g, 42.8 mmol) in dichloromethane (60 mL) was added imidazole (7.28 g, 107 mmol) and cooled to 5° C. tert-Butyldimethylsilyl chloride (6.45 g, 42.8 mmol) was added and the reaction mixture was stirred at 25° C. for 16 hours. Dichloromethane (100 mL) was added and the mixture was washed with water (2×50 mL) and brine (50 mL). The organic layer was dried over magnesium sulfate, filtered and concentrated in vacuo to afford compound 3.5 (7.73 g, 98%) as a colourless oil. 3.5: $C_{10}H_{20}OSi$ ($M_r$=184.35); $^1H$ NMR (400 MHz, $CDCl_3$) δ (ppm) 3.74 (t, J=7.1 Hz, 2H), 2.40 (td, J=7.1, 2.7 Hz, 2H), 1.95 (t, J=2.7 Hz, 1H), 0.90 (s, 9H), 0.07 (s, 6H); $^{13}C$ NMR (101 MHz, $CDCl_3$) δ (ppm) 81.6, 69.4, 61.9, 26.0, 23.0, 18.4, −5.2. Does not ionise in ESI-MS. Nb. $^1H$ NMR was consistent with literature data.

4-(5-(4-((tert-Butyldimethylsilyl)oxy)but-1-yn-1-yl)-2-(4-fluorophenyl)-4-iodothiophen-3-yl)pyridine (3.6)

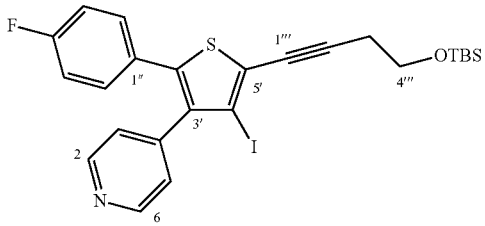 [SMILES: CC(C)(C)[Si](C)(C)OCCC#Cc1sc(-c2ccc(F)cc2)c(-c2ccncc2)c1I]

Negishi Coupling:

To a solution of alkyne 3.5 (2.06 mL, 9.97 mmol) in tetrahydrofuran (15 mL) was added dropwise n-butyllithium (1.2 M, 8.3 mL, 10 mmol) at 0° C. The reaction mixture was stirred for 15 minutes. Zinc chloride (1.63 g, 12.0 mmol) was added and the reaction mixture was stirred at 0° C. for 15 minutes, then allowed to warm to room temperature for 15 minutes, at which time the zinc had dissolved. Concurrently, compound 3.3 (1.23 g, 2.43 mmol) was dissolved in tetrahydrofuran (18 mL) and nitrogen was bubbled through the solution for 30 minutes. The metallated alkyne solution was added dropwise to the thiophene solution followed by addition of tetrakis(triphenylphosphine)palladium(0) (0.283 g, 0.245 mmol). The mixture was stirred at 25° C. for 70 hours. Saturated ammonium chloride (7.5 mL) was added and the mixture was stirred for 15 minutes. Ethyl acetate (150 mL) was added and the mixture was washed with saturated sodium carbonate (3×40 mL) and brine (3×40 mL). The organic layer was dried over magnesium sulfate, filtered and concentrated in vacuo. The product was purified by column chromatography using a gradient elution (0-50% ethyl acetate/petroleum spirits) to afford thiophene 3.6 as a pale yellow solid (1.27 g, 94%).

Sonogashira Coupling:

To a solution of compound 3.3 (1.30 g, 2.56 mmol) in tetrahydrofuran (13 mL) was added alkyne 3.5 (800 μL, 3.88 mmol), triphenylphosphine (0.010 g, 0.038 mmol), copper (I) iodide (0.027 g, 0.142 mmol), and bis(triphenyl-phosphine)palladium(II) dichloride (0.093 g, 0.132 mmol). The reaction mixture was bubbled with nitrogen for 15 minutes and heated at 120° C. for 2 hours. The reaction mixture was diluted with ethyl acetate (100 mL) and washed with water (3×50 mL) and brine (50 mL), dried over magnesium sulfate, filtered and concentrated in vacuo. The resulting oil was purified by column chromatography using a gradient elution (0-50% ethyl acetate/petroleum spirits) to afford compound 3.6 as a white solid. Trituration with petroleum spirits gave compound 3.6 (1.19 g, 82%) as a white powder. 3.6: $C_{25}H_{27}FINOSSi$ ($M_r$=563.54); mp 96.6-97.7° C.; $^1$H NMR (400 MHz, CDCl$_3$) δ (ppm) 8.60 (br. app. d, J=4.8 Hz, 2H, H2, H6), 7.13-7.11 (m, 2H), 7.10-7.05 (m, 2H), 6.94-6.89 (m, 2H), 3.87 (t, J=6.9 Hz, 2H), 2.73 (t, J=6.9 Hz, 2H), 0.92 (s, 9H, 0.11 (s, 6H); $^{13}$C NMR (101 MHz, CDCl$_3$) δ (ppm) 162.8 (d, $^1J_{CF}$=249.8 Hz), 150.1, 144.9, 140.1, 138.3, 130.9 (d, $^3J_{CF}$=8.3 Hz), 128.6 (d, $^4J_{CF}$=3.4 Hz), 125.7, 115.9 (d, $^2J_{CF}$=21.9 Hz), 96.9, 91.8, 75.7, 61.6, 26.1, 24.5, 18.5, −5.1; ESI-HRMS-TOF calcd for $C_{25}H_{28}FINOSSi^+$ (M+H)$^+$ 564.0684, found 564.0701; ESI-LCMS $R_t$=7.8 min, 564.1 (M+H)$^+$; RP-HPLC $R_t$=10.9 min, 97%.

General Method for Suzuki Coupling

To a solution of thiophene 3.6 (100 mg, 1.0 eq.) in tetrahydrofuran (3 mL) was added the boronic acid/pinacol ester (3.0 eq.) and sodium carbonate (1 M, 1 mL) in a 2-5 mL microwave vial. The reaction mixture was bubbled with nitrogen for 15 minutes. Bis(triphenylphosphine)palladium (II) dichloride (0.10 eq.) was added, the vial was capped and the mixture was heated at 100° C. for 90 minutes in the microwave. The mixture was extracted with diethyl ether and concentrated in vacuo. The product was purified by column chromatography.

Methyl 2-(2-(4-((tert-butyldimethylsilyl)oxy)but-1-yn-1-yl)-5-(4-fluorophenyl)-4-(pyridin-4-yl)thiophen-3-yl)benzoate (3.7)

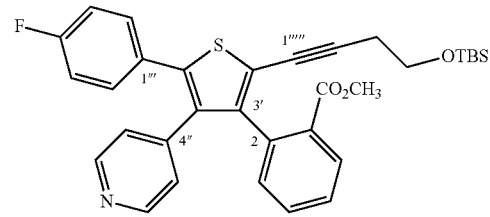 [SMILES: COC(=O)c1ccccc1-c1c(C#CCCO[Si](C)(C)C(C)(C)C)sc(-c2ccc(F)cc2)c1-c1ccncc1]

Compound 3.7 was synthesised using the general method for Suzuki coupling from thiophene 3.6 (67 mg, 0.12 mmol) and 2-(methoxycarbonyl)phenylboronic acid (65 mg, 0.36 mmol). The reaction time and temperature was changed to heating in the microwave at 100° C. for 1 hour, followed by 110° C. for a further hour. Purification using gradient column chromatography (0-50% ethyl acetate/petroleum spirits) gave compound 3.7 (14 mg, 21%) as a yellow oil. 3.7: $C_{33}H_{34}FNO_3SSi$ ($M_r$=571.78); $^1$H NMR (400 MHz, CDCl$_3$) δ (ppm) 8.31 (br. app. d, J=4.7 Hz, 2H), 7.84-7.82 (m, 1H), 7.39 (app. td, J=7.5, 1.6 Hz, 1H), 7.34 (app. td, J=7.6, 1.5 Hz, 1H), 7.19-7.14 (m, 2H), 7.10-7.08 (m, 1H), 6.97-6.91 (m, 2H), 6.83-6.81 (m, 2H), 3.69 (s, 3H), 3.62 (app. td, J=7.3, 3.9 Hz, 2H), 2.49 (t, J=7.2 Hz, 2H), 0.87 (s, 9H), 0.03 (s, 6H); $^{13}$C NMR (101 MHz, CDCl$_3$) δ (ppm) 167.4, 162.6 (d, $^1J_{CF}$=248.9 Hz), 149.6, 145.5, 143.9, 139.1, 136.3, 134.9, 132.0, 131.6, 131.4, 131.3 (d, $^3J_{CF}$=8.2 Hz), 130.2, 129.3 (d, $^4J_{CF}$=3.4 Hz), 127.9, 125.5, 120.1, 115.8 (d, $^2J_{CF}$=21.7 Hz), 94.7, 73.8, 61.6, 52.3, 26.0, 24.2, 18.4, −5.2; ESI-HRMS-TOF calcd for $C_{33}H_{35}FNO_3SSi^+$ (M+H)$^+$ 572.2086, found 572.2111; ESI-LCMS $R_t$=7.4 min, 572.2 (M+H)$^+$; RP-HPLC $R_t$=11.1 min, 95%.

Methyl 3-(2-(4-((tert-butyldimethylsilyl)oxy)but-1-yn-1-yl)-5-(4-fluorophenyl)-4-(pyridin-4-yl)thiophen-3-yl)benzoate (3.8)

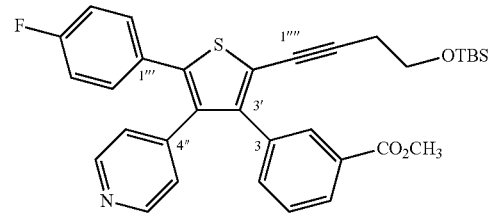 [SMILES: COC(=O)c1cccc(-c2c(C#CCCO[Si](C)(C)C(C)(C)C)sc(-c3ccc(F)cc3)c2-c2ccncc2)c1]

Compound 3.8 was synthesised using the general method for Suzuki coupling from thiophene 3.6 (250 mg, 0.444 mmol) and 3-(methoxycarbonyl)phenylboronic acid (240 mg, 1.33 mmol). Purification using gradient column chromatography (20-50% ethyl acetate/petroleum spirits) gave compound 3.8 (226 mg, 89%) as a yellow solid. 3.8: $C_{33}H_{34}FNO_3SSi$ ($M_r$=571.78); $^1$H NMR (400 MHz, CDCl$_3$) δ (ppm) 8.38-8.36 (m, 2H), 7.96-7.95 (m, 1H), 7.94-7.91 (m, 1H), 7.29 (app. td, J=7.7, 0.5 Hz, 1H), 7.23-7.21 (m, 1H), 7.15-7.10 (m, 2H), 6.98-6.92 (m, 2H), 6.83-6.82 (m, 2H), 3.87 (s, 3H), 3.70 (t, J=7.1 Hz, 2H), 2.56 (t, J=7.1 Hz, 2H), 0.87 (s, 9H), 0.04 (s, 6H); $^{13}$C NMR (101 MHz, CDCl$_3$) δ (ppm) 166.7, 162.7 (d, $^1J_{CF}$=249.3 Hz), 149.7, 144.1, 143.8, 139.9, 135.1, 134.7, 134.3, 131.4, 131.2 (d, $^3J_{CF}$=8.2 Hz), 130.1, 129.0 (d, $^4J_{CF}$=3.4 Hz), 128.7, 128.1, 125.7, 121.1, 115.9 (d, $^2J_{CF}$=21.8 Hz), 94.9, 74.0, 61.6, 52.2, 25.9, 24.3, 18.3, −5.2; ESI-HRMS-TOF calcd for $C_{33}H_{35}FNO_3SSi^+$ (M+H)$^+$ 572.2086, found 572.2103; ESI-LCMS $R_t$=7.6 min, 572.3 (M+H)$^+$; RP-HPLC $R_t$=10.9 min, 95%.

Methyl 4-(2-(4-(((tert-butyldimethylsilyl)oxy)but-1-yn-1-yl)-5-(4-fluorophenyl)-4-(pyridin-4-yl)thiophen-3-yl)benzoate (3.9)

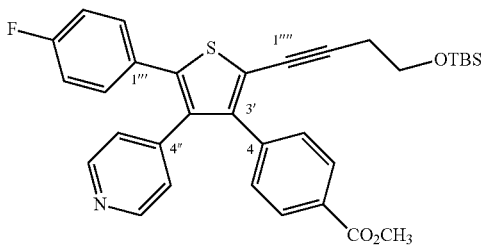 [SMILES: COC(=O)c1ccc(-c2c(C#CCCO[Si](C)(C)C(C)(C)C)sc(-c3ccc(F)cc3)c2-c2ccncc2)cc1]

Compound 3.9 was synthesised using the general method for Suzuki coupling from thiophene 3.6 (295 mg, 0.523 mmol) and 4-(methoxycarbonyl)phenylboronic acid (290 mg, 1.61 mmol). Purification using gradient column chromatography (0-50% ethyl acetate/petroleum spirits) gave compound 3.9 (299 mg, quant.) as a yellow solid. 3.9: $C_{33}H_{34}FNO_3SSi$ ($M_r$=571.78); $^1$H NMR (400 MHz, CDCl$_3$) δ (ppm) 8.38 (br. app. d, J=4.8 Hz, 2H), 7.94-7.91 (m, 2H), 7.23-7.20 (m, 2H), 7.15-7.10 (m, 2H), 7.00-6.93 (m, 2H), 6.85-6.83 (m, 2H), 3.91 (s, 3H), 3.71 (t, J=6.9 Hz, 2H), 2.57 (t, J=6.9 Hz, 2H), 0.88 (s, 9H), 0.05 (s, 6H); $^{13}$C NMR (101 MHz, CDCl$_3$) δ (ppm) 166.9, 162.8 (d, $^1J_{CF}$=249.4 Hz), 149.8, 144.1, 143.7, 140.2, 139.6, 134.7, 131.3 (d, $^3J_{CF}$=8.2 Hz), 130.1, 129.4, 129.2, 129.0 (d, $^4J_{CF}$=3.5 Hz), 125.7, 121.4, 116.0 (d, $^2J_{CF}$=21.8 Hz), 95.2, 73.9, 61.6, 52.2, 26.0, 24.4, 18.4, −5.2; ESI-LRMS 572.5 (M+H)$^+$; RP-HPLC $R_t$=10.1 min, 95%.

(3-(2-(4-((tert-Butyldimethylsilyl)oxy)but-1-yn-1-yl)-5-(4-fluorophenyl)-4-(pyridin-4-yl)thiophen-3-yl)phenyl)methanol (3.10)

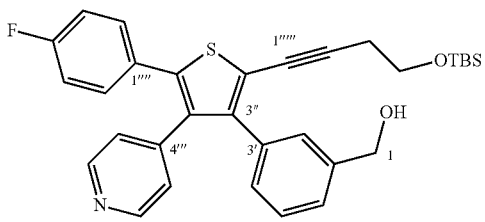 [SMILES: CC(C)(C)[Si](C)(C)OCCC#Cc1sc(-c2ccc(F)cc2)c(-c2ccncc2)c1-c1cccc(CO)c1]

Compound 3.10 was synthesised using the general method for Suzuki coupling from thiophene 3.6 (200 mg, 0.355 mmol) and 3-(hydroxymethyl)phenylboronic acid (162 mg, 1.06 mmol). Purification using gradient column chromatography (10-50% ethyl acetate/petroleum spirits) gave compound 3.10 (160 mg, 83%) as a yellow solid. 3.10: $C_{32}H_{34}FNO_2SSi$ ($M_r$=543.77); $^1$H NMR (400 MHz, CDCl$_3$) δ (ppm) 8.36-8.35 (m, 2H), 7.26-7.19 (m, 3H), 7.15-7.10 (m, 2H), 7.02 (app. dt, J=7.0, 1.8 Hz, 1H), 6.98-6.92 (m, 2H), 6.84-6.82 (m, 2H), 4.58 (s, 2H), 3.73 (t, J=6.9 Hz, 2H), 2.57 (t, J=6.9 Hz, 2H), 0.88 (s, 9H), 0.06 (s, 6H); $^{13}$C NMR (101 MHz, CDCl$_3$) δ (ppm) 162.6 (d, $^1J_{CF}$=248.6 Hz), 149.4, 145.1, 144.3, 141.3, 139.8, 134.9, 134.7, 131.3 (d, $^3J_{CF}$=7.8 Hz), 129.1, 128.7, 128.1, 126.1, 125.8, 120.6, 115.8 (d, $^2J_{CF}$=21.8 Hz), 94.4, 74.3, 64.8, 61.6, 26.0, 24.3, 18.4, −5.2; ESI-HRMS-TOF calcd for $C_{32}H_{35}FNO_2SSi^+$ (M+H)$^+$ 544.2136, found 544.2153; ESI-LCMS $R_t$=6.9 min, 544.2 (M+H)$^+$; RP-HPLC $R_t$=10.6 min, 98%.

4-(5-(4-((tert-Butyldimethysily)oxy)but-1-yn-1-yl)-4-(4-(((tert-butyldimethyl-silyl)oxy)methyl)phenyl)-2-(4-fluorophenyl)thiophen-3-yl)pyridine (3.11)

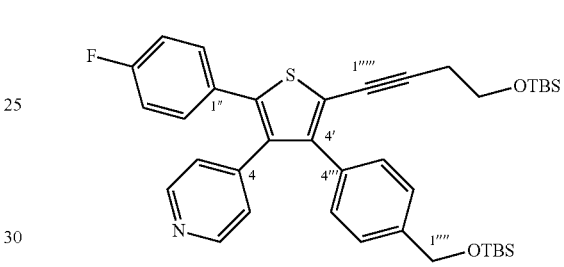

Compound 3.11 was synthesised using the general method for Suzuki coupling from thiophene 3.6 (110 mg, 0.195 mmol) and (4-(((tert-butyldimethylsilyl)oxy)methyl)phenyl)boronic acid (160 mg, 0.601 mmol). Purification using gradient column chromatography (0-40% ethyl acetate/petroleum spirits) gave thiophene 3.11 (113 mg, 88%) as a yellow solid. 3.11: $C_{38}H_{48}FNO_2SSi_2$ ($M_r$=658.04); $^1$H NMR (400 MHz, CDCl$_3$) δ (ppm) 8.36-8.35 (m, 2H), 7.19 (br. app. d, J=8.5 Hz, 2H), 7.15-7.08 (m, 4H), 6.97-6.91 (m, 2H), 6.82-6.81 (m, 2H), 4.72 (s, 2H), 3.72 (t, J=7.0 Hz, 2H), 2.57 (t, J=7.0 Hz, 2H), 0.94 (s, 9H), 0.90 (s, 9H), 0.09 (s, 6H), 0.06 (s, 6H); $^{13}$C NMR (101 MHz, CDCl$_3$) δ (ppm) 162.7 (d, $^1J_{CF}$=249.0 Hz), 149.8, 145.2, 144.1, 140.8, 139.7, 135.0, 133.4, 131.3 (d, $^3J_{CF}$=8.2 Hz), 130.0, 129.3 (d, $^4J_{CF}$=3.4 Hz), 125.8, 125.7, 120.5, 115.8 (d, $^2J_{CF}$=21.7 Hz), 94.3, 74.4, 64.9, 61.7, 26.1, 26.0, 24.4, 18.6, 18.5, −5.08, −5.13; ESI-LRMS 658.5 (M+H)$^+$; ESI-LCMS $R_t$=10.2 min, 658.3 (M+H)$^+$; RP-HPLC $R_t$=14.1 min, 99%.

4-(2-(4-((tert-Butyldimethylsilyl)oxy)but-1-yn-1-yl)-5-(4-fluorophenyl)-4-(pyridin-4-yl)thiophen-3-yl)benzamide (3.12)

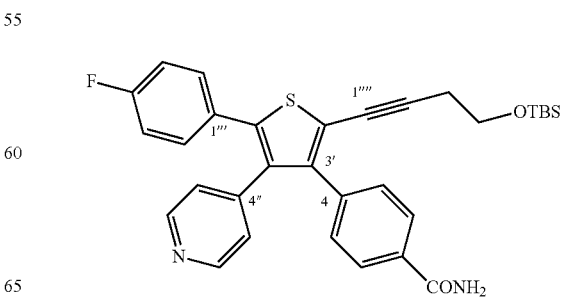

Compound 3.12 was synthesised using the general method for Suzuki coupling from thiophene 3.6 (87 mg, 0.15 mmol) and 4-aminocarbonylphenylboronic acid (76 mg, 0.46 mmol). Purification using gradient column chromatography (50-100% ethyl acetate/petroleum spirits) gave thiophene 3.12 (69 mg, 80%) as a yellow solid. 3.12: $C_{32}H_{33}FN_2O_2SSi$ ($M_r$=556.77); $^1H$ NMR (300 MHz, CDCl$_3$) δ (ppm) 8.39-8.37 (br. app. d, J=4.2 Hz, 2H), 7.69 (app. d, J=7.7 Hz, 2H), 7.23 (app. d, J=7.7 Hz, 2H), 7.14-7.10 (m, 2H), 6.98-6.93 (m, 2H), 6.81 (br. app. d, J=4.4 Hz, 2H), 6.04 (br. s, 1H), 5.70 (br. s, 1H), 3.72 (t, J=6.7 Hz, 2H), 2.57 (t, J=6.7 Hz, 2H), 0.89 (s, 9H), 0.06 (s, 6H); $^{13}C$ NMR (76 MHz, CDCl$_3$) δ (ppm) 169.1, 162.7 (d, $^1J_{CF}$=249.5 Hz), 149.9, 143.9, 143.7, 140.2, 138.7, 134.7, 132.3, 131.3 (d, $^3J_{CF}$=8.1 Hz), 130.4, 128.9 (d, $^4J_{CF}$=3.2 Hz), 127.2, 125.7, 121.4, 116.0 (d, $^2J_{CF}$=21.8 Hz), 95.2, 73.9, 61.6, 26.0, 24.4, 18.5, −5.1; ESI-LRMS 557.1 (M+H)$^+$; ESI-LCMS R$_t$=9.2 min, 557.2 (M+H)$^+$; RP-HPLC R$_t$=10.8 min, 83%.

3-(2-(4-((tert-Butyldimethylsilyl)oxy)but-1-yn-1-yl)-5-(4-fluorophenyl)-4-(pyridin-4-yl)thiophen-3-yl)aniline (3.13)

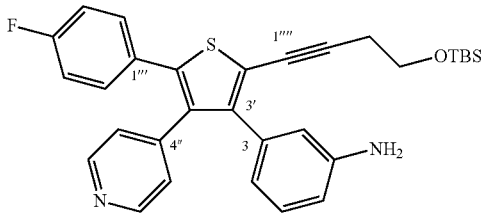 [SMILES: CC(C)(C)[Si](C)(C)OCCC#Cc1sc(-c2ccc(F)cc2)c(-c2ccncc2)c1-c1cccc(N)c1]

Compound 3.13 was synthesised using the general method for Suzuki from thiophene 3.6 (598 mg, 1.06 mmol) and 3-aminophenylboronic acid (430 mg, 3.14 mmol). Purification using column chromatography in ethyl acetate gave compound 3.13 (403 mg, 72%) as a yellow solid. 3.13: $C_{31}H_{33}FN_2OSSi$ ($M_r$=528.76); $^1H$ NMR (400 MHz, CDCl$_3$) δ (ppm) 8.37-8.36 (m, 2H), 7.14-7.09 (m, 2H), 7.00 (app. t, J=7.8 Hz, 1H), 6.97-6.91 (m, 2H), 6.85-6.83 (m, 2H), 6.56 (ddd, J=8.0, 2.4, 1.0 Hz, 1H), 6.50-6.49 (m, 1H), 6.48-6.45 (m, 1H), 3.74 (t, J=7.0 Hz, 2H), 3.56 (br. s, 2H), 2.58 (t, J=7.0 Hz, 2H), 0.90 (s, 9H), 0.07 (s, 6H); $^{13}C$ NMR (101 MHz, CDCl$_3$) δ (ppm) 162.6 (d, $^1J_{CF}$=248.9 Hz), 149.6, 146.1, 145.5, 144.0, 139.6, 135.8, 134.9, 131.3 (d, $^3J_{CF}$=8.2 Hz), 129.3 (d, $^4J_{CF}$=3.4 Hz), 128.9, 125.7, 120.6, 120.3, 116.8, 115.8 (d, $^2J_{CF}$=21.7 Hz), 114.4, 94.3, 74.4, 61.7, 26.0, 24.4, 18.4, −5.1; ESI-LRMS 529.3 (M+H)$^+$; ESI-LCMS R$_t$=9.1 min, 529.3 (M+H)$^+$.

4-(2-(4-((tert-Butyldimethylsilyl)oxy)but-1-yn-1-yl)-5-(4-fluorophenyl)-4-(pyridin-4-yl)thiophen-3-yl)aniline (3.14)

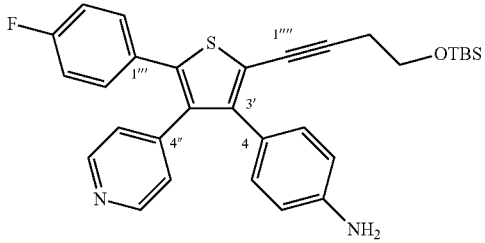

Compound 3.14 was synthesised using the general method for Suzuki from thiophene 3.6 (335 mg, 0.594 mmol) and 4-aminophenylboronic acid pinacol ester (392 mg, 1.79 mmol). Purification using gradient column chromatography (50-100% ethyl acetate/petroleum spirits) gave thiophene 3.14 (124 mg, 39%) as a beige solid. 3.14: $C_{31}H_{33}FN_2OSSi$ ($M_r$=528.76); $^1H$ NMR (400 MHz, CDCl$_3$) δ (ppm) 8.37-8.36 (m, 2H), 7.13-7.08 (m, 2H), 6.95-6.89 (m, 4H), 6.85-6.83 (m, 2H), 6.54-6.51 (m, 2H), 3.74 (t, J=7.0 Hz, 2H), 3.70 (br. s, 2H), 2.58 (t, J=7.0 Hz, 2H), 0.90 (s, 9H), 0.07 (s, 6H); $^{13}C$ NMR (101 MHz, CDCl$_3$) δ (ppm) 162.6 (d, $^1J_{CF}$=248.7 Hz), 149.6, 145.8, 145.5, 144.4, 139.5, 134.9, 131.3 (d, $^3J_{CF}$=8.2 Hz), 131.1, 129.4 (d, $^4J_{CF}$=3.4 Hz), 125.9, 124.8, 119.4, 115.8 (d, $^2J_{CF}$=21.7 Hz), 114.6, 93.9, 74.7, 61.8, 26.0, 24.4, 18.4, −5.1; ESI-LRMS 529.4 (M+H)$^+$; ESI-LCMS R$_t$=6.4 min, 529.2 (M+H)$^+$.

N-(3-(2-(4-((tert-butyldimethylsilyl)oxy)but-1-yn-1-yl)-5-(4-fluorophenyl)-4-(pyridin-4-yl)thiophen-3-yl)phenyl)acetamide (3.15)

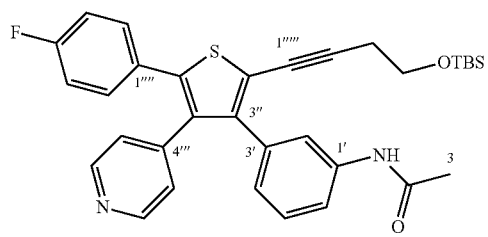 [SMILES: CC(=O)Nc1cccc(-c2c(C#CCCO[Si](C)(C)C(C)(C)C)sc(-c3ccc(F)cc3)c2-c2ccncc2)c1]

To a solution of thiophene 3.13 (82 mg, 0.16 mmol) in pyridine (2 mL) was added acetic anhydride (0.41 mL, 4.3 mmol). The reaction mixture was stirred at room temperature for 3 hours. Water was added and the precipitate was filtered and washed with water. The crude product was dried under vacuum to give compound 3.15 (73 mg, 82%) as a pale yellow powder. 3.15: $C_{33}H_{35}FN_2O_2SSi$ ($M_r$=570.80); $^1H$ NMR (300 MHz, CDCl$_3$) ((ppm) 8.38-8.36 (m, 2H), 7.51-7.49 (m, 1H), 7.26-7.05 (m, 5H), 6.98-6.90 (m, 2H), 6.87-6.81 (m, 3H), 3.73 (t, J=6.8 Hz, 2H), 2.58 (t, J=6.6 Hz, 2H), 2.13 (s, 3H), 0.89 (s, 9H), 0.07 (s, 6H); $^{13}C$ NMR (76 MHz, CDCl$_3$) ((ppm) 168.5, 162.6 (d, $^1J_{CF}$=249.6 Hz), 149.5, 144.7, 144.0, 139.8, 138.0, 135.5, 134.6, 131.3 (d, $^3J_{CF}$=7.9 Hz), 129.1, 128.6, 125.9, 125.8, 121.2, 120.8, 119.0, 115.8 (d, $^2J_{CF}$=21.8 Hz), 94.6, 74.2, 61.6, 26.0, 24.6, 24.3, 18.4, −5.1; ESI-LRMS 572.0 (M+H)$^+$; ESI-LCMS R$_t$=7.0 min, 571.3 (M+H)$^+$; RP-HPLC R$_t$=9.5 min, 93%.

N-(4-(2-(4-((tert-butyldimethylsilyl)oxy)but-1-yn-1-yl)-5-(4-fluorophenyl)-4-(pyridin-4-yl)thiophen-3-yl)phenyl)acetamide (3.16)

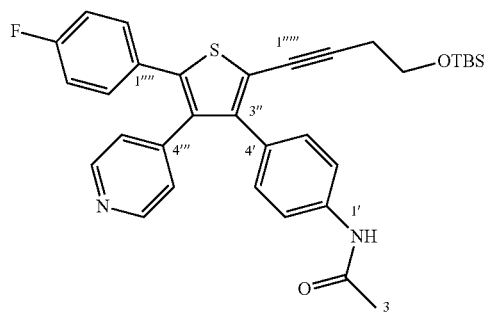 [SMILES: CC(=O)Nc1ccc(-c2c(C#CCCO[Si](C)(C)C(C)(C)C)sc(-c3ccc(F)cc3)c2-c2ccncc2)cc1]

Compound 3.16 was synthesised using the general method for Suzuki from thiophene 3.6 (100 mg, 0.177 mmol) and 4-acetamidophenylboronic acid pinacol ester (140 mg, 0.536 mmol). Purification using column chromatography in 5% methanol/dichloromethane gave compound 3.16 (90 mg, 89%) as a yellow solid. 3.16: $C_{33}H_{35}FN_2O_2SSi$ ($M_r$=570.79); $^1$H NMR (400 MHz, CDCl$_3$) δ (ppm) 8.35 (app. d, J=5.7 Hz, 2H), 8.06 (br. s, 1H), 7.40 (app. d, J=8.5 Hz, 2H), 7.14-7.09 (m, 2H), 7.06 (app. d, J=8.5 Hz, 2H), 6.96-6.91 (m, 2H), 6.83-6.82 (m, 2H), 3.72 (t, J=6.9 Hz, 2H), 2.57 (t, J=6.9 Hz, 2H), 2.15 (s, 3H), 0.89 (s, 9H), 0.06 (s, 6H); $^{13}$C NMR (101 MHz, CDCl$_3$) δ (ppm) 168.6, 162.6 (d, $^1J_{CF}$=249.1 Hz), 149.6, 144.6, 144.5, 139.8, 137.7, 134.7, 131.3 (d, $^3J_{CF}$=8.2 Hz), 130.7, 130.4, 129.2 (d, $^4J_{CF}$=3.4 Hz), 125.9, 120.4, 119.0, 115.9 (d, $^2J_{CF}$=21.8 Hz), 94.6, 74.2, 61.7, 26.0, 24.7, 24.4, 18.4, −5.1; ESI-LRMS 571.5 (M+H)$^+$; ESI-LCMS $R_t$=7.1 min, 571.3 (M+H)$^+$; RP-HPLC 9.4 min, 95%.

N-(3-(2-(4-((tert-butyldimethylsilyl)oxy)but-1-yn-1-yl)-5-(4-fluorophenyl)-4-(pyridin-4-yl)thiophen-3-yl)phenyl)benzamide (3.17)

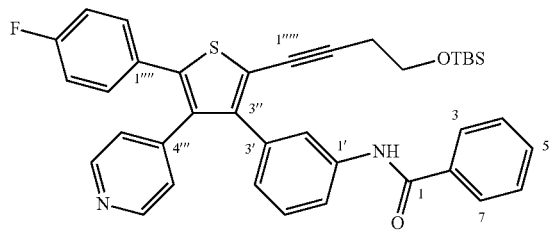 [SMILES: CC(C)(C)[Si](C)(C)OCCC#Cc1sc(-c2ccc(F)cc2)c(-c2ccncc2)c1-c1cccc(NC(=O)c2ccccc2)c1]

To a solution of thiophene 3.13 (100 mg, 0.189 mmol) in ethyl acetate (3 mL) was added triethylamine (28 µL, 0.20 mmol). Benzoyl chloride (23 µL, 0.20 mmol) was added to the reaction mixture at 0° C. The reaction mixture was stirred at room temperature for 4 hours. Ethyl acetate (20 mL) was added and the organic extract was washed with water (3×10 mL), brine (10 mL), dried over magnesium sulfate, filtered and concentrated in vacuo. Recrystallisation from methanol gave compound 3.17 (105 mg, 88%) as pale pink crystals. 3.17: $C_{38}H_{37}FN_2O_2SSi$ ($M_r$=632.87); mp 195.3-196.8° C.; $^1$H NMR (400 MHz, CDCl$_3$) δ (ppm) 8.39-8.37 (m, 2H), 7.84-7.81 (m, 2H), 7.67 (br. s, 1H), 7.61-7.44 (m, 5H), 7.26-7.22 (m, 1H), 7.16-7.11 (m, 2H), 7.00-6.93 (m, 2H), 6.89-6.86 (m, 3H), 3.73 (t, J=7.0 Hz, 2H), 2.59 (t, J=7.0 Hz, 2H), 0.87 (s, 9H), 0.04 (s, 6H); $^{13}$C NMR (101 MHz, CDCl$_3$) δ (ppm) 165.8, 162.6 (d, $^1J_{CF}$=249.0 Hz), 149.7, 144.7, 143.9, 139.7, 138.0, 135.8, 135.1, 134.8, 131.9, 131.3 (d, $^3J_{CF}$=8.2 Hz), 129.2 (d, $^4J_{CF}$=3.4 Hz), 128.8, 128.7, 127.2, 126.3, 125.7, 121.7, 120.9, 119.4, 115.8 (d, $^2J_{CF}$=21.8 Hz), 94.7, 74.2, 61.7, 26.0, 24.4, 18.4, −5.2; ESI-HRMS-TOF calcd for $C_3H_3FN_2O_2SSi^+$ (M+H)$^+$ 633.2402, found 633.2404; ESI-LCMS $R_t$=7.2 min, 633.3 (M+H)$^+$; RP-HPLC $R_t$=10.8 min, 98%.

N-(4-(2-(4-((tert-butyldimethylsilyl)oxy)but-1-yn-1-yl)-5-(4-fluorophenyl)-4-(pyridin-4-yl)thiophen-3-yl)phenyl)benzamide (3.18)

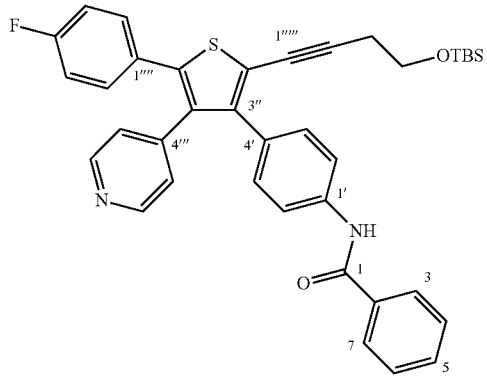 [SMILES: CC(C)(C)[Si](C)(C)OCCC#Cc1sc(-c2ccc(F)cc2)c(-c2ccncc2)c1-c1ccc(NC(=O)c2ccccc2)cc1]

To a solution of thiophene 3.14 (150 mg, 0.284 mmol) in ethyl acetate (6 mL) was added triethylamine (42 µL, 0.30 mmol). Benzoyl chloride (35 µL, 0.30 mmol) was added to the reaction mixture at 0° C. The reaction mixture was stirred at room temperature for 4 hours. Ethyl acetate (30 mL) was added and the organic extract was washed with water (3×15 mL), brine (15 mL), dried over magnesium sulfate, filtered and concentrated in vacuo. Recrystallisation from methanol/water (9:1) gave compound 3.18 (162 mg, 90%) as yellow crystals. 3.18: $C_{38}H_{37}FN_2O_2SSi$ ($M_r$=632.87); mp 168.9-169.6° C.; $^1$H NMR (400 MHz, CDCl$_3$) δ (ppm) 8.40-8.38 (m, 2H), 7.87-7.84 (m, 2H), 7.76 (br. s, 1H), 7.59-7.48 (m, 5H), 7.17-7.10 (m, 4H), 6.98-6.92 (m, 2H), 6.86-6.85 (m, 2H), 3.74 (t, J=7.0 Hz, 2H), 2.59 (t, J=7.0 Hz, 2H), 0.90 (s, 9H), 0.07 (s, 6H); $^{13}$C NMR (101 MHz, CDCl$_3$) δ (ppm) 166.0, 162.6 (d, $^1J_{CF}$=249.1 Hz), 149.7, 144.6, 144.1, 139.8, 137.6, 135.1, 134.8, 131.9, 131.3 (d, $^3J_{CF}$=8.2 Hz), 130.8, 129.2 (d, $^4J_{CF}$=3.3 Hz), 128.8, 127.2, 125.8, 120.5, 119.5, 115.8 (d, $^2J_{CF}$=21.8 Hz), 94.6, 74.3, 61.7, 26.0, 24.4, 18.4, −5.1; ESI-HRMS-TOF calcd for $C_{38}H_{38}FN_2O_2SSi^+$ (M+H)$^+$ 633.2402, found 633.2409; ESI-LCMS $R_t$=7.2 min, 633.3 (M+H)$^+$; RP-HPLC $R_t$=12.1 min, 97%.

N-(4-(2-(4-((tert-butyldimethylsilyl)oxy)but-1-yn-1-yl)-5-(4-fluorophenyl)-4-(pyridin-4-yl)thiophen-3-yphen-3-yl)phenyl)-4-methyenylbenzenesulfonamide (3.19)

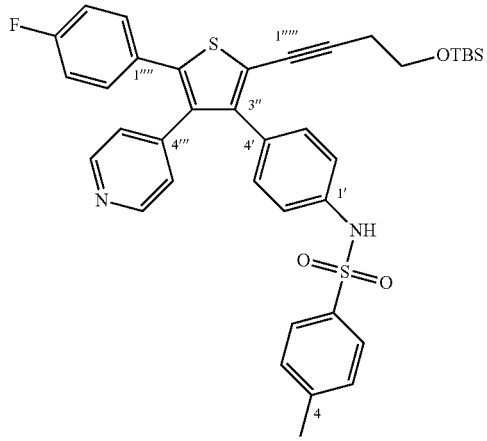 [SMILES: Cc1ccc(S(=O)(=O)Nc2ccc(-c3c(C#CCCO[Si](C)(C)C(C)(C)C)sc(-c4ccc(F)cc4)c3-c3ccncc3)cc2)cc1]

To a solution of thiophene 3.14 (100 mg, 0.189 mmol) in dichloromethane (5 mL) was added pyridine (137 μL, 1.70 mmol) and p-toluenesulfonyl chloride (59 mg, 0.31 mmol). The reaction mixture was stirred at room temperature for 20 hours. Aqueous hydrochloric acid (2.7 M, 20 mL) was added. The compound was extracted with dichloromethane (3×20 mL). The organic fractions were dried over magnesium sulfate, filtered and concentrated in vacuo. Purification by gradient column chromatography (0-50% ethyl acetate/petroleum spirits) gave thiophene 3.19 (119 mg, 92%) as a beige solid. 3.19: $C_{38}H_{39}FN_2O_3S_2Si$ ($M_r$=682.94); $^1H$ NMR (300 MHz, $CDCl_3$) δ (ppm) 8.33 (app. d, J=4.0 Hz, 2H), 7.64 (app. d, J=7.5 Hz, 2H), 7.59 (br. s, 1H), 7.24 (app. d, J=7.8 Hz, 2H), 7.12-7.08 (m, 2H), 7.00-6.92 (m, 6H), 6.76 (app. d, J=4.4 Hz, 2H), 3.72 (t, J=6.7 Hz, 2H), 2.56 (t, J=6.6 Hz, 2H), 2.41 (s, 3H), 0.90 (s, 9H), 0.07 (s, 6H); $^{13}C$ NMR (76 MHz, $CDCl_3$) δ (ppm) 162.7 (d, $^1J_{CF}$=249.2 Hz), 149.5, 144.2, 144.1, 144.0, 140.0, 136.4, 136.2, 134.6, 131.5, 131.3 (d, $^3J_{CF}$=8.1 Hz), 131.1, 129.7, 129.0 (d, $^4J_{CF}$=2.8 Hz), 127.4, 125.8, 120.7, 120.6, 115.9 (d, $^2J_{CF}$=21.7 Hz), 94.6, 74.1, 61.6, 26.0, 24.4, 21.7, 18.4, −5.1; ESI-LCMS $R_t$=7.3 min, 683.3 (M+H)$^+$; RP-HPLC $R_t$=9.9 min, 95%.

3-(2-(4-((tert-Butyldimethylsilyl)oxy)but-1-yn-1-yl)-5-(4-fluorophenyl)-4-(pyridin-4-yl)thiophen-3-yl)benzonitrile (3.20)

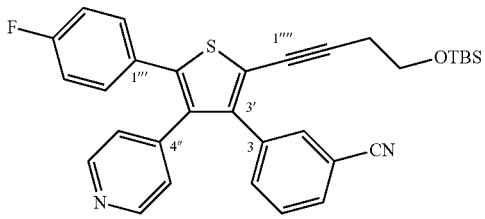 [SMILES: CC(C)(C)[Si](C)(C)OCCC#Cc1sc(-c2ccc(F)cc2)c(-c2ccncc2)c1-c1cccc(C#N)c1]

Compound 3.20 was synthesised using the general method for Suzuki coupling from thiophene 3.6 (154 mg, 0.273 mmol) and 3-cyanophenylboronic acid (119 mg, 0.810 mmol). Purification using gradient column chromatography (10-50% ethyl acetate/petroleum spirits) gave thiophene 3.20 (130 mg, 88%) as a yellow solid. 3.20: $C_{32}H_{31}FN_2OSSi$ ($M_r$=538.76); $^1H$ NMR (300 MHz, $CDCl_3$) δ (ppm) 8.42-8.40 (m, 2H), 7.60 (br. s, 1H), 7.58-7.52 (m, 1H), 7.32 (app. t, J=7.7 Hz, 1H), 7.26-7.21 (m, 1H), 7.15-7.10 (m, 2H), 6.99-6.94 (m, 2H), 6.82-6.80 (m, 2H), 3.73 (t, J=6.7 Hz, 2H), 2.59 (t, J=6.8 Hz, 2H), 0.88 (s, 9H), 0.06 (s, 6H); $^{13}C$ NMR (76 MHz, $CDCl_3$) δ (ppm) 162.8 (d, $^1J_{CF}$=249.6 Hz), 150.0, 143.3, 142.5, 140.4, 136.2, 134.4, 133.6, 131.3 (d, $^3J_{CF}$=8.4 Hz), 131.2, 129.0, 128.7 (d, $^4J_{CF}$=3.1 Hz), 125.6, 121.8, 118.6, 116.0 (d, $^2J_{CF}$=21.8 Hz), 112.4, 95.7, 73.6, 61.5, 26.0, 24.3, 18.4, −5.2; ESI-LRMS 538.9 (M+H)$^+$; ESI-LCMS $R_t$=7.7 min, 539.2 (M+H)$^+$; RP-HPLC $R_t$=9.9 min, 95%.

4-(5-(4-((tert-Butyldimethylsilyl)oxy)but-1-yn-1-yl)-2-(4-fluorophenyl)-4-(m-tolyl)thiophen-3-yl)pyridine (3.21)

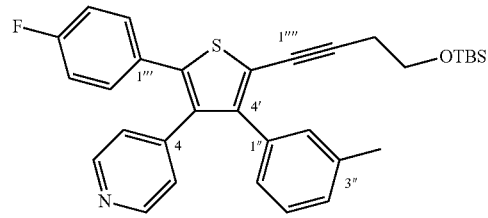 [SMILES: Cc1cccc(-c2c(C#CCCO[Si](C)(C)C(C)(C)C)sc(-c3ccc(F)cc3)c2-c2ccncc2)c1]

Compound 3.21 was synthesised using the general method for Suzuki coupling from thiophene 3.6 (158 mg, 0.280 mmol) and 3-tolylboronic acid (114 mg, 0.838 mmol). Purification using gradient column chromatography (0-40% ethyl acetate/petroleum spirits) gave compound 3.21 (144 mg, 97%) as a yellow solid. 3.21: $C_{32}H_{34}FNOSSi$ ($M_r$=527.77); $^1H$ NMR (300 MHz, $CDCl_3$) δ (ppm) 8.38-8.36 (m, 2H), 7.17-7.02 (m, 4H), 6.99-6.87 (m, 4H), 6.84-6.82 (m, 2H), 3.73 (t, J=7.1 Hz, 2H), 2.58 (t, J=7.1 Hz, 2H), 2.24 (s, 3H), 0.90 (s, 9H), 0.07 (s, 6H); $^{13}C$ NMR (76 MHz, $CDCl_3$) δ (ppm) 162.6 (d, $^1J_{CF}$=248.9 Hz), 149.7, 145.4, 144.1, 139.6, 137.4, 134.9, 134.6, 131.3 (d, $^3J_{CF}$=8.1 Hz), 130.8, 129.3 (d, $^4J_{CF}$=3.1 Hz), 128.3, 127.9, 127.1, 125.7, 120.3, 115.8 (d, $^2J_{CF}$=21.7 Hz), 94.1, 74.4, 61.7, 26.0, 24.4, 21.4, 18.4, −5.2; ESI-LCMS $R_t$=7.6 min, 528.3 (M+H)$^+$; RP-HPLC $R_t$=10.4 min, 90%.

4-(2-(4-(Tert-butyldimethylsilyloxy)but-1-ynyl)-5-(4-fluorophenyl)-4-(pyridin-4-yl)thiophen-3-yl)-N,N-dimethylaniline (3.22)

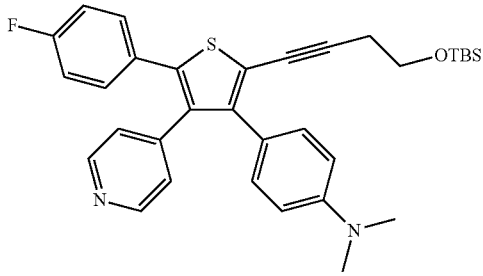 [SMILES: CN(C)c1ccc(-c2c(C#CCCO[Si](C)(C)C(C)(C)C)sc(-c3ccc(F)cc3)c2-c2ccncc2)cc1]

Compound 3.22 was synthesised using the general method for Suzuki coupling from thiophene 3.6 (158 mg, 0.280 mmol) and 4-(dimethylamino)phenylboronic acid (139 mg, 0.841 mmol). Purification using gradient column chromatography (20-50% EtOAc/hexane) gave compound 3.22 (130 mg, 83%) as a yellow solid. 3.22: $C_{33}H_{37}FN_2OSSi$ ($M_r$=556.81); $^1H$ NMR (300 MHz, $d_6$-DMSO) δ (ppm) 8.40-8.38 (m, 2H), 7.22-7.12 (m, 4H), 6.95-6.93 (m, 4H), 6.57 (d, J=8.9 Hz, 2H), 3.70 (t, J=6.4 Hz, 2H), 2.87 (s, 6H), 2.58 (t, J=6.4 Hz, 2H), 0.87 (s, 9H), 0.05 (s, 6H); ESI-LRMS 557.7 (M+H)$^+$.

4-(5-(4-(tert-Butyldimethylsilyloxy)but-1-ynyl)-2,4-bis(4-fluorophenyl)thiophen-3-yl)pyridine (3.23)

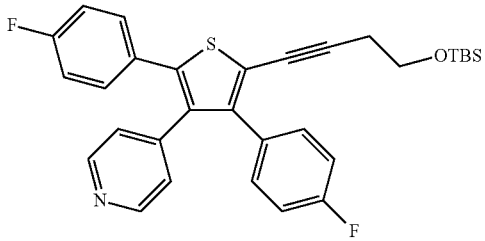 [SMILES: CC(C)(C)[Si](C)(C)OCCC#Cc1sc(-c2ccc(F)cc2)c(-c2ccncc2)c1-c1ccc(F)cc1]

Compound 3.23 was synthesised using the general method for Suzuki coupling from thiophene 3.6 (151 mg, 0.268 mmol) and 4-fluorophenylboronic acid (112 mg, 0.804 mmol). Purification using gradient column chromatography (20-50% EtOAc/hexane) gave compound 3.23 (123 mg, 86%) as a yellow solid. 3.23: $C_{31}H_{31}F_2NOSSi$ ($M_r$=531.73); $^1$H NMR (300 MHz, $d_6$-DMSO) δ (ppm) 8.40-8.38 (m, 2H), 7.25-7.07 (m, 8H), 6.96-6.94 (m, 2H), 3.67 (t, J=6.3 Hz, 2H), 2.58 (t, J=6.3 Hz, 2H), 0.85 (s, 9H), 0.02 (s, 6H); ESI-LRMS 532.1 (M+H)$^+$.

4-(5-(4-(tert-Butyldimethylsilyloxy)but-1-ynyl)-4-(4-chlorophenyl)-2-(4-fluorophenyl)thiophen-3-yl)pyridine (3.24)

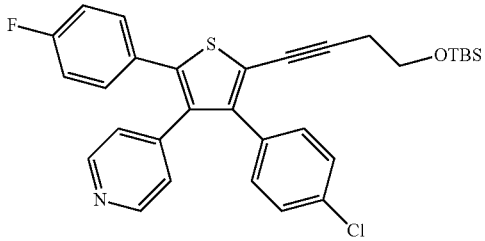 [SMILES: CC(C)(C)[Si](C)(C)OCCC#Cc1sc(-c2ccc(F)cc2)c(-c2ccncc2)c1-c1ccc(Cl)cc1]

Compound 3.24 was synthesised using the general method for Suzuki coupling from thiophene 3.6 (135 mg, 0.240 mmol) and 4-chlorophenylboronic acid (112 mg, 0.719 mmol). Purification using gradient column chromatography (20-50% EtOAc/hexane) gave compound 3.24 (80 mg, 61%) as a yellow solid. 3.24: $C_{31}H_{31}ClFNOSSi$ ($M_r$=548.19); $^1$H NMR (300 MHz, $d_6$-DMSO) δ (ppm) 8.41-8.39 (m, 2H), 7.34 (d, J=8.5 Hz, 2H), 7.25-7.14 (m, 6H), 6.97-6.95 (m, 2H), 3.67 (t, J=6.2 Hz, 2H), 2.59 (t, J=6.2 Hz, 2H), 0.84 (s, 9H), 0.02 (s, 6H); ESI-LRMS 548.0 (M+H)$^+$.

4-(5-(4-(tert-Butyldimethylsilyloxy)but 1-ynyl)-2-(4-fluorophenyl)-4-(4-(trifluoromethyl)phenyl)thiophen-3-yl)pyridine (3.25)

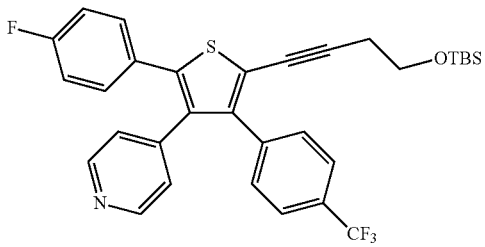 [SMILES: CC(C)(C)[Si](C)(C)OCCC#Cc1sc(-c2ccc(F)cc2)c(-c2ccncc2)c1-c1ccc(C(F)(F)F)cc1]

Compound 3.25 was synthesised using the general method for Suzuki coupling from thiophene 3.6 (125 mg, 0.222 mmol) and 4-(trifluoromethyl)phenylboronic acid (126 mg, 0.665 mmol). Purification using gradient column chromatography (20-50% EtOAc/hexane) gave compound 3.25 (90 mg, 70%) as a yellow solid. 3.25: $C_{32}H_{31}F_4NOSSi$ ($M_r$=581.74); $^1$H NMR (300 MHz, $d_6$-DMSO) δ (ppm) 8.41-8.39 (m, 2H), 7.65 (d, J=8.2 Hz, 2H), 7.35 (d, J=8.0 Hz, 2H), 7.26-7.15 (m, 4H), 6.99-6.97 (m, 2H), 3.65 (t, J=6.2 Hz, 2H), 2.59 (t, J=6.2 Hz, 2H), 0.82 (s, 9H), −0.01 (s, 6H); ESI-LRMS 582.0 (M+H)$^+$.

1-(4-(2-(4-(Tert-butyldimethylsilyloxy)but-1-ynyl)-5-(4-fluorophenyl)-4-(pyridin-4-yl)thiophen-3-yl)phenyl)ethanone (3.26)

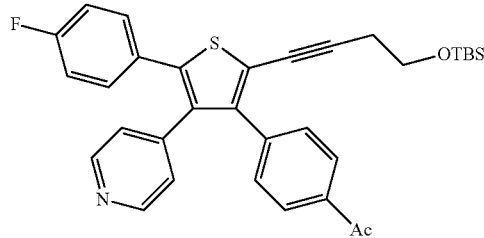 [SMILES: CC(=O)c1ccc(-c2c(C#CCCO[Si](C)(C)C(C)(C)C)sc(-c3ccc(F)cc3)c2-c2ccncc2)cc1]

Compound 3.26 was synthesised using the general method for Suzuki coupling from thiophene 3.6 (142 mg, 0.252 mmol) and 4-acetylphenylboronic acid (124 mg, 0.756 mmol). Purification using gradient column chromatography (20-50% EtOAc/hexane) gave compound 3.26 (63 mg, 45%) as a yellow solid. 3.26: $C_{33}H_{34}FNO_2SSi$ ($M_r$=555.78); $^1$H NMR (300 MHz, $d_6$-DMSO) δ (ppm) 8.39 (br. app. d, J=4.6 Hz, 2H), 7.85 (app. d, J=7.8 Hz, 2H), 7.29-7.15 (m, 6H), 6.98-6.96 (m, 2H), 3.66 (t, J=6.1 Hz, 2H), 2.58 (t, J=6.3 Hz, 2H), 2.54 (s, 3H), 0.83 (s, 9H), 0.01 (s, 6H); ESI-LRMS 556.3 (M+H)$^+$.

4-(2-(4-((tert-Butyldimethylsilyl)oxy)but-1-yn-1-yl)-5-(4-fluorophenyl)-4-(pyridin-4-yl)thiophen-3-yl)phenol (3.27)

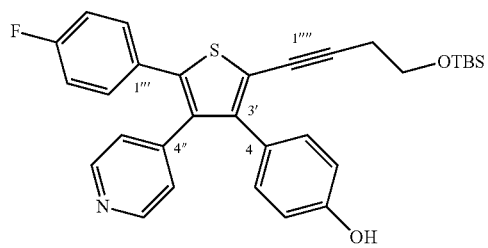 [SMILES: CC(C)(C)[Si](C)(C)OCCC#Cc1sc(-c2ccc(F)cc2)c(-c2ccncc2)c1-c1ccc(O)cc1]

Compound 3.27 was synthesised using the general method for Suzuki coupling from thiophene 3.6 (101 mg, 0.179 mmol) and 4-hydroxyphenylboronic acid (76 mg, 0.55 mmol). Purification using gradient column chromatography (20-50% ethyl acetate/petroleum spirits) gave thiophene 3.27 (67 mg, 71%) as a white solid. 3.27: $C_{31}H_{32}FNO_2SSi$ ($M_r$=529.75); $^1$H NMR (300 MHz, CDCl$_3$) δ (ppm) 9.90 (br. s, 1H), 8.36-8.34 (m, 2H), 7.16-7.10 (m, 2H), 6.99-6.89 (m, 6H), 6.65-6.61 (m, 2H), 3.75 (t, J=7.0 Hz, 2H), 2.60 (t, J=7.0 Hz, 2H), 0.90 (s, 9H), 0.08 (s, 6H); $^{13}$C NMR (76 MHz, $d_6$-DMSO) δ (ppm) 161.9 (d, $^1J_{CF}$=246.1 Hz), 156.9, 149.5, 145.2, 143.3, 138.5, 135.4, 131.3 (d, $^3J_{CF}$=8.3 Hz), 130.8, 128.9 (d, $^4J_{CF}$=2.7 Hz), 125.5, 124.7, 118.3, 115.8 (d, $^2J_{CF}$=21.8 Hz), 114.8, 94.9, 74.0, 61.1, 25.8, 23.6, 18.0, −5.3; ESI-LRMS 530.0 (M+H)$^+$; ESI-LCMS $R_t$=7.1 min, 530.3 (M+H)$^+$; RP-HPLC $R_t$=9.5 min, 95%.

Methyl 2-(5-(4-fluorophenyl)-2-(4-hydroxybut-1-yn-1-yl)-4-(pyridin-4-yl)thiophen-3-yl)benzoate (3.28)

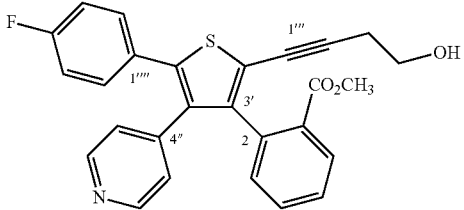 [SMILES: COC(=O)c1ccccc1-c1c(C#CCCO)sc(-c2ccc(F)cc2)c1-c1ccncc1]

Compound 3.28 was synthesised using the general method for Suzuki from thiophene 3.55 (50 mg, 0.11 mmol) and 2-(methoxycarbonyl)phenylboronic acid (65 mg, 0.36 mmol). After heating in the microwave at 100° C. for 90 minutes, the reaction was not complete. Therefore the reaction was heated in the microwave at 120° C. for a further hour. Purification using gradient column chromatography (0-6% methanol/chloroform) followed by preparative HPLC gave compound 3.28 (13 mg, 26%) as a yellow oil. 3.28: $C_{27}H_{20}FNO_3S$ ($M_r$=457.52); $^1$H NMR (400 MHz, $CD_3OD$) δ (ppm) 8.24 (br. app. d, J=4.7 Hz, 2H), 7.84-7.81 (m, 1H), 7.47 (app. td, J=7.5, 1.5 Hz, 1H), 7.41 (app. td, J=7.6, 1.4 Hz, 1H), 7.27-7.22 (m, 2H), 7.17-7.14 (m, 1H), 7.08-7.02 (m, 2H), 6.97-6.95 (m, 2H), 3.70 (s, 3H), 3.55 (td, J=6.9, 1.6 Hz, 2H), 2.49 (t, J=6.9 Hz, 2H); $^{13}$C NMR (101 MHz, $CD_3OD$) δ 169.1, 164.1 (d, $^1J_{CF}$=247.8 Hz), 149.7, 146.7, 146.2, 140.6, 137.2, 136.1, 133.2, 132.9, 132.8, 132.6 (d, $^3J_{CF}$=8.4 Hz), 131.1, 130.5 (d, $^4J_{CF}$=3.5 Hz), 129.2, 127.3, 121.4, 116.7 (d, $^2J_{CF}$=22.1 Hz), 95.7, 74.3, 61.3, 52.8, 24.4; ESI-HRMS-TOF calcd for $C_{27}H_{21}FNO_3S$ (M+H)$^+$ 458.1221, found 458.1222; ESI-LCMS $R_t$=5.3 min, 458.2 (M+H)$^+$; RP-HPLC $R_t$=7.0 min, 97%.

General Procedure for TBS Deprotection

To the TBS protected starting material (100 mg, 1.0 eq.) in methanol (10 mL) was added ammonium fluoride (3.0-4.0 eq.). The reaction mixture was refluxed for 16 hours. The crude product was concentrated, extracted into ethyl acetate and washed with water. The organic fraction was dried over magnesium sulfate, filtered and concentrated in vacuo. The crude product was purified by column chromatography.

Methyl 3-(5-(4-fluorophenyl)-2-(4-hydroxybut-1-yn-1-yl)-4-(pyridin-4-yl)thiophen-3-yl)benzoate (3.29)

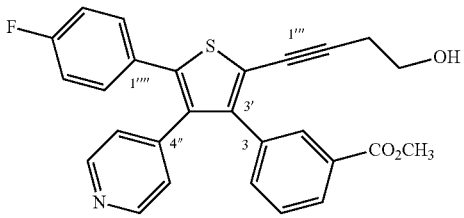 [SMILES: COC(=O)c1cccc(-c2c(C#CCCO)sc(-c3ccc(F)cc3)c2-c2ccncc2)c1]

Compound 3.29 was synthesised from compound 3.8 (462 mg, 0.808 mmol) following the general procedure for TBS deprotection. Purification by column chromatography in 10% methanol/chloroform afforded thiophene 3.29 (361 mg, 98%) as a white powder. 3.29: $C_{27}H_{20}FNO_3S$ ($M_r$=457.52); mp 148.6-150.1° C.; $^1$H NMR (400 MHz, $d_6$-DMSO) δ (ppm) 8.39-8.37 (m, 2H), 7.86-7.82 (m, 2H), 7.41 (app. t, J=7.7 Hz, 1H), 7.32 (app. dt, J=7.7, 1.6 Hz, 1H), 7.26-7.21 (m, 2H), 7.19-7.14 (m, 2H), 6.97-6.96 (m, 2H), 4.87 (t, J=5.6 Hz, 1H), 3.81 (s, 3H), 3.47 (td, J=6.9, 5.7 Hz, 2H), 2.52-2.48 (m, 2H); $^{13}$C NMR (101 MHz, $d_6$-DMSO) δ (ppm) 165.8, 162.0 (d, $^1J_{CF}$=247.0 Hz), 149.6, 143.8, 142.9, 139.0, 135.1, 134.6, 134.3, 131.3 (d, $^3J_{CF}$=8.5 Hz), 130.5, 129.4, 128.6, 128.6 (d, $^4J_{CF}$=5.4 Hz), 128.3, 125.5, 119.9, 115.9 (d, $^2J_{CF}$=21.9 Hz), 96.2, 73.3, 59.4, 52.2, 23.6; ESI-HRMS-TOF calcd for $C_{27}H_{21}FNO_3S^+$ (M+H)$^+$ 458.1221, found 458.1236; ESI-LCMS $R_t$=5.4 min, 458.2 (M+H)$^+$; RP-HPLC $R_t$=7.3 min, >99%.

Methyl 4-(5-(4-fluorophenyl)-2-(4-hydroxybut-1-yn-1-yl)-4-(pyridin-4-yl)thiophen-3-yl)benzoate (3.30)

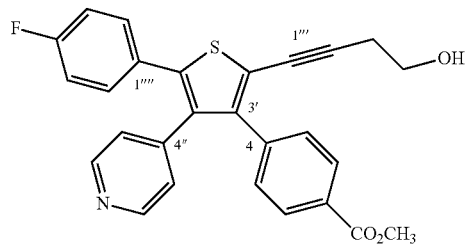 [SMILES: COC(=O)c1ccc(-c2c(C#CCCO)sc(-c3ccc(F)cc3)c2-c2ccncc2)cc1]

Compound 3.30 was synthesised from compound 3.9 (593 mg, 1.04 mmol) following the general procedure for TBS deprotection. Purification by column chromatography in 10% methanol/chloroform afforded compound 3.30 (478 mg, 99%) as a white powder. 3.30: $C_{27}H_{20}FNO_3S$ ($M_r$=457.52); mp 218.3-219.2° C.; $^1$H NMR (400 MHz, $CDCl_3$) δ (ppm) 8.38-8.37 (m, 2H), 7.95-7.92 (m, 2H), 7.24-7.21 (m, 2H), 7.15-7.10 (m, 2H), 6.99-6.93 (m, 2H), 6.81-6.80 (m, 2H), 3.90 (s, 3H), 3.71 (app. q, J=6.2 Hz, 2H), 2.64 (t, J=6.3 Hz, 2H), 1.64 (t, J=6.4 Hz, 1H); $^{13}$C NMR (101 MHz, $CDCl_3$) δ (ppm) 166.9, 162.8 (d, $^1J_{CF}$=249.3 Hz), 149.8, 144.5, 143.6, 140.4, 139.5, 134.7, 131.3 (d, $^3J_{CF}$=8.2 Hz), 130.1, 129.4, 129.3, 128.8 (d, $^4J_{CF}$=3.6 Hz), 125.6, 121.0, 116.0 (d, $^2J_{CF}$=21.8 Hz), 94.4, 74.7, 60.9, 52.3, 24.3; ESI-HRMS-TOF calcd for $C_{27}H_{21}FNO_3S$ (M+H)$^+$ 458.1221, found 458.1212; ESI-LCMS $R_t$=5.4 min, 458.1 (M+H)$^+$; RP-HPLC $R_t$=7.4 min, 99%.

3-(5-(4-Fluorophenyl)-2-(4-hydroxybut-1-yn-1-yl)-4-(pyridin-4-yl)thiophen-3-yl)benzoic acid (3.31)

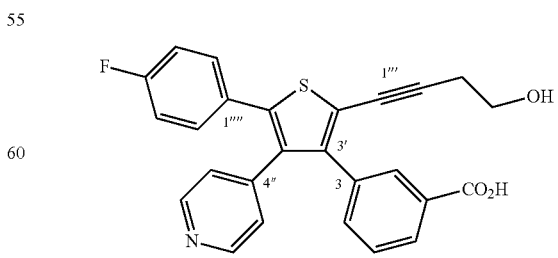

The starting thiophene 3.29 (200 mg, 0.47 mmol) was dissolved in ethanol (10 mL). Water (10 mL) was added followed by sodium hydroxide (70 mg, 1.75 mmol). The reaction mixture was heated at 50° C. for 2 hours. The reaction mixture was concentrated in vacuo to remove the ethanol. The mixture was acidified with hydrochloric acid (1 M) to pH 2. The resulting precipitate was filtered and dried under vacuum to afford compound 3.31 (155 mg, 80%) as a white powder. 3.31: $C_{26}H_{18}FNO_3S$ ($M_r$=443.49); mp 257.4-259.2° C.; $^1$H NMR (400 MHz, $d_6$-DMSO) δ (ppm) 8.43-8.42 (m, 2H), 7.84 (app. dt, J=7.7, 1.4 Hz, 1H), 7.78-7.76 (m, 1H), 7.40 (app. t, J=7.7 Hz, 1H), 7.34 (app. dt, J=7.8, 1.4 Hz, 1H), 7.26-7.23 (m, 2H), 7.20-7.16 (m, 2H), 7.04-7.03 (m, 2H), 3.47 (t, J=6.9 Hz, 2H), 2.52-2.49 (m, 2H); $^{13}$C NMR (101 MHz, $d_6$-DMSO) δ (ppm) 166.8, 162.1 (d, $^1J_{CF}$=246.8 Hz), 148.9, 144.0, 143.7, 139.1, 135.0, 134.3, 133.9, 131.4 (d, $^3J_{CF}$=8.5 Hz), 130.6, 130.6, 128.6 (d, $^4J_{CF}$=3.3 Hz), 128.5, 128.4, 125.8, 119.9, 115.9 (d, $^2J_{CF}$=21.8 Hz), 96.1, 73.3, 59.4, 23.6; ESI-HRMS-TOF calcd for $C_{26}H_{19}FNO_3S^+$ (M+H)$^+$ 444.1064, found 444.1075; ESI-LCMS $R_t$=5.1 min, 444.1 (M+H)$^+$; RP-HPLC $R_t$=6.7 min, >99%.

4-(5-(4-Fluorophenyl)-2-(4-hydroxybut-1-yn-1-yl)-4-(pyridin-4-yl)thiophen-3-yl)benzoic acid (3.32)

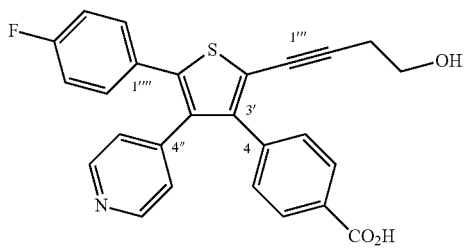 [SMILES: O=C(O)c1ccc(-c2c(C#CCCO)sc(-c3ccc(F)cc3)c2-c2ccncc2)cc1]

The starting thiophene 3.30 (100 mg, 0.219 mmol) was dissolved in ethanol (5 mL). Water (5 mL) was added followed by sodium hydroxide (35 mg, 0.87 mmol). The reaction mixture was heated at 50° C. for 2 hours. The reaction mixture was concentrated in vacuo to remove the ethanol. The mixture was acidified with hydrochloric acid (1 M) to pH 2. The resulting precipitate was filtered and dried under vacuum to afford compound 3.32 (89 mg, 92%) as a white powder. 3.32: $C_{26}H_{18}FNO_3S$ ($M_r$=443.49); $^1$H NMR (400 MHz, $d_6$-DMSO) δ (ppm) 8.71 (br. app. d, J=5.3 Hz, 2H), 7.87 (app. d, J=8.2 Hz, 2H), 7.48 (br. app. d, J=5.9 Hz, 2H), 7.30-7.26 (m, 4H), 7.23-7.18 (m, 2H), 3.50 (t, J=6.7 Hz, 2H), 2.53 (t, J=6.7 Hz, 2H); $^{13}$C NMR (101 MHz, $d_6$-DMSO) δ (ppm) 166.9, 162.4 (d, $^1J_{CF}$=247.7 Hz), 150.3, 143.6, 143.2, 141.1, 137.8, 133.2, 131.8 (d, $^3J_{CF}$=8.7 Hz), 130.11, 130.07, 129.2, 128.1, 127.8 (d, $^4J_{CF}$=3.0 Hz), 120.8, 116.2 (d, $^2J_{CF}$=21.9 Hz), 97.1, 72.8, 59.3, 23.6; ESI-HRMS-TOF calcd for $C_{26}H_{19}FNO_3S^+$ (M+H)$^+$ 444.1064, found 444.1071; ESI-LCMS $R_t$=5.1 min, 444.1 (M+H)$^+$; RP-HPLC $R_t$=6.7 min, 98%.

4-(5-(4-Fluorophenyl)-3-(3-(hydroxymethyl)phenyl)-4-(pyridin-4-yl)thiophen-2-yl)but-3-yn-1-ol (3.33)

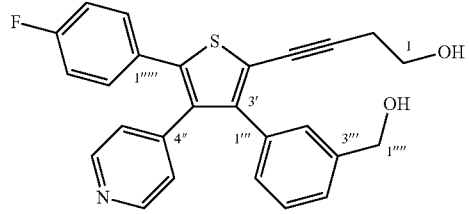 [SMILES: OCCC#Cc1sc(-c2ccc(F)cc2)c(-c2ccncc2)c1-c1cccc(CO)c1]

Compound 3.33 was synthesised from compound 3.10 (119 mg, 0.219 mmol) following the general procedure for TBS deprotection. Purification by column chromatography in 5% methanol/chloroform afforded compound 3.33 (78 mg, 83%) as a white powder. 3.33: $C_{26}H_{20}FNO_2S$ ($M_r$=429.51); mp 189.0-190.6° C.; $^1$H NMR (400 MHz, $CD_3OD$) δ (ppm) 8.29-8.28 (m, 2H), 7.27-7.20 (m, 5H), 7.07-7.01 (m, 2H), 6.99-6.96 (m, 3H), 4.53 (s, 2H), 3.63 (t, J=6.7 Hz, 2H), 2.57 (t, J=6.7 Hz, 2H); $^{13}$C NMR (101 MHz, $CD_3OD$) δ (ppm) 164.1 (d, $^1J_{CF}$=247.9 Hz), 149.8, 146.7, 146.5, 142.7, 141.1, 136.2, 136.1, 132.7 (d, $^3J_{CF}$=8.4 Hz), 130.5 (d, $^4J_{CF}$=3.5 Hz), 130.0, 129.8, 129.0, 127.6, 127.2, 121.8, 116.7 (d, $^2J_{CF}$=22.1 Hz), 95.5, 74.9, 64.9, 61.4, 24.5; ESI-HRMS-TOF calcd for $C_{26}H_{21}FNO_2S$ (M+H)$^+$ 430.1272, found 430.1259; ESI-LCMS $R_t$=5.0 min, 430.2 (M+H)$^+$; RP-HPLC $R_t$=6.7 min, >99%.

4-(5-(4-Fluorophenyl)-3-(4-(hydroxymethyl)phenyl)-4-(pyridin-4-yl)thiophen-2-yl)but-3-yn-1-ol (3.34)

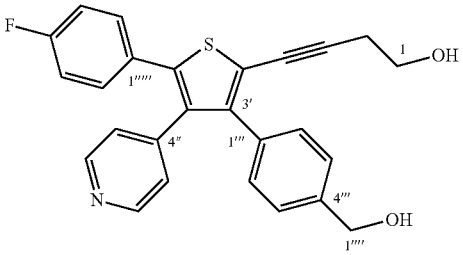 [SMILES: OCCC#Cc1sc(-c2ccc(F)cc2)c(-c2ccncc2)c1-c1ccc(CO)cc1]

Compound 3.34 was synthesised from compound 3.11 (98 mg, 0.15 mmol) following the general procedure for TBS deprotection.

Recrystallisation from methanol afforded thiophene 3.34 (37 mg, 58%) as white crystals. 3.34: $C_{26}H_{20}FNO_2S$ ($M_r$=429.51); mp 235-236.7° C.; $^1$H NMR (400 MHz, $d_6$-DMSO) δ (ppm) 8.39-8.38 (m, 2H), 7.24-7.14 (m, 6H), 7.09 (app. d, J=8.2 Hz, 2H), 6.96-6.95 (m, 2H), 5.18 (br. s, 1H), 4.88 (br. s, 1H), 4.46 (s, 2H), 3.50 (t, J=6.8 Hz, 2H), 2.53-2.49 (m, 2H); $^{13}$C NMR (101 MHz, $d_6$-DMSO) δ (ppm) 162.0 (d, $^1J_{CF}$=246.6 Hz), 149.3, 144.8, 143.5, 141.9, 138.8, 135.3, 132.4, 131.3 (d, $^3J_{CF}$=8.5 Hz), 129.4, 128.8 (d, $^4J_{CF}$=3.0 Hz), 126.0, 125.6, 119.3, 115.8 (d, $^2J_{CF}$=21.9 Hz), 95.5, 73.6, 62.6, 59.5, 23.6; ESI-HRMS-TOF calcd for $C_{26}H_{21}FNO_2S$ (M+H)$^+$ 430.1272, found 430.1285; ESI-LCMS $R_t$=5.0 min, 430.2 (M+H)$^+$; RP-HPLC $R_t$=6.2 min, >99%.

3-(5-(4-Fluorophenyl)-2-(4-hydroxybut-1-yn-1-yl)-4-(pyridin-4-yl)thiophen-3-yl)benzamide (3.35)

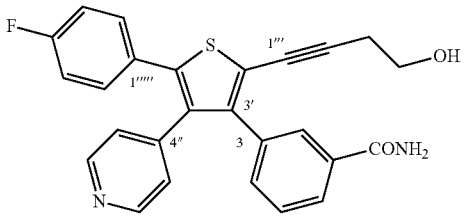 [SMILES: NC(=O)c1cccc(-c2c(C#CCCO)sc(-c3ccc(F)cc3)c2-c2ccncc2)c1]

To a suspension of acid 3.31 (80 mg, 0.18 mmol) in dimethylformamide (2 mL) was added (benzotriazol-1-yloxy)tris(dimethylamino)phosphonium hexafluorophosphate (119 mg, 0.269 mmol), N,N-diisopropylethylamine (46 µL, 0.27 mmol) and ammonium carbonate (90 mg, 0.93 mmol). The reaction mixture was stirred at room temperature for 16 hours. The solvent was evaporated in vacuo. Purification by column chromatography in 5% methanol/chloroform followed by recrystallisation from methanol afforded compound 3.35 (44 mg, 55%) as white crystals. 3.35: $C_{26}H_{19}FN_2O_2S$ ($M_r$=442.51); mp 239.4-240.8° C.; $^1$H NMR (400 MHz, $d_6$-DMSO) δ (ppm) 8.38-8.37 (m, 2H), 7.88 (br. s, 1H), 7.78-7.75 (m, 2H), 7.35-7.31 (m, 2H), 7.26-7.15 (m, 5H), 6.95-6.94 (m, 2H), 4.88 (br. s, 1H), 3.47 (t, J=6.8 Hz, 2H), 2.51-2.48 (m, 2H); $^{13}$C NMR (101 MHz, $d_6$-DMSO) δ (ppm) 167.4, 162.0 (d, $^1J_{CF}$=247.2 Hz), 149.6, 144.6, 142.9, 138.8, 135.3, 134.2, 134.0, 132.3, 131.3 (d, $^3J_{CF}$=8.5 Hz), 129.1, 128.7 (d, $^4J_{CF}$=3.3 Hz), 127.9, 126.7, 125.5, 119.7, 115.9 (d, $^2J_{CF}$=21.9 Hz), 95.9, 73.4, 59.4, 23.6; ESI-HRMS-TOF calcd for $C_{26}H_{20}FN_2O_2S^+$ (M+H)$^+$ 443.1224, found 443.1244; ESI-LCMS $R_t$=4.9 min, 443.2 (M+H)$^+$; RP-HPLC $R_t$=6.4 min, 99%.

4-(5-(4-Fluorophenyl)-2-(4-hydroxybut-1-yn-1-yl)-4-(pyridin-4-yl)thiophen-3-yl)benzamide (3.36)

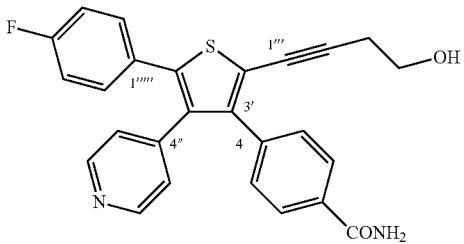 [SMILES: NC(=O)c1ccc(-c2c(C#CCCO)sc(-c3ccc(F)cc3)c2-c2ccncc2)cc1]

Compound 3.36 was synthesised from compound 3.12 (49 mg, 0.09 mmol) following the general procedure for TBS deprotection. Purification by column chromatography in 5% methanol/chloroform gave thiophene 3.36 (27 mg, 70%) as a white powder. 3.36: $C_{26}H_{19}FN_2O_2S$ ($M_r$=442.51); mp 251.3-254.2° C.; $^1$H NMR (400 MHz, $d_6$-DMSO) δ (ppm) 8.40-8.39 (m, 2H), 7.95 (br. s, 1H), 7.77-7.74 (m, 2H), 7.37 (br. s, 1H), 7.25-7.15 (m, 6H), 6.97-6.95 (m, 2H), 4.89 (t, J=5.6 Hz, 1H), 3.49 (td, J=6.9, 5.6 Hz, 2H), 2.54-2.49 (m, 2H); $^{13}$C NMR (101 MHz, $d_6$-DMSO) δ (ppm) 167.5, 162.0 (d, $^1J_{CF}$=246.6 Hz), 149.6, 144.2, 143.0, 138.9, 137.0, 135.2, 133.2, 131.4 (d, $^3J_{CF}$=8.4 Hz), 129.6, 128.6 (d, $^4J_{CF}$=3.2 Hz), 127.2, 125.5, 119.9, 115.9 (d, $^2J_{CF}$=21.9 Hz), 96.1, 73.4, 59.4, 23.6; ESI-HRMS-TOF calcd for $C_{26}H_{20}FN_2O_2S$ (M+H)$^+$ 443.1224, found 443.1242; ESI-LCMS $R_t$=4.9 min, 443.2 (M+H)$^+$; RP-HPLC $R_t$=6.4 min, 97%.

3-(5-(4-Fluorophenyl)-2-(4-hydroxybut-1-yn-1-yl)-4-(pyridin-4-yl)thiophen-3-yl)-N-(2-hydroxyethyl)benzamide (3.37)

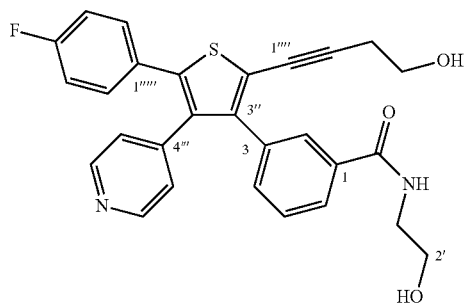 [SMILES: O=C(NCCO)c1cccc(-c2c(C#CCCO)sc(-c3ccc(F)cc3)c2-c2ccncc2)c1]

To a suspension of compound 3.31 (80 mg, 0.18 mmol) in acetonitrile (2 mL) was added (benzotriazol-1-yloxy)tris(dimethylamino)phosphonium hexafluorophosphate (120 mg, 0.271 mmol), N,N-diisopropylethylamine (47 µL, 0.27 mmol) and ethanolamine (50 µL, 0.90 mmol). The reaction mixture was stirred at room temperature for 16 hours. Ethyl acetate (10 mL) was added and the mixture was washed with water (3×10 mL) and the aqueous fraction further extracted with ethyl acetate (3×10 mL). The combined organic fractions were dried over magnesium sulfate, filtered and concentrated in vacuo. Purification by gradient column chromatography (0-10% methanol/chloroform) afforded compound 3.37 (50 mg, 57%) as a white powder. 3.37: $C_{28}H_{23}FN_2O_3S$ ($M_r$=486.56); mp 140.0-142.5° C.; $^1$H NMR (400 MHz, $d_6$-DMSO) δ (ppm) 8.38-8.34 (m, 3H), 7.80 (s, 1H), 7.75 (d, J=7.8 Hz, 1H), 7.33 (app. t, J=7.7 Hz, 1H), 7.25-7.14 (m, 5H), 6.96-6.94 (m, 2H), 4.88 (t, J=5.6 Hz, 1H), 4.71 (t, J=5.6 Hz, 1H), 3.51-3.44 (m, 4H), 3.34-3.28 (m, 2H), 2.51-2.48 (m, 2H); $^{13}$C NMR (101 MHz, $d_6$-DMSO) δ (ppm) 165.8, 162.0 (d, $^1J_{CF}$=246.7 Hz), 149.6, 144.5, 142.9, 138.8, 135.3, 134.3, 134.2, 132.1, 131.3 (d, $^3J_{CF}$=8.5 Hz), 128.8, 128.7 (d, $^4J_{CF}$=3.1 Hz), 127.9, 126.4, 125.5, 119.8, 115.9 (d, $^2J_{CF}$=21.8 Hz), 96.0, 73.4, 59.7, 59.4, 42.2, 23.6; ESI-HRMS-TOF calcd for $C_{28}H_{24}FN_2O_3S^+$ (M+H)$^+$ 487.1486, found 487.1508; ESI-LCMS $R_t$=4.9 min, 487.2 (M+H)$^+$; RP-HPLC $R_t$=6.2 min, >99%.

4-(5-(4-Fluorophenyl)-2-(4-hydroxybut-1-yn-1-yl)-4-(pyridin-4-yl)thiophen-3-yl)-N-(2-hydroxyethyl)benzamide (3.38)

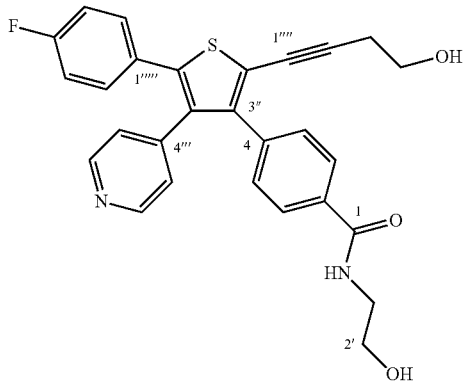 [SMILES: O=C(NCCO)c1ccc(-c2c(C#CCCO)sc(-c3ccc(F)cc3)c2-c2ccncc2)cc1]

To a suspension of compound 3.32 (60 mg, 0.14 mmol) in acetonitrole (1.5 mL) was added (benzotriazol-1-yloxy)tris(dimethylamino)phosphonium hexafluorophosphate (90 mg, 0.20 mmol), N,N-diisopropylethylamine (35 μL, 0.20 mmol) and ethanolamine (38 μL, 0.68 mmol). The reaction mixture was stirred at room temperature for 16 hours. Ethyl acetate (10 mL) was added and the mixture was washed with water (3×10 mL) and the aqueous fraction further extracted with ethyl acetate (3×10 mL). The combined organic fractions was dried over magnesium sulfate, filtered and concentrated in vacuo. Purification by gradient column chromatography (0-10% methanol/chloroform) afforded compound 3.38 (30 mg, 45%) as a white powder. 3.38: $C_{28}H_{23}FN_2O_3S$ ($M_r$=486.56); mp 218.7-220.9° C.; $^1$H NMR (400 MHz, d$_6$-DMSO) δ (ppm) 8.43-8.39 (m, 3H), 7.74 (app. d, J=8.5 Hz, 2H), 7.25-7.15 (m, 6H), 6.96-6.95 (m, 2H), 4.88 (t, J=5.6 Hz, 1H), 4.70 (t, J=5.7 Hz, 1H), 3.52-3.46 (m, 4H), 3.35-3.28 (m, 2H), 2.53-2.49 (m, 2H); $^{13}$C NMR (101 MHz, d$_6$-DMSO) δ (ppm) 165.8, 162.0 (d, $^1J_{CF}$=247.0 Hz), 149.6, 144.1, 142.9, 138.9, 136.8, 135.2, 133.5, 131.3 (d, $^3J_{CF}$=8.5 Hz), 129.5, 128.6 (d, $^4J_{CF}$=3.2 Hz), 126.9, 125.5, 119.8, 115.9 (d, $^2J_{CF}$=21.8 Hz), 96.1, 73.3, 59.7, 59.4, 42.2, 23.6; ESI-HRMS-TOF calcd for $C_{28}H_{24}FN_2O_3S^+$ (M+H)$^+$ 487.1486, found 487.1483; ESI-LCMS $R_t$=4.9 min, 487.2 (M+H)$^+$; RP-HPLC $R_t$=6.1 min, 97%.

4-(3-(3-Aminophenyl)-5-(4-fluorophenyl)-4-(pyridin-4-yl)thiophen-2-yl)but-3-yn-1-ol (3.39)

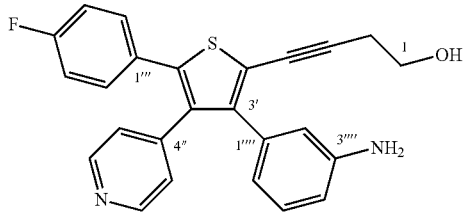 [SMILES: Nc1cccc(-c2c(C#CCCO)sc(-c3ccc(F)cc3)c2-c2ccncc2)c1]

Compound 3.39 was synthesised from compound 3.13 (100 mg, 0.189 mmol) following the general procedure for TBS deprotection. Purification using gradient column chromatography (0-5% methanol/ethyl acetate) gave compound 3.39 (48 mg, 62%) as a yellow powder. 3.39: $C_{25}H_{19}FN_2OS$ ($M_r$=414.50); mp 142.5-143.8° C.; $^1$H NMR (300 MHz, CD$_3$OD) δ (ppm) 8.29-8.27 (m, 2H), 7.22-7.16 (m, 2H), 7.05-6.93 (m, 5H), 6.64-6.61 (m, 2H), 6.37 (d, J=7.5 Hz, 2H), 3.64 (t, J=6.8 Hz, 2H), 2.58 (t, J=6.8 Hz, 2H); $^{13}$C NMR (76 MHz, CD$_3$OD) δ (ppm) 164.1 (d, $^1J_{CF}$=247.8 Hz), 149.7, 148.5, 147.3, 146.6, 140.9, 136.9, 136.2, 132.6 (d, $^3J_{CF}$=8.3 Hz), 130.6 (d, $^4J_{CF}$=3.1 Hz), 129.6, 127.5, 121.5, 121.0, 118.2, 116.7 (d, $^2J_{CF}$=22.1 Hz), 115.8, 95.2, 75.0, 61.4, 24.6; ESI-HRMS-TOF calcd for $C_{25}H_{20}FN_2OS^+$ (M+H)$^+$ 415.1275, found 415.1293; ESI-LCMS $R_t$=4.9 min, 415.2 (M+H)$^+$; RP-HPLC $R_t$=5.5 min, 96%.

4-(3-(4-Aminophenyl)-5-(4-fluorophenyl)-4-(pyridin-4-yl)thiophen-2-yl)but-3-yn-1-ol (3.40)

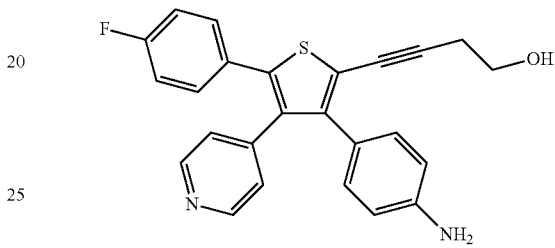

Compound 3.40 was synthesised from compound 3.14 (83 mg, 0.16 mmol) following the general procedure for TBS deprotection. Purification by gradient column chromatography (20-50% EtOAc/hexane) afforded compound 3.40 (56 mg, 86%) as yellow powder. 3.40: $C_{25}H_{19}FN_2OS$ ($M_r$=414.49); $^1$H NMR (300 MHz, CD$_3$OD) δ (ppm) 8.30-8.28 (m, 2H), 7.23-7.16 (m, 2H), 7.06-6.96 (m, 4H), 6.90-6.86 (m, 2H), 6.61-6.56 (m, 2H), 3.65 (t, J=6.9 Hz, 2H), 2.58 (t, J=6.9 Hz, 2H); $^{13}$C NMR (76 MHz, d$_6$-DMSO) δ (ppm) 161.9 (d, $^1J_{CF}$=246.3 Hz), 149.4, 148.1, 145.8, 143.6, 138.2, 135.3, 131.3 (d, $^3J_{CF}$=8.4 Hz), 130.4, 129.1 (d, $^4J_{CF}$=2.6 Hz), 125.6, 121.2, 117.5, 115.8 (d, $^2J_{CF}$=21.8 Hz), 113.1, 94.7, 74.2, 59.6, 23.7; ESI-HRMS-TOF calcd for $C_{25}H_{20}FN_2OS^+$ (M+H)$^+$ 415.1275, found 415.1273; RP-HPLC $R_t$=5.3 min, 90%.

N-(3-(5-(4-fluorophenyl)-2-(4-hydroxybut-1-yn-1-yl)-4-(pyridin-4-yl)thiophen-3-yl)phenyl)acetamide (3.41)

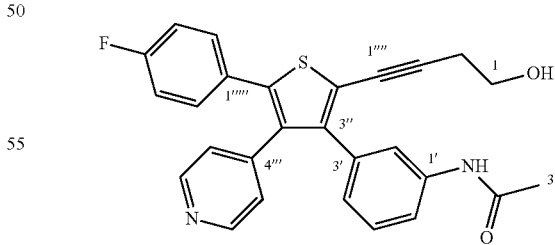

Compound 3.41 was synthesised from compound 3.15 (65 mg, 0.11 mmol) following the general procedure for TBS deprotection. Purification by gradient column chromatography (0-10% methanol/chloroform) afforded compound 3.41 (47 mg, 90%) as white powder. 3.41: $C_{27}H_{21}FN_2O_2S$ ($M_r$=456.54); mp 139.4-143.2° C.; $^1$H NMR (400 MHz, d$_6$-DMSO) δ (ppm) 9.89 (s, 1H), 8.38-8.36 (m, 2H), 7.53 (s, 1H), 7.46 (d, J=8.1 Hz, 1H), 7.24-7.13 (m, 5H), 6.93-6.91 (m, 2H), 6.69 (d, J=7.7 Hz, 1H), 4.87 (t, J=5.6 Hz, 1H), 3.48 (app. q, J=6.5 Hz, 2H), 2.51 (t, J=6.9 Hz, 2H), 2.00 (s, 3H); $^{13}$C NMR (101 MHz, d$_6$-DMSO) δ (ppm) 168.3, 162.0 (d, $^{1}J_{CF}$=246.8 Hz), 149.5, 145.0, 143.0, 139.1, 138.7, 135.3, 134.6, 131.4 (d, $^{3}J_{CF}$=8.4 Hz), 128.8 (d, $^{4}J_{CF}$=3.2 Hz), 128.2, 125.4, 124.3, 120.2, 119.4, 118.1, 115.8 (d, $^{2}J_{CF}$=21.9 Hz), 95.7, 73.5, 59.5, 24.0, 23.6; ESI-HRMS-TOF calcd for C$_{27}$H$_{22}$FN$_2$O$_2$S+(M+H)$^+$ 457.1381, found 457.1394; ESI-LCMS R$_t$=5.0 min, 457.2 (M+H)$^+$; RP-HPLC R$_t$=6.5 min, >99%.

N-(4-(5-(4-fluorophenyl)-2-(4-hydroxybut-1-yn-1-yl)-4-(pyridin-4-yl)thiophen-3-yl)phenyl)acetamide (3.42)

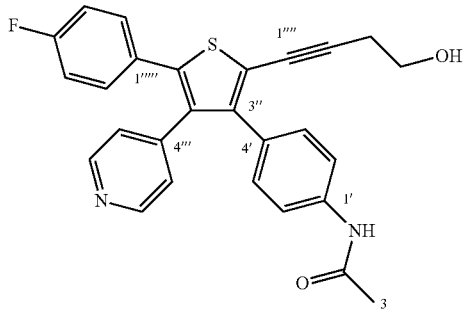 [SMILES: CC(=O)Nc1ccc(-c2c(C#CCCO)sc(-c3ccc(F)cc3)c2-c2ccncc2)cc1]

Compound 3.42 was synthesised from compound 3.16 (84 mg, 0.15 mmol) following the general procedure for TBS deprotection. Purification by gradient column chromatography (0-10% methanol/chloroform) afforded thiophene 3.42 (52 mg, 77%) as a white powder. 3.42: C$_{27}$H$_{21}$FN$_2$O$_2$S (M$_r$=456.53); mp 251.4-253.3° C.; $^1$H NMR (400 MHz, d$_6$-DMSO) δ (ppm) 9.96 (s, 1H), 8.39-8.38 (m, 2H), 7.46 (app. d, J=8.7 Hz, 2H), 7.23-7.14 (m, 4H), 7.04 (app. d, J=8.7 Hz, 2H), 6.94-6.92 (m, 2H), 4.88 (t, J=5.6 Hz, 1H), 3.50 (app. q, J=6.3 Hz, 2H), 2.53-2.49 (m, 2H), 2.02 (s, 3H); $^{13}$C NMR (101 MHz, d$_6$-DMSO) δ (ppm) 168.4, 162.0 (d, $^{1}J_{CF}$=246.7 Hz), 149.5, 144.8, 143.2, 138.7, 138.6, 135.3, 131.3 (d, $^{3}J_{CF}$=8.4 Hz), 130.1, 128.8 (d, $^{4}J_{CF}$=3.2 Hz), 128.7, 125.5, 118.9, 118.2, 115.8 (d, $^{2}J_{CF}$=21.9 Hz), 95.5, 73.7, 59.5, 24.0, 23.6; ESI-HRMS-TOF calcd for C$_{27}$H$_{22}$FN$_2$O$_2$S (M+H)$^+$ 457.1381, found 457.1390; ESI-LCMS R$_t$=5.1 min, 457.2 (M+H)$^+$; RP-HPLC R$_t$=6.6 min, >99%.

N-(3-(5-(4-fluorophenyl)-2-(4-hydroxybut-1-yn-1-yl)-4-(pyridin-4-yl)thiophen-3-yl)phenyl)benzamide (3.43)

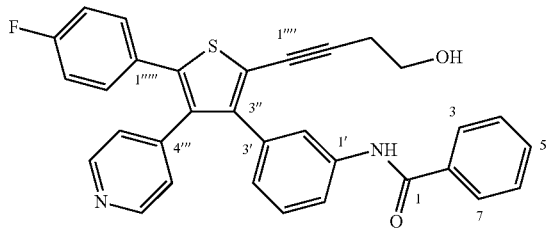 [SMILES: O=C(Nc1cccc(-c2c(C#CCCO)sc(-c3ccc(F)cc3)c2-c2ccncc2)c1)c1ccccc1]

Compound 3.43 was synthesised from compound 3.17 (100 mg, 0.158 mmol) following the general procedure for TBS deprotection. Purification by gradient column chromatography (0-5% methanol/chloroform) afforded thiophene 3.43 (78 mg, 95%) as a white powder. 3.43: C$_{32}$H$_{23}$FN$_2$O$_2$S (M$_r$=518.61); mp 204.4-206.3° C.; $^1$H NMR (400 MHz, d$_6$-DMSO) δ (ppm) 10.23 (s, 1H), 8.40-8.38 (m, 2H), 7.92-7.90 (m, 2H), 7.82 (br. s, 1H), 7.67 (br. d, J=8.1 Hz, 1H), 7.61-7.51 (m, 3H), 7.26-7.15 (m, 5H), 6.97-6.96 (m, 2H), 6.75 (d, J=7.7 Hz, 1H), 4.86 (t, J=5.6 Hz, 1H), 3.50 (app. q, J=6.4 Hz, 2H), 2.53 (t, J=7.0 Hz, 2H); $^{13}$C NMR (101 MHz, d$_6$-DMSO) δ (ppm) 165.6, 162.0 (d, $^{1}J_{CF}$=246.5 Hz), 149.5, 145.0, 143.0, 139.0, 138.7, 135.3, 135.0, 134.6, 131.6, 131.4 (d, $^{3}J_{CF}$=8.4 Hz), 128.8 (d, $^{4}J_{CF}$=3.2 Hz), 128.4, 128.1, 127.7, 125.4, 124.9, 121.5, 119.5, 119.4, 115.8 (d, $^{2}J_{CF}$=21.9 Hz), 95.8, 73.5, 59.5, 23.7; ESI-HRMS-TOF calcd for C$_{32}$H$_{24}$FN$_2$O$_2$S$^+$ (M+H)$^+$ 519.1537, found 519.1525; ESI-LCMS R$_t$=5.4 min, 519.2 (M+H)$^+$; RP-HPLC R$_t$=8.1 min, 99%.

N-(4-(5-(4-fluorophenyl)-2-(4-hydroxybut-1-yn-1-yl)-4-(pyridin-4-yl)thiophen-3-yl)phenyl)benzamide (3.44)

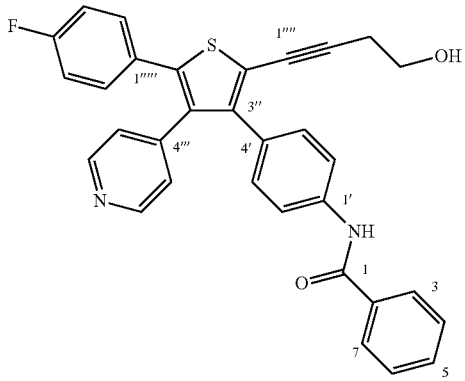 [SMILES: O=C(Nc1ccc(-c2c(C#CCCO)sc(-c3ccc(F)cc3)c2-c2ccncc2)cc1)c1ccccc1]

Compound 3.44 was synthesised from compound 3.18 (150 mg, 0.237 mmol) following the general procedure for TBS deprotection. Purification by gradient column chromatography (0-5% methanol/chloroform) afforded compound 3.44 (110 mg, 89%) as white powder. 3.44: C$_{32}$H$_{23}$FN$_2$O$_2$S (M$_r$=518.61); mp 248.6-250.5° C.; $^1$H NMR (400 MHz, d$_6$-DMSO) δ (ppm) 10.28 (s, 1H), 8.42-8.40 (m, 2H), 7.93-7.91 (m, 2H), 7.68 (app. d, J=8.6 Hz, 2H), 7.61-7.50 (m, 3H), 7.27-7.15 (m, 4H), 7.12 (app. d, J=8.6 Hz, 2H), 6.98-6.96 (m, 2H), 4.90 (t, J=5.5 Hz, 1H), 3.52 (app. q, J=6.4 Hz, 2H), 2.54 (t, J=6.8 Hz, 2H); $^{13}$C NMR (101 MHz, d$_6$-DMSO) δ (ppm) 165.7, 162.0 (d, $^{1}J_{CF}$=246.8 Hz), 149.6, 144.7, 143.2, 138.6, 138.5, 135.3, 134.9, 131.6, 131.3 (d, $^{3}J_{CF}$, J=8.5 Hz), 130.0, 129.4, 128.8 (d, $^{4}J_{CF}$=3.3 Hz), 128.4, 127.6, 125.6, 119.6, 119.1, 115.8 (d, $^{2}J_{CF}$=21.9 Hz), 95.6, 73.7, 59.5, 23.7; ESI-HRMS-TOF calcd for C$_{32}$H$_{24}$FN$_2$O$_2$S (M+H)$^+$ 519.1537, found 519.1559; ESI-LCMS R$_t$=5.4 min, 519.2 (M+H)$^+$; RP-HPLC R$_t$=7.1 min, 98%.

N-(3-(5-(4-fluorophenyl)-2-(4-hydroxybut-1-yn-1-yl)-4-(pyridin-4-yl)thiophen-3-yl)phenyl)-4-methylbenzenesulfonamide (3.45)

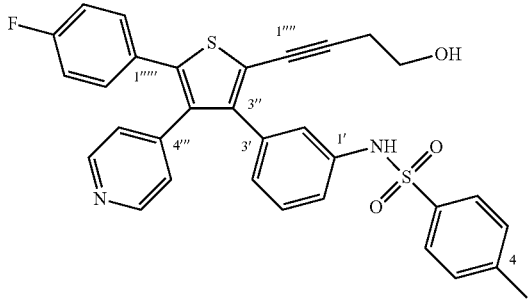 [SMILES: Cc1ccc(S(=O)(=O)Nc2cccc(-c3c(C#CCCO)sc(-c4ccc(F)cc4)c3-c3ccncc3)c2)cc1]

To a solution of thiophene 3.13 (98 mg, 0.19 mmol) in dichloromethane (5 mL) was added pyridine (91 μL, 1.1 mmol) and p-toluenesulfonyl chloride (45 mg, 0.23 mmol). The reaction mixture was stirred at room temperature for 24 hours. Aqueous hydrochloric acid (2.7 M, 20 mL) was added. The compound was extracted with dichloromethane (3×20 mL). The organic fractions were combined and dried over magnesium sulfate, filtered and concentrated in vacuo. Purification by gradient column chromatography (0-50% ethyl acetate/petroleum spirits) gave compound 3.45 (62 mg, 59%) as a beige powder. 3.45: $C_{32}H_{25}FN_2O_3S_2$ ($M_r$=568.68); mp 212.7-214.6° C.; $^1$H NMR (400 MHz, $d_6$-DMSO) δ (ppm) 10.18 (s, 1H), 8.34-8.33 (m, 2H), 7.51 (app. d, J=8.3 Hz, 2H), 7.34 (app. d, J=8.0 Hz, 2H), 7.23-7.14 (m, 4H), 7.08 (app. t, J=7.9 Hz, 1H), 7.00 (br. app. t, J=1.8 Hz, 1H), 6.95 (ddd, J=8.1, 2.1, 0.9 Hz, 1H), 6.83-6.82 (m, 2H), 6.71 (app. dt, J=7.7, 1.2 Hz, 1H), 4.88 (br. s, 1H), 3.47 (t, J=6.9 Hz, 2H), 2.50-2.46 (m, 2H), 2.36 (s, 3H); $^{13}$C NMR (101 MHz, $d_6$-DMSO) δ (ppm) 162.0 (d, $^1J_{CF}$=246.6 Hz), 149.3, 144.4, 143.2, 142.9, 138.8, 137.6, 136.6, 135.2, 135.1, 131.3 (d, $^3J_{CF}$=8.5 Hz), 129.6, 128.7, 128.7 (d, $^4J_{CF}$=3.4 Hz), 126.5, 125.4, 125.3, 121.4, 119.6, 119.0, 115.8 (d, $^2J_{CF}$=21.8 Hz), 95.8, 73.2, 59.5, 23.6, 21.0; ESI-HRMS-TOF calcd for $C_{32}H_{26}FN_2O_3S_{2+}$ (M+H)$^+$ 569.1363, found 569.1370; ESI-LCMS $R_t$=5.6 min, 569.2 (M+H)$^+$; RP-HPLC $R_t$=7.6 min, >99%.

N-(4-(5-(4-fluorophenyl)-2-(4-hydroxybut-1-yn-1-yl)-4-(pyridin-4-yl)thiophen-3-yl)phenyl)-4-methylbenzenesulfonamide (3.46)

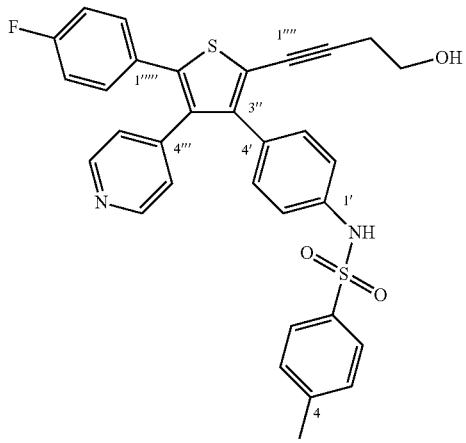 [SMILES: Cc1ccc(S(=O)(=O)Nc2ccc(-c3c(C#CCCO)sc(-c4ccc(F)cc4)c3-c3ccncc3)cc2)cc1]

Compound 3.46 was synthesised from compound 3.19 (119 mg, 0.174 mmol) following the general procedure for TBS deprotection. Purification by gradient column chromatography (20-100% ethyl acetate/petroleum spirits) followed by recrystallisation from methanol afforded compound 3.46 (68 mg, 69%) as white crystals. 3.46: $C_{32}H_{25}FN_2O_3S_2$ ($M_r$=568.68); mp 244.3-246.4° C.; $^1$H NMR (400 MHz, $d_6$-DMSO) (ppm) 10.24 (s, 1H), 8.34 (br. app. d, J=3.9 Hz, 2H), 7.59 (app. d, J=8.3 Hz, 2H), 7.33 (app. d, J=8.1 Hz, 2H), 7.21-7.13 (m, 4H), 6.99-6.94 (m, 4H), 6.87 (br. app. d, J=5.6 Hz, 2H), 4.90 (br. s, 1H), 3.45 (t, J=6.9 Hz, 2H), 2.51-2.46 (m, 2H), 2.36 (s, 3H); $^{13}$C NMR (101 MHz, $d_6$-DMSO) δ (ppm) 162.0 (d, $^1J_{CF}$=246.7 Hz), 149.4, 144.5, 143.3, 143.0, 138.6, 137.2, 136.5, 135.2, 131.3 (d, $^3J_{CF}$=8.4 Hz), 130.5, 129.7, 129.6, 128.7 (d, $^4J_{CF}$=3.2 Hz), 126.7, 125.4, 119.2, 119.1, 115.8 (d, $^2J_{CF}$=21.8 Hz), 95.6, 73.5, 59.4, 23.6, 21.0; ESI-HRMS-TOF calcd for $C_{32}H_{26}FN_2O_3S_{2+}$ (M+H)$^+$ 569.1363, found 569.1382; ESI-LCMS $R_t$=5.7 min, 569.2 (M+H)$^+$; RP-HPLC $R_t$=7.3 min, 95%.

3-(5-(4-Fluorophenyl)-2-(4-hydroxybut-1-yn-1-yl)-4-(pyridin-4-yl)thiophen-3-yl)benzonitrile (3.47)

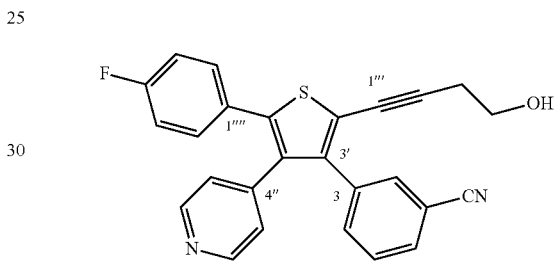

Compound 3.47 was synthesised from compound 3.20 (53 mg, 0.10 mmol) following the general procedure for TBS deprotection. Purification by column chromatography in 3% methanol/dichloromethane afforded compound 3.47 (40 mg, 96%) as a yellow solid. 3.47: $C_{26}H_{17}FN_2OS$ ($M_r$=424.49); mp 184.0-185.9° C.; $^1$H NMR (300 MHz, CD$_3$OD) δ (ppm) 8.34 (app. d, J=3.5 Hz, 2H), 7.65-7.61 (m, 2H), 7.46-7.39 (m, 2H), 7.25-7.21 (m, 2H), 7.07-7.01 (m, 4H), 3.65 (t, J=6.5 Hz, 2H), 2.59 (t, J=6.5 Hz, 2H); $^{13}$C NMR (76 MHz, CD$_3$OD) δ (ppm) 164.2 (d, $^1J_{CF}$=248.2 Hz), 150.1, 145.9, 144.1, 141.7, 137.5, 135.9, 135.8, 134.7, 132.7 (d, $^3J_{CF}$=8.4 Hz), 132.3, 130.3, 130.1 (d, $^4J_{CF}$=2.5 Hz), 127.5, 122.9, 119.3, 116.8 (d, $^2J_{CF}$=22.2 Hz), 113.3, 96.6, 74.2, 61.3, 24.5; ESI-HRMS-TOF calcd for $C_{26}H_{18}FN_2OS^+$ (M+H)$^+$ 425.1118, found 425.1118; ESI-LCMS $R_t$=5.5 min, 425.2 (M+H)$^+$; RP-HPLC $R_t$=7.2 min, 99%.

4-(5-(4-Fluorophenyl)-4-(pyridin-4-yl)-3-(m-tolyl)thiophen-2-yl)but-3-yn-1-ol (3.48)

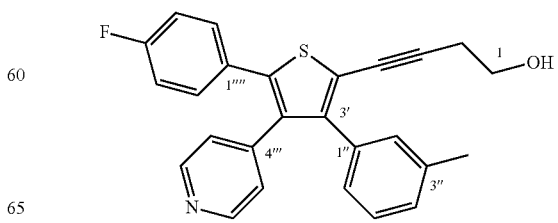

Compound 3.48 was synthesised from compound 3.21 (50 mg, 0.10 mmol) following the general procedure for TBS deprotection. Purification by column chromatography in 3% methanol/dichloromethane afforded thiophene 3.48 (37 mg, 94%) as a yellow powder. 3.48: $C_{26}H_{20}FNOS$ ($M_r$=413.51); mp 177.1-179.0° C.; $^1$H NMR (400 MHz, CD$_3$OD) δ (ppm) 8.30-8.28 (m, 2H), 7.24-7.19 (m, 2H), 7.14-7.00 (m, 5H), 6.98-6.96 (m, 2H), 6.89 (d, J=7.4 Hz, 1H), 3.63 (t, J=6.8 Hz, 2H), 2.57 (t, J=6.8 Hz, 2H), 2.24 (s, 3H); $^{13}$C NMR (101 MHz, CD$_3$OD) δ (ppm) 164.1 (d, $^1J_{CF}$=247.7 Hz), 149.8, 146.9, 146.6, 141.1, 138.8, 136.2, 136.0, 132.6 (d, $^3J_{CF}$=8.4 Hz), 131.8, 130.5 (d, $^4J_{CF}$=3.4 Hz), 129.3, 128.9, 128.2, 127.6, 121.6, 116.7 (d, $^2J_{CF}$=22.1 Hz), 95.2, 75.0, 61.4, 24.5, 21.3; ESI-HRMS-TOF calcd for $C_{26}H_{21}FNOS^+$ (M+H)$^+$ 414.1322, found 414.1317; ESI-LCMS R$_t$=5.5 min, 414.2 (M+H)$^+$; RP-HPLC R$_t$=7.0 min, 98%.

4-(3-(4-(Dimethylamino)phenyl)-5-(4-fluorophenyl)-4-(pyridin-4-yl)thiophen-2-yl)but-3-yn-1-ol (3.49)

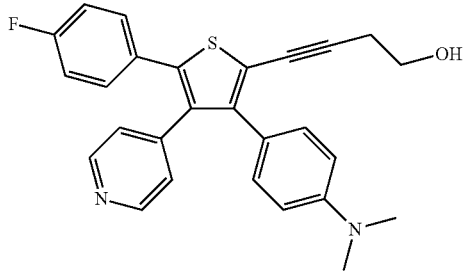 [SMILES: CN(C)c1ccc(-c2c(C#CCCO)sc(-c3ccc(F)cc3)c2-c2ccncc2)cc1]

Compound 3.49 was synthesised from compound 3.22 (63 mg, 0.11 mmol) following the general procedure for TBS deprotection. Purification by gradient column chromatography (20-50% EtOAc/hexane) afforded compound 3.49 (31 mg, 62%) as yellow powder. 3.49: $C_{27}H_{23}FN_2OS$ ($M_r$=442.55); $^1$H NMR (300 MHz, d$_6$-DMSO) δ (ppm) 8.40-8.38 (m, 2H), 7.22-7.12 (m, 4H), 6.96-6.93 (m, 4H), 6.57 (d, J=8.9 Hz, 2H), 4.88 (t, J=5.5 Hz, 1H), 3.52 (app. q, J=6.4 Hz, 2H), 2.87 (s, 6H), 2.55-2.49 (m, 2H); ESI-HRMS-TOF calcd for $C_{27}H_{24}FN_2OS^+$ (M+H)$^+$ 443.1588, found 443.1566.

4-(3,5-bis(4-Fluorophenyl)-4-(pyridin-4-yl)thiophen-2-yl)but-3-yn-1-ol (3.50)

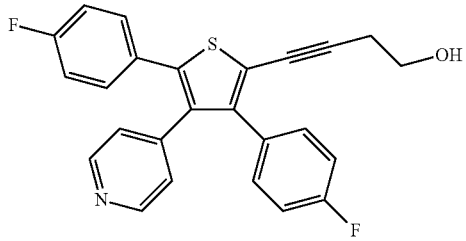 [SMILES: OCCC#Cc1sc(-c2ccc(F)cc2)c(-c2ccncc2)c1-c1ccc(F)cc1]

Compound 3.50 was synthesised from compound 3.23 (110 mg, 0.207 mmol) following the general procedure for TBS deprotection. Purification by gradient column chromatography (20-50% EtOAc/hexane) afforded compound 3.50 (81 mg, 94%) as yellow powder. 3.50: $C_{25}H_{17}F_2NOS$ ($M_r$=417.47); $^1$H NMR (300 MHz, CD$_3$OD) δ (ppm) 8.33-8.31 (m, 2H), 7.25-7.15 (m, 4H), 7.08-6.97 (m, 6H), 3.66 (t, J=6.8 Hz, 2H), 2.60 (t, J=6.8 Hz, 2H); $^{13}$C NMR (151 MHz, CD$_3$OD) δ (ppm) 164.1 (d, $^1J_{CF}$=247.8 Hz), 163.6 (d, $^1J_{CF}$=246.3 Hz), 149.9, 146.4, 145.6, 141.2, 136.1, 133.1 (d, $^3J_{CF}$=8.2 Hz), 132.6 (d, $^3J_{CF}$=8.5 Hz), 132.3 (d, $^4J_{CF}$=3.3 Hz), 130.4 (d, $^4J_{CF}$=3.4 Hz), 127.6, 122.0, 116.7 (d, $^2J_{CF}$=22.0 Hz), 115.9 (d, $^2J_{CF}$=21.8 Hz), 95.7, 74.7, 61.3, 24.5; ESI-HRMS-TOF calcd for $C_{25}H_{18}F_2NOS^+$ (M+H)$^+$ 418.1072, found 418.1063; RP-HPLC R$_t$=6.9 min, 95%.

4-(3-(4-Chlorophenyl)-5-(4-fluorophenyl)-4-(pyridin-4-yl)thiophen-2-yl)but-3-yn-1-ol (3.51)

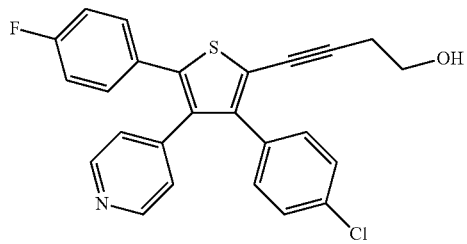 [SMILES: OCCC#Cc1sc(-c2ccc(F)cc2)c(-c2ccncc2)c1-c1ccc(Cl)cc1]

Compound 3.51 was synthesised from compound 3.24 (81 mg, 0.15 mmol) following the general procedure for TBS deprotection. Purification by gradient column chromatography (20-50% EtOAc/hexane) afforded compound 3.51 (60 mg, 94%) as yellow powder. 3.51: $C_{25}H_{17}ClFNOS$ ($M_r$=433.93); $^1$H NMR (400 MHz, DMSO) δ 8.42-8.40 (m, 2H), 7.37-7.33 (m, 2H), 7.24-7.13 (m, 6H), 6.96 (dd, J=4.4, 1.6 Hz, 2H), 4.89 (br. s, 1H), 3.50 (dd, J=10.2, 6.4 Hz, 2H), 2.54-2.49 (m, 2H); $^{13}$C NMR (101 MHz, DMSO) δ 162.0 (d, $^1J_{CF}$=246.8 Hz), 149.6, 143.6, 142.9, 138.9, 135.1, 133.0, 132.4, 131.5, 131.3 (d, $^3J_{CF}$=8.5 Hz), 128.6 (d, $^4J_{CF}$=3.1 Hz), 128.1, 125.5, 119.7, 115.9 (d, $^2J_{CF}$=21.9 Hz), 96.2, 73.2, 59.4, 23.6; ESI-HRMS-TOF calcd for $C_{25}H_{18}ClFNOS^+$ (M+H)$^+$ 434.0776, found 434.0784; RP-HPLC R$_t$=7.2 min, 95%.

4-(5-(4-Fluorophenyl)-4-(pyridin-4-yl)-3-(4-(trifluoromethyl)phenyl)thiophen-2-yl)but-3-yn-1-ol (3.52)

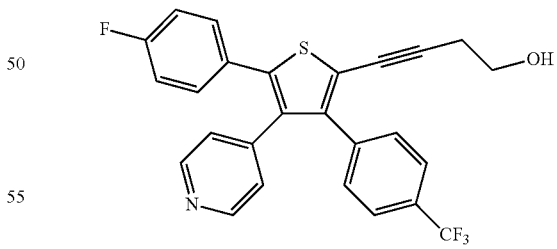

Compound 3.52 was synthesised from compound 3.25 (91 mg, 0.16 mmol) following the general procedure for TBS deprotection. Purification by gradient column chromatography (20-50% EtOAc/hexane) afforded compound 3.52 (58 mg, 79%) as yellow powder. 3.52: $C_{26}H_{17}F_4NOS$ ($M_r$=467.48); $^1$H NMR (300 MHz, CD$_3$OD) δ (ppm) 8.33 (br. app. d, J=5.1 Hz, 2H), 7.58 (app. d, J=8.3 Hz, 2H), 7.37 (app. d, J=8.1 Hz, 2H), 7.25-7.21 (m, 2H), 7.08-6.99 (m, 4H), 3.64 (t, J=6.7 Hz, 2H), 2.59 (t, J=6.7 Hz, 2H); $^{13}$C NMR (76 MHz, MeOH) δ 164.2 (d, $^1J_{CF}$=248.0 Hz), 150.1, 146.1, 144.9, 141.6, 140.1, 136.0, 132.7 (d, $^3J_{CF}$=8.5 Hz), 131.8, 130.6 (d, $^2J_{CF}$=32.3 Hz), 130.1 (d, $^4J_{CF}$=3.5 Hz), 127.5, 126.0 (q, $^3J_{CF}$=3.8 Hz), 125.6 (d, $^1J_{CF}$=271.2 Hz), 122.8, 116.8 (d, $^2J_{CF}$=22.1 Hz), 96.3, 74.3, 61.3, 24.5; ESI-HRMS-TOF calcd for $C_{26}H_{18}F_4NOS^+$ (M+H)$^+$ 468.1040, found 468.1051; RP-HPLC $R_t$=7.4 min, >99%.

1-(4-(5-(4-Fluorophenyl)-2-(4-hydroxybut-1-yn-1-yl)-4-(pyridin-4-yl)thiophen-3-yl)phenyl)ethanone (3.53)

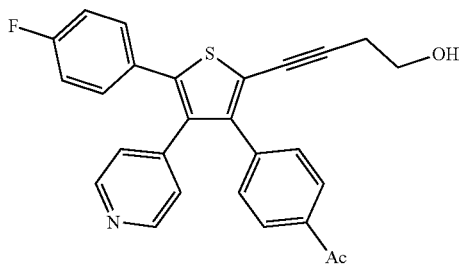 [SMILES: CC(=O)c1ccc(-c2c(C#CCCO)sc(-c3ccc(F)cc3)c2-c2ccncc2)cc1]

Compound 3.53 was synthesised from compound 3.26 (60 mg, 0.11 mmol) following the general procedure for TBS deprotection. Purification by gradient column chromatography (20-50% EtOAc/hexane) afforded compound 3.53 (31 mg, 65%) as yellow powder. 3.53: $C_{27}H_{20}FNO_2S$ ($M_r$=441.52); $^1$H NMR (300 MHz, CD$_3$OD) δ (ppm) 8.31 (br. app. d, J=5.3 Hz, 2H), 7.92-7.88 (m, 2H), 7.34-7.30 (m, 2H), 7.26-7.20 (m, 2H), 7.09-6.99 (m, 4H), 3.64 (t, J=6.7 Hz, 2H), 2.60-2.56 (m, 2H); $^{13}$C NMR (151 MHz, CD$_3$OD) δ (ppm) 199.9, 164.2 (d, $^1J_{CF}$=248.0 Hz), 150.0, 146.1, 145.3, 141.7, 141.1, 137.3, 135.9, 132.7 (d, $^3J_{CF}$=8.3 Hz), 131.5, 130.2 (d, $^4J_{CF}$=3.3 Hz), 129.2, 127.5, 122.6, 116.8 (d, $^2J_{CF}$=22.1 Hz), 96.3, 74.5, 61.3, 26.7, 24.5; ESI-HRMS-TOF calcd for $C_{27}H_{21}FNO_2S^+$ (M+H)$^+$ 442.1272, found 442.1288; RP-HPLC $R_t$=6.6 min, 95%.

4-(5-(4-Fluorophenyl)-2-(4-hydroxybut-1-yn-1-yl)-4-(pyridin-4-yl)thiophen-3-yl)phenol (3.54)

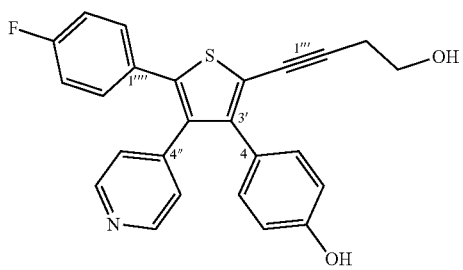 [SMILES: OCCC#Cc1sc(-c2ccc(F)cc2)c(-c2ccncc2)c1-c1ccc(O)cc1]

Compound 3.54 was synthesised from compound 3.27 (53 mg, 0.10 mmol) following the general procedure for TBS deprotection. Purification by column chromatography in 3% methanol/dichloromethane afforded compound 3.54 (40 mg, 96%) as a white powder. 3.54: $C_{25}H_{28}FNO_2S$ ($M_r$=415.48); mp 248.1-251.0° C.; $^1$H NMR (300 MHz, d$_6$-DMSO) δ (ppm) 9.53 (s, 1H), 8.37 (app. d, J=4.3 Hz, 2H), 7.21-7.11 (m, 4H), 6.98-6.87 (m, 4H), 6.62 (app. d, J=8.5 Hz, 2H), 4.87 (t, J=5.5 Hz, 1H), 3.48 (app. q, J=6.7 Hz, 2H), 2.52-2.48 (m, 2H); $^{13}$C NMR (76 MHz, CD$_3$OD) δ (ppm) 162.0 (d, $^1J_{CF}$=246.8 Hz), 156.9, 149.5, 145.2, 143.4, 138.5, 135.4, 131.4 (d, $^3J_{CF}$=8.4 Hz), 130.9, 129.0 (d, $^4J_{CF}$=2.4 Hz), 125.6, 124.8, 118.4, 115.9 (d, $^2J_{CF}$=21.8 Hz), 114.9, 95.2, 73.9, 59.6, 23.7; ESI-HRMS-TOF calcd for $C_{25}H_{19}FNO_2S^+$ (M+H)$^+$ 416.1115, found 416.1120; ESI-LCMS $R_t$=5.1 min, 416.2 (M+H)$^+$; RP-HPLC $R_t$=6.6 min, 99%.

4-(5-(4-Fluorophenyl)-3-iodo-4-(pyridin-4-yl)thiophen-2-yl)but-3-yn-1-ol (3.55)

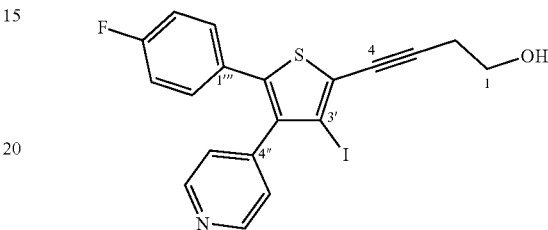

Compound 3.55 was synthesised from compound 3.6 (155 mg, 0.275 mmol) following the general procedure for TBS deprotection. Purification by gradient column chromatography (0-10% methanol/chloroform) followed by recrystallisation from methanol afforded compound 3.55 (117 mg, 95%) as a yellow crystals. 3.55: $C_{19}H_{13}FINOS$ ($M_r$=449.28); mp 187.2-189.3° C.; $^1$H NMR (400 MHz, d$_6$-DMSO) δ (ppm) 8.61-8.59 (m, 2H), 7.22-7.12 (m, 6H), 4.98 (t, J=5.6 Hz, 1H), 3.63 (td, J=6.8, 5.7 Hz, 2H), 2.67 (t, J=6.8 Hz, 2H); $^{13}$C NMR (101 MHz, d$_6$-DMSO) δ (ppm) 162.1 (d, $^1J_{CF}$=247.2 Hz), 149.8, 144.3, 139.2, 138.9, 131.0 (d, $^3J_{CF}$=8.6 Hz), 128.2 (d, $^4J_{CF}$=3.3 Hz), 125.5, 124.2, 115.9 (d, $^2J_{CF}$=21.9 Hz), 97.6, 94.8, 75.1, 59.5, 23.8; ESI-HRMS-TOF calcd for $C_{19}H_{14}FINOS^+$ (M+H)$^+$ 449.9819, found 449.9833; ESI-LCMS $R_t$=5.4 min, 450.0 (M+H)$^+$; RP-HPLC $R_t$=6.5 min, 99%.

4-(5-(4-((tert-Butyldimethylsilyl)oxy)but-1-yn-1-yl)-2-(4-fluorophenyl)thiophen-3-yl)pyridine (4.3)

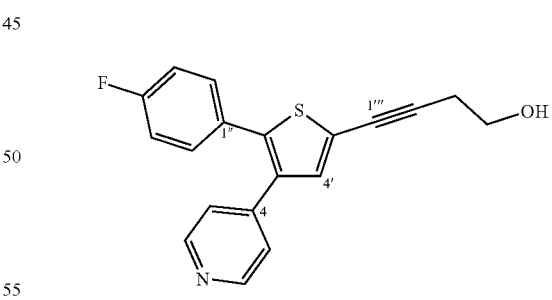

To a solution of thiophene 3.6 (50 mg, 0.089 mmol) in anhydrous tetrahydrofuran (1 mL) was added isopropylmagnesium chloride lithium chloride complex solution (0.83 M in tetrahydrofuran, 0.12 mL, 0.10 mmol) at −78° C. The reaction mixture was stirred for 1 hour at −78° C. Methanol (1 mL) was added and the mixture was diluted with diethyl ether (10 mL), washed with water (3×10 mL) and aqueous layer further extracted with diethyl ether (3×10 mL). The organic layers were dried over magnesium sulfate, filtered and concentrated in vacuo. The crude product was purified by gradient column chromatography (0-50% ethyl acetate/ petroleum spirits) to give compound 4.3 as a yellow oil (30 mg, 77%). 4.3: $C_{25}H_{28}FNOSSi$ ($M_r$=437.65); $^1$H NMR (400 MHz, CDCl$_3$) δ (ppm) 8.51 (app. d, J=5.8 Hz, 2H), 7.25-7.19 (m, 2H), 7.17 (s, 1H), 7.12-7.10 (m, 2H), 7.03-6.97 (m, 2H), 3.83 (t, J=6.9 Hz, 2H), 2.68 (t, J=6.9 Hz, 2H), 0.93 (s, 9H), 0.11 (s, 6H); $^{13}$C NMR (100 MHz, CDCl$_3$) δ (ppm) 162.9 (d, $^1J_{CF}$=247.9 Hz), 150.2, 143.5, 140.1, 135.0, 133.3, 131.3 (d, $^3J_{CF}$=8.2 Hz), 129.1 (d, $^4J_{CF}$=3.4 Hz), 123.8, 123.7, 116.1 (d, $^2J_{CF}$=21.7 Hz), 93.4, 74.1, 61.6, 26.1, 24.3, 18.5, −5.1; ESI-HRMS-TOF calcd for $C_{25}H_{29}FNOSSi^+$ (M+H)$^+$ 438.1718, found 438.1724.

1-(2-(4-((tert-Butyldimethylsilyl)oxy)but-1-yn-1-yl)-5-(4-fluorophenyl)-4-(pyridin-4-yl)thiophen-3-yl)-3-phenylpropan-1-ol (4.4)

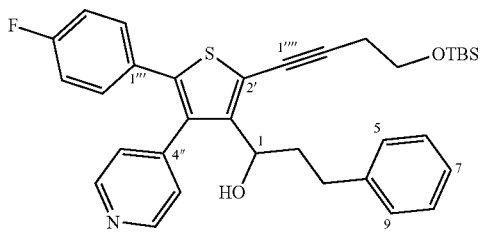 [SMILES: CC(C)(C)[Si](C)(C)OCCC#Cc1sc(-c2ccc(F)cc2)c(-c2ccncc2)c1C(O)CCc1ccccc1]

To a solution of thiophene 3.6 (0.22 g, 0.39 mmol) in tetrahydrofuran (0.4 mL) was added isopropylmagnesium chloride lithium chloride complex solution (0.83 M in tetrahydrofuran, 0.53 mL) at −78° C. The reaction mixture was stirred at −78° C. for 30 minutes. Hydrocinnamaldehyde (55 μL, 0.42 mmol) was added and the reaction mixture was stirred at 0° C. for 1 hour. Saturated ammonium chloride was added and the mixture was extracted with diethyl ether, dried over magnesium sulfate, filtered and concentrated in vacuo. The resulting oil was purified by flash chromatography using gradient elution (0-70% ethyl acetate/hexane) to afford compound 4.4 as a yellow oil (0.14 g, 64%). 4.4: $C_{34}H_{38}FNO_2SSi$ ($M_r$=571.83); $^1$H NMR (400 MHz, CDCl$_3$) (ppm) 8.46-8.45 (m, 2H), 7.24-7.14 (m, 3H), 7.06-7.01 (m, 4H), 6.99-6.97 (m, 2H), 6.93-6.82 (m, 2H), 4.54 (td, J=8.8, 5.2 Hz, 1H), 3.83 (t, J=6.6 Hz, 2H), 2.70 (t, J=6.6 Hz, 2H), 2.69-2.52 (m, 2H), 2.29-2.18 (m, 1H), 2.04-1.95 (m, 1H), 0.93 (s, 9H), 0.11 (s, 6H); $^{13}$C NMR (101 MHz, CDCl$_3$) δ (ppm) 162.5 (d, $^1J_{CF}$=247.7 Hz), 149.8, 147.6, 144.1, 141.4, 140.0, 135.0, 131.0 (d, $^3J_{CF}$=8.1 Hz), 128.9 (d, $^4J_{CF}$=3.3 Hz), 128.4 (s, 2C), 126.0, 125.7, 119.5, 115.7 (d, $^2J_{CF}$=21.6 Hz), 97.9, 73.6, 68.8, 61.6, 38.6, 32.2, 26.0, 24.5, 18.4, −5.1; ESI-HRMS-TOF calcd for $C_{34}H_{39}FNO_2SSi^+$ (M+H)$^+$ 572.2449, found 572.2462; ESI-LCMS R$_t$=7.2 min, 572.3 (M+H)$^+$; RP-HPLC R$_t$=11.9 min, 96%.

4-(5-(4-Fluorophenyl)-4-(pyridin-4-yl)thiophen-2-yl)but-3-yn-1-ol (4.5)

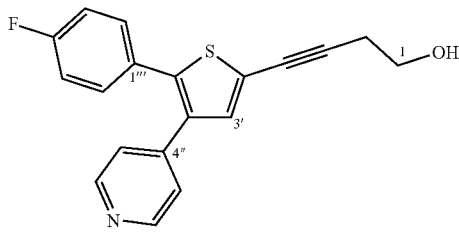 [SMILES: OCCC#Cc1cc(-c2ccncc2)c(-c2ccc(F)cc2)s1]

T To a solution of aryl iodide 5.1 (2.57 g, 6.74 mmol) in tetrahydrofuran (26 mL) was added 3-butyn-1-ol (0.77 mL, 10 mmol), triphenylphosphine (18 mg, 0.07 mmol), copper (I) iodide (64 mg, 0.34 mmol) and triethylamine (9.4 mL, 67 mmol). The reaction mixture was bubbled with nitrogen for 15 minutes. Bis(triphenylphosphine)palladium(II) dichloride (237 mg, 0.338 mmol) was added and the reaction mixture was refluxed for 2 hours. The reaction mixture was diluted with ethyl acetate (10 mL) and washed with water (3×10 mL) and brine (10 mL), dried over magnesium sulfate, filtered and concentrated in vacuo. The resulting crude product was purified by gradient column chromatography (50-100% ethyl acetate/petroleum spirits) to afford compound 4.5 (1.90 g, 87%) as a yellow solid. Recrystallisation from methanol gave white crystals. 4.5: $C_{19}H_{14}FNOS$ ($M_r$=323.39); mp 153.2-155.7° C.; $^1$H NMR (400 MHz, CDCl$_3$) δ (ppm) 8.52-8.50 (m, 2H), 7.25-7.20 (m, 3H), 7.12-7.10 (m, 2H), 7.03-6.97 (m, 2H), 3.84 (app. q, J=5.5 Hz, 2H), 2.75 (t, J=6.3 Hz, 2H), 1.82 (br. s, 1H); $^{13}$C NMR (101 MHz, CDCl$_3$) δ (ppm) 162.8 (d, $^1J_{CF}$=249.4 Hz), 149.9, 143.6, 140.3, 134.8, 133.4, 131.1 (d, $^3J_{CF}$=8.2 Hz), 128.8 (d, $^4J_{CF}$=3.5 Hz), 123.6, 123.4, 116.0 (d, $^2J_{CF}$=21.8 Hz), 93.1, 74.4, 60.8, 24.3; ESI-HRMS-TOF calcd for $C_{19}H_{15}FNOS^+$ (M+H)$^+$ 324.0853, found 324.0862; ESI-LCMS R$_t$=4.9 min, 324.2 (M+H)$^+$; RP-HPLC R$_t$=6.3 min, 96%.

4-(5-(4-Fluorophenyl)-3-(1-hydroxy-3-phenylpropyl)-4-(pyridin-4-yl)thiophen-2-yl)but-3-yn-1-ol (4.6)

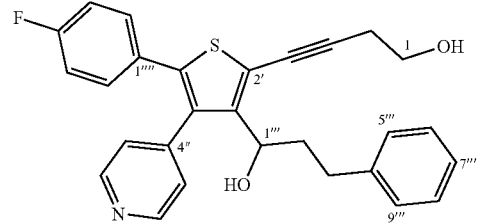 [SMILES: OCCC#Cc1sc(-c2ccc(F)cc2)c(-c2ccncc2)c1C(O)CCc1ccccc1]

Compound 4.6 was synthesised from compound 4.4 (44 mg, 0.08 mmol) following the general procedure for TBS deprotection. Purification by gradient column chromatography (0-5% methanol/dichloromethane) afforded 4.6 as a yellow oil (35 mg, 99%). 4.6: $C_{28}H_{24}FNO_2S$ ($M_r$=457.56); $^1$H NMR (400 MHz, CDCl$_3$) δ (ppm) 8.46-8.45 (m, 2H), 7.26-7.15 (m, 3H), 7.08-7.01 (m, 4H), 6.96-6.94 (m, 2H), 6.92-6.86 (m, 2H), 4.53 (dd, J=9.1, 4.6 Hz, 1H), 3.85 (t, J=5.9 Hz, 2H), 2.74 (t, J=5.6 Hz, 2H, 2.73-2.67 (m, 1H), 2.62-2.55 (m, 1H), 2.40-2.30 (m, 1H), 2.04-1.95 (m, 1H); $^{13}$C NMR (101 MHz, CDCl$_3$) δ (ppm) 162.6 (d, $^1J_{CF}$=249.2 Hz), 150.0, 148.1, 143.9, 141.3, 139.8, 134.9, 131.0 (d, $^3J_{CF}$=8.2 Hz), 128.9 (d, $^4J_{CF}$=3.4 Hz), 128.533, 128.526, 126.1, 125.6, 119.3, 115.9 (d, $^2J_{CF}$=21.8 Hz), 97.6, 75.0, 68.8, 61.1, 38.5, 32.2, 24.5; ESI-HRMS-TOF calcd for $C_{28}H_{25}FNO_2S^+$ (M+H)$^+$ 458.1585, found 458.1599; ESI-LCMS R$_t$=5.5 min, 458.2 (M+H)$^+$; RP-HPLC R$_t$=7.2 min, >99%.

4-(2-(4-Fluorophenyl)-4-iodothiophen-3-yl)pyridine (4.16)

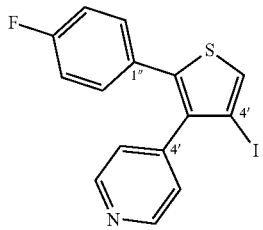 [SMILES: Fc1ccc(-c2scc(I)c2-c2ccncc2)cc1]

To a solution of thiophene 3.3 (0.20 g, 0.39 mmol) in anhydrous tetrahydrofuran (5 mL) was added isopropylmagnesium chloride lithium chloride complex solution (0.95 M in tetrahydrofuran, 0.45 mL, 0.43 mmol) at −78° C. The reaction mixture was stirred at −78° C. for 1 hour. Methanol (5 mL) was added and the mixture was concentrated in vacuo. The crude product was diluted with diethyl ether (10 mL), washed with water (10 mL) and extracted with diethyl ether (3×10 mL). The organic layers were dried over magnesium sulfate, filtered and concentrated in vacuo. Purification by flash column chromatography using gradient elution (0-50% ethyl acetate/petroleum spirits) gave compound 4.16 (0.14 g, 95%) as a yellow powder. 4.16: $C_{15}H_9FINS$ ($M_r$=381.21); mp 129.3-131.9° C.; $^1$H NMR (400 MHz, CDCl$_3$) δ (ppm) 8.60-8.58 (app. d, J=4.5 Hz, 2H), 7.53 (s, 1H), 7.13-7.07 (m, 4H), 6.94-6.89 (m, 2H); $^{13}$C NMR (101 MHz, CDCl$_3$) δ (ppm) 162.7 (d, $^1J_{CF}$=249.3 Hz), 149.9, 144.6, 140.3, 138.2, 130.9 (d, $^3J_{CF}$=8.3 Hz), 128.8 (d, $^4J_{CF}$=3.4 Hz), 128.6, 125.8, 115.8 (d, $^2J_{CF}$=21.8 Hz), 83.2; ESI-HRMS-TOF calcd for $C_{15}H_{10}FINS^+$ (M+H)$^+$ 381.9557, found 381.9559; ESI-LCMS $R_t$=5.9 min, 382.0 (M+H)$^+$; RP-HPLC $R_t$=7.2 min, 95%.

4-(2-(4-Fluorophenyl)-4-(3-phenylprop-1-yn-1-yl)thiophen-3-yl)pyridine (4.19)

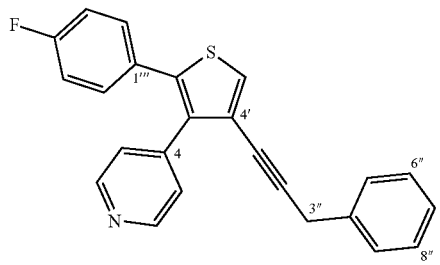 [SMILES: Fc1ccc(-c2scc(C#CCc3ccccc3)c2-c2ccncc2)cc1]

Compound 4.16 (0.55 g, 1.4 mmol) was dissolved in tetrahydrofuran (5.5 mL). Copper(I) iodide (15 mg, 0.079 mmol), triphenylphosphine (8 mg, 0.001 mmol), 3-phenyl-1-propyne (0.27 mL, 2.2 mmol) and triethylamine (5.5 mL) were added. The reaction mixture was bubbled with nitrogen for 30 minutes. Bis(triphenylphosphine)palladium(II) dichloride (60 mg, 0.085 mmol) was added and the reaction mixture was heated at reflux for 4 hours. Water (20 mL) was added and the mixture was extracted with ethyl acetate (3×20 mL). The organic layers were concentrated in vacuo and the product was purified by flash column chromatography using gradient elution (0-40% ethyl acetate/petroleum spirits) to give compound 4.19 as a yellow oil (0.15 g, 28%). 4.19: $C_{24}H_{16}FNS$ ($M_r$=369.46); $^1$H NMR (400 MHz, CDCl$_3$) δ (ppm) 8.49-8.48 (m, 2H), 7.49 (s, 1H), 7.29-7.13 (m, 9H), 6.99-6.93 (m, 2H), 3.71 (s, 2H); $^{13}$C NMR (101 MHz, CDCl$_3$) δ (ppm) 162.7 (d, $^1J_{CF}$=248.9 Hz), 149.6, 143.4, 140.1, 136.4, 136.3, 131.2 (d, $^3J_{CF}$=8.2 Hz), 129.3 (d, $^4J_{CF}$=3.4 Hz), 128.7, 128.1, 128.0, 126.9, 125.3, 124.0, 116.0 (d, $^2J_{CF}$=21.8 Hz), 89.8, 77.4, 25.9; ESI-HRMS-TOF calcd for $C_{24}H_{17}FNS^+$ (M+H)$^+$ 370.1060, found 370.1068; ESI-LCMS $R_t$=5.9 min, 370.2 (M+H)$^+$; RP-HPLC $R_t$=8.4 min, 95%.

4-(2-(4-Fluorophenyl)-4-(3-phenylpropyl)thiophen-3-yl)pyridine (4.18)

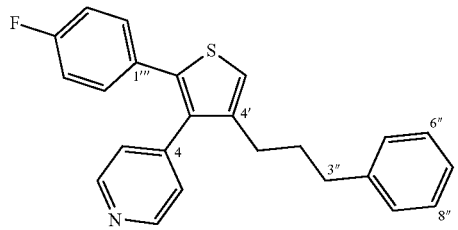 [SMILES: Fc1ccc(-c2scc(CCCc3ccccc3)c2-c2ccncc2)cc1]

To a dry three-neck round bottom flask was added a solution of thiophene 4.19 (105 mg, 0.284 mmol) in ethanol (20 mL). The round bottom flask was evacuated and flushed with nitrogen. Palladium on carbon (10% w/w, approx. 10 mg) was added and the round bottom flask was evacuated and flushed with nitrogen three times, then evacuated and flushed with hydrogen three times. The reaction mixture was stirred at room temperature for 3 days under hydrogen. The product was filtered through celite and the solvent was evaporated in vacuo to afford thiophene 4.18 (106 mg, quant.) as a yellow oil. 4.18: $C_{24}H_{20}FNS$ ($M_r$=373.49); $^1$H NMR (400 MHz, CDCl$_3$) δ (ppm) 8.54-8.53 (m, 2H), 7.27-7.23 (m, 2H), 7.19-7.16 (m, 1H), 7.13-7.05 (m, 7H), 6.93-6.88 (m, 2H), 2.57 (t, J=7.6 Hz, 2H), 2.50 (t, J=7.8 Hz, 2H), 1.79 (app. p, J=7.7 Hz, 2H); $^{13}$C NMR (101 MHz, CDCl$_3$) δ (ppm) 162.2 (d, $^1J_{CF}$=248.1 Hz), 149.9, 145.1, 142.2, 141.8, 140.3, 135.8, 130.9 (d, $^3J_{CF}$=8.1 Hz), 129.9 (d, $^4J_{CF}$=3.4 Hz), 128.39, 128.35, 125.9, 125.3, 120.4, 115.6 (d, $^2J_{CF}$=21.6 Hz), 35.4, 31.4, 29.1; ESI-HRMS-TOF calcd for $C_{24}H_{21}FNS^+$ (M+H)$^+$ 374.1373, found 374.1380; ESI-LCMS $R_t$=6.1 min, 374.2 (M+H)$^+$; RP-HPLC $R_t$=8.7 min, 97%.

4-(2-(4-Fluorophenyl)-5-iodo-4-(3-phenylpropyl)thiophen-3-yl)pyridine (4.20)

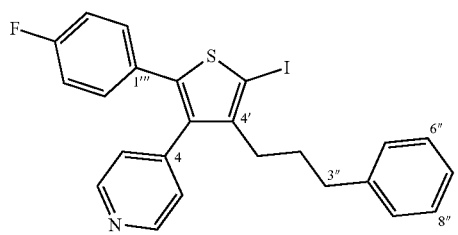 [SMILES: Fc1ccc(-c2sc(I)c(CCCc3ccccc3)c2-c2ccncc2)cc1]

To a solution of compound 4.18 (81 mg, 0.22 mmol) in acetonitrile (3 mL) was added iodine (65 mg, 0.26 mmol).

The reaction mixture was stirred until the iodine had dissolved. Silver nitrate (48 mg, 0.28 mmol) was added to the solution resulting in formation of a yellow precipitate. The reaction mixture was stirred at room temperature for 1 hour and the precipitate filtered. The resulting filtrate was evaporated in vacuo and the crude product was diluted with ethyl acetate (20 mL), washed with saturated sodium thiosulfate (20 mL) and extracted with ethyl acetate (3×20 mL). The combined organic layers were dried over magnesium sulfate, filtered and concentrated in vacuo to give compound 4.20 (108 mg, quant.). Recrystallisation in methanol afforded the desired compound 4.20 as yellow crystals. 4.20: $C_{24}H_{19}FINS$ ($M_r$=499.39); mp 140.1-141.9; $^1$H NMR (400 MHz, $d_6$-DMSO+NaOH) δ (ppm) 8.51-8.50 (m, 2H), 7.21-7.08 (m, 9H), 6.99-6.97 (m, 2H), 2.46-2.37 (m, 4H), 1.56-1.49 (m, 2H); $^{13}$C NMR (101 MHz, $d_6$-DMSO) δ (ppm) 161.8 (d, $^1J_{CF}$=246.1 Hz), 149.9, 145.7, 143.7 (2C), 141.1, 136.1, 130.8 (d, $^3J_{CF}$=8.4 Hz), 129.1 (d, $^4J_{CF}$=3.2 Hz), 128.3, 128.1, 125.8, 125.1, 115.8 (d, $^2J_{CF}$=21.8 Hz), 77.6, 34.8, 30.4, 30.3; ESI-HRMS-TOF calcd for $C_{24}H_{20}FINS^+$ (M+H)$^+$ 500.0340, found 500.0360; ESI-LCMS $R_t$=6.8 min, 500.1 (M+H)$^+$; RP-HPLC $R_t$=10.1 min, 99%. Nb. NaOH added to $d_6$-DMSO sample to remove broadening of the pyridyl proton signals.

4-(5-(4-((tert-Butyldimethylsilyl)oxy)but-1-yn-1-yl)-2-(4-fluorophenyl)-4-(3-phenylpropyl)thiophen-3-yl)pyridine (4.2)

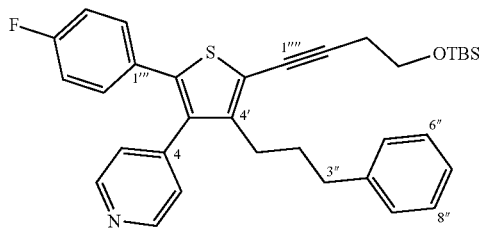 [SMILES: CC(C)(C)[Si](C)(C)OCCC#Cc1sc(-c2ccc(F)cc2)c(-c2ccncc2)c1CCCc1ccccc1]

Compound 4.20 (80 mg, 0.16 mmol) was dissolved in tetrahydrofuran (1 mL). Copper(I) iodide (3 mg, 0.02 mmol), triphenylphosphine (1 mg, 0.004 mmol), alkyne 3.5 (19 μL, 0.24 mmol) and triethylamine (1 mL) were added. The reaction mixture was bubbled with nitrogen for 15 minutes. Bis(triphenylphosphine)palladium(II) dichloride (8 mg, 0.01 mmol) was added and the reaction mixture was heated at reflux for 2 hours. Water (10 mL) was added and the mixture was extracted with ethyl acetate (3×10 mL). The organic layers were concentrated in vacuo and the product was purified by column chromatography using gradient elution (0-40% ethyl acetate/petroleum spirits) to give compound 4.2 as a yellow solid (52 mg, 58%). 4.2: $C_{34}H_{38}FNOSSi$ ($M_r$=555.83); $^1$H NMR (400 MHz, CDCl$_3$) δ (ppm) 8.52 (br. s, 2H), 7.24-7.20 (m, 2H), 7.17-7.13 (m, 1H), 7.08-7.00 (m, 6H), 6.92-6.86 (m, 2H), 3.82 (t, J=7.0 Hz, 2H), 2.68 (t, J=7.0 Hz, 2H), 2.60-2.56 (m, 2H), 2.51 (t, J=7.4 Hz, 2H), 1.71-1.62 (m, 2H), 0.93 (s, 9H), 0.11 (s, 6H); $^{13}$C NMR (101 MHz, CDCl$_3$) δ (ppm) 162.4 (d, $^1J_{CF}$=248.6 Hz), 150.1, 146.0, 144.8, 141.8, 139.2, 135.6, 130.9 (d, $^3J_{CF}$=8.1 Hz), 129.4 (d, $^4J_{CF}$=3.5 Hz), 128.4 (2C), 125.9, 125.2, 119.5, 115.7 (d, $^2J_{CF}$=21.7 Hz), 95.2, 74.0, 61.9, 35.6, 31.2, 28.2, 26.0, 24.4, 18.5, −5.1; ESI-HRMS-TOF calcd for $C_{34}H_{39}FNOSSi^+$ (M+H)$^+$ 556.2500, found 556.2508; ESI-LCMS $R_t$=8.5 min, 556.3 (M+H)$^+$; RP-HPLC $R_t$=12.8 min, 99%.

4-(5-(4-Fluorophenyl)-3-(3-phenylpropyl)-4-(pyridin-4-yl)thiophen-2-yl)but-3-yn-1-ol (4.1)

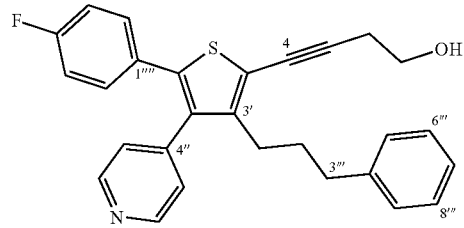 [SMILES: OCCC#Cc1sc(-c2ccc(F)cc2)c(-c2ccncc2)c1CCCc1ccccc1]

Compound 4.1 was synthesised from compound 4.2 (46 mg, 0.083 mmol) following the general procedure for TBS deprotection. Purification by column chromatography in 50% ethyl acetate/petroleum spirits afforded 4.1 (35 mg, 96%) as a yellow solid. 4.1: $C_{28}H_{24}FNOS$ ($M_r$=441.56); $^1$H NMR (400 MHz, CDCl$_3$) δ (ppm) 8.54 (br. s, 2H), 7.25-7.21 (m, 2H), 7.18-7.14 (m, 1H), 7.08-7.00 (m, 6H), 6.92-6.86 (m, 2H), 3.80 (br. s, 2H), 2.74 (t, J=6.3 Hz, 2H), 2.60-2.56 (m, 2H), 2.52 (t, J=7.4 Hz, 1H), 1.85 (br. s, 1H), 1.72-1.63 (m, 2H); $^{13}$C NMR (101 MHz, CDCl$_3$) δ (ppm) 162.5 (d, $^1J_{CF}$=248.9 Hz), 150.0, 146.3, 144.8, 141.7, 139.5, 135.5, 130.9 (d, $^3J_{CF}$=8.2 Hz), 129.2 (d, $^4J_{CF}$=3.4 Hz), 128.4 (2C), 125.9, 125.3, 119.1, 115.7 (d, $^2J_{CF}$=21.7 Hz), 94.5, 74.6, 61.1, 35.6, 31.2, 28.2, 24.4; ESI-HRMS-TOF calcd for $C_{28}H_{25}FNOS^+$ (M+H)$^+$ 442.1635, found 442.1625; ESI-LCMS $R_t$=5.8 min, 442.2 (M+H)$^+$; RP-HPLC $R_t$=8.5 min, 99%.

1-(5-(4-Fluorophenyl)-4-(pyridin-4-yl)thiophen-3-yl)-3-phenylpropan-1-ol (4.17)

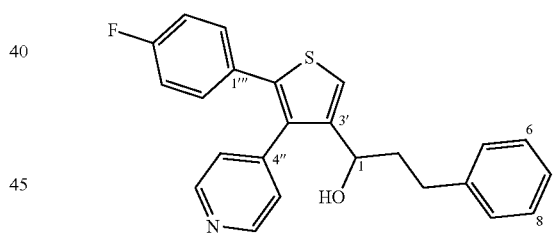

To a solution of thiophene 4.16 (97 mg, 0.25 mmol) in anhydrous tetrahydrofuran (1 mL) was added isopropylmagnesium chloride lithium chloride complex solution (1.2 M in THF, 0.24 mL, 0.29 mmol) at −78° C. The reaction mixture was stirred at −78° C. for 30 minutes. Hydrocinnamaldehyde (36 μL, 0.28 mmol) was added and the mixture was stirred at 0° C. for 1 hour. Saturated ammonium chloride (5 mL) was added and the mixture was extracted with ethyl acetate (3×5 mL). The organic layers were dried over magnesium sulfate, filtered and concentrated in vacuo. The crude product was purified by gradient column chromatography (20-60% ethyl acetate/petroleum spirits) to give compound 4.17 (62 mg, 63%) as a yellow oil. 4.17: $C_{24}H_{20}FNOS$ ($M_r$=389.49); $^1$H NMR (400 MHz, CDCl$_3$) δ 8.49-8.47 (m, 2H), 7.41 (d, J=0.6 Hz, 1H), 7.25-7.13 (m, 3H), 7.12-7.06 (m, 2H), 7.06-7.00 (m, 4H), 6.94-6.87 (m, 2H), 4.56 (app. dd, J=8.4, 4.4 Hz, 1H), 2.78-2.54 (m, 2H), 2.06-1.85 (m, 2H), 1.66 (br. s, 1H); $^{13}$C NMR (101 MHz, CDCl$_3$) δ (ppm) 162.4 (d, $^1J_{CF}$=248.5 Hz), 149.7, 145.8, 144.7, 141.4, 141.1, 134.5, 131.0 (d, $^3J_{CF}$=8.1 Hz), 129.6 (d, $^4J_{CF}$=3.5 Hz), 128.5, 128.4, 126.0, 125.5, 121.1, 115.7 (d, $^2J_{CF}$=21.7 Hz), 67.7, 39.5, 32.1; ESI-HRMS-TOF calcd for $C_{24}H_{21}FNOS^+$ (M+H)$^+$ 390.1322, found 390.1342; ESI-LRMS 390.4 (M+H)$^+$; ESI-LCMS $R_t$=5.3 min, 390.2 (M+H)$^+$; RP-HPLC $R_t$=7.9 min, 93%.

4-(2-(4-Fluorophenyl)-5-iodothiophen-3-yl)pyridine (5.1)

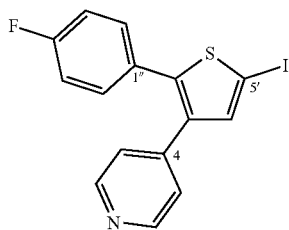 [SMILES: Fc1ccc(-c2sc(I)cc2-c2ccncc2)cc1]

To a solution of compound 3.2 (2.88 g, 11.3 mmol) in acetonitrile (87 mL) was added iodine (3.15 g, 12.4 mmol). Silver nitrate (2.30 g, 13.6 mmol) was added to the suspension resulting in formation of a yellow precipitate. The reaction mixture was stirred at room temperature for 16 hours. The reaction mixture was filtered and the resulting filtrate was evaporated in vacuo. Chloroform (100 mL) was added and the mixture was washed with aqueous sodium thiosulfate (100 mL). The organic layer was evaporated in vacuo and the crude compound was purified by column chromatography in diethyl ether to afford compound 5.1. Recrystallisation in methanol afforded the desired compound 5.1 (3.20 g, 74%) as white crystals. 5.1: $C_{15}H_9FINS$ ($M_r$=381.21); mp 147.6-149.4° C.; $^1H$ NMR (400 MHz, CDCl$_3$) δ (ppm) 8.52-8.50 (m, 2H), 7.32 (s, 1H), 7.22-7.17 (m, 2H), 7.11-7.09 (m, 2H), 7.03-6.98 (m, 2H); $^{13}C$ NMR (101 MHz, CDCl$_3$) δ (ppm) 163.0 (d, $^1J_{CF}$=249.4 Hz), 150.2, 145.8, 142.6, 139.0, 137.2, 131.1 (d, $^3J_{CF}$=8.2 Hz), 128.6 (d, $^4J_{CF}$=3.5 Hz), 123.5, 116.1 (d, $^2J_{CF}$=21.8 Hz), 73.2; ESI-HRMS-TOF calcd for $C_{15}H_{10}FINS^+$ (M+H)$^+$ 381.9557, found 381.9568; ESI-LCMS $R_t$=5.6 min, 381.9 (M+H)$^+$; RP-HPLC $R_t$=6.8 min, 99%.

3-(5-(4-Fluorophenyl)-4-(pyridin-4-yl)thiophen-2-yl) prop-2-yn-1-ol (5.2)

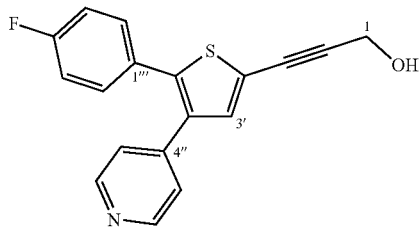 [SMILES: OCC#Cc1cc(-c2ccncc2)c(-c2ccc(F)cc2)s1]

To a solution of aryl iodide 5.1 (500 mg, 1.31 mmol) in tetrahydrofuran (5 mL) was added propargyl alcohol (116 μL, 1.97 mmol), triphenylphosphine (3 mg, 0.01 mmol), copper(I) iodide (13 mg, 0.068 mmol) and triethylamine (5.0 mL, 36 mmol). The reaction mixture was bubbled with nitrogen for 15 minutes. Bis(triphenylphosphine)palladium (II) dichloride (46 mg, 0.066 mmol) was added and the reaction mixture was refluxed for 2 hours. The reaction mixture was diluted with ethyl acetate (10 mL) and washed with water (3×10 mL), brine (10 mL), dried over magnesium sulfate, filtered and concentrated in vacuo. The resulting crude product was purified by column chromatography in 50% ethyl acetate/petroleum spirits to afford compound 5.2 (308 mg, 76%) as a yellow foam. 5.2: $C_{18}H_{12}FNOS$ ($M_r$=309.36); $^1H$ NMR (400 MHz, CDCl$_3$) δ (ppm) 8.53-8.51 (m, 2H), 7.24 (s, 1H), 7.24-7.20 (m, 2H), 7.12-7.11 (m, 2H), 7.03-6.98 (m, 2H), 4.54 (s, 2H), 2.17 (br. s, 1H); $^{13}C$ NMR (101 MHz, CDCl$_3$) δ (ppm) 162.9 (d, $^1J_{CF}$=249.7 Hz), 149.9, 143.6, 141.3, 134.9, 134.1, 131.2 (d, $^3J_{CF}$=8.3 Hz), 128.7 (d, $^4J_{CF}$=3.5 Hz), 123.7, 122.6, 116.1 (d, $^2J_{CF}$=21.8 Hz), 93.7, 77.6, 51.3; ESI-HRMS-TOF calcd for $C_{18}H_{13}FNOS^+$ (M+H)$^+$ 310.0696, found 310.0710; ESI-LCMS $R_t$=4.9 min, 310.0 (M+H)$^+$; RP-HPLC $R_t$=5.5 min, 99%.

5-(5-(4-Fluorophenyl)-4-(pyridin-4-yl)thiophen-2-yl) pent-4-yn-1-ol (5.3)

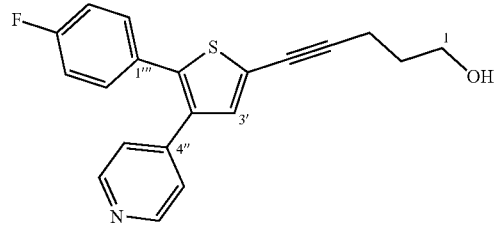 [SMILES: OCCCC#Cc1cc(-c2ccncc2)c(-c2ccc(F)cc2)s1]

To a solution of aryl iodide 5.1 (200 mg, 0.525 mmol) in tetrahydrofuran (2 mL) was added 4-pentyn-1-ol (73 μL, 0.79 mmol), triphenylphosphine (1.4 mg, 5.0 μmol), copper (I) iodide (5.0 mg, 0.026 mmol) and triethylamine (2.0 mL, 14 mmol). The reaction mixture was bubbled with nitrogen for 15 minutes. Bis(triphenylphosphine)palladium(II) dichloride (18 mg, 0.026 mmol) was added and the reaction mixture was refluxed for 2 hours. The reaction mixture was diluted with ethyl acetate (10 mL) and washed with water (3×10 mL), brine (10 mL), dried over magnesium sulfate, filtered and concentrated in vacuo. The resulting crude product was purified by column chromatography in chloroform to afford compound 5.3 (151 mg, 85%) as a yellow foam. 5.3: $C_{20}H_{16}FNOS$ ($M_r$=337.41); $^1H$ NMR (400 MHz, CDCl$_3$) δ (ppm) 8.50 (app. d, J=5.6 Hz, 2H), 7.24-7.18 (m, 2H), 7.18 (s, 1H), 7.12-7.10 (m, 2H), 7.03-6.97 (m, 2H), 3.82 (br. t, J=5.9 Hz, 2H), 2.60 (t, J=7.0 Hz, 2H), 1.92-1.85 (m, 2H), 1.55 (br. s, 1H); $^{13}C$ NMR (101 MHz, CDCl$_3$) δ (ppm) 162.8 (d, $^1J_{CF}$=249.3 Hz), 150.0, 143.6, 140.0, 134.9, 133.2, 131.2 (d, $^3J_{CF}$=8.2 Hz), 128.9 (d, $^4J_{CF}$=3.5 Hz), 123.8, 123.7, 116.0 (d, $^2J_{CF}$=21.8 Hz), 95.6, 73.4, 61.4, 31.4, 16.4; ESI-HRMS-TOF (M+H)$^+$ calcd for $C_{20}H_{17}FNOS^+$ (M+H)$^+$ 338.1009, found 338.1026; ESI-LCMS $R_t$=5.1 min, 338.0 (M+H)$^+$; RP-HPLC $R_t$=6.2 min, >99%.

2-(3-(5-(4-Fluorophenyl)-4-(pyridin-4-yl)thiophen-2-yl)prop-2-yn-1-yl)isoindoline-1,3-dione (5.4)

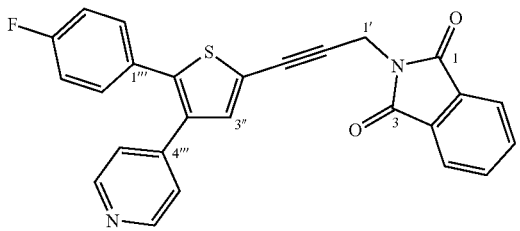 [SMILES: O=C1c2ccccc2C(=O)N1CC#Cc1cc(-c2ccncc2)c(-c2ccc(F)cc2)s1]

Compound 5.2 (188 mg, 0.608 mmol) was dissolved in tetrahydrofuran (6.1 mL). The solution was cooled to 0° C. Phthalimide (179 mg, 1.22 mmol) and triphenylphosphine (239 mg, 0.911 mmol) were added. Diisopropyl azodicarboxylate (179 µL, 0.909 mmol) was added over 15 minutes. The reaction mixture was stirred at room temperature for 20 hours. Water (100 µL) was added and the solvent evaporated in vacuo. The crude compound was purified by column chromatography in ethyl acetate to afford compound 5.4 (136 mg, 51%) as a yellow foam. 5.4: $C_{26}H_{15}FN_2O_2S$ ($M_r$=438.48); $^1$H NMR (400 MHz, CDCl$_3$) δ (ppm) 8.50-8.49 (m, 2H), 7.91 (app. dd, J=5.5, 3.0 Hz, 2H), 7.76 (app. dd, J=5.5, 3.1 Hz, 2H), 7.26 (s, 1H), 7.22-7.17 (m, 2H), 7.09-7.07 (m, 2H), 7.02-6.96 (m, 2H), 4.72 (s, 2H); $^{13}$C NMR (101 MHz, CDCl$_3$) δ (ppm) 167.1, 162.8 (d, $^1J_{CF}$=249.5 Hz), 150.1, 143.1, 141.3, 135.0, 134.8, 134.3, 132.1, 131.2 (d, $^3J_{CF}$=8.3 Hz), 128.7 (d, $^4J_{CF}$=3.5 Hz), 123.7, 123.5, 121.8, 116.0 (d, $^2J_{CF}$=21.8 Hz), 88.3, 75.7, 28.0; ESI-HRMS-TOF calcd for $C_{26}H_{16}FN_2O_2S^+$ (M+H)$^+$ 439.0911, found 439.0910; ESI-LCMS $R_t$=5.7 min, 439.1 (M+H)$^+$; RP-HPLC $R_t$=7.3 min, 95%.

2-(4-(5-(4-Fluorophenyl)-4-(pyridin-4-yl)thiophen-2-yl)but-3-yn-1-yl)isoindoline-1,3-dione (5.5)

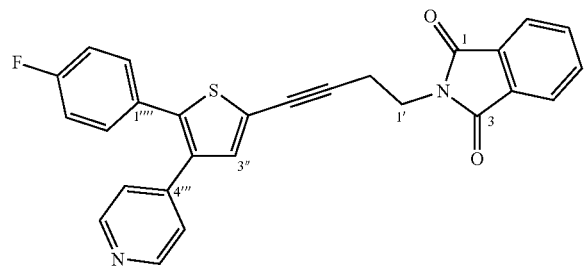 [SMILES: O=C1c2ccccc2C(=O)N1CCC#Cc1cc(-c2ccncc2)c(-c2ccc(F)cc2)s1]

Compound 4.5 (200 mg, 0.618 mmol) was dissolved in tetrahydrofuran (6.2 mL). The solution was cooled to 0° C. Phthalimide (182 mg, 1.24 mmol) and triphenylphosphine (243 g, 0.926 mmol) were added. Diisopropyl azodicarboxylate (183 µL, 0.929 mmol) was added over 15 minutes. The reaction mixture was stirred at room temperature for 20 hours. Water (100 µL) was added and the solvent evaporated in vacuo. The crude compound was purified by column chromatography in ethyl acetate to afford compound 5.5 (261 mg, 93%) as a yellow foam. 5.5: $C_{27}H_{17}FN_2O_2S$ ($M_r$=452.50); $^1$H NMR (400 MHz, CDCl$_3$) δ (ppm) 8.51-8.49 (m, 2H), 7.88 (app. dd, J=5.5, 3.0 Hz, 2H), 7.73 (app. dd, J=5.5, 3.1 Hz, 2H), 7.22-7.17 (m, 2H), 7.13 (s, 1H), 7.10-7.08 (m, 2H), 7.02-6.96 (m, 2H), 3.98 (t, J=7.1 Hz, 2H), 2.88 (t, J=7.0 Hz, 2H); $^{13}$C NMR (101 MHz, CDCl$_3$) δ (ppm) 168.0, 162.7 (d, $^1J_{CF}$=249.3 Hz), 149.7, 143.5, 140.4, 134.8, 134.1, 133.5, 132.0, 131.1 (d, $^3J_{CF}$=8.2 Hz), 128.8 (d, $^4J_{CF}$=3.5 Hz), 123.6, 123.4, 123.0, 115.9 (d, $^2J_{CF}$=21.8 Hz), 91.7, 74.8, 36.5, 19.7; ESI-HRMS-TOF calcd for $C_{27}H_{18}FN_2O_2S^+$ (M+H)$^+$ 453.1068, found 453.1066; ESI-LCMS $R_t$=5.7 min, 453.1 (M+H)$^+$; RP-HPLC $R_t$=7.3 min, 95%.

3-(5-(4-Fluorophenyl)-4-(pyridin-4-yl)thiophen-2-yl)prop-2-yn-1-amine (5.6)

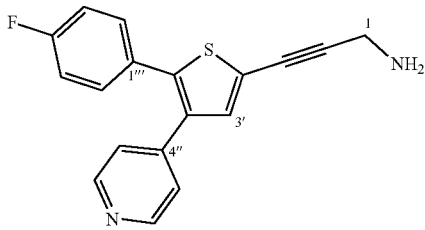 [SMILES: NCC#Cc1cc(-c2ccncc2)c(-c2ccc(F)cc2)s1]

Compound 5.4 (136 mg, 0.310 mmol) was dissolved in methanol (6.1 mL). Hydrazine monohydrate (151 µL, 3.10 mmol) was added and the reaction mixture was stirred at room temperature for 20 hours. The solvent was evaporated in vacuo and the crude product was purified by column chromatography in ethyl acetate/methanol/triethylamine (15:4:1) to afford compound 5.6 (62 mg, 65%) as a brown foam. 5.6: $C_{18}H_{13}FN_2S$ ($M_r$=308.37); $^1$H NMR (400 MHz, CDCl$_3$) δ (ppm) 8.52-8.51 (m, 2H), 7.25-7.20 (m, 3H), 7.12-7.11 (m, 2H), 7.03-6.97 (m, 2H), 3.70 (s, 2H); $^{13}$C NMR (101 MHz, CDCl$_3$) δ (ppm) 162.9 (d, $^1J_{CF}$=249.4 Hz), 150.2, 143.4, 140.7, 135.1, 133.7, 131.2 (d, $^3J_{CF}$=8.2 Hz), 128.9 (d, $^4J_{CF}$=3.5 Hz), 123.7, 123.0, 116.1 (d, $^2J_{CF}$=21.8 Hz), 95.8, 75.1, 32.5; ESI-HRMS-TOF calcd for $C_{18}H_{14}FN_2S$ (M+H) 309.0856, found 309.0855; ESI-LCMS $R_t$=4.1 min, 309.1 (M+H)$^+$; RP-HPLC $R_t$=4.7 min, 82%.

4-(5-(4-Fluorophenyl)-4-(pyridin-4-yl)thiophen-2-yl)but-3-yn-1-amine (5.7)

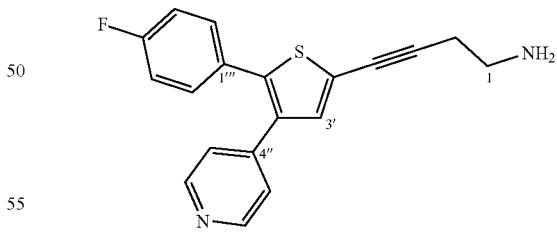

Compound 5.5 (149 mg, 0.329 mmol) was dissolved in methanol (6.6 mL). Hydrazine monohydrate (160 mL, 3.29 mmol) was added and the reaction mixture was stirred at room temperature for 20 hours. The solvent was evaporated in vacuo and the crude product was purified by column chromatography in ethyl acetate/methanol/triethylamine (15:4:1) to afford compound 5.7 (70 mg, 69%) as a yellow foam. 5.7: $C_{19}H_{15}FN_2S$ ($M_r$=322.40); $^1$H NMR (400 MHz, CDCl$_3$) δ (ppm) 8.51 (app. d, J=5.6 Hz, 2H), 7.24-7.20 (m, 3H), 7.12-7.10 (m, 2H), 7.02-6.97 (m, 2H), 2.95 (br. s, 2H), 2.61 (t, J=6.4 Hz, 2H) 1.59 (br. s, 2H); $^{13}$C NMR (101 MHz, CDCl$_3$) δ (ppm) 162.8 (d, $^1J_{CF}$=249.2 Hz), 150.1, 143.4, 140.1, 135.0, 133.5, 131.2 (d, $^3J_{CF}$=8.2 Hz), 128.9 (d, $^4J_{CF}$=3.5 Hz), 123.6, 123.4, 116.0 (d, $^2J_{CF}$=21.8 Hz), 93.8, 74.4, 41.0, 24.8; ESI-HRMS-TOF calcd for C$_{19}$H$_{16}$FN$_2$S (M+H)$^+$ 323.1013, found 323.1013; ESI-LCMS R$_t$=4.2 min, 323.1 (M+H)$^+$; RP-HPLC R$_t$=4.1 min, 98%.

4-(4-(5-(4-Fluorophenyl)-4-(pyridin-4-yl)thiophen-2-yl)but-3-yn-1-yl)morpholine (5.8)

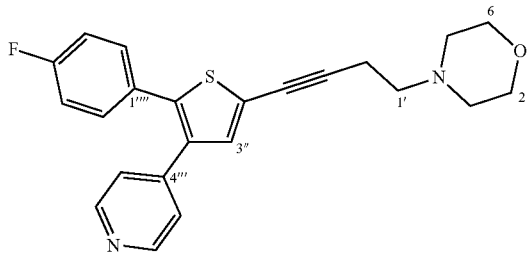 [SMILES: Fc1ccc(-c2sc(C#CCCN3CCOCC3)cc2-c2ccncc2)cc1]

To a solution of thiophene 4.5 (195 mg, 0.603 mmol) in chloroform (5 mL) was added triethylamine (112 µL, 0.804 mmol). The reaction mixture was cooled to 0° C. and methanesulfonyl chloride (57 µL, 0.74 mmol) was added. The reaction mixture was stirred for 1 hour. Saturated sodium hydrogen carbonate (20 mL) was added and the mixture was extracted with chloroform (3×20 mL). The organic layers were dried over magnesium sulfate, filtered and concentrated in vacuo. Morpholine (2.0 mL, 23 mmol) was added and the reaction mixture was stirred at 100° C. for 1 hour. The mixture was diluted with diethyl ether (20 mL) and filtered. The filtrate was extracted with hydrochloric acid (3 M, 20 mL). The aqueous layer was made basic with sodium hydroxide and extracted with ethyl acetate (3×20 mL). The organic layers were dried over magnesium sulfate, filtered and concentrated in vacuo. The product was purified by column chromatography using 5% methanol/chloroform to give thiophene 5.8 as a yellow oil (75 mg, 32%). 5.8: C$_{23}$H$_{21}$FN$_2$OS (M$_r$=392.49); $^1$H NMR (400 MHz, CDCl$_3$) δ (ppm) 8.50 (app. d, J=5.8 Hz, 2H), 7.24-7.17 (m, 2H), 7.17 (s, 1H), 7.11-7.10 (m, 2H), 7.02-6.96 (m, 2H), 3.74-3.72 (m, 4H), 2.71-2.62 (m, 4H), 2.54-2.52 (m, 4H); $^{13}$C NMR (101 MHz, CDCl$_3$) δ (ppm) 162.8 (d, $^1J_{CF}$=249.2 Hz), 150.1, 143.4, 140.1, 135.0, 133.3, 131.2 (d, $^3J_{CF}$=8.2 Hz), 128.9 (d, $^4J_{CF}$=3.5 Hz), 123.6, 123.6, 116.0 (d, $^2J_{CF}$=21.8 Hz), 94.1, 73.9, 67.0, 57.3, 53.5, 18.1; ESI-HRMS-TOF calcd for C$_{23}$H$_{22}$FN$_2$OS$^+$ (M+H)$^+$ 393.1431, found 393.1430; ESI-LCMS R$_t$=4.3 min, 393.1 (M+H)$^+$; RP-HPLC R$_t$=5.0 min, 99%.

4-(5-(4-Fluorophenyl)-4-(pyridin-4-yl)thiophen-2-yl)butan-1-ol (5.9)

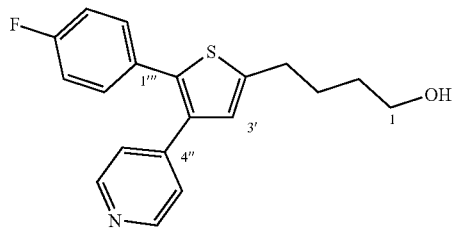 [SMILES: OCCCCc1cc(-c2ccncc2)c(-c2ccc(F)cc2)s1]

To a dry three-neck round bottom flask was added a solution of thiophene 4.5 (200 mg, 0.618 mmol) in ethanol (20 mL). The round bottom flask was evacuated and flushed with nitrogen. Palladium on carbon (10% w/w, approx. 10 mg) was added and the round bottom flask was evacuated and flushed with nitrogen three times, then evacuated and flushed with hydrogen three times. The reaction mixture was stirred at room temperature for 3 days. The product was filtered through celite and the solvent was evaporated in vacuo. The resulting crude product was purified by column chromatography 10% methanol/chloroform to afford thiophene 5.9 as a white solid (82 mg, 40%). 5.9: C$_{19}$H$_{18}$FNOS (M$_r$=327.42); $^1$H NMR (400 MHz, CDCl$_3$) δ (ppm) 8.47 (app. d, J=5.9 Hz, 2H), 7.24-7.19 (m, 2H), 7.14-7.12 (m, 2H), 7.01-6.95 (m, 2H), 6.87 (br. s, 1H), 3.71 (t, J=6.4 Hz, 2H), 2.88 (t, J=7.4 Hz, 2H), 1.86-1.67 (m, 4H); $^{13}$C NMR (101 MHz, CDCl$_3$) δ (ppm) 162.6 (d, $^1J_{CF}$=248.2 Hz), 150.0, 145.2, 144.3, 137.6, 134.9, 131.1 (d, $^3J_{CF}$=8.1 Hz), 129.9 (d, $^4J_{CF}$=3.5 Hz), 126.8, 123.7, 115.9 (d, $^2J_{CF}$=21.7 Hz), 62.6, 32.2, 29.9, 27.9; ESI-HRMS-TOF calcd for C$_{19}$H$_{19}$FNOS$^+$ (M+H)$^+$ 328.1166, found 328.1165; ESI-LCMS R$_t$=4.8 min, 328.0 (M+H)$^+$; RP-HPLC R$_t$=5.8 min, 98%.

1-(5-(4-Fluorophenyl)-4-(pyridin-4-yl)thiophen-2-yl)-4-hydroxybutan-1-one (5.10)

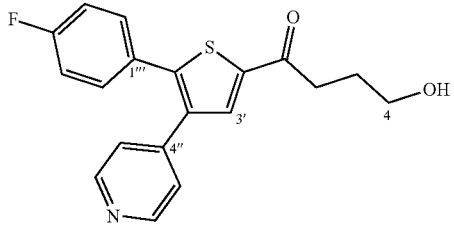 [SMILES: O=C(CCCO)c1cc(-c2ccncc2)c(-c2ccc(F)cc2)s1]

A solution of compound 4.5 (100 mg, 0.309 mmol) was dissolved in acetone (10 mL) and added dropwise to sulfuric acid (10 M, 0.77 mL) at 0° C. in an ice bath. The reaction mixture was allowed to warm to room temperature and stirred for 1.5 hours. The reaction mixture was concentrated in vacuo and then diluted with ethyl acetate (20 mL). The mixture was washed with water (20 mL) and extracted with ethyl acetate (3×20 mL). The combined organic extracts were dried over magnesium sulfate, filtered and concentrated in vacuo. The crude product was purified by column chromatography 10% methanol/chloroform to afford thiophene 5.10 as a pale yellow solid (75 mg, 71%). 5.10: C$_{19}$H$_{16}$FNO$_2$S (M$_r$=341.40); mp 126.2-128.1° C.; $^1$H NMR (400 MHz, CDCl$_3$) δ (ppm) 8.56-8.54 (m, 2H), 7.78 (s, 1H), 7.29-7.24 (m, 2H), 7.15-7.14 (m, 2H), 7.06-7.01 (m, 2H), 3.77 (br. t, J=5.7 Hz, 2H), 3.10 (t, J=7.0 Hz, 2H), 2.08-2.02 (m, 2H), 1.84 (br. s, 1H); $^{13}$C NMR (101 MHz, CDCl$_3$) δ (ppm) 193.2, 163.1 (d, $^1J_{CF}$=250.5 Hz), 150.0, 147.7, 143.1, 142.7, 136.1, 133.7, 131.1 (d, $^3J_{CF}$=8.4 Hz), 128.5 (d, $^4J_{CF}$=3.5 Hz), 123.6, 116.2 (d, $^2J_{CF}$=21.9 Hz), 61.6, 35.6, 27.3; ESI-HRMS-TOF calcd for C$_{19}$H$_{17}$FNO$_2$S (M+H) 342.0959, found 342.0960; ESI-LCMS R$_t$=4.5 min, 342.2 (M+H)$^+$; RP-HPLC R$_t$=5.0 min, 95%.

Ethyl 5-(4-fluorophenyl)-4-(pyridin-4-yl)thiophene-2-carboxylate (5.11)

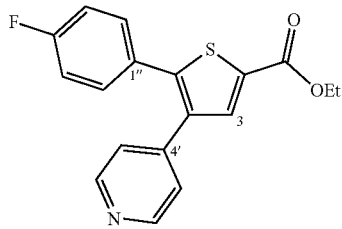 [SMILES: CCOC(=O)c1cc(-c2ccncc2)c(-c2ccc(F)cc2)s1]

A solution of n-butyllithium in hexanes (1.1 M, 4.0 mL, 4.4 mmol) was added to a solution of thiophene 3.2 (1.0 g, 3.9 mmol) in tetrahydrofuran (50 mL) at −78° C. The reaction mixture was stirred for 30 minutes. Ethyl chloroformate (0.42 mL, 4.4 mmol) was added and the reaction mixture was stirred for 3 hours. Water (50 mL) was added and the tetrahydrofuran was evaporated in vacuo. The mixture was extracted with ethyl acetate (3×50 mL) and the combined organic extracts were washed with brine (50 mL), dried over magnesium sulfate, filtered and concentrated in vacuo. The crude product was purified by column chromatography in 50% ethyl acetate/petroleum spirits to afford compound 5.11 (0.71 g, 55%) as a yellow oil. 5.11: $C_{18}H_{14}FNO_2S$ ($M_r$=327.37); $^1$H NMR (400 MHz, CDCl$_3$) δ (ppm) 8.54-8.52 (m, 2H), 7.84 (s, 1H), 7.29-7.24 (m, 2H), 7.15-7.14 (m, 2H), 7.06-7.00 (m, 2H), 4.39 (q, J=7.1 Hz, 2H), 1.40 (t, J=7.1 Hz, 3H); $^{13}$C NMR (101 MHz, CDCl$_3$) δ (ppm) 163.1 (d, $^1J_{CF}$=250.1 Hz), 161.8, 150.2, 146.2, 143.0, 135.9, 135.0, 132.9, 131.2 (d, $^3J_{CF}$=8.3 Hz), 128.7 (d, $^4J_{CF}$=3.5 Hz), 123.5, 116.2 (d, $^2J_{CF}$=21.9 Hz), 61.6, 14.4; ESI-HRMS-TOF calcd for $C_{18}H_{15}FNO_2S$ (M+H)$^+$ 328.0802, found 328.0800; ESI-LCMS $R_t$=5.4 min, 328.0 (M+H)$^+$; RP-HPLC $R_t$=6.3 min, 99%.

5-(4-Fluorophenyl)-4-(pyridin-4-yl)thiophene-2-carboxylic acid (5.12)

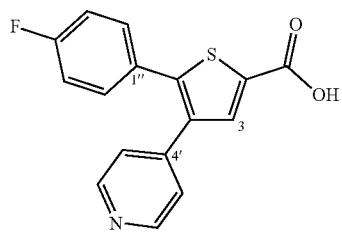

A mixture of ester 5.11 (600 mg, 1.83 mmol) and sodium hydroxide (290 mg, 7.25 mmol) in ethanol/water (1:1, 60 mL) was heated at 50° C. for 2 hours. The reaction mixture was concentrated in vacuo to remove the ethanol. The mixture was acidified with 1 M hydrochloric acid. The resulting precipitate was filtered and dried under vacuum to afford 5.12 as a white powder (468 mg, 85%). 5.12: $C_{16}H_{10}FNO_2S$ ($M_r$=299.32); mp 294.0-296.2° C.; $^1$H NMR (400 MHz, d$_6$-DMSO) δ (ppm) 8.52-8.51 (m, 2H), 7.89 (s, 1H), 7.40-7.35 (m, 2H), 7.29-7.23 (m, 4H); $^{13}$C NMR (101 MHz, d$_6$-DMSO) δ (ppm) 162.5, 162.5 (d, $^1J_{CF}$=247.3 Hz), 150.0, 145.1, 142.2, 136.0, 134.8, 133.8, 131.4 (d, $^3J_{CF}$=8.6 Hz), 128.7 (d, $^4J_{CF}$=3.2 Hz), 123.5, 116.2 (d, $^2J_{CF}$=21.9 Hz); ESI-HRM-TOF calcd for $C_{16}H_{11}FNO_2S^+$ (M+H)$^+$ 300.0489, found 300.0498; ESI-LCMS $R_t$=4.7 min, 300.0 (M+H)$^+$; RP-HPLC $R_t$=4.9 min, 99%.

tert-Butyl 4-(5-(4-fluorophenyl)-4-(pyridin-4-yl)thiophene-2-carbonyl)piperazine-1-carboxylate (5.13)

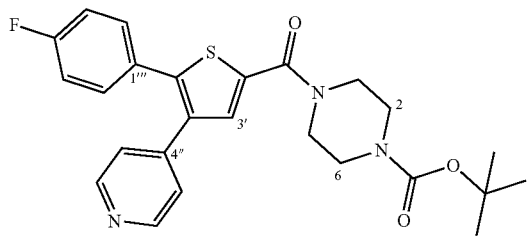 [SMILES: CC(C)(C)OC(=O)N1CCN(C(=O)c2cc(-c3ccncc3)c(-c3ccc(F)cc3)s2)CC1]

Dimethylformamide (20 μL) was added to a compound 5.12 (170 mg, 0.570 mmol) in dichloromethane (10 mL). Oxalyl chloride (195 μL, 2.27 mmol) was added dropwise under nitrogen. The reaction mixture was stirred at room temperature for 2 hours forming an orange solution. The solvent was evaporated in vacuo to give the acid chloride intermediate. Dichloromethane (5 mL) was added to the acid chloride intermediate followed by N,N-diisopropylethylamine (129 μL, 0.739 mmol) and 1-Boc-piperazine (116 mg, 0.623 mmol). The reaction mixture was stirred at room temperature for 4 hours and then poured into water (15 mL) and acidified to pH 1 with 1 M hydrochloric acid. The mixture was extracted with dichloromethane (3×20 mL) and the combined organic layers were concentrated in vacuo. The crude product was purified by flash column chromatography with gradient elution (0-10% methanol/chloroform) to afford compound 5.13 as a white solid (160 mg, 61%). 5.13: $C_{25}H_{26}FN_3O_3S$ ($M_r$=467.56); $^1$H NMR (400 MHz, CDCl$_3$) δ (ppm) 8.54-8.53 (m, 2H), 7.36 (s, 1H), 7.28-7.23 (m, 2H), 7.14-7.12 (m, 2H), 7.06-7.00 (m, 2H), 3.80-3.77 (m, 4H), 3.55-3.52 (m, 4H), 1.48 (s, 9H); $^{13}$C NMR (101 MHz, CDCl$_3$) δ (ppm) 163.1, 163.0 (d, $^1J_{CF}$=249.9 Hz), 154.6, 150.2, 143.2, 143.1, 135.9, 135.1, 131.2 (d, $^3J_{CF}$=8.3 Hz), 131.0, 128.5 (d, $^4J_{CF}$=3.4 Hz), 123.6, 116.2 (d, $^2J_{CF}$=21.9 Hz), 80.6, 43.6, 43.4, 28.4; ESI-LCMS $R_t$=5.3 min, 468.1 (M+H)$^+$; RP-HPLC $R_t$=6.6 min, 98%. Nb. $^{13}$C NMR signals at 43.6 and 43.4 ppm were identified from the HSQC experiment.

(5-(4-Fluorophenyl)-4-(pyridin-4-yl)thiophen-2-yl)(piperazin-1-yl)methanone (5.14)

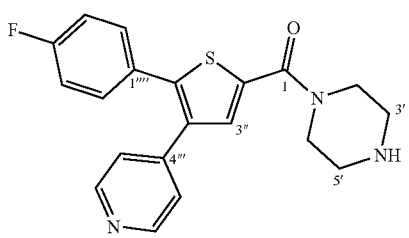 [SMILES: O=C(c1cc(-c2ccncc2)c(-c2ccc(F)cc2)s1)N1CCNCC1]

Compound 5.13 (93 mg, 0.20 mmol) was dissolved in dichloromethane (5 mL). Trifluoroacetic acid (1 mL) was added and the reaction mixture was stirred at room temperature for 2 hours. The mixture was poured into aqueous sodium hydroxide (1 M, 30 mL) and extracted with dichloromethane (3×20 mL). The combined organic extracts were dried over magnesium sulfate, filtered and concentrated in vacuo. The crude product was purified by flash column chromatography with gradient elution (10-20% methanol/chloroform) to afford compound 5.14 (53 mg, 72%) as a yellow oil. 5.14: $C_{20}H_{18}FN_3OS$ ($M_r$=367.44); $^1H$ NMR (400 MHz, CDCl$_3$) δ (ppm) 8.54-8.52 (m, 2H), 7.36 (s, 1H), 7.28-7.22 (m, 2H), 7.14-7.12 (m, 2H), 7.06-7.00 (m, 2H), 3.97-3.95 (m, 4H), 3.14-3.10 (m, 4H). $^{13}C$ NMR (101 MHz, CDCl$_3$) δ (ppm) 163.1 (d, $^1J_{CF}$=250.0 Hz), 163.1, 150.2, 143.4, 143.2, 135.6, 135.1, 131.3 (d, $^3J_{CF}$=8.3 Hz), 131.2, 128.5 (d, $^4J_{CF}$=3.5 Hz), 123.6, 116.3 (d, $^2J_{CF}$=21.9 Hz), 45.3 (2C); ESI-HRMS-TOF calcd for $C_{20}H_{19}FN_3OS^+$ (M+H)$^+$ 368.1227, found 368.1228; ESI-LCMS $R_t$=3.8 min, 368.1 (M+H)$^+$; RP-HPLC 5.7 min, 97%.

1-(5-(4-Fluorophenyl)-4-(pyridin-4-yl)thiophen-2-yl)ethanone (5.15)

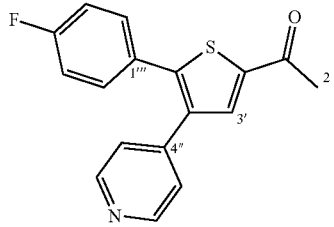 [SMILES: CC(=O)c1cc(-c2ccncc2)c(-c2ccc(F)cc2)s1]

A mixture of acetyl chloride (84 μL, 1.2 mmol) and aluminium chloride (329 mg, 2.46 mmol) in dichloromethane (10 mL) was stirred at room temperature for 30 minutes. Thiophene 3.2 (201 mg, 0.787 mmol) in dichloromethane (5 mL) was added and the reaction mixture was refluxed for 16 hours. The reaction mixture was poured into ice water (100 mL) and extracted with dichloromethane (3×50 mL). The combined organic extracts were washed with brine (50 mL), dried over magnesium sulfate, filtered and concentrated in vacuo. The resulting product was purified by gradient column chromatography (50-70% diethyl ether/petroleum spirits) to afford compound 5.15 (155 mg, 66%). 5.15: $C_{17}H_{12}FNOS$ ($M_r$=297.35); mp 167.7-168.9° C.; $^1H$ NMR (400 MHz, CDCl$_3$) δ (ppm) 8.56 (app. d, J=5.4 Hz, 2H), 7.72 (s, 1H), 7.30-7.25 (m, 2H), 7.16-7.14 (m, 2H), 7.06-7.00 (m, 2H), 2.60 (s, 3H); $^{13}C$ NMR (101 MHz, CDCl$_3$) δ (ppm) 190.4, 163.3 (d, $^1J_{CF}$=250.5 Hz), 150.4, 147.9, 143.14, 143.06, 136.4, 134.2, 131.2 (d, $^3J_{CF}$=8.4 Hz), 128.7 (d, $^4J_{CF}$=3.6 Hz), 123.6, 116.3 (d, $^2J_{CF}$=21.9 Hz), 26.8; ESI-HRMS-TOF (M+H)$^+$ calcd for $C_{17}H_{13}FNOS^+$ (M+H)$^+$ 298.0696, found 298.0699; ESI-LCMS $R_t$=5.0 min, 298.0 (M+H)$^+$; RP-HPLC $R_t$=5.4 min, >99%.

(5-(4-Fluorophenyl)-4-(pyridin-4-yl)thiophen-2-yl)(phenyl)methanone (5.16)

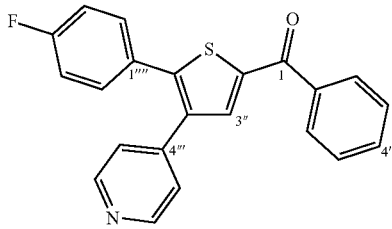 [SMILES: O=C(c1ccccc1)c1cc(-c2ccncc2)c(-c2ccc(F)cc2)s1]

A mixture of benzoyl chloride (136 μL, 1.17 mmol) and aluminium chloride (320 mg, 2.40 mmol) in dichloromethane (10 mL) was stirred at room temperature for 30 minutes. Thiophene 3.2 (195 mg, 0.764 mmol) in dichloromethane (5 mL) was added and the reaction mixture was refluxed for 16 hours. The reaction mixture was poured into ice water (100 mL) and extracted with dichloromethane (3×50 mL). The combined organic extracts were washed with brine (50 mL), dried over magnesium sulfate, filtered and concentrated in vacuo. The resulting product was purified by column chromatography (50% diethyl ether/petroleum spirits) to afford compound 5.16 (243 mg, 89%). 5.16: $C_{22}H_{14}FNOS$ ($M_r$=359.42); mp 151.4-153.2° C.; $^1H$ NMR (400 MHz, CDCl$_3$) δ (ppm) 8.55 (app. d, J=5.2 Hz, 2H), 7.93-7.90 (m, 2H), 7.68 (s, 1H), 7.65-7.61 (m, 1H), 7.56-7.51 (m, 2H), 7.34-7.29 (m, 2H), 7.16-7.14 (m, 2H), 7.08-7.02 (m, 2H); $^{13}C$ NMR (101 MHz, CDCl$_3$) δ (ppm) 187.8, 163.4 (d, $^1J_{CF}$=250.6 Hz), 150.4, 148.3, 143.1, 142.3, 137.7, 136.4, 136.3, 132.7, 131.3 (d, $^3J_{CF}$=8.4 Hz), 129.3, 128.8, 128.7 (d, $^4J_{CF}$=3.5 Hz), 123.7, 116.4 (d, $^2J_{CF}$=21.9 Hz); ESI-HRMS-TOF calcd for $C_{22}H_{14}FNOS^+$ (M+H)$^+$ 360.0853, found 360.0860; ESI-LCMS $R_t$=5.6 min, 360.0 (M+H)$^+$; RP-HPLC $R_t$=6.8 min, 99%.

(5-(4-Fluorophenyl)-4-(pyridin-4-yl)thiophen-2-yl)(furan-2-yl)methanone (5.17)

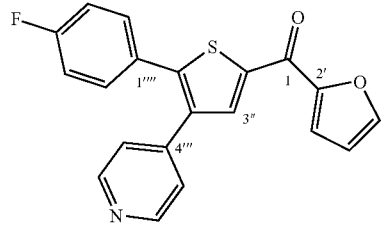 [SMILES: O=C(c1ccco1)c1cc(-c2ccncc2)c(-c2ccc(F)cc2)s1]

A mixture of furoyl chloride (116 μL, 1.18 mmol) and aluminium chloride (313 mg, 2.35 mmol) in dichloromethane (10 mL) was stirred at room temperature for 30 minutes. Thiophene 3.2 (200 mg, 0.783 mmol) in dichloromethane (5 mL) was added and the reaction mixture was refluxed for 16 hours. The reaction mixture was poured into ice water (100 mL) and extracted with dichloromethane (3×50 mL). The combined organic extracts were washed with brine (50 mL), dried over magnesium sulfate, filtered and concentrated in vacuo. The resulting product was purified in 50% diethyl ether/petroleum spirits to afford compound 5.17 (233 mg, 85%). 5.17: $C_{20}H_{12}FNO_2S$ ($M_r$=349.38); mp 157.6-158.9° C.; $^1H$ NMR (400 MHz, CDCl$_3$) δ (ppm) 8.58-8.56 (m, 2H), 8.23 (s, 1H), 7.71 (dd, J=1.7, 0.8 Hz, 1H), 7.47 (dd, J=3.6, 0.8 Hz, 1H), 7.34-7.29 (m, 2H), 7.21-7.20 (m, 2H), 7.08-7.02 (m, 2H), 6.65 (dd, J=3.6, 1.7 Hz, 1H); $^{13}C$ NMR (101 MHz, CDCl$_3$) δ (ppm) 172.9, 163.3 (d, $^1J_{CF}$=250.5 Hz), 152.5, 150.3, 148.2, 146.8, 143.3, 140.8, 136.5, 135.7, 131.3 (d, $^3J_{CF}$=8.3 Hz), 128.7 (d, $^4J_{CF}$=3.5 Hz), 123.7, 119.3, 116.3 (d, $^2J_{CF}$=21.9 Hz), 112.9; ESI-HRMS-TOF (M+H)$^+$ calcd for $C_{20}H_{13}FNO_2S^+$ (M+H)$^+$ 350.0646, found 350.0660; ESI-LCMS $R_t$=5.3 min, 350.0 (M+H)$^+$; RP-HPLC $R_t$=6.2 min, 99%.

4-(2-(4-Fluorophenyl)-5-(furan-2-yl)thiophen-3-yl)pyridine (5.18)

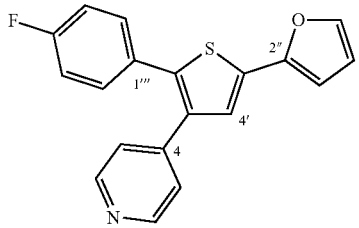 [SMILES: Fc1ccc(-c2sc(-c3ccco3)cc2-c2ccncc2)cc1]

To a solution of thiophene 5.1 (200 mg, 0.525 mmol) in tetrahydrofuran (6 mL) was added furan-2-boronic acid (178 mg, 1.59 mmol) and sodium carbonate (1 M, 2 mL). The mixture was bubbled with nitrogen for 5 minutes. Bis(triphenylphosphine)palladium(II) dichloride (39 mg, 0.056 mmol) was added. The reaction mixture was heated in the microwave at 100° C. for 1.5 hours. Diethyl ether (20 mL) was added and the reaction mixture was washed with water (2×20 mL). The aqueous layer was further extracted with diethyl ether (2×20 mL) and the combined organic layers were evaporated in vacuo. The crude product was purified by gradient column chromatography (50-80% diethyl ether/petroleum spirits) to afford compound 5.18 (154 mg, 91%) as a yellow foam. 5.18: $C_{19}H_{12}FNOS$ ($M_r$=321.37); $^1H$ NMR (400 MHz, CDCl$_3$) δ (ppm) 8.53 (br. s, 2H), 7.45 (dd, J=1.8, 0.7 Hz, 1H), 7.31 (s, 1H), 7.31-7.23 (m, 2H), 7.20-7.18 (m, 2H), 7.04-6.99 (m, 2H), 6.57 (dd, J=3.4, 0.6 Hz, 1H), 6.48 (dd, J=3.4, 1.8 Hz, 1H); $^{13}C$ NMR (101 MHz, CDCl$_3$) δ (ppm) 162.8 (d, $^1J_{CF}$=249.0 Hz), 150.1, 148.6, 143.9, 142.3, 138.3, 135.8, 133.2, 131.1 (d, $^3J_{CF}$=8.2 Hz), 129.3 (d, $^4J_{CF}$=3.5 Hz), 124.6, 123.7, 116.1 (d, $^2J_{CF}$=21.8 Hz), 112.0, 105.9; ESI-HRMS-TOF calcd for $C_{19}H_{13}FNOS^+$ (M+H)$^+$ 322.0696, found 322.0712; ESI-LCMS $R_t$=5.5 min, 322.0 (M+H)$^+$; RP-HPLC $R_t$=6.9 min, 95%.

2,3,5,6-Tetrafluoro-4-(5-(4-fluorophenyl)-4-(pyridin-4-yl)thiophen-2-yl)pyridine (5.19)

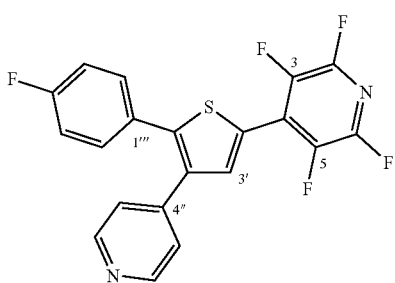 [SMILES: Fc1ccc(-c2sc(-c3c(F)c(F)nc(F)c3F)cc2-c2ccncc2)cc1]

To a solution of thiophene 3.2 (350 g, 1.37 mmol) in tetrahydrofuran (13.7 mL) was added n-butyllithium in hexanes (1.06 M, 1.42 mL, 1.51 mmol) dropwise at −78° C. The reaction mixture was stirred for 30 minutes and pentafluoropyridine (180 μL, 1.65 mmol) was added. The reaction mixture was stirred for a further 2 hours. The solvent was evaporated and the resulting product was taken up in water (40 mL) and extracted with ethyl acetate (3×40 mL). The combined organic extracts were dried over magnesium sulfate, filtered and concentrated in vacuo. The crude product was purified by column chromatography in 50% ethyl acetate/petroleum spirits to afford compound 5.19 (365 mg, 65%) as a yellow solid. 5.19: $C_{20}H_9F_5N_2S$ ($M_r$=404.36); mp 137.5-139.4° C.; $^1H$ NMR (400 MHz, CDCl$_3$) δ (ppm) 8.61-8.59 (m, 2H), 7.94 (s, 1H), 7.35-7.30 (m, 4H), 7.12-7.06 (m, 2H); $^{13}C$ NMR (101 MHz, CDCl$_3$) δ (ppm) 163.4 (d, $^1J_{CF}$=250.7 Hz), 150.2, 145.8-143.0 (m, 2C), 143.0, 138.5 (app. dd, $^1J_{CF}$=261.1 Hz, $^2J_{CF}$=35.1 Hz), 136.2, 134.7 (t, $^4J_{CF}$=7.2 Hz), 131.3 (d, $^3J_{CF}$=8.4 Hz), 128.0 (d, $^4J_{CF}$=3.6 Hz), 126.0, 123.7, 116.4 (d, $^2J_{CF}$=21.9 Hz); ESI-HRMS-TOF calcd for $C_{20}H_{10}F_5N_2S^+$ (M+H)$^+$ 405.0479, found 405.0478; ESI-LCMS $R_t$=6.3 min, 405.1 (M+H)$^+$; RP-HPLC $R_t$=7.3 min, >99%.

3,5,6-Trifluoro-4-(5-(4-fluorophenyl)-4-(pyridin-4-yl)thiophen-2-yl)pyridin-2-amine (5.20)

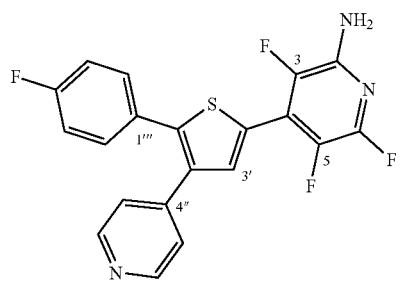 [SMILES: Nc1nc(F)c(F)c(-c2cc(-c3ccncc3)c(-c3ccc(F)cc3)s2)c1F]

To a solution of compound 5.19 (100 mg, 0.247 mmol) in N-methyl-2-pyrrolidone (3 mL) was added aqueous ammonia (25%, 9 mL) in a microwave vial. The reaction mixture was sealed and heated on a hotplate at 120° C. for 1 hour. The resulting precipitate was filtered and dried to give compound 5.20 (99 mg, quant.) as a yellow solid. 5.20: $C_{20}H_{11}F_4N_3S$ ($M_r$=401.38); mp 209.7-211.1° C.; $^1H$ NMR (400 MHz, CDCl$_3$) δ (ppm) 8.57-8.55 (m, 2H), 7.84 (s, 1H), 7.36-7.28 (m, 4H), 7.11-7.04 (m, 2H), 4.61 (br. s, 2H); $^{13}C$ NMR (101 MHz, CDCl$_3$) δ 163.2 (d, $^1J_{CF}$=250.0 Hz), 150.0, 147.8-145.2 (m), 143.9-143.8 (m), 143.6, 143.9-141.2 (m), 140.0-137.4 (m), 135.7, 133.6 (t, $^4J_{CF}$=6.8 Hz), 131.3 (d, $^3J_{CF}$=8.3 Hz), 128.4 (d, $^4J_{CF}$=3.5 Hz), 127.41-127.37 (m), 123.8, 121.9, 116.3 (d, $^2J_{CF}$=21.9 Hz); ESI-HRMS-TOF calcd for $C_{20}H_{12}F_4N_3S^+$ (M+H)$^+$ 402.0683, found 402.0682; ESI-LCMS $R_t$=5.4 min, 402.1 (M+H)*; RP-HPLC $R_t$=6.8 min, 96%.

3,5-Difluoro-4-(5-(4-fluorophenyl)-4-(pyridin-4-yl)thiophen-2-yl)pyridine-2,6-diamine (5.21)

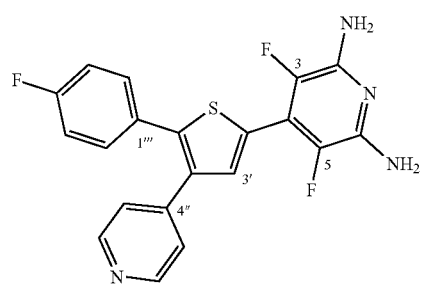 [SMILES: Nc1nc(N)c(F)c(-c2cc(-c3ccncc3)c(-c3ccc(F)cc3)s2)c1F]

To a solution of compound 5.19 (100 mg, 0.247 mmol) in N-methyl-2-pyrrolidone (3 mL) was added aqueous ammonia (25%, 9 mL) in a microwave vial. The reaction mixture was sealed and heated on a hotplate at 150° C. for 3 days. Ethyl acetate (20 mL) was added and the mixture was washed with water (3×20 mL). The aqueous fraction was extracted with ethyl acetate (20 mL). The combined organic layer was dried over magnesium sulfate, filtered and concentrated in vacuo. The crude product was purified by column chromatography in 10% methanol/chloroform to afford compound 5.21 (35 mg, 36%). 5.21: $C_{20}H_{13}F_3N_4S$ ($M_r$=398.41); mp 228.2-230.1° C.; $^1$H NMR (400 MHz, CDCl$_3$) δ (ppm) 8.55-8.54 (m, 2H), 7.75 (s, 1H), 7.33-7.28 (m, 2H), 7.21-7.19 (m, 2H), 7.07-7.01 (m, 2H), 4.31 (br. s, 4H); $^{13}$C NMR (101 MHz, CDCl$_3$) δ (ppm) 163.0 (d, $^1J_{CF}$=249.4 Hz), 150.2, 143.6, 142.6-142.2 (m), 135.5, 135.3 (d, $^1J_{CF}$=245.2 Hz), 132.9 (t, $^4J_{CF}$=6.6 Hz), 131.3 (d, $^3J_{CF}$=8.3 Hz), 128.9 (d, $^4J_{CF}$=3.5 Hz), 128.6, 123.8, 118.6, 116.2 (d, $^2J_{CF}$=21.8 Hz); ESI-HRMS-TOF calcd for $C_{20}H_{14}F_3N_2S$ (M+H)$^+$ 399.0886, found 399.0883; ESI-LCMS $R_t$=5.0 min, 399.1 (M+H)$^+$; RP-HPLC $R_t$=5.8 min, 99%.

4-(5-(4-Fluorophenyl)-4-(pyridin-4-yl)thiophen-2-yl)morpholine (5.23)

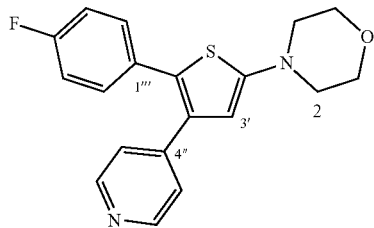 [SMILES: Fc1ccc(-c2sc(N3CCOCC3)cc2-c2ccncc2)cc1]

A mixture of compound 5.1 (150 mg, 0.393 mmol), tris(dibenzylideneacetone)dipalladium(0) (7.2 mg, 7.9 μmol, 2 mol %), xantphos (4.6 mg, 7.9 μmol, 2 mol %), sodium tert-butoxide (53 mg, 0.55 mmol), toluene (1.2 mL) and morpholine (41 μL, 0.47 mmol) was stirred at 60° C. for 32 hours in a sealed tube. Ethyl acetate (10 mL) was added and the mixture was washed with water (3×10 mL). The organic layer was dried over magnesium sulfate, filtered and concentrated in vacuo. The crude product was purified by gradient column chromatography (50-100% ethyl acetate/petroleum spirits, then 1% methanol/ethyl acetate) to afford compound 5.23 (7.5 mg, 6%). 5.23: $C_{19}H_{17}FN_2OS$ ($M_r$=340.41); $^1$H NMR (400 MHz, CDCl$_3$) δ (ppm) 8.50-8.48 (m, 2H), 7.21-7.12 (m, 4H), 7.00-6.91 (m, 2H), 6.19 (s, 1H), 3.90-3.83 (m, 4H), 3.20-3.15 (m, 4H).

Biochemistry

Fluorescence polarisation (FP) assay

FP signals were measured with a PHERAstar microplate reader (BMG Labtech) using black, low-binding half-area 96 well plates (Corning). Each binding data point was carried out in duplicate or triplicate. Data were recorded in millipolarisation (mP) units and measured at an excitation wavelength of 485 nm and an emission wavelength of 520 nm. Tris(hydroxymethyl)aminomethane (Tris) assay buffer was used in all binding experiments and consisted of 10 mM Tris, 50 nM potassium chloride, and 3.5 mM 3-((3-cholamidopropyl)dimethylammonium)-1-propanesulfonate (Chaps) at pH 8.0. The recombinant inactive and active His-tag p38α MAPK used in the ligand binding assays were prepared as described by Bukhtiyarova et al.

Determination of $K_d$ for the Fluorescently Labelled Ligand

The method used to determine the $K_d$ for the fluorescently labelled ligand was similar to the method by Munoz et al. 5 nM of the fluoroprobe was incubated at room temperature for 1 hour with increasing concentrations of inactive non-phosphorylated p38α MAPK (0-1000 nM) in the presence of 10% dimethylsulfoxide. The $K_d$ value to inactive p38α MAPK was calculated from 3 independent experiments and determined to be 13±1 nM. To determine the affinity of the fluoroprobe to active phosphorylated p38α MAPK, 5 nM of fluoroprobe was incubated at room temperature for 2 hours with increasing concentrations of active phosphorylated p38α MAPK (0-500 nM) in the presence of 10% dimethylsulfoxide. The $K_d$ value to active p38α MAPK was calculated from 3 independent experiments and determined to be 36±2 nM.

Ligand Binding Experiments

Test compounds were prepared from dimethylsulfoxide stocks (10 mM). To determine the $K_i$ values, the test compounds (final concentration ranging from 10 nM-500 μM), 5 nM of fluoroprobe and 50 nM of inactive p38α MAPK were added to each well. Plates were incubated at room temperature for 1 hour and FP signals were recorded. For binding experiments to active p38α MAPK, the FP signals were recorded after 2 hours incubation at room temperature. Data is represented as mean±SEM from two to three independent experiments. A list of $K_i$ values for the synthesised analogues is given below in table 6.

TABLE 6

Complete binding affinity and enzyme inhibition data of synthesised analogues

| Compound | $K_i$ ± SEM (μM) to inactive p38α | $K_i$ ± SEM (μM) to active p38α | IC$_{50}$ (mean, μM) |
|---|---|---|---|
| RWJ67657 | 0.21 ± 0.04 | 0.013 ± 0.006 | n.d. |
| 3.2 | 5.0 ± 0.4 | 0.6 ± 0.1 | n.d. |
| 3.3 | >10 | >10 | n.d. |
| 3.28 | >10 | 8.7 | n.d. |
| 3.29 | >10 | 3.0 | n.d. |
| 3.30 | >10 | >10 | n.d. |
| 3.31 | >10 | 7.1 | n.d. |
| 3.32 | >10 | >10 | n.d. |
| 3.33 | >10 | 1.3 ± 0.2 | n.d. |
| 3.34 | >10 | 3.5 | n.d. |
| 3.35 | >10 | 2.2 ± 0.3 | n.d. |
| 3.36 | >10 | 2 ± 1 | n.d. |
| 3.37 | 1.9 ± 0.2 | 2 ± 1 | n.d. |
| 3.38 | >10 | 1.7 ± 0.2 | n.d. |
| 3.39 | >10 | 3.2 | n.d. |
| 3.40 | >10 | >10 | n.d. |
| 3.41 | 2.6 ± 0.6 | 2.0 ± 0.1 | n.d. |
| 3.42 | >10 | >10 | n.d. |
| 3.43 | >10 | >10 | n.d. |
| 3.44 | >10 | >10 | n.d. |
| 3.45 | >10 | >10 | n.d. |
| 3.46 | >10 | >10 | n.d. |
| 3.47 | >10 | 1.8 ± 0.4 | n.d. |
| 3.48 | >10 | >10 | n.d. |
| 3.49 | >10 | >10 | n.d. |
| 3.50 | >10 | 0.9 ± 0.4 | n.d. |
| 3.51 | >10 | >10 | n.d. |
| 3.52 | >10 | >10 | n.d. |
| 3.53 | >10 | 2.2 ± 0.3 | n.d. |
| 3.54 | >10 | 3.4 | n.d. |
| 3.55 | >10 | >10 | n.d. |
| 4.1 | 2.3 ± 0.2 | 0.6 ± 0.1 | 0.18 |
| 4.5 | 2.0 ± 0.2 | 0.56 ± 0.06 | 0.16 |
| 4.6 | >10 | 3.9 | 4.72 |
| 4.17 | 1.9 ± 0.3 | 0.99 ± 0.09 | 0.26 |

TABLE 6-continued

Complete binding affinity and enzyme inhibition data of synthesised analogues

| Compound | $K_i \pm$ SEM (μM) to inactive p38α | $K_i \pm$ SEM (μM) to active p38α | $IC_{50}$ (mean, μM) |
|---|---|---|---|
| 4.18 | 1.5 ± 0.5 | 0.72 ± 0.03 | 0.27 |
| 4.19 | >10 | 9.4 | n.d. |
| 5.1 | 1.9 ± 0.4 | 2.3 | n.d. |
| 5.2 | 2.1 ± 0.3 | 0.63 ± 0.04 | n.d. |
| 5.3 | 1.7 ± 0.2 | 0.80 ± 0.04 | n.d. |
| 5.6 | >10 | n.d. | n.d. |
| 5.7 | 1.1 ± 0.2 | 0.19 ± 0.04 | n.d. |
| 5.8 | 2.2 ± 0.2 | 2.5 | n.d. |
| 5.9 | 0.98 ± 0.02 | 0.25 ± 0.04 | n.d. |
| 5.10 | 2.7 ± 0.3 | 0.67 ± 0.03 | n.d. |
| 5.11 | 6 ± 1 | 2.2 | n.d. |
| 5.12 | 17 ± 2 | 1.4 | n.d. |
| 5.14 | 6.3 ± 0.4 | 0.9 ± 0.1 | n.d. |
| 5.15 | 6.4 ± 0.6 | 1.4 | n.d. |
| 5.16 | 5 ± 2 | 2.8 ± 0.1 | n.d. |
| 5.17 | 5.9 ± 0.7 | 2.5 | n.d. |
| 5.18 | >10 | 1.7 | n.d. |
| 5.19 | 3.01 ± 0.03 | 0.8 ± 0.1 | n.d. |
| 5.20 | 0.66 ± 0.06 | 0.21 ± 0.01 | n.d. |
| 5.21 | 0.47 ± 0.01 | 0.16 ± 0.02 | n.d. |

Competition Experiments

Competition experiments were carried out to determine whether the synthesised analogues were competing with the fluoroprobe for the ATP binding pocket of p38α MAPK. In these experiments, the test compounds were analysed at two concentrations, with a constant concentration of fluoroprobe and increasing concentration of inactive p38α MAPK. Test compounds were prepared from dimethylsulfoxide stocks (10 mM). The test compound (final concentration differs between ligands) and SB203580-fluoroscein (5 nM) were added to each well. The competition binding assay was started by the addition of inactive p38α MAPK (final concentration 0.03-1000 nM), and the FP signals were measured after 1 hour of incubation at room temperature, where each binding data point was performed in duplicate. Graphs for the competition experiments are shown in FIG. 14 indicating that all compounds bind competitively with SB203580-fluoroscein ligand to inactive p38α MAPK.

In Vitro Activation Assay (Phosphorylation of p38α MAPK)

Inactive p38 MAPK (500 ng) was pre-incubated with test inhibitors (1 and 10 μM) for 30 minutes in Tris buffer. The reaction was started by the addition of active MKK6 (5 ng) and ATP (100 μM). After 30 minutes incubation at room temperature, the reaction was stopped with ethylenediaminetetraacetic acid (EDTA) (10 mM). Phosphorylation of p38 MAPK was analysed by Western blotting.

Western Blotting

Reaction samples were mixed 1:1 with Laemmli loading buffer, including β-mercaptoethanol (Biorad). Samples were heated at 95° C. for 5 minutes and 80 ng of protein was resolved using sodium dodecyl sulfate polyacrylamide gel electrophoresis (SDS-PAGE) gels (Biorad) at 200 V for 90 minutes. Proteins were transferred (100 V, 1 hour) to a polyvinylidene difluoride (PVDF) membrane (Merck). Membranes were incubated in blocking buffer (5% skim milk in Tris-buffered saline with Tween 20 (TBST), 1 hour, room temperature) and washed in TBST. Membranes were incubated with primary antibodies against total and phosphorylated p38 MAPK (1:1,000, Cell Signaling Technology) overnight at 4° C. Membranes were washed 4×15 minutes in TBST and probed with a secondary anti-mouse antibody at 1:2,000 dilution for 1 hour at room temperature, followed by washing in TBST (4×15 minutes). Signal detection was done with Western Lightning plus-ECL enhanced chemiluminescent substrate (Perkin Elmer) with the ChemiDoc Imaging System (BioRad).

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

ITEMISED LISTING OF EMBODIMENTS

1. A compound of formula (I), or a pharmaceutically acceptable salt thereof:

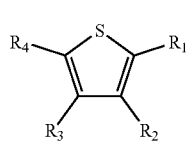

Formula (I)

wherein, $R_1$ is selected from the group consisting of hydrogen, alkyl, alkenyl, alkynyl, alkanoyl, carboalkoxy, acyloxy, aryl, aroyl, heteroaryl, heteroaroyl, heterocyclyl, heterocycloyl, cycloalkyl, O-alkyl and O-aryl, O-heteroaryl, amino and amido, all of which groups may be substituted or unsubstituted;

$R_2$ is selected from the group consisting of hydrogen, alkyl, alkenyl, alkynyl, aryl, alkylaryl, heterocyclyl and heteroaryl, all of which may be substituted or unsubstituted; and $R_3$ and $R_4$ are independently selected from the group consisting of aryl, heteroaryl, heterocyclyl and cycloalkyl, all of which groups may be substituted or unsubstituted.

2. The compound of item 1 wherein the compound is a compound of formula (II), or a pharmaceutically acceptable salt thereof:

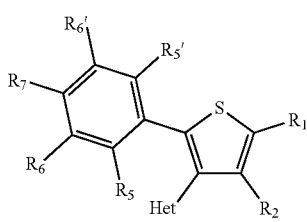

Formula (II)

wherein $R_1$ and $R_2$ are as described in item 1;

Het is selected from the group consisting of $C_5$-$C_7$ heteroaryl and $C_5$-$C_7$ heterocyclyl, each of which groups may be substituted or unsubstituted; and $R_5$, $R_5'$, $R_6$, $R_6'$ and $R_7$ are independently selected from the group consisting of hydrogen, halo, haloalkyl, hydroxy and nitro.

3. The compound of item 1 or item 2 wherein the compound is a compound of formula (III), or a pharmaceutically acceptable salt thereof:

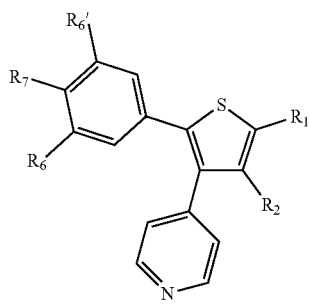

Formula (III)

wherein $R_1$, $R_2$, $R_6$, $R_6'$ and $R_7$ are as described in item 1 or item 2 for formula (I) or formula (II).

4. The compound of any one of the preceding items wherein $R_1$ is selected from the group consisting of hydrogen, $C_1$-$C_{12}$ alkyl, $C_2$-$C_{12}$ alkenyl, $C_2$-$C_{12}$ alkynyl, $C_2$-$C_{12}$ alkanoyl, $C_5$-$C_7$ aryl, $C_5$-$C_7$ aroyl, $C_5$-$C_7$ heteroaryl, $C_5$-$C_7$ heteroaroyl, $C_5$-$C_7$ heterocyclyl, $C_5$-$C_7$ heterocycloyl and $C_5$-$C_7$ cycloalkyl, all of which groups may be substituted or unsubstituted.

5. The compound of any one of the preceding items wherein $R_1$ is selected from the group consisting of $C_2$-$C_6$ alkynyl, $C_2$-$C_6$ alkanoyl, $C_5$-$C_6$ aryl, $C_5$-$C_6$ aroyl, $C_5$-$C_6$ heteroaryl, $C_5$-$C_6$ heteroaroyl, $C_5$-$C_6$ heterocyclyl and $C_5$-$C_6$ heterocycloyl, all of which groups may be substituted or unsubstituted.

6. The compound of any one of the preceding items wherein $R_2$ is selected from the group consisting of hydrogen, $C_1$-$C_{12}$ alkyl, $C_2$-$C_{12}$ alkenyl, $C_2$-$C_{12}$ alkynyl, $C_5$-$C_7$ aryl and alkyl-$C_5$-$C_7$ aryl, all of which may be substituted or unsubstituted.

7. The compound of any one of the preceding items wherein $R_2$ is hydrogen.

8. The compound of any one of the preceding items wherein $R_3$ is selected from the group consisting of $C_5$-$C_7$ heteroaryl and $C_5$-$C_7$ heterocyclyl, each of which groups may be substituted or unsubstituted.

9. The compound of any one of the preceding items wherein $R_3$ is selected from the group consisting of $C_6$ nitrogen heteroaryl and $C_6$ nitrogen heterocycyl, each of which groups may be substituted or unsubstituted.

10. The compound of any one of the preceding items wherein $R_3$ is selected from the group consisting of pyridyl, piperidyl, pyrazyl, pyrimidyl and pyridazyl, each of which groups may be substituted or unsubstituted.

11. The compound of any one of the preceding items wherein $R_4$ is substituted or unsubstituted $C_5$-$C_7$ aryl or $C_5$-$C_7$ heteroaryl.

12. The compound of any one of the preceding items wherein $R_4$ is substituted or unsubstituted phenyl.

13. The compound of any one of the preceding items wherein $R_4$ is phenyl substituted with a substituent selected from the group consisting of halo, haloalkyl, hydroxy and nitro.

14. The compound of any one of the preceding items wherein Het is selected from the group consisting of pyridyl, piperidyl, pyrazyl, pyrimidyl and pyridazyl, each of which groups may be substituted or unsubstituted.

15. The compound of any one of the preceding items wherein Het is selected from the group consisting of pyridyl, piperidyl and pyrimidyl, each of which groups may be substituted or unsubstituted.

16. The compound of any one of the preceding items wherein $R_5$, $R_5'$, $R_6$, $R_6'$ and $R_7$ are independently selected from the group consisting of hydrogen, halo, haloalkyl, hydroxy and nitro 17. The compound of any one of the preceding items wherein $R_5$, $R_5'$, $R_6$, $R_6'$ and $R_7$ are independently selected from the group consisting of hydrogen, halo and haloalkyl.

18. The compound of any one of the preceding items wherein $R_5$, $R_5'$, $R_6$ and $R_6'$ are hydrogen.

19. The compound of any one of the preceding items wherein $R_7$ is selected from the group consisting of halo and haloalkyl.

20. The compound of any one of the preceding items wherein the compound is a compound of the below formula, or a pharmaceutically acceptable salt thereof:

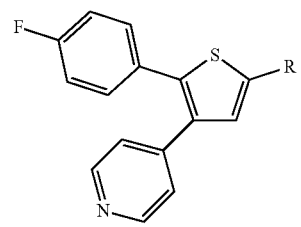

wherein R is selected from the groups shown in the below table

| R |
| --- |
| ![alkynyl-NH2] |
| ![alkynyl-piperazine-NH] |
| ![piperidine-N-benzyl-NH] |
| ![alkyl-OH] |
| ![alkynyl-NH2] |
| ![alkynyl-morpholine] |

US 11,273,153 B2
| 99 -continued | 100 -continued |
|---|---|
| R | R |
| 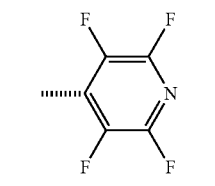 |  |
| 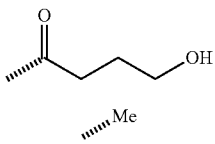 | 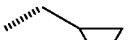 |
| 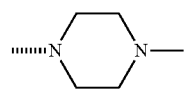 |  |
| 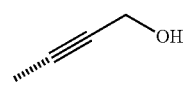 |  |
| 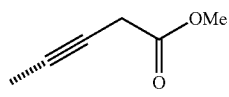 | 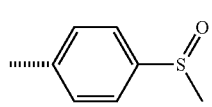 |
| 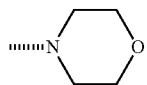 | 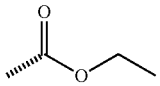 |
| 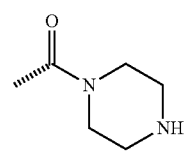 |  |
| 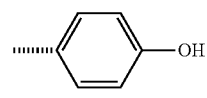 | 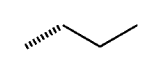 |
| 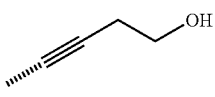 | 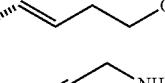 |
| 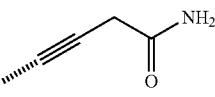 | 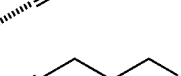 |
| 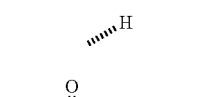 |  |
| 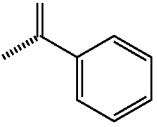 | 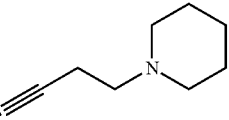 |
| 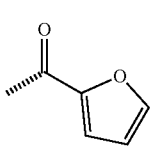 |  |

-continued

R

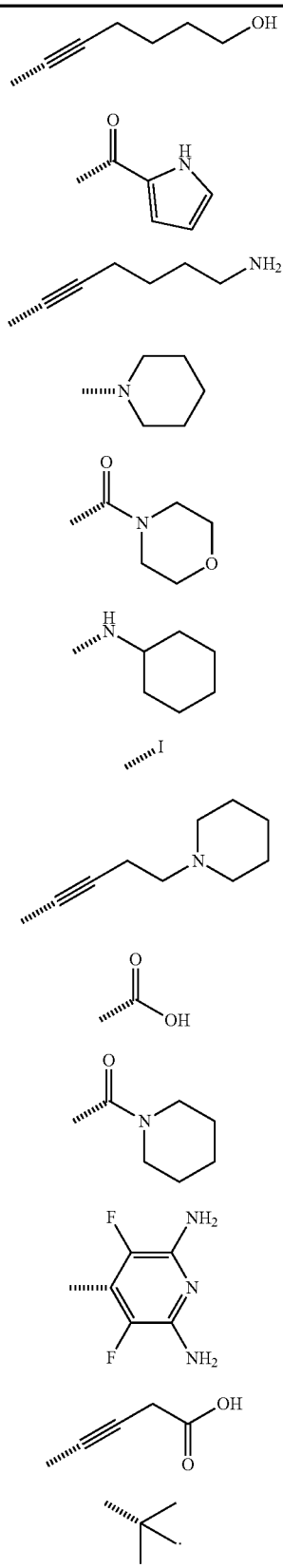

21. The compound of any one of the preceding items wherein the compound, or a pharmaceutically acceptable salt thereof, is selected from the group consisting of:

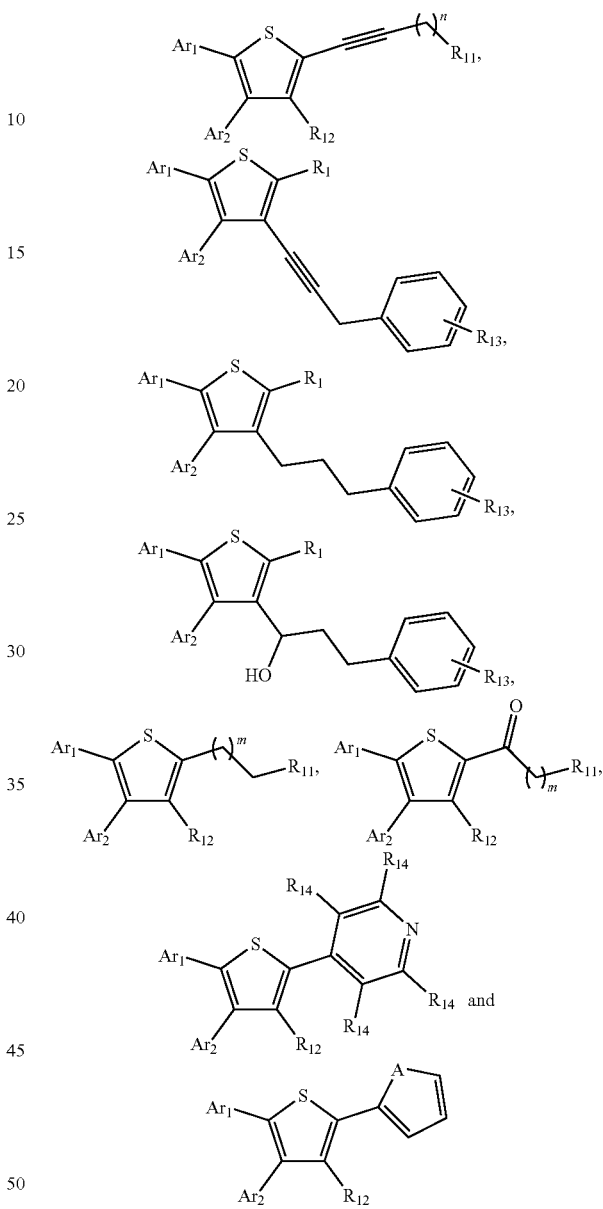

wherein, $Ar_1$ and $Ar_2$ are independently substituted or unsubstituted aryl or heteroaryl, A is selected from oxygen, sulphur or nitrogen, n is 1 or 2, m is 0 to 6, $R_1$ is as described in any one of the embodiments for formula (I) to (III), $R_{11}$ is selected from the group consisting of hydroxy, amino, $C_1$-$C_6$ alkyl, phenyl, furan, morpholine, piperazine and N-phthalimide;

$R_{12}$ is selected from the group consisting of hydrogen, alkylphenyl and hydroxyalkyl phenyl wherein the phenyl ring may be substituted with $R_{13}$;

$R_{13}$, when present, is selected from the group consisting of halo, amino, hydroxy, haloalkyl, $C_1$-$C_6$ alkyl and $C_1$-$C_6$ alkanoyl; and each incidence of $R_{14}$ is independently selected from the group consisting of hydrogen, fluoro, chloro, bromo, iodo, amino and aminoalkyl.

22. The compound of any one of the preceding items wherein $Ar_2$ is substituted or unsubstituted pyridyl.
23. The compound of any one of the preceding items wherein A is preferably oxygen.
24. The compound of any one of the preceding items wherein $R_{12}$ is preferably hydrogen.
25. The compound of any one of the preceding items wherein it is preferred that $R_{13}$ is not present, that is, only hydrogens are attached to the ring carbons.
26. The compound of any one of the preceding items wherein each incidence of $R_{14}$ is independently selected from fluoro or amino.
27. The compound of any one of the preceding items wherein $Ar_1$ is 4-fluorophenyl.
28. The compound of any one of the preceding items wherein $Ar_2$ is 4-pyridyl.
29. The compound of any one of the preceding items wherein the compound is selected from the group consisting of:

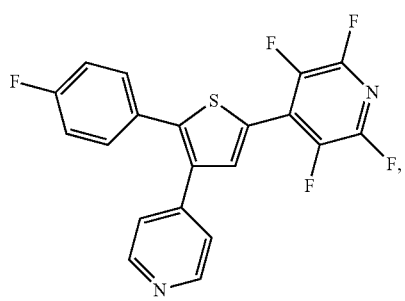

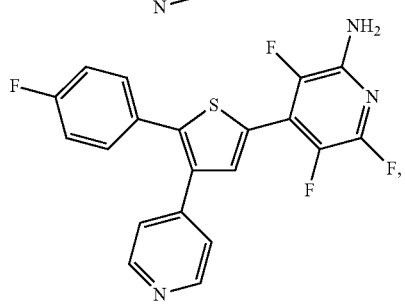

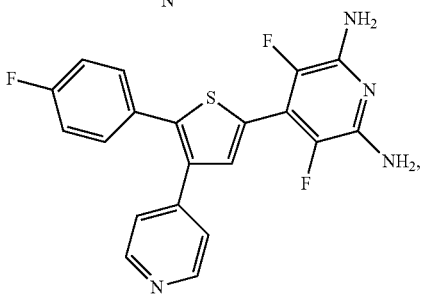

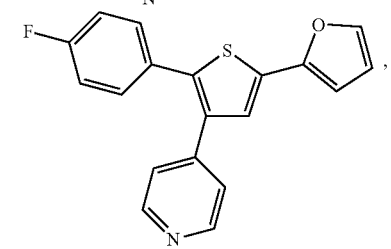

-continued

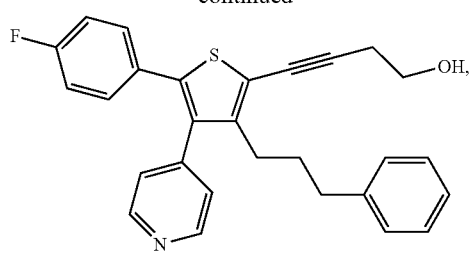

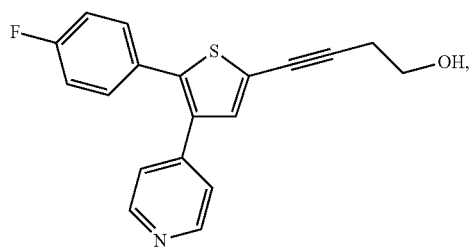

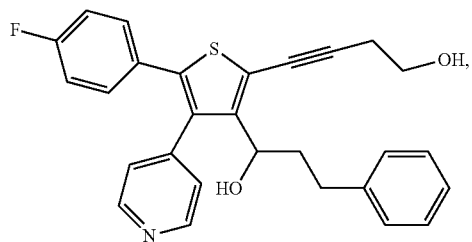

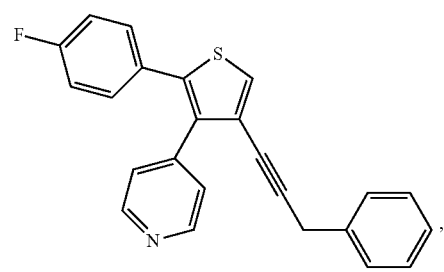

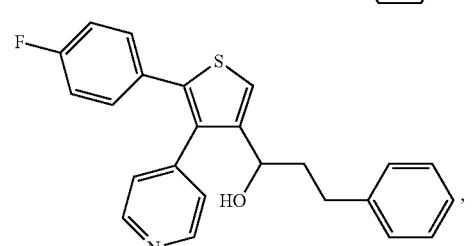

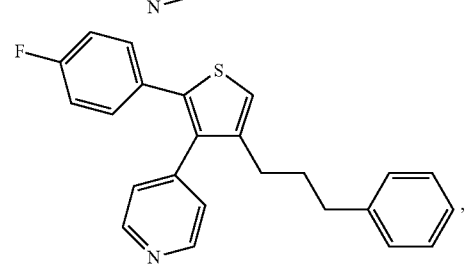

105
-continued

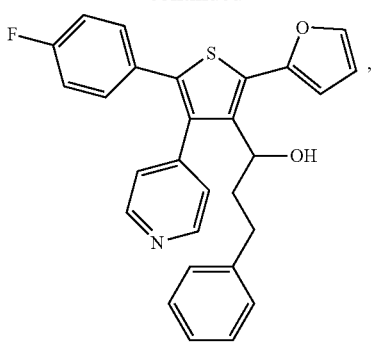

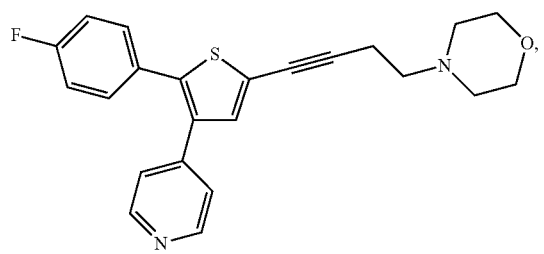

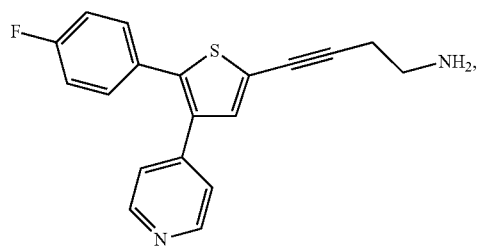

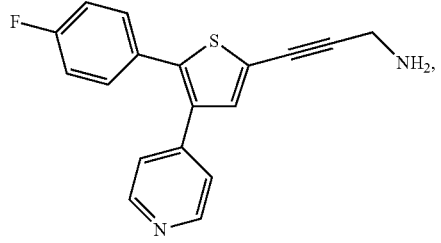

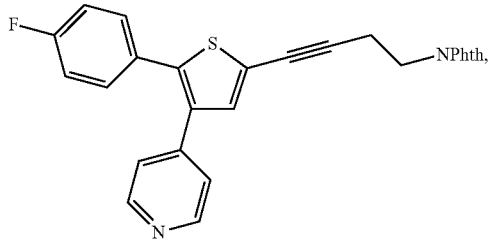

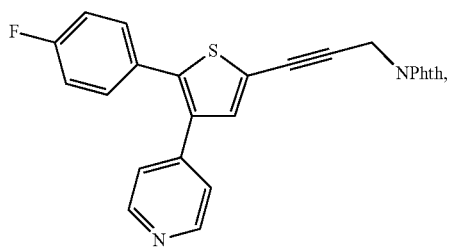

106
-continued

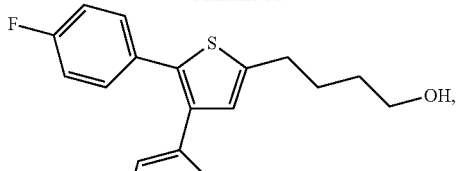

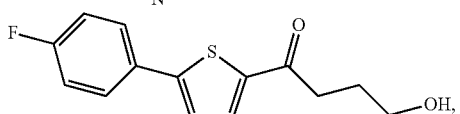

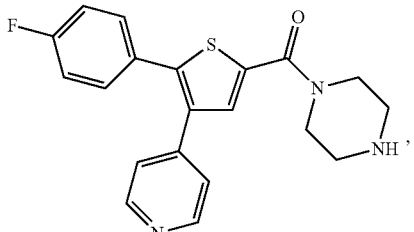

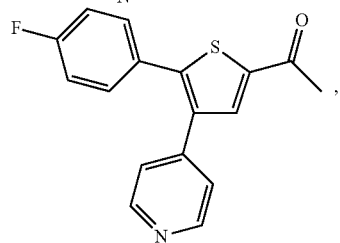

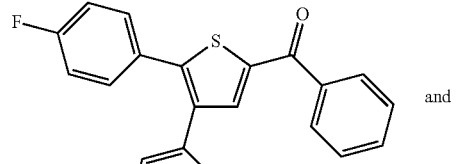

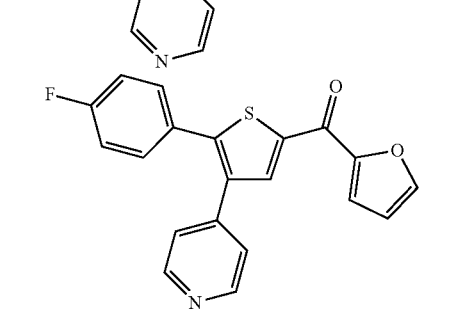

and or a pharmaceutically acceptable salt thereof.

30. The compound of any one of the preceding items wherein the compound of the first aspect is a non-naturally occurring compound 31. A pharmaceutical composition comprising an effective amount of a compound of any one of items 1 to 30, or a pharmaceutically acceptable salt thereof, and a pharmaceutically acceptable carrier, diluent and/or excipient.

32. The pharmaceutical composition of any one of items 1 to 30 wherein the pharmaceutical composition is for the treatment or prophylaxis of a disease, disorder or condition responsive to MAPK inhibition, preferably p38 MAPK inhibition, more preferably p38α MAPK inhibition.

33. A method of treating a patient suffering from a disease, disorder or condition responsive to MAPK inhibition including the step of administering an effective amount of a compound of any one of items 1 to 30, or a pharmaceutically effective salt thereof, or the pharmaceutical composition of any one of items 31 or 32, to the patient.

34. A compound of any one of items 1 to 30, or a pharmaceutically effective salt thereof, or the pharmaceutical composition of any one of items 31 or 32 for use in the treatment of a disease, disorder or condition responsive to MAPK inhibition.

35. Use of a compound of any one of items 1 to 30, or a pharmaceutically effective salt thereof, in the manufacture of a medicament for the treatment of a disease, disorder or condition responsive to MAPK inhibition.

36. The method, compound or use of any one of items 33 to 35 wherein the disease, disorder or condition is responsive to p38 MAPK inhibition.

37. The method, compound or use of any one of items 33 to 36 wherein the disease, disorder or condition is responsive to p38α MAPK inhibition.

38. The method, compound or use of any one of items 33 to 37 wherein the method is a method of reducing inflammation, or use is a use in treating inflammation, in a patient by inhibiting MAPK, particularly by inhibiting p38 MAPK, more particularly by inhibiting p38α MAPK.

39. The method, compound or use of any one of items 33 to 38 wherein the disease, disorder or condition is selected from the group consisting of arthritis, inflammatory bowel disease, asthma, psoriasis, myocardial injury, stroke, cancer, Alzheimer's disease, HIV, COPD, multiple myeloma, myelodysplastic syndrome, acute respiratory distress syndrome, coronary heart disease, acute coronary syndrome, major depressive disorder, dental pain, artherosclerosis, neuropathic pain and inflammation associated with any one or more of the aforementioned diseases, disorders or conditions.

40. The method, compound or use of any one of items 33 to 39 wherein the patient is a domestic or livestock animal or a human.

41. A complex of a compound of any one of items 1 to 30, or a pharmaceutically effective salt thereof, with a p38 MAPK enzyme.

42. The complex of embodiment 40 wherein the p38 MAPK enzyme is a p38α MAPK enzyme.

The invention claimed is:

1. A compound of formula (I), or a pharmaceutically acceptable salt thereof:

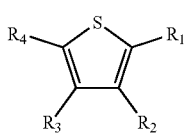

Formula (I)

wherein,
$R_2$ is selected from the group consisting of hydrogen, alkyl, alkenyl, alkynyl, aryl, and alkylaryl, all of which may be substituted or unsubstituted;
$R_1$ is selected from the group consisting of hydrogen, alkyl, alkenyl, alkynyl, carboalkoxy, aryl, and cycloalkyl, all of which may be substituted or unsubstituted;
wherein one of $R_1$ and $R_2$ is alkynyl, which may be substituted or unsubstituted;
$R_3$ is pyridyl, which may be substituted or unsubstituted;
$R_4$ is phenyl, which may be substituted or unsubstituted;
each substituent is independently selected from the group consisting of: $C_{1-8}$ alkyl, $C_{1-8}$ alkoxy, $C_{2-8}$ alkenyl, $C_{2-8}$ alkynyl, $C_6$ aryl, aryloxy, halo, hydroxyl, halogenated alkyl, $NR_{10}H$, $NR_{10}R_{10}$, CN, $NO_2$, $N_3$, $CH_2OH$, $CONH_2$, $CONR_{10}R_{10}$, $CO_2R_{10}$, $CH_2OR_{10}$, $NHCOR_{10}$, $NHCO_2R_{10}$, $CF_3S$, and $CF_3SO_2$;
wherein each $R_{10}$ is independently selected from H or $C_{1-6}$ alkyl, each $C_{1-6}$ alkyl may be unsubstituted or substituted with one or more substituents independently selected from the group consisting of: halo, hydroxyl and $NH_2$;
wherein each $C_{1-8}$ alkyl may be unsubstituted or substituted with one or more substituents independently selected from the group consisting of: $C_{1-8}$ alkoxy, $C_{2-8}$ alkenyl, $C_{2-8}$ alkynyl, $C_6$ aryl, aryloxy, halo, hydroxyl, halogenated alkyl, $NR_{10}H$, $NR_{10}R_{10}$, CN, $NO_2$, $N_3$, $CH_2OH$, $CONH_2$, $CONR_{10}R_{10}$, $CO_2R_{10}$, $CH_2OR_{10}$, $NHCOR_{10}$, $NHCO_2R_{10}$, $CF_3S$, and $CF_3SO_2$;
wherein each $C_{1-8}$ alkoxy substituent may be unsubstituted or substituted with one or more substituent independently selected from the group consisting of: $C_{1-8}$ alkyl, $C_{2-8}$ alkenyl, $C_{2-8}$ alkynyl, $C_6$ aryl, aryloxy, halo, hydroxyl, halogenated alkyl, $NR_{10}H$, $NR_{10}R_{10}$, CN, $NO_2$, $N_3$, $CH_2OH$, $CONH_2$, $CONR_{10}R_{10}$, $CO_2R_{10}$, $CH_2OR_{10}$, $NHCOR_{10}$, $NHCO_2R_{10}$, $CF_3S$, and $CF_3SO_2$;
wherein each $C_{2-8}$ alkenyl may be unsubstituted or substituted with one or more substituents independently selected from the group consisting of: $C_{1-8}$ alkoxy, $C_{2-8}$ alkynyl, $C_6$ aryl, aryloxy, halo, hydroxyl, halogenated alkyl, $NR_{10}H$, $NR_{10}R_{10}$, CN, $NO_2$, $N_3$, $CH_2OH$, $CONH_2$, $CONR_{10}R_{10}$, $CO_2R_{10}$, $CH_2OR_{10}$, $NHCOR_{10}$, $NHCO_2R_{10}$, $CF_3S$, and $CF_3SO_2$;
wherein each $C_{2-8}$ alkynyl may be unsubstituted or substituted with one or more substituents independently selected from the group consisting of: $C_{1-8}$ alkoxy, $C_{2-8}$ alkenyl, $C_6$ aryl, aryloxy, halo, hydroxyl, halogenated alkyl, $NR_{10}H$, $NR_{10}R_{10}$, CN, $NO_2$, $N_3$, $CH_2OH$, $CONH_2$, $CONR_{10}R_{10}$, $CO_2R_{10}$, $CH_2OR_{10}$, $NHCOR_{10}$, $NHCO_2R_{10}$, $CF_3S$, and $CF_3SO_2$;
wherein each $C_6$ aryl may be unsubstituted or substituted with one or more substituents independently selected from the group consisting of: $C_{1-8}$ alkyl, $C_{1-8}$ alkoxy, $C_{2-8}$ alkenyl, $C_{2-8}$ alkynyl, aryloxy, halo, hydroxyl, halogenated alkyl, $NR_{10}H$, $NR_{10}R_{10}$, CN, $NO_2$, $N_3$, $CH_2OH$, $CONH_2$, $CONR_{10}R_{10}$, $CO_2R_{10}$, $CH_2OR_{10}$, $NHCOR_{10}$, $NHCO_2R_{10}$, $CF_3S$, and $CF_3SO_2$.

2. A pharmaceutical composition comprising an effective amount of a compound according to claim 1, or a pharmaceutically acceptable salt thereof, and a pharmaceutically acceptable carrier, diluent and/or excipient.

3. A method of treating a disease, disorder or condition responsive to p38α MAPK inhibition, the method including the step of administering to a subject in need thereof an effective amount of a compound according to claim 1, or a pharmaceutically effective salt thereof, to the patient, wherein the disease, disorder or condition is selected from a group consisting of arthritis, inflammatory bowel disease, asthma, psoriasis, myocardial injury, cardiac remodeling, renal fibrosis, stroke, cancer associated with p38α MAPK activation, Alzheimer's disease, HIV, COPD, multiple myeloma, myelodysplastic syndrome, acute respiratory distress syndrome, coronary heart disease, acute coronary syndrome, major depressive disorder, dental pain, artherosclerosis, neuropathic pain, and inflammation associated with any one or more of these diseases, disorders or conditions, wherein the inflammation is associated with p38α MAPK activation.

4. The method of claim 3 wherein the disease, disorder or condition is inflammation associated with any one or more of arthritis, inflammatory bowel disease, asthma, psoriasis, myocardial injury, cardiac remodeling, renal fibrosis, stroke, cancer associated with p38α MAPK activation, Alzheimer's disease, HIV, COPD, multiple myeloma, myelodysplastic syndrome, acute respiratory distress syndrome, coronary heart disease, acute coronary syndrome, major depressive disorder, dental pain, artherosclerosis, and neuropathic pain, wherein the inflammation is associated with p38α MAPK activation.

5. The method of claim 3 wherein the patient is a human.

6. The compound of claim 1 wherein $R_3$ is unsubstituted pyridyl.

7. The compound of claim 1 wherein the compound is a compound of formula (III), or a pharmaceutically acceptable salt thereof:

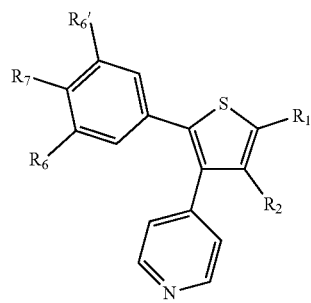

Formula (III)

wherein $R_1$ and $R_2$ are as described in claims 1; and $R_6$, $R_6'$ and $R_7$ are independently selected from the group consisting of hydrogen, halo, haloalkyl, hydroxy and nitro.

8. The compound of claim 1 wherein the compound is selected from the group consisting of:

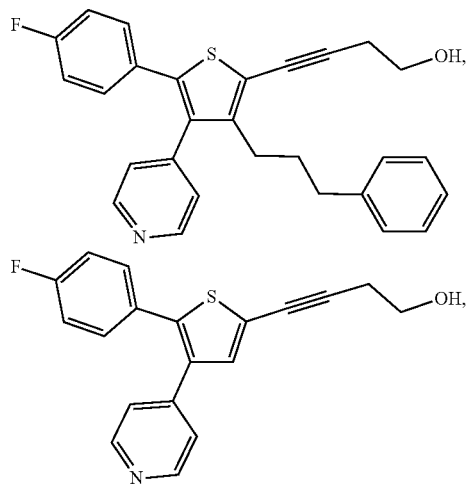

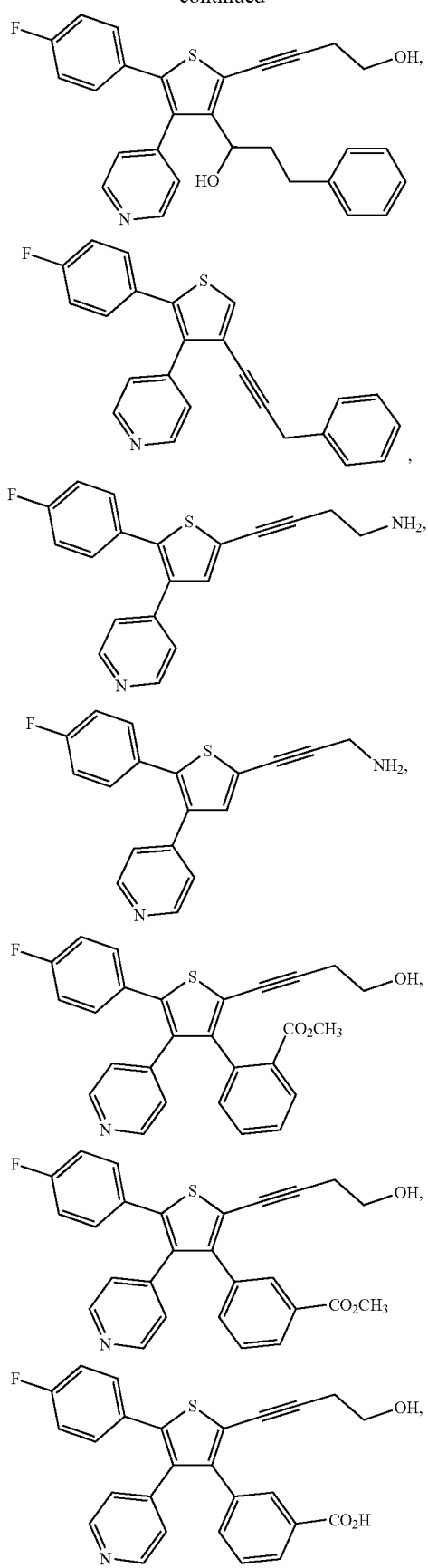

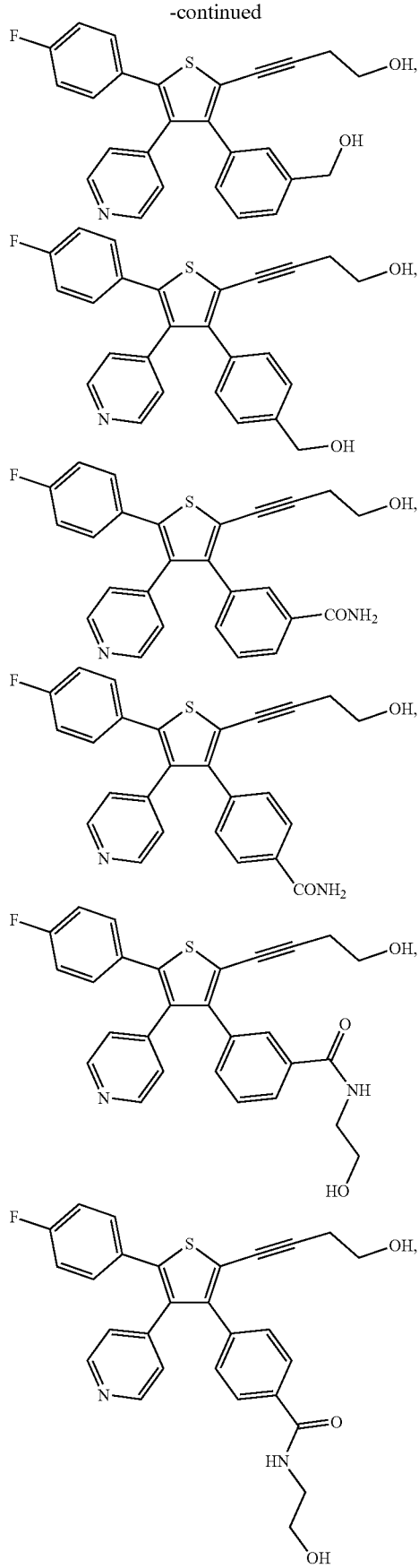
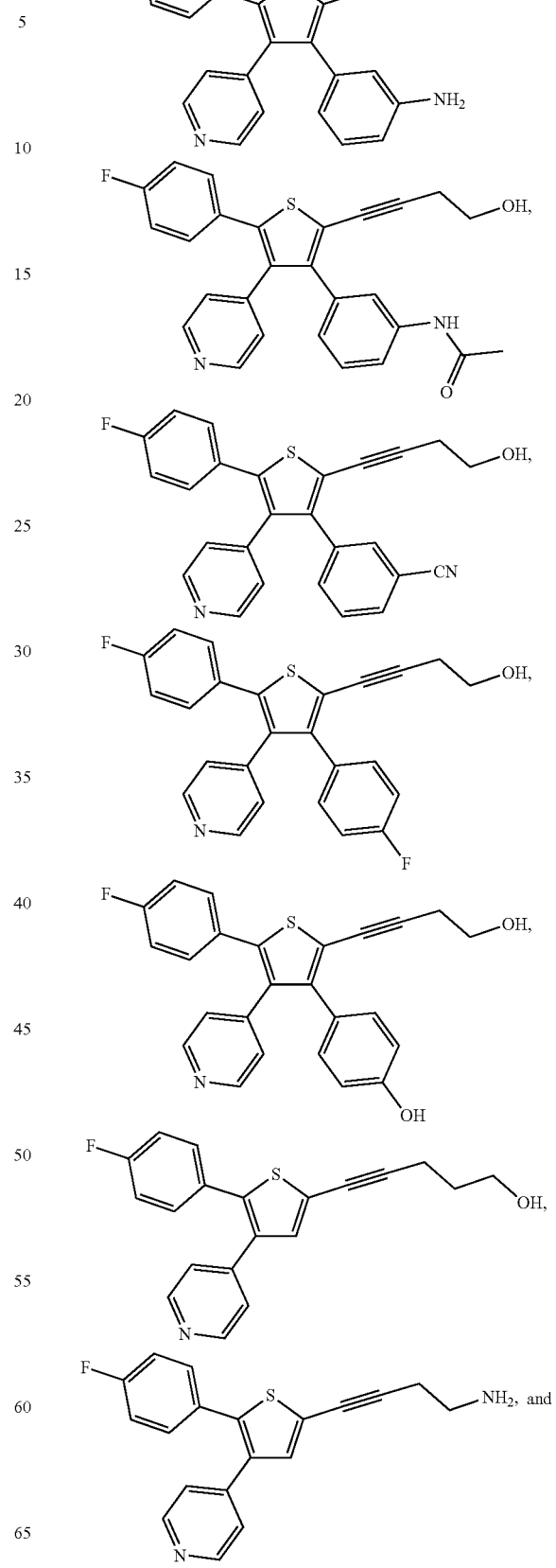

-continued

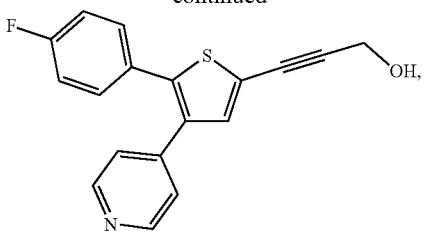

or a pharmaceutically acceptable salt thereof.

9. The compound of claim 1 wherein the compound is selected from the group consisting of:

-continued

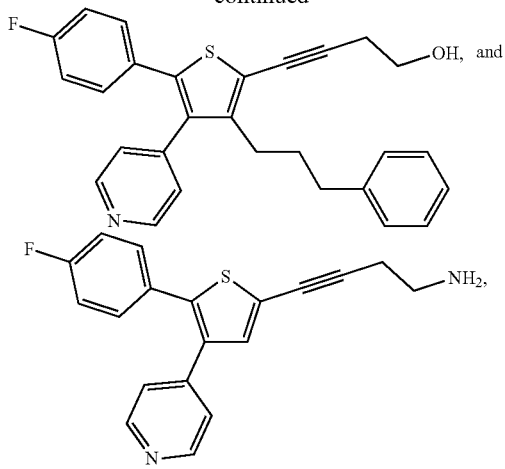

or a pharmaceutically acceptable salt thereof.

10. The compound of claim 1 wherein $R_1$ is alkynyl.
11. The compound of claim 1 wherein $R_2$ is selected from the group consisting of hydrogen, aryl, and alkylaryl.
12. The compound of claim 1 wherein $R_2$ is hydrogen.
13. The compound of claim 1 wherein $R_2$ is aryl.
14. The compound of claim 1 wherein $R_2$ is alkylaryl.
15. The compound of claim 1 wherein $R_2$ is alkynyl.
16. The compound of claim 1 wherein $R_1$ is selected from the group consisting of hydrogen, aryl and alkylaryl.
17. The compound of claim 1 wherein $R_1$ is hydrogen.
18. The compound of claim 1 wherein $R_3$ is 4-pyridyl and $R_4$ is 4-fluorophenyl.

* * * * *